United States Patent
Hoveyda et al.

(10) Patent No.: US 9,475,814 B2
(45) Date of Patent: *Oct. 25, 2016

(54) CHIRAL N-ACYL-5,6,7(8-SUBSTITUTED)-TETRA HYDRO-[1,2,4]TRIAZOLO[4,3-A]PYRAZINES AS SELECTIVE NK-3 RECEPTOR ANTAGONISTS, PHARMACEUTICAL COMPOSITION, METHODS FOR USE IN NK-3 RECEPTOR MEDIATED DISORDERS AND CHIRAL SYNTHESIS THEREOF

(71) Applicant: Euroscreen S.A., Charleroi (BE)

(72) Inventors: Hamid R. Hoveyda, Brussels (BE); Guillaume Dutheuil, Vedrin (BE); Graeme L. Fraser, Bousval (BE); Marie-Odile Roy, Paris (FR); Mohamed El Bousmaqui, Aulnoy-lez-Valenciennes (FR); Frederic Batt, Lyons (FR)

(73) Assignee: Euroscreen S.A., Charleroi (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/349,595

(22) PCT Filed: Oct. 3, 2012

(86) PCT No.: PCT/EP2012/069546
§ 371 (c)(1),
(2) Date: Apr. 3, 2014

(87) PCT Pub. No.: WO2013/050424
PCT Pub. Date: Apr. 11, 2013

(65) Prior Publication Data
US 2014/0275097 A1    Sep. 18, 2014

Related U.S. Application Data

(60) Provisional application No. 61/543,611, filed on Oct. 5, 2011.

(30) Foreign Application Priority Data

Oct. 3, 2011 (EP) .................................. 11183678
Oct. 3, 2011 (EP) .................................. 11183679
Oct. 3, 2011 (EP) .................................. 11183681
Oct. 3, 2011 (EP) .................................. 11183692

(51) Int. Cl.
C07D 487/04    (2006.01)

(52) U.S. Cl.
CPC .............. *C07D 487/04* (2013.01); *Y02P 20/55* (2015.11)

(58) Field of Classification Search
CPC .................................................. C07D 487/04
See application file for complete search history.

(56) References Cited

U.S. PATENT DOCUMENTS

| 6,414,149 | B1 | 7/2002 | Chu-Moyer et al. |
| 2007/0219181 | A1 | 9/2007 | Kimura et al. |
| 2008/0275052 | A1 | 11/2008 | Dhar et al. |
| 2008/0318935 | A1 | 12/2008 | Beckett et al. |
| 2011/0046096 | A1 | 2/2011 | Pouzet et al. |
| 2012/0142672 | A1 | 6/2012 | Koike et al. |
| 2013/0023530 | A1 | 1/2013 | Hoveyda et al. |

FOREIGN PATENT DOCUMENTS

| EP | 2085398 A1 | 8/2009 |
| JP | H06128261 A | 5/1994 |
| WO | WO-00/43008 A1 | 7/2000 |
| WO | WO-03/082817 A2 | 10/2003 |
| WO | WO-2004/014914 A1 | 2/2004 |
| WO | WO-2004/021984 A2 | 3/2004 |
| WO | WO-2004/080958 A2 | 9/2004 |
| WO | WO-2005/032464 A2 | 4/2005 |
| WO | WO-2005/080397 A2 | 9/2005 |

(Continued)

OTHER PUBLICATIONS

Fassihi, 1993, vol. 92, p. 1-14.*

(Continued)

*Primary Examiner* — Michael Barker
*Assistant Examiner* — Karen Cheng
(74) *Attorney, Agent, or Firm* — Locke Lord LLP; Ralph A. Loren; Nicholas J. DiCeglie, Jr.

(57) ABSTRACT

The present invention relates to novel compounds of Formula I and their use in therapeutic treatments. The invention further relates to a novel chiral synthesis of 5,6,7,(8-substituted)-tetrahydro-[1,2,4]triazolo[4,3-a]pyrazines using N-sp3 protective groups. The invention also provides intermediates for use in the synthesis of compounds of Formula I.

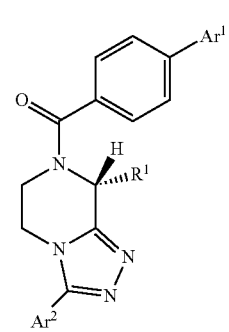

20 Claims, 3 Drawing Sheets

(56) References Cited

FOREIGN PATENT DOCUMENTS

| WO | WO-2006/120478 A2 | 11/2006 |
|---|---|---|
| WO | WO-2007/138351 A2 | 12/2007 |
| WO | WO-2009/072643 A1 | 6/2009 |
| WO | WO-2009/089462 A1 | 7/2009 |
| WO | WO-2009/090055 A1 | 7/2009 |
| WO | WO-2009/095253 A1 | 8/2009 |
| WO | WO-2009/095254 A1 | 8/2009 |
| WO | WO-2010/125101 A1 | 11/2010 |
| WO | WO-2010/125102 A1 | 11/2010 |
| WO | WO-2011/121137 A1 | 10/2011 |
| WO | WO-2013/050424 A1 | 4/2013 |

OTHER PUBLICATIONS

Jeffrey A.S., "Neurokinin antagonists and their potential role in treating depression and other stress disorders", Expert Opinion on Therapeutics Patents, Informa Healthcare, vol. 14, N°10, 2004, pp. 1421-1433.

Granik, V. et al. "Properties of lactim aster of 3-carbomethoxy-4-acetyl-2-piperazinone and the synthesis of 3-oxo-5-acetyl-1,2,3,4,5,6,7,8-octahydropyrazino[2,3-c]pyridazine", Kimiko-Farmatsevticheskii Zhurnal, vol. 2, N°2, 1968, pp. 16-18. [XP002663277].

Fioramonti, J. et al., "Intestinal anti-nociceptive behaviour of NK3 receptor antagonism in conscious rats: evidence to support a peripheral mechanism of action", Neurogastroenterol Motil, vol. 15, Mar. 2003, pp. 363-369.

Shafton, A.D. et al., "Effects of the peripherally acting NK3 receptor antagonist, SB-235375, on intestinal and somatic nociceptive responses and on intestinal motility in anaesthetized rats", Neurogastroenterol Motil, vol. 16, Oct. 2003, pp. 223-231.

Nelson, P.J. et al., "1,2,4-Triazoles. V1.I the Synthesis of Some s-Triazolo[4,3-a]pyrazines", J. Org. Chem., vol. 27, Mar. 1962, pp. 3243-3248.

Hansen, K. B. et al. "First Generation Process for the Preparation of the DPP-IV Inhibitor Sitagliptin", Org. Process Res. Dev., vol. 9, N°5, Aug. 2005, pp. 634-639.

Kowalchick, J. E. et al., "Design, synthesis, and biological evaluation of triazolopiperazine-based b-amino amides as potent, orally active dipeptidyl peptidase IV (DPP-4) inhibitors", Bioorg. Med. Chem. Lett., vol. 17, Jul. 2007, pp. 5934-5939.

Balsells, J. et al., "Synthesis of [1,2,4]Triazolo[4,3-alpha]piperazines via Highly Reactive Chloromethyloxadiazoles", Org. Lett., vol. 7, N°6, Feb. 2005, pp. 1039-1042.

Houghton, L.A. et al., "Effect of the NK3 receptor antagonist, talnetant, on rectal sensory function and compliance in healthy humans", Neurogastroenterol Motil, vol. 19, Feb. 2007, pp. 732-743.

Scolnick, M.D. et al., "Comparative Study of Experimentally Induced Benign and Atypical Hyperplasia in the Ventral Prostate of Differents Rat Strains", J. Andrology, vol. 15, N°4, Jul./Aug. 1994, pp. 287-297.

Rick, F.G. et al., "Combining Growth Hormone-Releasing Hormone AntagonistWith Luteinizing Hormone-Releasing Hormone Antagonist Greatly Augments Benign Prostatic Hyperplasia Shrinkage", J. Urol., vol. 187, Apr. 2012, pp. 1498-1504.

Lomax, A.E. et al., "Neurochemical classification of enteric neurons in the guinea-pig distal colon", Cell Tissue Res, vol. 302, Aug. 2000, pp. 59-72.

Copel, C. et al.,"Activation of neurokinin 3 receptor increases Nav 1.9 current in enteric neurons", J. Physiol., vol. 587, Feb. 2009, pp. 1461-1479.

McCort, G.A. et al., "A rapid and efficient synthesis of imidazo [1,2-a] and [1,2,4]triazolo[4,3-a]piperazine carboxylic acids", Tetrahedron Letters, vol. 33, N°31, Feb. 1992, pp. 4443-4446.

International Search Report of PCT/EP2012/069546.

International Search Report of PCT/EP2011/055218 (published as WO2013/050424).

Navarro, V. M. et al. "Regulation of Gonadotropin-Releasing Hormone Secretion by Kisspeptin/Dynorphin/Neurokinin B Neurons in the Arcuate Nucleus of the Mouse," The Journal of Neuroscience 29(38):11866-11859 (2009).

Murali Dhar, T.G. et al. "Synthesis and SAR of p38x MAP kinase inhibitors based on heterobicyclic scaffolds," Biorganic & Medicinal Chemistry Letters 17, 5019-5024 (2007).

Meltzer, H. Y. et al., "Placebo-Controlled Evaluation of Four Novel Compounds for the Treatment of Schizophrenia and Schizoaffective Disorder," Am J. Psychiatry 161:6, (2004).

Krajewski, S. J. et al. "Morphologic Evidence That Neurokinin B Modulates Gonadotropin-Releasing Hormone Secretion via Neurokinin 3 Receptors in the Rat Median Eminence," The Journal of Comparative Neurology 489:372-386, (2005).

Giardina, G. AM, et al. "Recent advances in neurokinin-3 receptor antagonists," Exp. Opin. Ther. Patents 10(6):939-960, (2000).

Dawson, L. A et al. "Therapeutic Utility of NK3 Receptor Antagonists for the Treatment of Schizophrenia," Current Pharmaceutical Design 16, 344-357, (2010).

Bottomley, M. J. et al. "Structural and Functional Analysis of the Human HDAC4 Catalytic Domain Reveals a Regulatory Structural Zinc-binding Domain," Journal of Biological Chemistry, vol. 283, No. 39, 26694-26704, (2008).

Burke, M. C. et al. "Coexpression of Dynorphin and Neurokinin B Immunoreactivity in the Rat Hypothalamus: Morphologic Evidence of Interrelated Function Within the Arcuate Nucleus," The Journal of Comparative Neurology 498: 712-726, (2006).

Goodman, R. L. et al. "Evidence That Dynorphin Plays a Major Role in Mediating Progesterone Negative Feedback on Gonadotropin-Releasing Hormone Neurons in Sheep," Endocrinology 145(+6): 2959-2967, (2004).

XP-002597351 Chemical Abstract.
XP-002597352 Chemical Abstract.
XP-002597353 Chemical Abstract.
XP-002597354 Chemical Abstract.
XP-002597355 Chemical Abstract.
XP-002597356 Chemical Abstract.
XP-002597357 Chemical Abstract.
XP-002663277 Chemical Abstract.

* cited by examiner

*p = 0.0125 for comparison of Cmpd n°1 to vehicle group at T = 1h, unpaired t-test
**p = 0.0057 in Cmpd n°1 group, comparison of basal versus T = 1h, paired t-test

*p = 0.0163 for comparison of Cmpd n°19 to vehicle group at T = 1h, unpaired t-test
**p = 0.0065 in Cmpd n°1 group, comparison of basal versus T = 1h, paired t-test

CHIRAL N-ACYL-5,6,7(8-SUBSTITUTED)-TETRA HYDRO-[1,2,4]TRIAZOLO[4,3-A]PYRAZINES AS SELECTIVE NK-3 RECEPTOR ANTAGONISTS, PHARMACEUTICAL COMPOSITION, METHODS FOR USE IN NK-3 RECEPTOR MEDIATED DISORDERS AND CHIRAL SYNTHESIS THEREOF

CROSS-REFERENCE TO RELATED APPLICATIONS

This application is a 35 U.S.C. §371 National Phase Application of International PCT Patent Application No. PCT/EP2012/069546, filed Oct. 3, 2012, which application claims priority to European Patent Application Serial Nos. EP 11183678.9, filed Oct. 3, 2011, EP11183692.0, filed Oct. 3, 2011, EP 11183681.3, filed Oct. 3, 2011, EP 11183679.7, filed Oct. 3, 2011, and U.S. Provisional Patent Application No. 61/543,611, filed Oct. 5, 2011, the contents of each of which are incorporated herein by reference in their entireties.

FIELD OF INVENTION

The present invention relates to novel N-acyl-5,6,7,(8-substituted)-tetrahydro-[1,2,4]triazolo[4,3-a]pyrazines including their pharmaceutically acceptable salts and solvates that are selective antagonists to neurokinin-3 receptor (NK-3) and are useful as therapeutic compounds, particularly in the treatment and/or prevention of a broad array of CNS and peripheral diseases or disorders.

The present invention also relates to a novel chiral synthesis of 5,6,7,(8-substituted)-tetrahydro-[1,2,4]triazolo[4,3-a]pyrazine intermediates for use in the synthesis of pharmaceutical active ingredients, such as selective antagonists to the neurokinin 3 receptor (NK-3), especially the N-acyl-5,6,7,(8-substituted)-tetrahydro-[1,2,4]triazolo[4,3-a]pyrazines of the invention. The invention also pertains to novel stereoisomerically pure 5,6,7,(8-substituted)-tetrahydro-[1,2,4]triazolo[4,3-a]pyrazine intermediates obtained by the chiral synthesis of the invention as well as to novel intermediates of this synthesis.

BACKGROUND OF INVENTION

Tachykinin receptors are the targets of a family of structurally related peptides which include substance P (SP), neurokinin A (NKA) and neurokinin B (NKB), named collectively "tachykinins". Tachykinins are synthesized in the central nervous system (CNS) and peripheral tissues, where they exert a variety of biological activities. Three tachykinin receptors are known which are named neurokinin-1 (NK-1), neurokinin-2 (NK-2) and neurokinin-3 (NK-3) receptors. Tachykinin receptors belong to the rhodopsin-like seven membrane G-protein coupled receptors. SP has the highest affinity and is believed to be the endogenous ligand of NK-1, NKA for NK-2 receptor and NKB for NK-3 receptor, although cross-reactivity amongst these ligands does exist. The NK-1, NK-2 and NK-3 receptors have been identified in different species. NK-1 and NK-2 receptors are expressed in a wide variety of peripheral tissues and NK-1 receptors are also expressed in the CNS; whereas NK-3 receptors are primarily expressed in the CNS.

The neurokinin receptors mediate a variety of tachykinin-stimulated biological effects that include transmission of excitatory neuronal signals in the CNS and periphery (e.g. pain), modulation of smooth muscle contractile activity, modulation of immune and inflammatory responses, induction of hypotensive effects via dilatation of the peripheral vasculature and stimulation of endocrine and exocrine gland secretions.

In the CNS, the NK-3 receptor is expressed in regions including the medial prefrontal cortex, the hippocampus, the thalamus and the amygdala. Moreover, NK-3 receptors are expressed on dopaminergic neurons. Activation of NK-3 receptors has been shown to modulate dopamine, acetylcholine and serotonin release suggesting a therapeutic utility for NK-3 receptor modulators for the treatment of a variety of disorders including psychotic disorders, anxiety, depression, schizophrenia as well as obesity, pain or inflammation (Exp. Opinion Ther. Patents (2000), 10(6), 939-960; Current Opinion in Investigational Drugs, 2001, 2(7), 950-956 and Current Pharmaceutical Design, 2010, 16, 344-357).

Schizophrenia is classified into subgroups. The paranoid type is characterized by delusions and hallucinations and absence of thought disorder, disorganized behavior, and affective flattening. In the disorganized type, which is also named 'hebephrenic schizophrenia' in the International Classification of Diseases (ICD), thought disorder and flat affect are present together. In the catatonic type, prominent psychomotor disturbances are evident, and symptoms may include catatonic stupor and waxy flexibility. In the undifferentiated type, psychotic symptoms are present but the criteria for paranoid, disorganized, or catatonic types have not been met. The symptoms of schizophrenia normally manifest themselves in three broad categories, i.e. positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as a lack of sustained attention and deficits in decision making. The current antipsychotic drugs (APDs) are fairly successful in treating the positive symptoms but fare less well for the negative and cognitive symptoms. Contrary to that, NK3 antagonists have been shown clinically to improve on both positive and negative symptoms in schizophrenics (Meltzer et al, Am. J. Psychiatry, 161, 975-984, 2004) and ameliorate cognitive behavior of schizophrenics (Curr. Opinion. Invest. Drug, 6, 717-721, 2005).

In rat, morphological studies provide evidence for putative interactions between NKB neurons and the hypothalamic reproductive axis (Krajewski et al, J. Comp. Neurol., 489(3), 372-386, 2005). In arcuate nucleus neurons, NKB expression co-localizes with estrogen receptor cc and dynorphin, implicated in progesterone feedback to Gonadotropin Releasing Hormone (GnRH) secretion (Burke et al., J. Comp. Neurol., 498(5), 712-726, 2006; Goodman et al., Endocrinology, 145, 2959-2967, 2004). Moreover, NK-3 receptor is highly expressed in the hypothalamic arcuate nucleus in neurons which are involved in the regulation of GnRH release.

WO 00/43008 discloses a method of suppressing gonadotropin and/or androgen production with specific NK-3 receptor antagonists. More particularly, the WO 00/43008 application relates to lowering luteinizing hormone (LH) blood level by administering an NK-3 receptor antagonist. Concurrently or alternatively with gonadotropin suppression, WO 00/43008 also relates to suppression of androgen production with NK-3 receptor antagonists. Recently it has been postulated that NKB acts autosynaptically on kisspeptin neurons in the arcuate nucleus to synchronize and shape the pulsatile secretion of kisspeptin and drive the release of GnRH from fibers in the median eminence (Navarro et al., J. of Neuroscience, 23, 2009-pp 11859-11866). All these observations suggest a therapeutic utility for NK-3 receptor modulators for sex hormone-dependent diseases.

Non-peptide ligands have been developed for each of the tachykinin receptors. Some of them have been described as dual modulators able to modulate both NK-2 and NK-3 receptors (WO 06/120478). However, known non-peptide NK-3 receptor antagonists suffer from a number of drawbacks, notably poor safety profile and limited CNS penetrability that may limit the success of these compounds in clinical development.

On this basis, new potent and selective antagonists of NK-3 receptor may be of therapeutic value for the preparation of drugs useful in the treatment and/or prevention of CNS and peripheral diseases or disorders in which NKB and the NK-3 receptors are involved.

Antagonists to Neurokinin-3 Receptor (NK-3)

The invention thus encompasses compounds of general Formula I, their pharmaceutically acceptable salts and solvates as well as methods of use of such compounds or compositions comprising such compounds as antagonists to the NK-3 receptor. Compounds of Formula I are N-acyl-5, 6,7,(8-substituted)-tetrahydro-[1,2,4]triazolo[4,3-a]pyrazines. The compounds of the invention are generally disclosed in international patent application PCT/EP2011/055218 but none is specifically exemplified therein.

In a general aspect, the invention provides compounds of general Formula I:

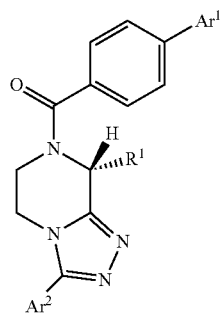

I and pharmaceutically acceptable salts and solvates thereof, wherein

Ar¹ is unsubstituted thiophen-2-yl, unsubstituted phenyl, or 4-fluorophenyl;

R¹ is H or methyl;

Ar² is of general Formula (i), (ii) or (iii):

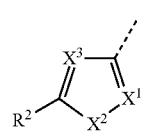

(i)

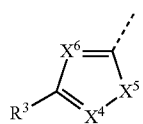

(ii)

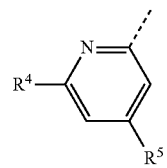

(iii)

wherein

R² is linear or branched C1-C4 alkyl, C1-C2 haloalkyl, linear or branched C2-C3 alkenyl, C3-C4 cycloalkyl or di(C1-C2 alkyl)amino;

X¹ is N or C—R⁶ wherein R⁶ is H, fluoro or C1-C2 alkyl;

X² is O or S;

X³ is N, or X³ is CH under the condition that X¹ is N and X² is N—R⁷ wherein R⁷ is linear or branched C1-C3 alkyl or cyclopropyl;

R³ is linear or branched C1-C4 alkyl or C3-C4 cycloalkyl;

X⁴ is N or C—R⁸ wherein R⁸ is H or C1-C2 alkyl;

X⁵ is O or S;

X⁶ is N, or X⁶ is CH under the condition that X⁴ is N and X⁵ is N—R⁹ wherein R⁹ is linear or branched C1-C3 alkyl or cyclopropyl;

R⁴ is halo, cyano, methyl, or hydroxyl;

R⁵ is H or halo;

with the condition that when Ar² is of Formula (iii), then R¹ is methyl; and the compound of Formula I is not (3-(2-isobutylthiazol-4-yl)-5,6-dihydro-[1,2,4]triazolo[4,3-a]pyrazin-7(8H)-yl)(4-(thiophen-2-yl)phenyl)methanone;

[1,1'-biphenyl]-4-yl(8-methyl-3-(6-methylpyridin-2-yl)-5,6-dihydro-[1,2,4]triazolo[4,3-a]pyrazin-7 (8H)-yl)methanone;

(8-methyl-3-(6-methylpyridin-2-yl)-5,6-dihydro-[1,2,4]triazolo[4,3-a]pyrazin-7(8H)-yl)(4-(thiophen-2-yl)phenyl)methanone.

In another aspect, the present invention provides a pharmaceutical composition comprising at least one compound according to the invention or a pharmaceutically acceptable salts or solvate thereof.

The invention also relates to the use of the above compounds or their pharmaceutically acceptable salts and solvates as modulators of NK-3 receptors, preferably as antagonists of NK-3 receptors.

The invention further provides methods of treatment and/or prevention of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carninoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a therapeutically effective amount of a compound or pharmaceutically acceptable salts or solvate of Formula I, to a patient in need thereof. Preferably the patient is a warm-blooded animal, more preferably a human.

The invention further provides methods of treatment for gynecological disorders and infertility. In particular, the invention provides methods to suppress the LH-surge in assisted conception comprising the administration of a therapeutically effective amount of a compound or pharmaceutically acceptable salts or solvate of Formula I, to a patient in need thereof. Preferably the patient is a warm-blooded animal, more preferably a woman.

The invention further provides methods to affect androgen production to cause male castration and to inhibit the sex drive in male sexual offenders comprising the administration of a therapeutically effective amount of a compound or pharmaceutically acceptable salts or solvate of Formula I, to a patient in need thereof. Preferably the patient is a warm-blooded animal, more preferably a man.

The invention also provides the use of a compound of Formula I or a pharmaceutically acceptable salts or solvate thereof as a medicament. Preferably, the medicament is used for the treatment and/or prevention of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carninoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. The medicament may also be used for the treatment of gynecologic disorders, infertility and to affect androgen production to cause male castration.

Chiral synthesis of 5,6,7,(8-substituted)-tetrahydro-[1,2,4]triazolo[4,3-a]pyrazine compounds The N-acyl-5,6,7,(8-substituted)-tetrahydro-[1,2,4]triazolo[4,3-a]pyrazine of general Formula I of the invention can be prepared by different ways with reactions known to a person skilled in the art.

The Applicant further proposes therein a new chiral synthesis for the compounds of the invention and especially for (R)-8-substituted-5,6,7,8-tetrahydro-[1,2,4]triazolo[4,3-a]pyrazine intermediates that may be converted into compounds of Formula I by N-acylation.

Different synthetic approaches that are of general relevance to the synthesis of (R)-8-methyl-5,6,7,8-tetrahydro-[1,2,4]triazolo[4,3-a]pyrazine are known in the literature. The below examples and experimental conditions of relevant approaches provided are illustrative only.

In Method A(i) (see Scheme A), the [1,2,4]triazolopyrazine core IIIa(i) is formed by acetylation of 2-hydrazidopyrazine (step 1) followed by a cyclodehydration reaction (step 2), using procedures familiar to those skilled in the art. This methodology was initially developed by Nelson and Potts (*J. Org. Chem.* 1962, 27, 3243-3248). Subsequent reduction of the pyrazine ring with $H_2$/Pd affords the [1,2,4]triazolo[4,3-a]piperazine (step 3). This method is well described in the literature and has been used, for example, in the Merck synthesis of Sitagliptin (Hansen, K. B. et al. *Org. Process Res. Dev.* 2005, 9, 634-639 and references therein). However, i) perusal of the existing literature indicates that this procedure is generally used with substrates wherein $R^1$=H (i.e. non-chiral analogs, cf. Scheme A), and ii) that the application of this method to prepare chiral [1,2,4]triazolo[4,3-a]piperazine variant of general Formula IVa(i) (in Method A(i)) has not been disclosed. The dearth of examples of pyrazine substrates wherein $R^1 \neq H$ in this methodology may be due to the difficulty of pyrazine reduction step; noteworthy in this regard is the fact that in the optimized process scale-up procedure reported by Hansen et al., the pyrazine ($R^1$=H) reduction (step 3, Scheme A) proceeded in merely 51% yield. In addition to the issue of chemical yield, access to chiral substrates through reduction of [1,2,4]triazolopyrazine substrates wherein $R^1 \neq H$ would require the additional challenge of efficient asymmetric hydrogenation conditions (in terms of both yield and chiral purity); this is currently not a known procedure to the best of Applicant's knowledge. Thus application of Method A(i) for chiral synthesis of [1,2,4]triazolo[4,3-a]piperazine structures is hitherto unknown.

Scheme A: Method A(i)

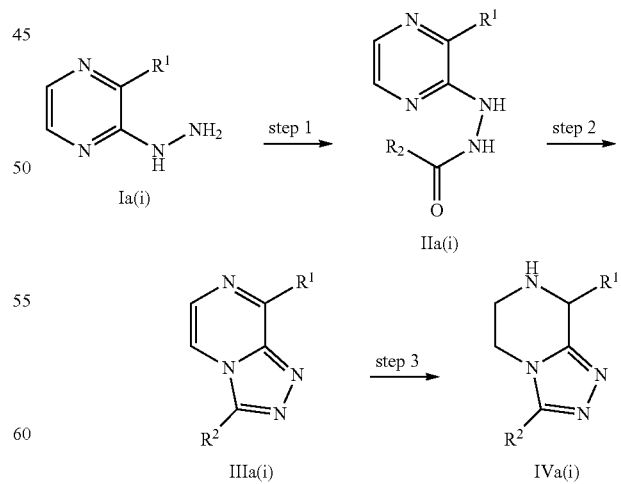

Method A(ii) (cf. Scheme B) is a variation on Method A(i) whereby the reduction of $R^1 \neq H$ substituted [1,2,4]triazolopyrazine substrates is circumvented. This method has been reported by the Merck group in their studies related to Sitagliptin (see, for example, Kowalchick, J. E. et al. *Bioorg. Med. Chem. Lett.* 2007, 17, 5934-5939), wherein Boc-protected intermediates depicted by general Formula IVa(ii) are deprotonated with a strong base, such as n-butyllithium, in the presence of tetramethylethylenediamine (TMEDA), followed by treatment of the thus generated anion with an electrophile such as an alkyl halide (step 4, Scheme B). The chiral variant of this methodology has not been reported in the literature.

Scheme B: Method A(ii)

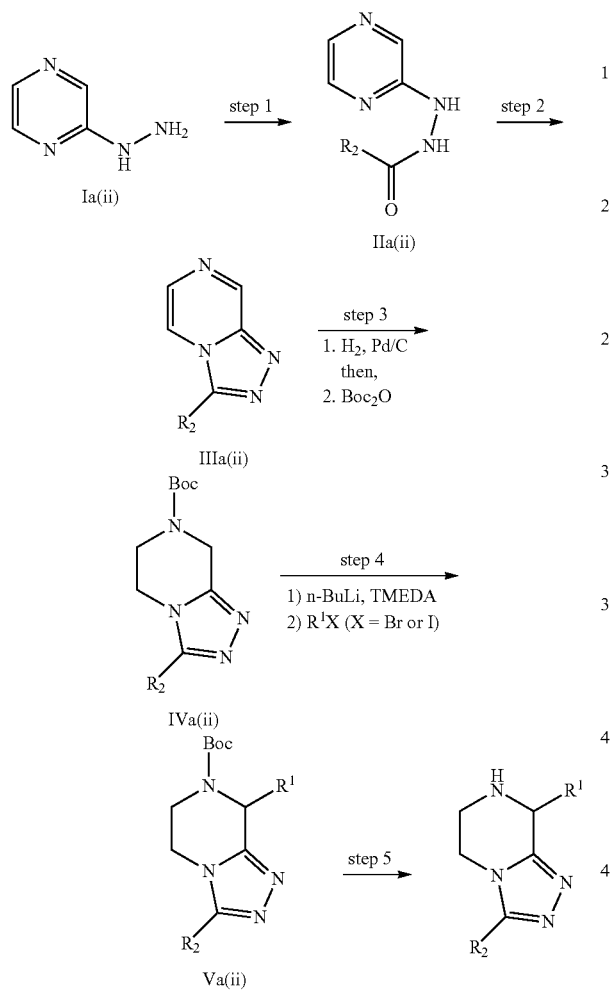

Inspired by the earlier work by Makino and Kato (JP016128261(A), 1994), yet another alternative approach to the synthesis of [1,2,4]triazolo[4,3-a]piperazines was developed using chloromethyloxadiazoles as a key reagent (Balsells, J. et al. *Org. Lett.* 2005, 7, 1039-1042). This methodology (Method B) is depicted in Scheme C below. As reported by Balsells et al., however, this approach proceeds in high yield mainly when the strong electron-withdrawing $R_2$=$CF_3$ group is present in the chloromethyloxadiazole reagent. In addition, the mechanism suggested by the said authors would render application of this strategy unlikely, if not impossible, for a chiral synthesis of IVb intermediates (cf. Scheme C). Indeed, in the current literature only racemic or achiral products are described using such an approach. Thus, application of Method B towards preparation of chiral [1,2,4]triazolo[4,3-a]piperazine structures has never been disclosed.

Scheme C: Method B

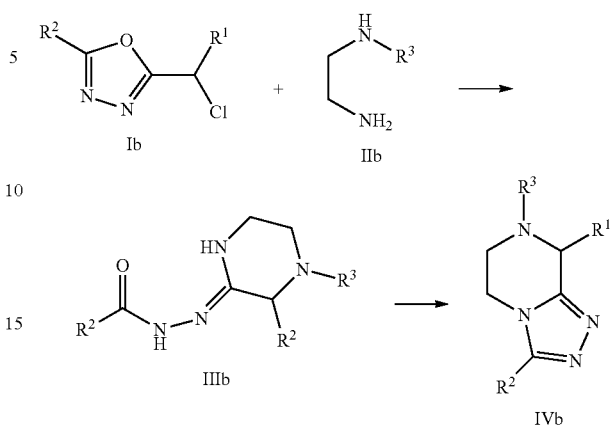

Another well-known method for the preparation of [1,2,4]triazolo[4,3-a]piperazine containing structures is shown in Scheme D below (Method C). Addition of acetylhydrazide to piperazinoimidate (step 1) is followed by cyclodehydration to form the fused triazolo ring (step 2). This method is well documented in the literature although exemplified only through racemic or achiral structures; e.g.: McCort, G. A.; Pascal, J. C. *Tetrahedron Lett.*, 1992, 33, 4443-4446; Brockunier, L. L. et al. WO 03/082817 A2; Chu-Moyer, M. Y. et al. U.S. Pat. No. 6,414,149 B1; Banka, A. et al. WO2009/089462 A1. To the best of his knowledge, the Applicant is unaware of any published reports of the application of this method for obtaining chiral products by starting from chiral piperazinones (Id in Scheme D).

Scheme D: Method C

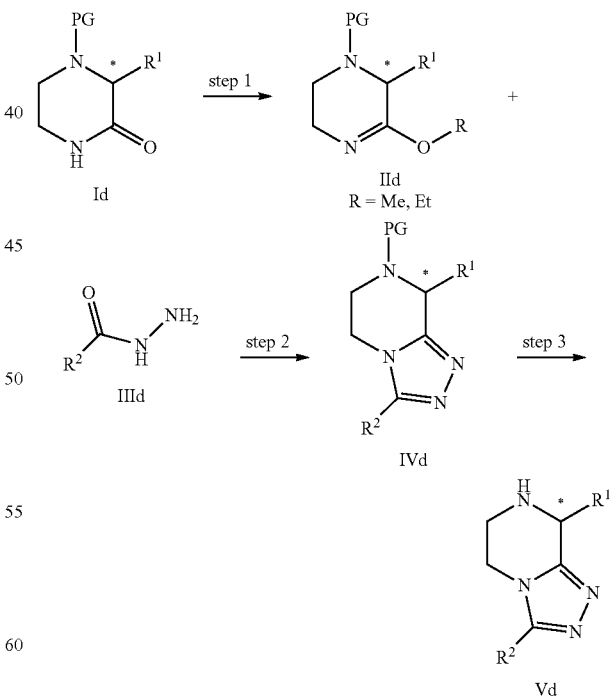

The symbol * denotes a well-defined configuration at the carbon center next to which the said symbol is placed, i.e. the carbon atom to which the $R^1$ group is attached in the this Scheme.

A synthesis of (R)-8-methyl-5,6,7,8-tetrahydro-[1,2,4]triazolo[4,3-a]pyrazine compounds through general Method C has been previously described in international patent application PCT/EP2011/055218 which is in the name of the Applicant. The preparation disclosed therein is depicted in Scheme E:

of Formula I of the present invention, in what is considered essentially racemic by those skilled in the art. As such, the said method cannot be used in practice to prepare a pharmaceutically active ingredient as this method does not reliably furnish chiral intermediates (IIIe, Ve, VIe; Scheme E) and thus cannot be reliably used for obtaining chiral Scheme E: Synthesis of (R)-8-methyl-5,6,7,8-tetrahydro-[1,2,4]triazolo[4,3-a]pyrazine intermediates according to PCT/EP2011/055218.

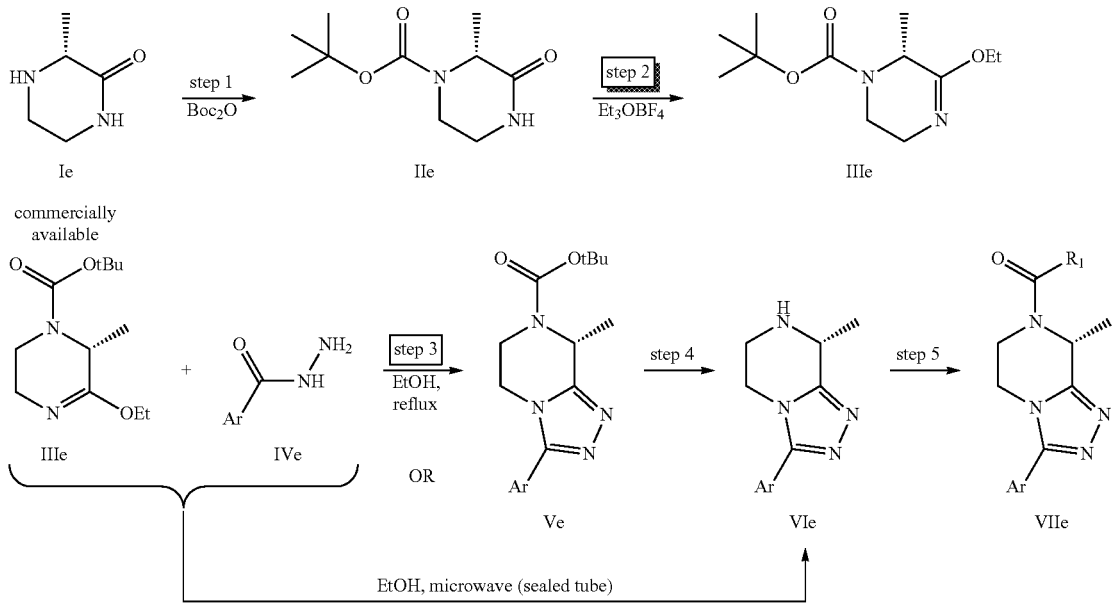

NB: Steps 2 and 3 are particularly prone to racemization despite the graphic depiction of chiral products for each of these steps in the above Scheme. Thus, obtaining intermediates/products in high chiral purity (>80% ee) is feasible but not in a reproducible fashion.

Boc-protected ketopiperazine IIe was prepared and then converted to iminoether IIIe by using the Meerwein reagent (e.g. Et$_3$OBF$_4$). Cyclodehydration reaction between the acyl hydrazide IVe and the iminoether aforementioned was conducted either under forcing thermal reflux conditions, or by applying excessive microwave irradiation in a sealed tube typically for rather protracted reaction times (often days). When using microwave irradiation, N-Boc deprotection occurred during the said cyclodehydration step; thus, a deprotection step was typically not necessary to conduct (i.e., IIIe+IVe→VIein Scheme E). However, when thermal cyclodehydration conditions were applied, Boc-deprotection step was required (i.e., IIIe+IVe→Ve→VIe).

As noted in Scheme E above, steps 2 and 3 have shortcomings that significantly limit the application of the said procedure for uses wherein generation of chiral intermediates or products are required in a reproducible fashion, as with the preparation of pharmaceutically active ingredient, for instance. Step 1 is the piperazinoimidate formation (i.e., IIe→IIIe) and step 2 is the cyclodehydration step between the said imidate and acetylhydrazide (i.e., IIIe+IVe→Ve).

An important disadvantage of the Scheme E procedure is that racemization of the stereogenic carbon center occurred frequently in steps 2-3. Consequently, the said procedure furnished final products that were only infrequently of acceptable chiral purity; in fact, much more frequently, the Scheme E procedure produced final products represented by the general Formula VIIe, which correspond to compounds products represented by the general Formula VIIe, which correspond to compounds of Formula I of the present invention.

Another disadvantage of the Scheme E procedure is the excessively protracted reaction time required for the cyclodehydration step (Scheme E, IIIe+IVe→Ve). Up to several days (under forcing reaction conditions—see below) were always required with substrates represented by the general Formula IId (Scheme D) wherein R≠H, i.e. the more sterically congested analogs, unlike the case with achiral substrates represented by the general Formula IId (Scheme D) wherein R=H. Such significantly protracted reaction times (several days) are not practical for such cases as a cGMP scale-up synthesis required to prepare a pharmaceutically active ingredient for clinical studies.

As adumbrated in the above paragraph, in the Scheme E procedure, the cyclodehydration step required extremely forcing conditions. Thus, use of elevated temperatures at reflux (for protracted durations), or additionally with application of essentially maximally feasible (within margin of experimental safety) microwave irradiation (sealed vessel) were often required.

Applicant resorted to a racemic synthesis from racemic 5,6,7,(8-methyl)-tetrahydro-[1,2,4]triazolo[4,3-a]pyrazine followed by an additional chiral preparative HPLC purification step after forming the final product of interest depicted by the general Formula VIIe in Scheme E. While feasible on small scale for the initial research and development phase, such an approach poses the problems of scalability in terms of time, cost and general applicability to such needs as cGMP scale-up of a pharmaceutically active ingredients, for instance.

Therefore, there is a need for improving the synthetic procedure for preparing stereoisomeric ally pure 5,6,7,(8-substituted)-tetrahydro-[1,2,4]triazolo[4,3-a]pyrazine intermediates for the synthesis of compounds of general Formula I of the present invention.

The invention thus also relates to a process of preparing 5,6,7,(8-substituted)-tetrahydro-[1,2,4]triazolo[4,3-a]pyrazine intermediates compounds of Formula II

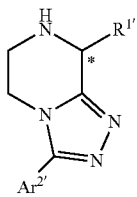

or salts or solvates thereof, wherein
$R^{1'}$ is linear or branched C1-C4 alkyl or C3-C4 cycloalkyl, each of said alkyl or cycloalkyl groups, groups being optionally substituted by one or more group(s) selected from halo or esters; and
$Ar^{2'}$ is a 5- to 6-membered aryl or heteroaryl group, each of the aryl, or heteroaryl groups being optionally substituted by one or more group(s) selected from halo, alkyl, haloalkyl, cycloalkyl, heteroalkyl, heterocyclyl, aryl, heteroaryl, hydroxyl, alkoxy, alkylamino, carbamoyl, alkylcarbamoyl, carbamoylalkyl, carbamoylamino, alkylcarbamoylamino, alkylsulfonyl, haloalkylsulfonyl, arylsulfonylalkyl, sulfamoyl, alkylsulfamoyl, alkylsulfonylamino, haloalkylsulfonylamino, fused to the aryl or heteroaryl group may be one or more cycloalkyl, aryl, heterocyclyl or heteroaryl moiety, each of said substituents being optionally substituted by one or more further substituent(s) selected from halo, alkyl, haloalkyl, alkoxy, haloalkoxy;
said process comprising the following steps:
  a) reacting a compound of Formula A

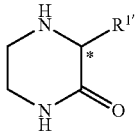

wherein
$R^{1'}$ is as defined above;
with a reagent resulting in a N-sp³ protective group (PG) on the amine nitrogen of compound of Formula A,
to obtain a compound of Formula C

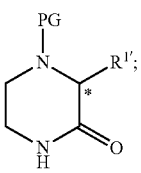

b) converting the compound of Formula C with a tri(C1-C2 alkyl) oxonium salt so as to obtain a compound of Formula D

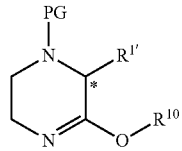

wherein $R^{1'}$ and PG are as defined above, and $R^{10}$ is C1-C2 alkyl,
in the presence of a base;
  c) reacting the compound of Formula D with a compound of Formula E

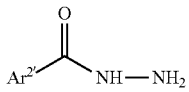

or a salt or solvate thereof, wherein
$Ar^{2'}$ is defined as above with respect to Formula II;
so as to obtain a compound of Formula F

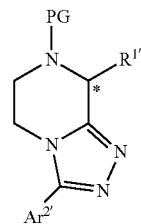

wherein $R^{1'}$, PG, and $Ar^{2'}$ are as defined above; and
  d) deprotecting the compound of Formula F with a suitable deprotection reagent to afford a compound of Formula II or a salt or solvate thereof.

The process of the invention provides compounds of Formula II or a salt or solvate thereof having good enantiomeric excess of up to 98% and possibly more in a reproducible fashion.

The process of the invention proceeds with the retention of stereochemistry with respect to the chiral (3-substituted)-piperazin-2-one starting material except to the extent that racemization occurs as a minor side-reaction; thus the configuration at position 8 of the ring is defined by the configuration of the aforesaid chiral starting material.

According to an advantageous embodiment, through the use of chiral 3-substituted-piperazin-2-one starting material, the process of the invention provides access to 5,6,7, ((R)-8-substituted)-tetrahydro-[1,2,4]triazolo[4,3-a]pyrazine compounds by minimizing any intervening racemization during the process.

In another aspect, the invention provides compounds of Formula D

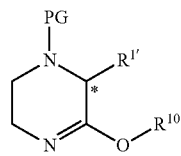

wherein $R^{1'}$ is as defined above with respect to Formula II;
PG is a protective group wherein the amine nitrogen remains as tertiary amine (i.e. sp$^3$ hybridized nitrogen), hereafter referred to as N-sp$^3$ protective group; and
$R^{10}$ is C1-C2 alkyl, preferably ethyl.

In still another aspect, the invention provides compounds of Formula III

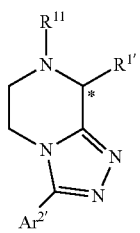

or salts or solvates thereof, wherein
$R^{1'}$ and $Ar^{2'}$ are as defined above with respect to Formula II; and
$R^{11}$ is H or a N-sp$^3$ protective group,
with the proviso that the compound of Formula III is not
(R)-4-(8-methyl-5,6,7,8-tetrahydro-[1,2,4]triazolo[4,3-a]pyrazin-3-yl)-2-phenylthiazole hydrochloride,
(R)-8-methyl-3-(pyridin-2-yl)-5,6,7,8-tetrahydro-[1,2,4]triazolo[4,3-a]pyrazine dihydrochloride salt,
(R)-2-(4-chlorophenyl)-4-(8-methyl-5,6,7,8-tetrahydro-[1,2,4]triazolo[4,3-a]pyrazin-3-yl)thiazole hydrochloride salt,
(R)-2-(4-fluorophenyl)-4-(8-methyl-5,6,7,8-tetrahydro-[1,2,4]triazolo[4,3-a]pyrazin-3-yl)thiazole hydrochloride salt,
(S)-8-methyl-3-(pyridin-2-yl)-5,6,7,8-tetrahydro-[1,2,4]triazolo[4,3-a]pyrazine,
(S)-2-(4-fluorophenyl)-4-(8-methyl-5,6,7,8-tetrahydro-[1,2,4]triazolo[4,3-a]pyrazin-3-yl)thiazole,
(S)-4-(4-(8-methyl-5,6,7,8-tetrahydro-[1,2,4]triazolo[4,3-a]pyrazin-3-yl)thiazol-2-yl)morpholine.

DETAILED DESCRIPTION

Compounds

As noted above, the invention relates to compounds of Formula I, as well as their pharmaceutically acceptable salts or solvates.

According to one embodiment, the invention provides compounds of general Formula I':

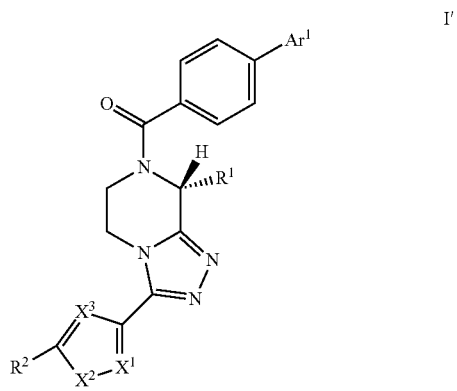

and pharmaceutically acceptable solvates thereof, wherein
$Ar^1$ is unsubstituted thiophen-2-yl, unsubstituted phenyl, or 4-fluorophenyl;
$R^1$ is H or methyl;
$R^2$ is linear or branched C1-C4 alkyl, C1-C2 haloalkyl, linear or branched C2-C3 alkenyl, C3-C4 cycloalkyl or di(C1-C2 alkyl)amino;
$X^1$ is N or C—$R^6$ wherein $R^6$ is H, fluoro or C1-C2 alkyl;
$X^2$ is O or S;
$X^3$ is N, or $X^3$ is CH under the condition that $X^1$ is N and $X^2$ is N—$R^7$ wherein $R^7$ is linear or branched C1-C3 alkyl or cyclopropyl;
with the condition that the compound of Formula I' is not (3-(2-isobutylthiazol-4-yl)-5,6-dihydro-[1,2,4]triazolo[4,3-a]pyrazin-7(8H)-yl)(4-(thiophen-2-yl)phenyl)methanone.

Preferred compounds of Formula I' and pharmaceutically acceptable solvates thereof are those wherein $Ar^1$ is unsubstituted thiophen-2-yl or unsubstituted phenyl, preferably $Ar^1$ is unsubstituted thiophen-2-yl; and/or
$R^1$ is H or methyl, preferably $R^1$ is methyl; and/or
$R^2$ is linear or branched C1-C3 alkyl, C1-C2 haloalkyl, linear or branched C2-C3 alkenyl, cyclopropyl or di(C1-C2 alkyl)amino, preferably $R^2$ is methyl, ethyl, vinyl, iso-propyl, iso-butyl, C1 fluoroalkyl, cyclopropyl or dimethylamino, more preferably $R^2$ is methyl, ethyl, iso-propyl, trifluoromethyl or cyclopropyl, still more preferably $R^2$ is methyl, ethyl or iso-propyl; even more preferably $R^2$ is methyl and/or
$X^1$ is C—$R^6$ wherein $R^6$ is H or methyl, preferably $X^1$ is CH; and/or
$X^2$ is O or S, preferably $X^2$ is S; and/or
$X^3$ is N.

In one embodiment, preferred compounds of Formula I' are those of Formula I'1

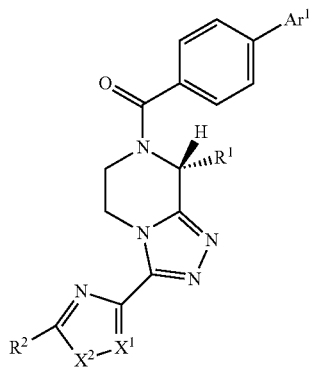

I′1

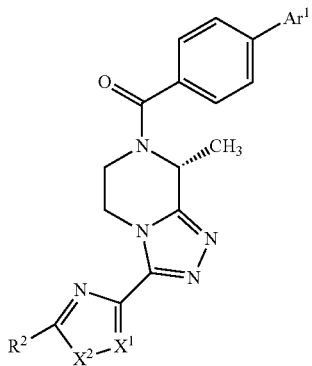

I′b and pharmaceutically acceptable solvates thereof, wherein Ar¹, R¹, R², X¹ and X² are as defined above with respect to Formula I′.

Preferred compounds of Formula I′1 and pharmaceutically acceptable solvates thereof are those wherein Ar¹ is unsubstituted thiophen-2-yl or unsubstituted phenyl, preferably Ar¹ is unsubstituted thiophen-2-yl; and/or R¹ is H or methyl, preferably R¹ is methyl; and/or R² is linear or branched C1-C3 alkyl, C1-C2 haloalkyl, linear or branched C2-C3 alkenyl, cyclopropyl or di(C1-C2 alkyl)amino, preferably R² is methyl, ethyl, vinyl, iso-propyl, iso-butyl, C1 fluoroalkyl, cyclopropyl or dimethylamino, more preferably R² is methyl, ethyl, iso-propyl, trifluoromethyl or cyclopropyl; still more preferably R² is methyl, ethyl or iso-propyl; even more preferably R² is methyl and/or X¹ is C—R⁶ wherein R⁶ is H or methyl, preferably X¹ is CH; and/or X² is O or S, preferably X² is S.

In one embodiment, preferred compounds of Formula I′1 are those of Formulae I′a and I′b:

and pharmaceutically acceptable solvates thereof, wherein Ar¹, R², X¹ and X² are as defined above in respect to Formula I′.

Preferred compounds of Formulae I′a and I′b are those wherein

Ar¹ is unsubstituted thiophen-2-yl or unsubstituted phenyl, preferably Ar¹ is unsubstituted thiophen-2-yl; and/or R² is linear or branched C1-C3 alkyl, C1-C2 haloalkyl, linear or branched C2-C3 alkenyl, cyclopropyl or di(C1-C2 alkyl)amino, preferably R² is methyl, ethyl, vinyl, iso-propyl, iso-butyl, C1 fluoroalkyl, cyclopropyl or dimethylamino, more preferably R² is methyl, ethyl, iso-propyl, trifluoromethyl or cyclopropyl, still more preferably R² is methyl, ethyl or iso-propyl; even more preferably R² is methyl and/or X¹ is C—R⁶ wherein R⁶ is H or methyl, preferably X¹ is CH; and/or X² is O or S, preferably X² is S.

In one embodiment, preferred compounds of Formula I′1 are those of Formulae I′c and I′d:

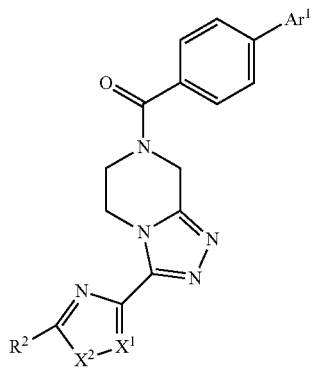

I′a

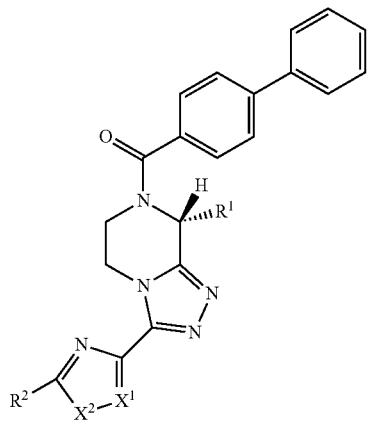

I′c

-continued

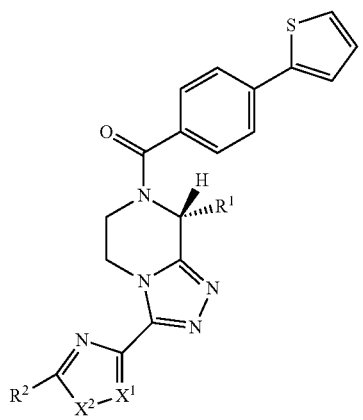

I'd and pharmaceutically acceptable solvates thereof, wherein $R^1$, $R^2$, $X^1$ and $X^2$ are as defined above in respect to Formula I'.

Preferred compounds of Formulae I'c and I'd are those wherein $R^1$ is H or methyl, preferably $R^1$ is methyl; and/or $R^2$ is linear or branched C1-C3 alkyl, C1-C2 haloalkyl, linear or branched C2-C3 alkenyl, cyclopropyl or di(C1-C2 alkyl)amino, preferably $R^2$ is methyl, ethyl, vinyl, iso-propyl, iso-butyl, C1 fluoroalkyl, cyclopropyl or dimethylamino, more preferably $R^2$ is methyl, ethyl, iso-propyl, trifluoromethyl or cyclopropyl, still more preferably $R^2$ is methyl, ethyl or iso-propyl; even more preferably $R^2$ is methyl and/or $X^1$ is C—$R^6$ wherein $R^6$ is H or methyl, preferably $X^1$ is CH; and/or $X^2$ is O or S, preferably $X^2$ is S.

In one embodiment, preferred compounds of Formula I'1 are those of Formulae I'e and I'f:

-continued

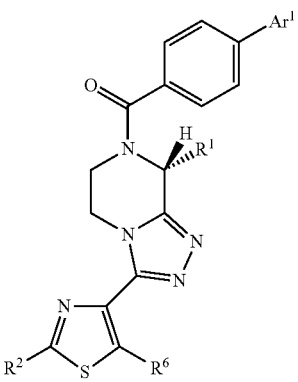

I'f and pharmaceutically acceptable solvates thereof, wherein $Ar^1$, $R^1$, $R^2$ and $R^6$ are as defined above in respect to Formula I'.

Preferred compounds of Formulae I'e and I'f are those wherein $Ar^1$ is unsubstituted thiophen-2-yl or unsubstituted phenyl, preferably $Ar^1$ is unsubstituted thiophen-2-yl; and/or $R^1$ is H or methyl, preferably $R^1$ is methyl; and/or $R^2$ is linear or branched C1-C3 alkyl, C1-C2 haloalkyl, linear or branched C2-C3 alkenyl, cyclopropyl or di(C1-C2 alkyl)amino, preferably $R^2$ is methyl, ethyl, vinyl, iso-propyl, iso-butyl, C1 fluoroalkyl, cyclopropyl or dimethylamino, more preferably $R^2$ is methyl, ethyl, iso-propyl, trifluoromethyl or cyclopropyl, still more preferably $R^2$ is methyl, ethyl or iso-propyl; even more preferably $R^2$ is methyl and/or $R^6$ is H or methyl, preferably $R^6$ is H.

Among the compounds of Formulae I'e and I'f, those of Formula I'f are preferred.

Other preferred compounds of Formulae I'e and I'f are those of Formulae I'e-1, I'f-1, I'e-2 and I'f-2

I'e

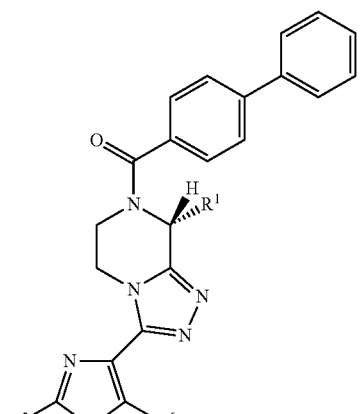

I'e-1

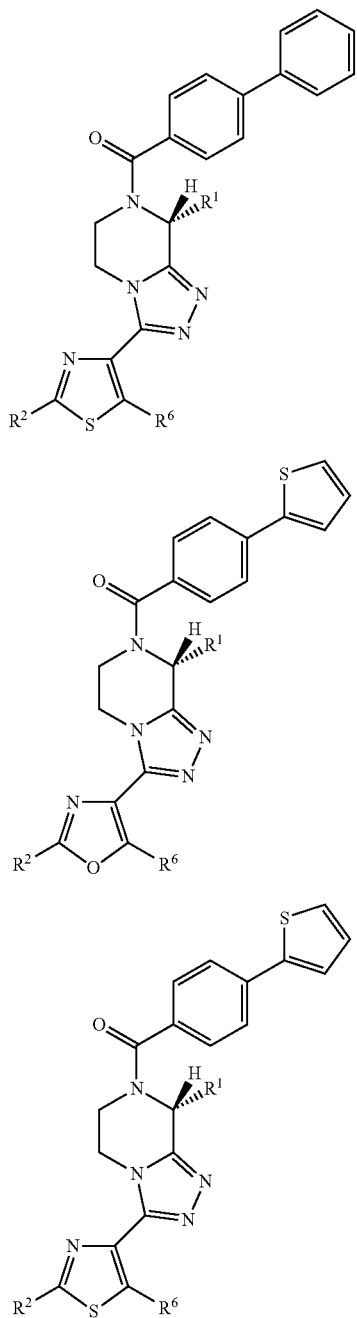

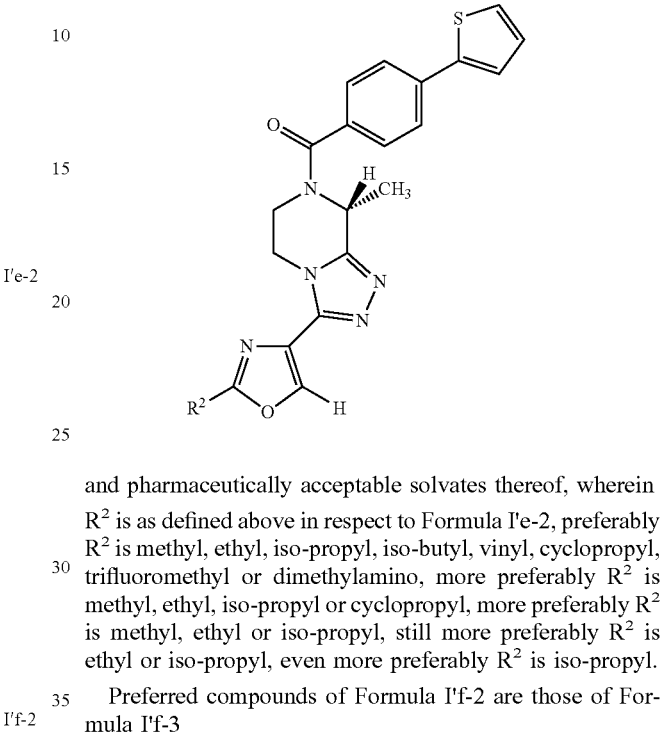

Among the compounds of Formulae I'e-1, I'f-1, I'e-2 and I'f-2, those of Formulae I'f-1 and I'f-2 are preferred, those of Formula I'f-2 are further preferred.

Preferred compounds of Formula I'e-2 are those of Formula I'e-3 and pharmaceutically acceptable solvates thereof, wherein

R² is as defined above in respect to Formula I'e-2, preferably R² is methyl, ethyl, iso-propyl, iso-butyl, vinyl, cyclopropyl, trifluoromethyl or dimethylamino, more preferably R² is methyl, ethyl, iso-propyl or cyclopropyl, more preferably R² is methyl, ethyl or iso-propyl, still more preferably R² is ethyl or iso-propyl, even more preferably R² is iso-propyl.

Preferred compounds of Formula I'f-2 are those of Formula I'f-3

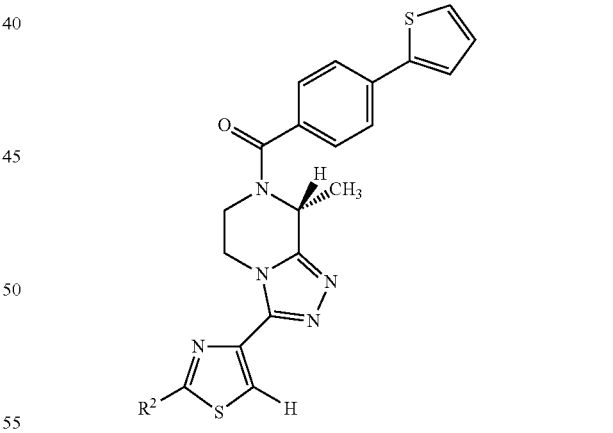

and pharmaceutically acceptable solvates thereof, wherein

R² is as defined above in respect to Formula I'e-2, preferably R² is methyl, ethyl, iso-propyl, iso-butyl, vinyl, cyclopropyl, trifluoromethyl or dimethylamino more preferably R² is methyl, ethyl, iso-propyl, vinyl, cyclopropyl or dimethylamino more preferably R² is methyl, ethyl, iso-propyl, vinyl or dimethylamino, still more preferably R² is methyl or ethyl, even more preferably R² is methyl.

In one embodiment, compounds of Formula I'1 are those of Formulae I'g, I'h and I'i and pharmaceutically acceptable solvates thereof, wherein R¹, R² and R⁶ are as defined above in respect to Formula I'.

Preferred compounds of Formulae I'e-1, I'f-1, I'e-2 and I'f-2 are those wherein

R¹ is H or methyl, preferably R¹ is methyl; and/or

R² is linear or branched C1-C3 alkyl, C1-C2 haloalkyl, linear or branched C2-C3 alkenyl, cyclopropyl or di(C1-C2 alkyl)amino, preferably R² is methyl, ethyl, vinyl, iso-propyl, iso-butyl, C1 fluoroalkyl, cyclopropyl or dimethylamino, more preferably R² is methyl, ethyl, iso-propyl, trifluoromethyl or cyclopropyl, still more preferably R² is methyl, ethyl or iso-propyl; even more preferably R² is methyl and/or R⁶ is H or methyl, preferably R⁶ is H.

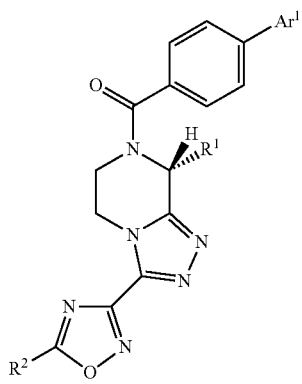

I'g

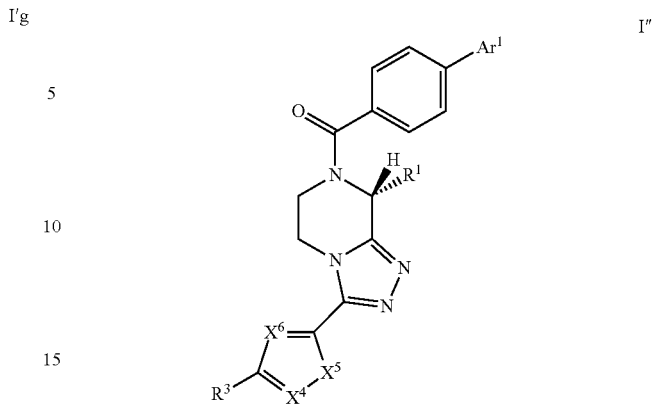

I'' and pharmaceutically acceptable solvates thereof, wherein

Ar¹ is unsubstituted thiophen-2-yl, unsubstituted phenyl, or 4-fluorophenyl;

$R^1$ is H or methyl;

$R^3$ is linear or branched C1-C4 alkyl or C3-C4 cycloalkyl;

$X^4$ is N or C—$R^8$ wherein $R^8$ is H or C1-C2 alkyl;

$X^5$ is O or S;

$X^6$ is N, or $X^6$ is CH under the condition that $X^4$ is N and $X^5$ is N—$R^9$ wherein $R^9$ is linear or branched C1-C3 alkyl or cyclopropyl.

Preferred compounds of Formula I'' and pharmaceutically acceptable solvates thereof are those wherein Ar¹ is unsubstituted thiophen-2-yl or unsubstituted phenyl, preferably Ar¹ is unsubstituted thiophen-2-yl; and/or $R^1$ is H or methyl, preferably $R^1$ is methyl; and/or $R^3$ is methyl or iso-propyl, and/or $X^4$ is N or C—$R^8$ wherein $R^8$ is H or methyl, $X^5$ is O or S and $X^6$ is N, preferably $X^4$ is N or C—$R^8$ wherein $R^8$ is H or methyl, $X^5$ is S and $X^6$ is N; and/or $X^4$ is N, $X^5$ is N—$R^9$ wherein $R^9$ is methyl and $X^6$ is CH.

In one embodiment, preferred compounds of Formula I'' are those of Formulae I''a and I''b:

I'h

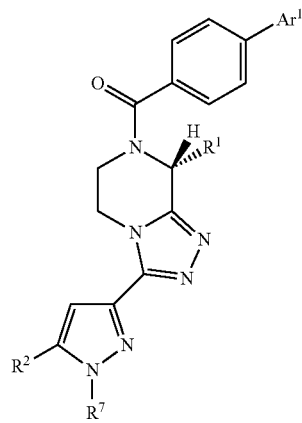

I'i

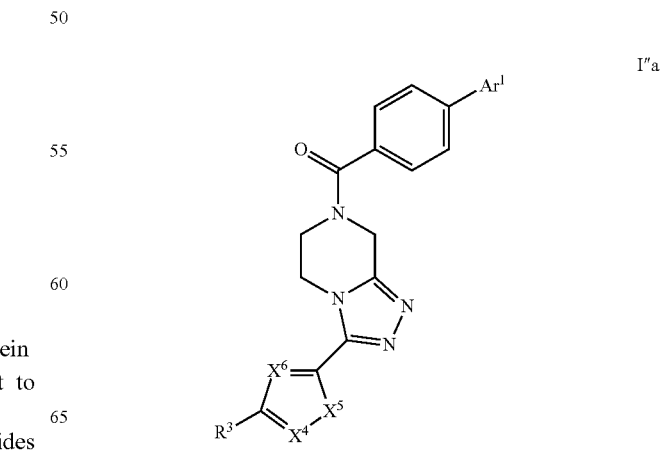

I''a and pharmaceutically acceptable solvates thereof, wherein Ar¹, $R^1$, $R^2$ and $R^7$ are as defined above in respect to Formula I'.

According to one embodiment, the invention provides compounds of general Formula I'':

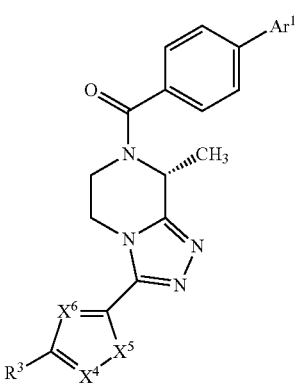

and pharmaceutically acceptable solvates thereof, wherein Ar¹, R³, X⁴, X⁵ and X⁶ are as defined above in respect to Formula I″.

Among the compounds of Formulae I″a and I″b, those of Formula I″b are preferred.

In one embodiment, preferred compounds of Formula I″ are those of Formulae I″c and I″d:

and pharmaceutically acceptable solvates thereof, wherein R¹, R³, X⁴, X⁵ and X⁶ are as defined above in respect to Formula I″.

Preferred compounds of Formulae I″c and I″d are those wherein

R¹ is H or methyl, preferably R¹ is methyl; and/or
R³ is methyl or iso-propyl; and/or
X⁴ is N or C—R⁸ wherein R⁸ is H or methyl, X⁵ is O or S and X⁶ is N, preferably X⁴ is N or C—R⁸ wherein R⁸ is H or methyl, X⁵ is S and X⁶ is N; and/or
X⁴ is N, X⁵ is N—R⁹ wherein R⁹ is methyl and X⁶ is CH.

In one embodiment, preferred compounds of Formula I″ are those of Formulae I″e, I″f, I″g, I″h and I″i:

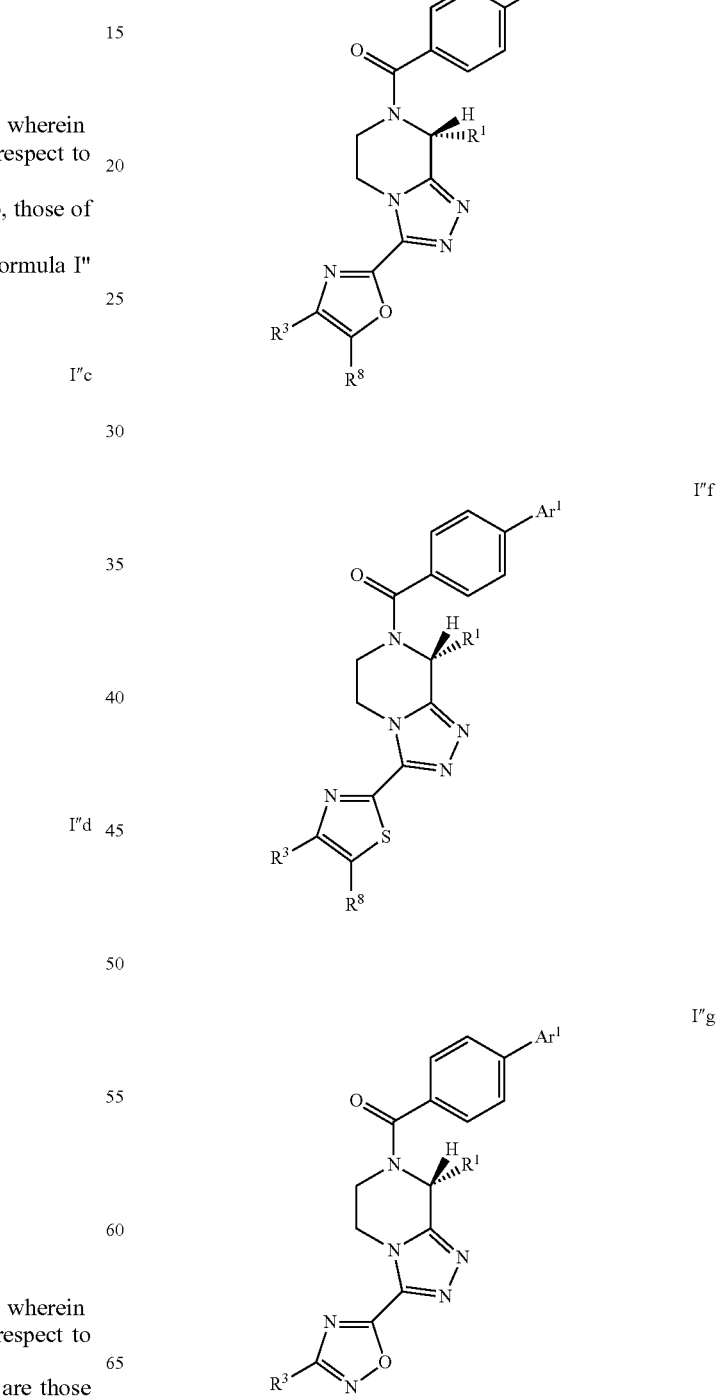

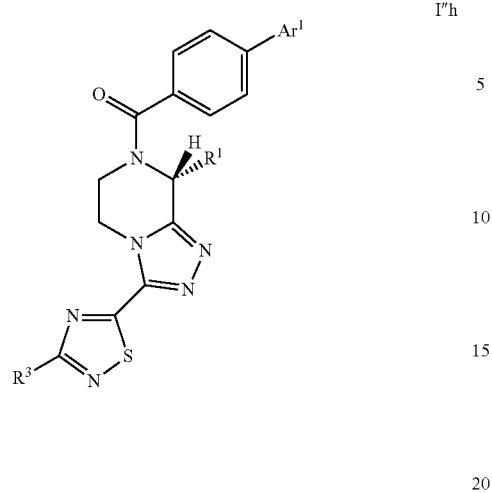

I″h

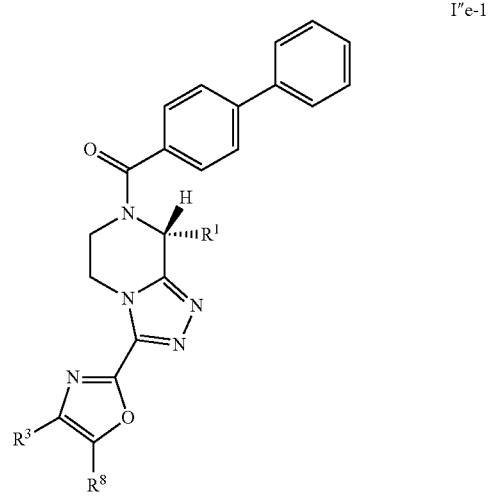

I″e-1

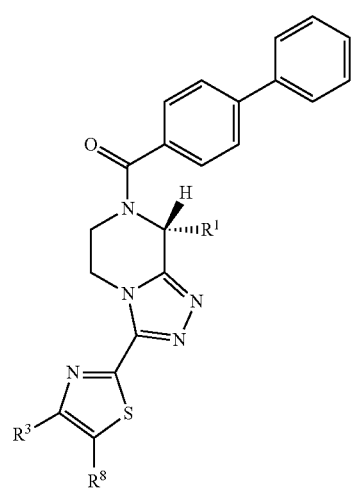

I″i

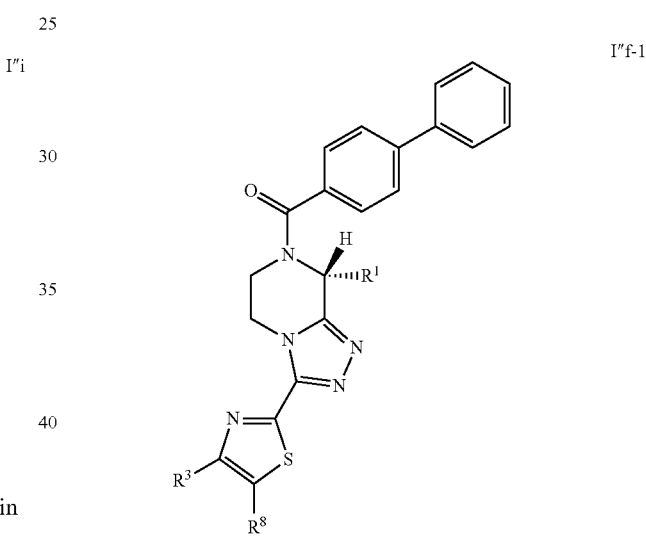

I″f-1 and pharmaceutically acceptable solvates thereof, wherein $Ar^1$, $R^1$, $R^3$, $R^8$ and $R^9$ are as defined above in respect to Formula I″.

Preferred compounds of Formulae I″e, I″f, I″g, I″h and I″i are those wherein $Ar^1$ is unsubstituted thiophen-2-yl or unsubstituted phenyl, preferably $Ar^1$ is unsubstituted thiophen-2-yl; and/or $R^1$ is H or methyl, preferably $R^1$ is methyl; and/or $R^3$ is methyl or iso-propyl; and/or $R^8$ is H or methyl, preferably H; and/or $R^9$ is methyl.

Among the compounds of Formulae re, I″f, I″g, I″h and I″i, those of Formulae I″e, I″f, I″g and I″h are preferred, in particular those of Formulae I″f and I″h are further preferred.

Other preferred compounds of Formulae I″e, I″f, I″g, I″h and I″i are those of Formulae I″e-1, I″f-1, I″g-1, I″h-1, I″i-1, I″e-2, I″f-2, I″g-2, I″h-2 and I″i-2

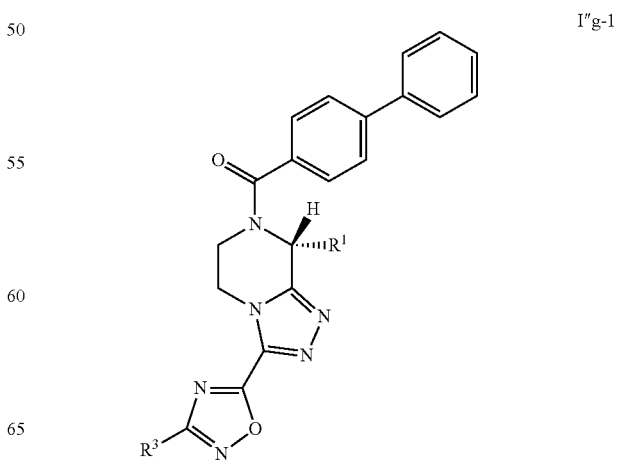

I″g-1

I″h-1
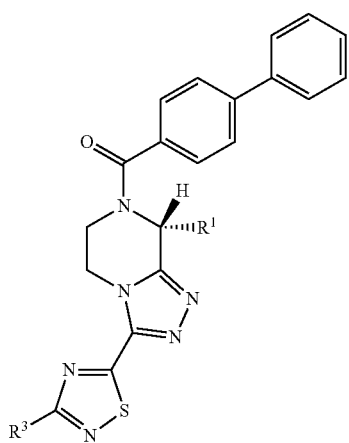
I″i-1
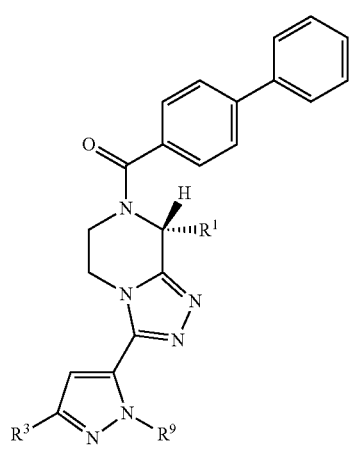
I″e-2
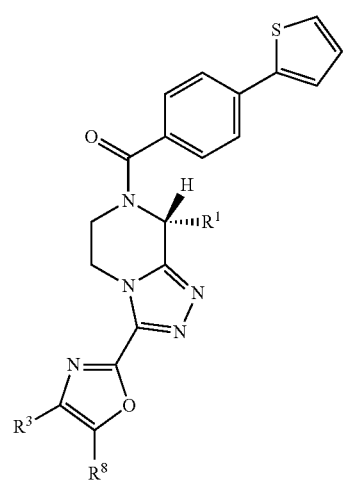
I″f-2
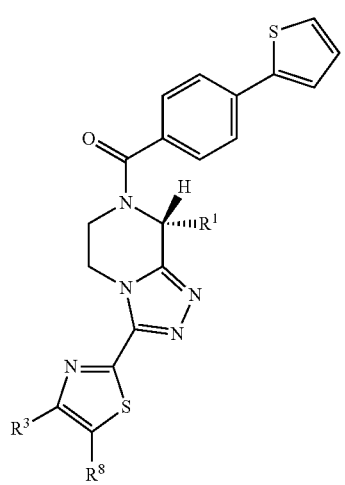
I″g-2
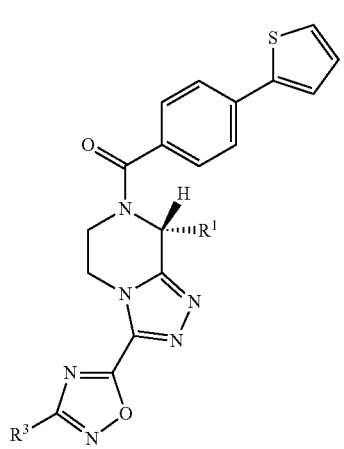
I″h-2
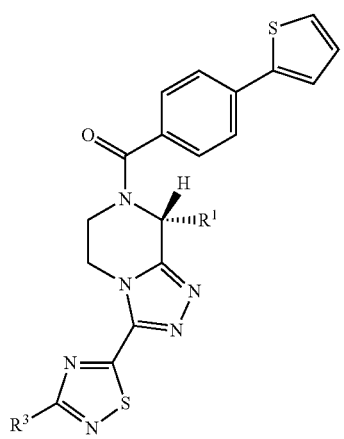

-continued

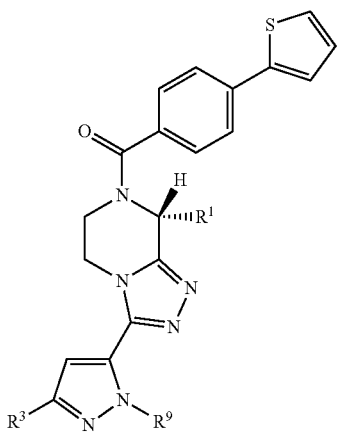

I″i-2 and pharmaceutically acceptable solvates thereof, wherein $R^1$, $R^3$, $R^8$ and $R^9$ are as defined above in respect to Formula I″.

Preferred compounds of Formulae I″e-1, I″f-1, I″g-1, I″h-1, I″i-1, I″e-2, I″f-2, I″g-2, I″h-2 and I″i-2 are those wherein
$R^1$ is H or methyl, preferably $R^1$ is methyl; and/or
$R^3$ is methyl or iso-propyl; and/or
$R^8$ is H or methyl, preferably H; and/or
$R^9$ is methyl.

Among the compounds of Formulae I″e-1, I″f-1, I″g-1, I″h-1, I″i-1, I″e-2, I″f-2, I″g-2, I″h-2 and I″i-2, those of Formulae I″e-1, I″f-1, I″g-1, I″h-1, I″e-2, I″f-2, I″g-2 and I″h-2 are preferred, in particular those of Formulae I″f-1, I″h-1, I″f-2 and I″h-2 are further preferred.

According to one embodiment, the invention provides compounds of general Formula I‴:

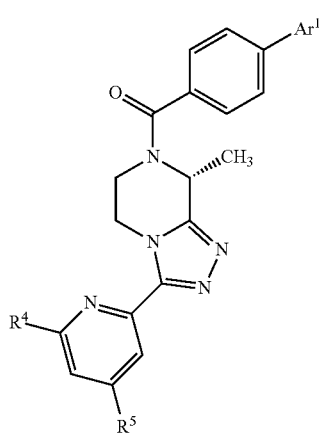

I‴ and pharmaceutically acceptable salts and solvates thereof, wherein
$Ar^1$ is unsubstituted phenyl, unsubstituted thiophen-2-yl, or 4-fluorophenyl;
$R^4$ is halo, cyano, methyl, or hydroxyl;
$R^5$ is H or halo;
with the condition that the compound of Formula I‴ is not [1,1′-biphenyl]-4-yl(8-methyl-3-(6-methylpyridin-2-yl)-5,6-dihydro-[1,2,4]triazolo[4,3-a]pyrazin-7(8H)-yl)methanone;

(8-methyl-3-(6-methylpyridin-2-yl)-5,6-dihydro-[1,2,4]triazolo[4,3-a]pyrazin-7(8H)-yl)(4-(thiophen-2-yl)phenyl)methanone.

Preferred compounds of Formula I‴ and pharmaceutically acceptable salts and solvates thereof are those wherein
$Ar^1$ is unsubstituted phenyl, or unsubstituted thiophen-2-yl more preferably $Ar^1$ is unsubstituted phenyl; and/or
$R^4$ is cyano, methyl or hydroxy, preferably $R^4$ is cyano or methyl, more preferably $R^4$ is methyl, and $R^5$ is H; and/or
$R^4$ is methyl and $R^5$ is chloro.

In one embodiment, preferred compounds of Formula I‴ are those of Formulae I‴a and I‴b:

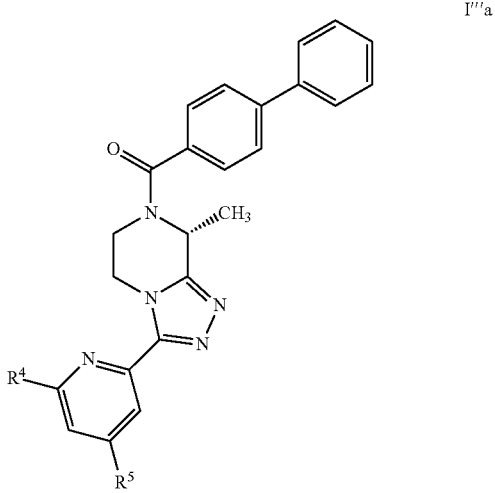

I‴a

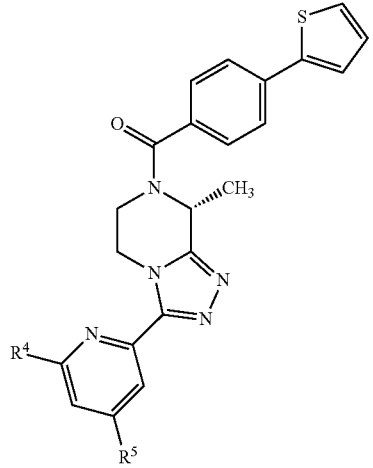

I‴b and pharmaceutically acceptable salts and solvates thereof, wherein
$R^4$ and $R^5$ are as defined above in respect to Formula I‴.

Preferred compounds of Formulae I‴a and I‴b are those wherein
$R^4$ is cyano, methyl or hydroxy, preferably $R^4$ is cyano or methyl, more preferably $R^4$ is methyl, and $R^5$ is H; and/or
$R^4$ is methyl and $R^5$ is chloro.

Particularly preferred compounds of Formula I of the invention are those listed in Table 1 hereafter:

TABLE 1

| Cpd n° | Structure | Chemical name | MW |
|---|---|---|---|
| 1 | 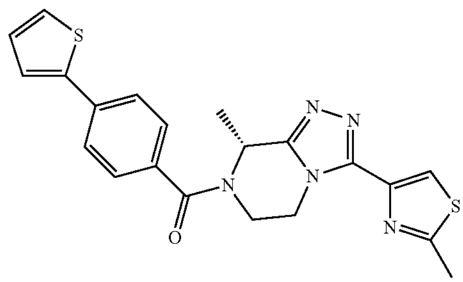 [SMILES: Cc1nc(-c2nnc3n2CCN(C(=O)c2ccc(-c4cccs4)cc2)[C@@H]3C)cs1] | (R)-(8-methyl-3-(2-methylthiazol-4-yl)-5,6-dihydro-[1,2,4]triazolo[4,3-a]pyrazin-7(8H)-yl)(4-(thiophen-2-yl)phenyl)methanone | 421.53 |
| 2 | 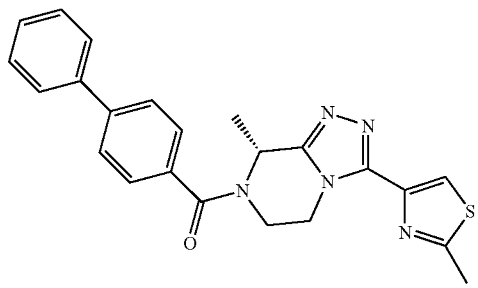 [SMILES: Cc1nc(-c2nnc3n2CCN(C(=O)c2ccc(-c4ccccc4)cc2)[C@@H]3C)cs1] | (R)-[1,1'-biphenyl]-4-yl(8-methyl-3-(2-methylthiazol-4-yl)-5,6-dihydro-[1,2,4]triazolo[4,3-a]pyrazin-7(8H)-yl)methanone | 415.51 |
| 3 | 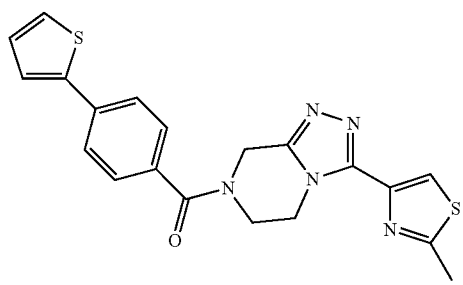 [SMILES: Cc1nc(-c2nnc3n2CCN(C(=O)c2ccc(-c4cccs4)cc2)C3)cs1] | (3-(2-methylthiazol-4-yl)-5,6-dihydro-[1,2,4]triazolo[4,3-a]pyrazin-7(8H)-yl)(4-(thiophen-2-yl)phenyl)methanone | 407.51 |
| 4 | 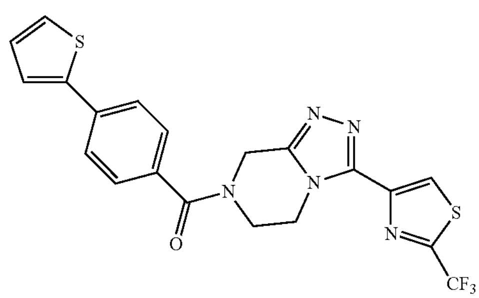 [SMILES: O=C(c1ccc(-c2cccs2)cc1)N1CCn2c(nnc2-c2csc(C(F)(F)F)n2)C1] | (4-(thiophen-2-yl)phenyl)(3-(2-(trifluoromethyl)thiazol-4-yl)-5,6-dihydro-[1,2,4]triazolo[4,3-a]pyrazin-7(8H)-yl)methanone | 461.48 |
| 5 | 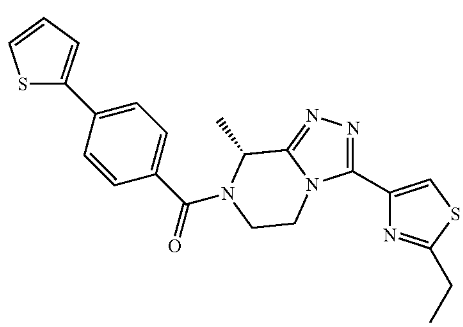 [SMILES: CCc1nc(-c2nnc3n2CCN(C(=O)c2ccc(-c4cccs4)cc2)[C@@H]3C)cs1] | (R)-(3-(2-ethylthiazol-4-yl)-8-methyl-5,6-dihydro-[1,2,4]triazolo[4,3-a]pyrazin-7(8H)-yl)(4-(thiophen-2-yl)phenyl)methanone | 435.56 |

TABLE 1-continued

| Cpd n° | Structure | Chemical name | MW |
|---|---|---|---|
| 6 | 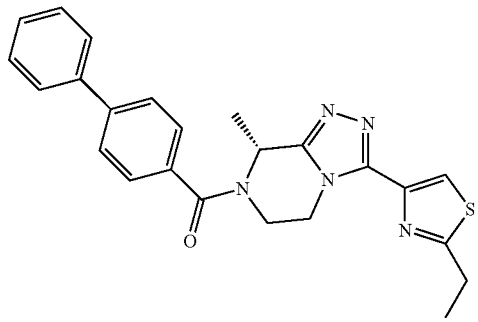 [SMILES: CCc1nc(-c2nnc3n2CCN(C(=O)c2ccc(-c4ccccc4)cc2)[C@@H]3C)cs1] | (R)-[1,1'-biphenyl]-4-yl(3-(2-ethylthiazol-4-yl)-8-methyl-5,6-dihydro-[1,2,4]triazolo[4,3-a]pyrazin-7(8H)-yl)methanone | 429.53 |
| 7 | 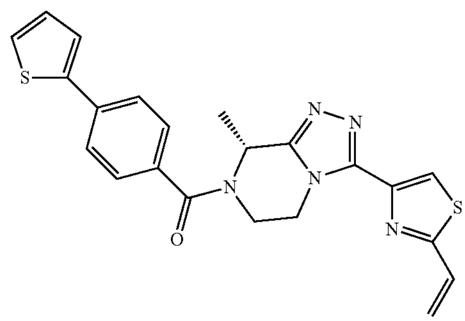 [SMILES: C=Cc1nc(-c2nnc3n2CCN(C(=O)c2ccc(-c4cccs4)cc2)[C@@H]3C)cs1] | (R)-(8-methyl-3-(2-vinylthiazol-4-yl)-5,6-dihydro-[1,2,4]triazolo[4,3-a]pyrazin-7(8H)-yl)(4-(thiophen-2-yl)phenyl)methanone | 433.54 |
| 8 | 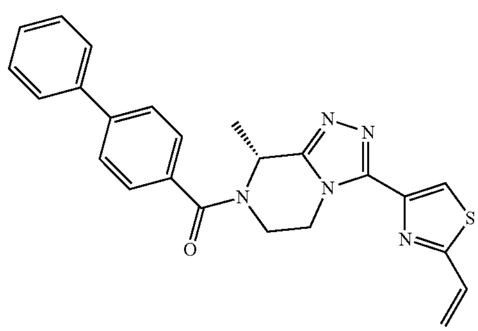 [SMILES: C=Cc1nc(-c2nnc3n2CCN(C(=O)c2ccc(-c4ccccc4)cc2)[C@@H]3C)cs1] | (R)-[1,1'-biphenyl]-4-yl(8-methyl-3-(2-vinylthiazol-4-yl)-5,6-dihydro-[1,2,4]triazolo[4,3-a]pyrazin-7(8H)-yl)methanone | 427.52 |
| 9 | 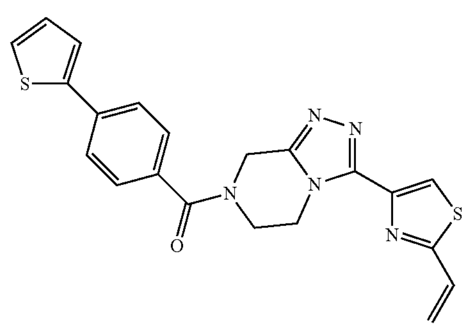 [SMILES: C=Cc1nc(-c2nnc3n2CCN(C(=O)c2ccc(-c4cccs4)cc2)C3)cs1] | (4-(thiophen-2-yl)phenyl)(3-(2-vinylthiazol-4-yl)-5,6-dihydro-[1,2,4]triazolo[4,3-a]pyrazin-7(8H)-yl)methanone | 419.52 |

TABLE 1-continued

| Cpd n° | Structure | Chemical name | MW |
|---|---|---|---|
| 10 | 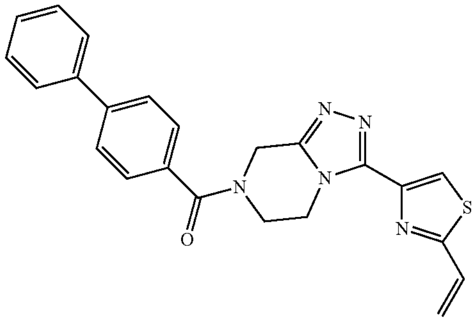 [SMILES: C=Cc1nc(-c2nnc3n2CCN(C(=O)c2ccc(-c4ccccc4)cc2)C3)cs1] | [1,1'-biphenyl]-4-yl(3-(2-vinylthiazol-4-yl)-5,6-dihydro-[1,2,4]triazolo[4,3-a]pyrazin-7(8H)-yl)methanone | 413.50 |
| 11 | 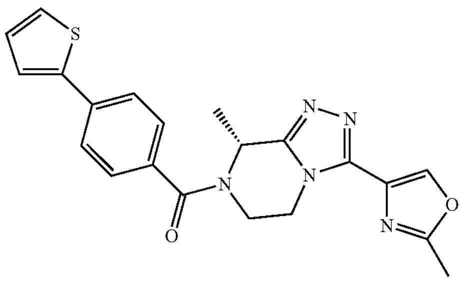 [SMILES: Cc1nc(-c2nnc3n2CCN(C(=O)c2ccc(-c4cccs4)cc2)[C@@H]3C)co1] | (R)-(8-methyl-3-(2-methyloxazol-4-yl)-5,6-dihydro-[1,2,4]triazolo[4,3-a]pyrazin-7(8H)-yl)(4-(thiophen-2-yl)phenyl)methanone | 405.47 |
| 12 | 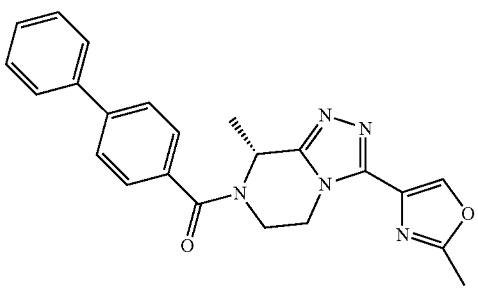 [SMILES: Cc1nc(-c2nnc3n2CCN(C(=O)c2ccc(-c4ccccc4)cc2)[C@@H]3C)co1] | (R)-[1,1'-biphenyl]-4-yl(8-methyl-3-(2-methyloxazol-4-yl)-5,6-dihydro-[1,2,4]triazolo[4,3-a]pyrazin-7(8H)-yl)methanone | 399.44 |
| 13 | 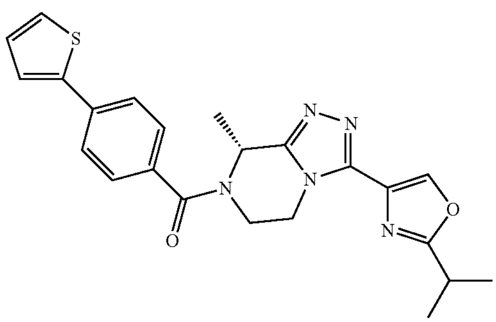 [SMILES: CC(C)c1nc(-c2nnc3n2CCN(C(=O)c2ccc(-c4cccs4)cc2)[C@@H]3C)co1] | (R)-(3-(2-isopropyloxazol-4-yl)-8-methyl-5,6-dihydro-[1,2,4]triazolo[4,3-a]pyrazin-7(8H)-yl)(4-(thiophen-2-yl)phenyl)methanone | 433.52 |
| 14 | 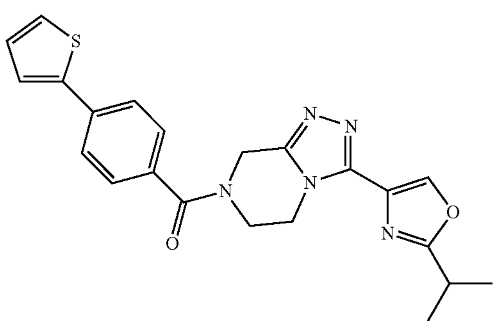 [SMILES: CC(C)c1nc(-c2nnc3n2CCN(C(=O)c2ccc(-c4cccs4)cc2)C3)co1] | (3-(2-isopropyloxazol-4-yl)-5,6-dihydro-[1,2,4]triazolo[4,3-a]pyrazin-7(8H)-yl)(4-(thiophen-2-yl)phenyl)methanone | 419.50 |

TABLE 1-continued

| Cpd n° | Structure | Chemical name | MW |
|---|---|---|---|
| 15 | 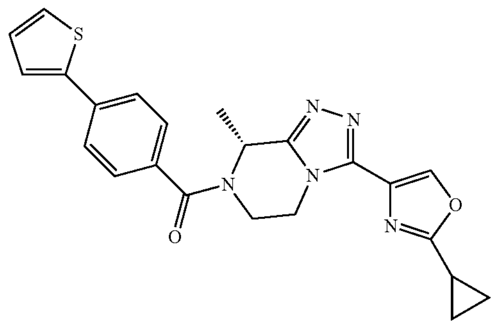 [SMILES: C[C@@H]1c2nnc(-c3coc(C4CC4)n3)n2CCN1C(=O)c1ccc(-c2cccs2)cc1] | (R)-(3-(2-cyclopropyloxazol-4-yl)-8-methyl-5,6-dihydro-[1,2,4]triazolo[4,3-a]pyrazin-7(8H)-yl)(4-(thiophen-2-yl)phenyl)methanone | 431.51 |
| 16 | 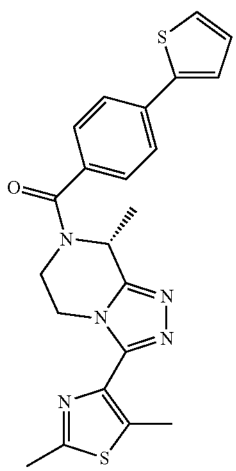 [SMILES: Cc1nc(-c2nnc3n2CCN(C(=O)c2ccc(-c4cccs4)cc2)[C@@H]3C)c(C)s1] | (R)-(3-(2,5-dimethylthiazol-4-yl)-8-methyl-5,6-dihydro-[1,2,4]triazolo[4,3-a]pyrazin-7(8H)-yl)(4-(thiophen-2-yl)phenyl)methanone | 435.56 |
| 17 | 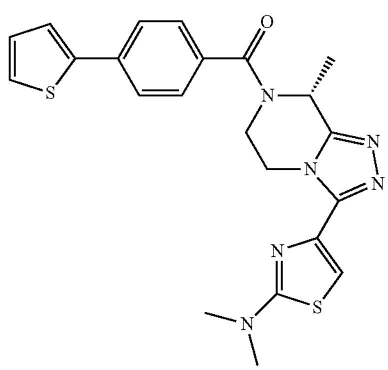 [SMILES: C[C@@H]1c2nnc(-c3csc(N(C)C)n3)n2CCN1C(=O)c1ccc(-c2cccs2)cc1] | (R)-(3-(2-(dimethylamino)thiazol-4-yl)-8-methyl-5,6-dihydro-[1,2,4]triazolo[4,3-a]pyrazin-7(8H)-yl)(4-(thiophen-2-yl)phenyl)methanone | 450.58 |
| 18 | 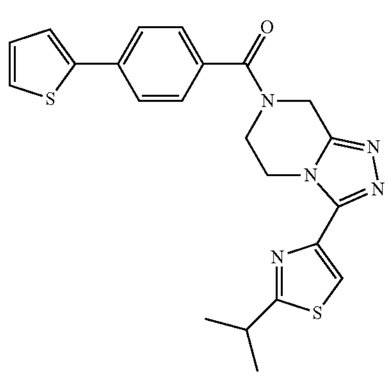 [SMILES: CC(C)c1nc(-c2nnc3n2CCN(C(=O)c2ccc(-c4cccs4)cc2)C3)cs1] | (3-(2-isopropylthiazol-4-yl)-5,6-dihydro-[1,2,4]triazolo[4,3-a]pyrazin-7(8H)-yl)(4-(thiophen-2-yl)phenyl)methanone | 435.56 |

TABLE 1-continued

| Cpd n° | Structure | Chemical name | MW |
|---|---|---|---|
| 19 | 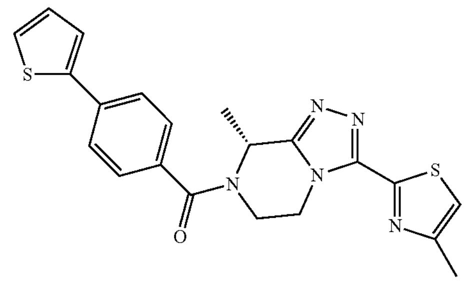 [SMILES: Cc1csc(-c2nnc3n2CCN(C(=O)c2ccc(-c4cccs4)cc2)[C@@H]3C)n1] | (R)-(8-methyl-3-(4-methylthiazol-2-yl)-5,6-dihydro-[1,2,4]triazolo[4,3-a]pyrazin-7(8H)-yl)(4-(thiophen-2-yl)phenyl)methanone | 421.54 |
| 20 | 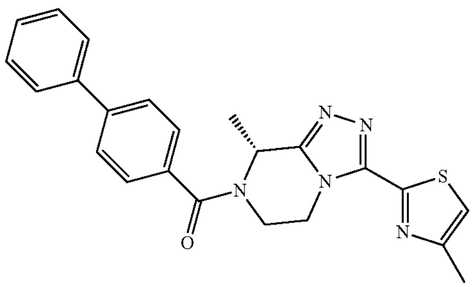 | (R)-[1,1'-biphenyl]-4-yl(8-methyl-3-(4-methylthiazol-2-yl)-5,6-dihydro-[1,2,4]triazolo[4,3-a]pyrazin-7(8H)-yl)methanone | 415.51 |
| 21 | 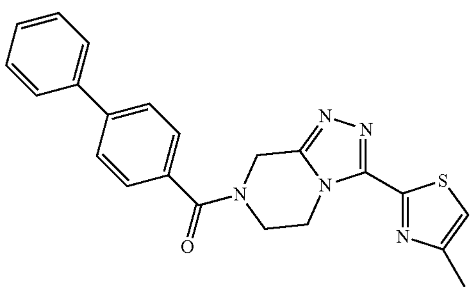 [SMILES: Cc1csc(-c2nnc3n2CCN(C(=O)c2ccc(-c4ccccc4)cc2)C3)n1] | [1,1'-biphenyl]-4-yl(3-(4-methylthiazol-2-yl)-5,6-dihydro-[1,2,4]triazolo[4,3-a]pyrazin-7(8H)-yl)methanone | 401.48 |
| 22 | 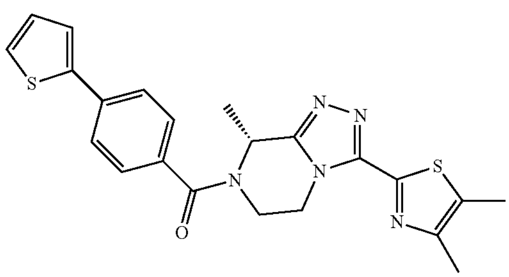 [SMILES: Cc1nc(-c2nnc3n2CCN(C(=O)c2ccc(-c4cccs4)cc2)[C@@H]3C)sc1C] | (R)-(3-(4,5-dimethylthiazol-2-yl)-8-methyl-5,6-dihydro-[1,2,4]triazolo[4,3-a]pyrazin-7(8H)-yl)(4-(thiophen-2-yl)phenyl)methanone | 435.57 |
| 23 | 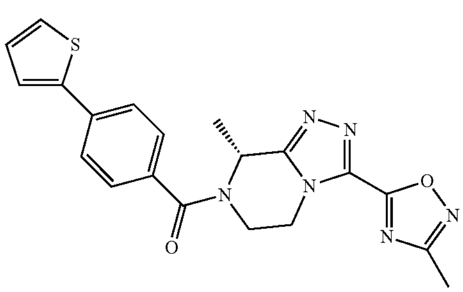 [SMILES: Cc1noc(-c2nnc3n2CCN(C(=O)c2ccc(-c4cccs4)cc2)[C@@H]3C)n1] | (R)-(8-methyl-3-(3-methyl-1,2,4-oxadiazol-5-yl)-5,6-dihydro-[1,2,4]triazolo[4,3-a]pyrazin-7(8H)-yl)(4-(thiophen-2-yl)phenyl)methanone | 406.46 |

TABLE 1-continued

| Cpd n° | Structure | Chemical name | MW |
|---|---|---|---|
| 24 | 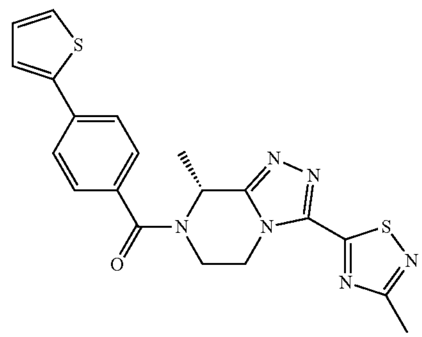 [SMILES: Cc1nsc(-c2nnc3n2CCN(C(=O)c2ccc(-c4cccs4)cc2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(4-(thiophen-2-yl)phenyl)methanone | 422.53 |
| 25 | 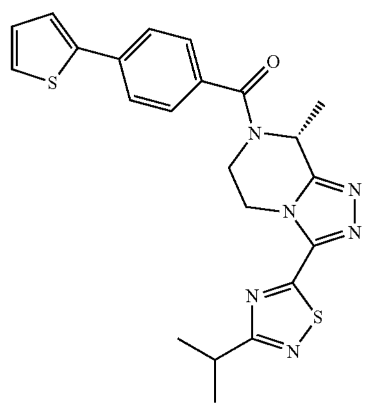 [SMILES: CC(C)c1nsc(-c2nnc3n2CCN(C(=O)c2ccc(-c4cccs4)cc2)[C@@H]3C)n1] | (R)-(3-(3-isopropyl-1,2,4-thiadiazol-5-yl)-8-methyl-5,6-dihydro-[1,2,4]triazolo[4,3-a]pyrazin-7(8H)-yl)(4-(thiophen-2-yl)phenyl)methanone | 450.58 |
| 26 | | (R)-(8-methyl-3-(4-methyloxazol-2-yl)-5,6-dihydro-[1,2,4]triazolo[4,3-a]pyrazin-7(8H)-yl)(4-(thiophen-2-yl)phenyl)methanone | 405.47 |
| 26 | | (R)-[1,1'-biphenyl]-4-yl(8-methyl-3-(4-methyloxazol-2-yl)-5,6-dihydro-[1,2,4]triazolo[4,3-a]pyrazin-7(8H)-yl)methanone | 399.45 |

TABLE 1-continued

| Cpd n° | Structure | Chemical name | MW |
|---|---|---|---|
| 28 | 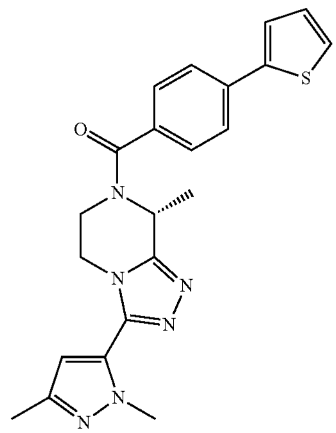 [SMILES: Cc1cc(-c2nnc3n2CCN(C(=O)c2ccc(-c4cccs4)cc2)[C@@H]3C)n(C)n1] | (R)-(3-(1,3-dimethyl-1H-pyrazol-5-yl)-8-methyl-5,6-dihydro-[1,2,4]triazolo[4,3-a]pyrazin-7(8H)-yl)(4-(thiophen-2-yl)phenyl)methanone | 418.51 |
| 29 | 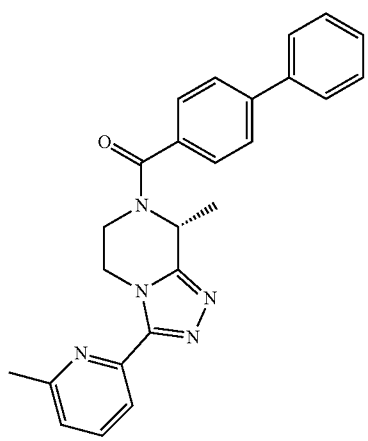 [SMILES: Cc1cccc(-c2nnc3n2CCN(C(=O)c2ccc(-c4ccccc4)cc2)[C@@H]3C)n1] | (R)-[1,1'-biphenyl]-4-yl(8-methyl-3-(6-methylpyridin-2-yl)-5,6-dihydro-[1,2,4]triazolo[4,3-a]pyrazin-7(8H)-yl)methanone | 409.48 |
| 30 | 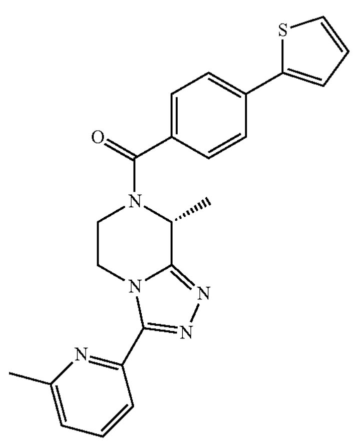 [SMILES: Cc1cccc(-c2nnc3n2CCN(C(=O)c2ccc(-c4cccs4)cc2)[C@@H]3C)n1] | (R)-(8-methyl-3-(6-methylpyridin-2-yl)-5,6-dihydro-[1,2,4]triazolo[4,3-a]pyrazin-7(8H)-yl)(4-(thiophen-2-yl)phenyl)methanone | 415.51 |

TABLE 1-continued

| Cpd n° | Structure | Chemical name | MW |
|---|---|---|---|
| 31 | 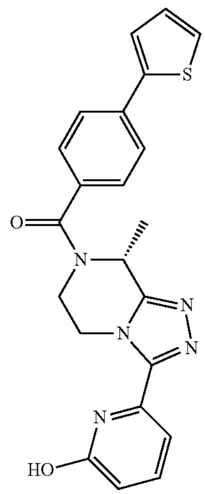 [SMILES: C[C@@H]1c2nnc(-c3cccc(O)n3)n2CCN1C(=O)c1ccc(-c2cccs2)cc1] | (R)-(3-(6-hydroxypyridin-2-yl)-8-methyl-5,6-dihydro-[1,2,4]triazolo[4,3-a]pyrazin-7(8H)-yl)(4-(thiophen-2-yl)phenyl)methanone | 417.48 |
| 32 | 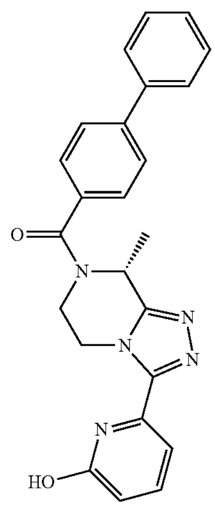 [SMILES: C[C@@H]1c2nnc(-c3cccc(O)n3)n2CCN1C(=O)c1ccc(-c2ccccc2)cc1] | (R)-[1,1'-biphenyl]-4-yl(3-(6-hydroxypyridin-2-yl)-8-methyl-5,6-dihydro-[1,2,4]triazolo[4,3-a]pyrazin-7(8H)-yl)methanone | 411.45 |
| 33 | 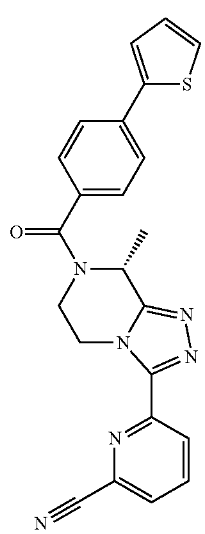 [SMILES: C[C@@H]1c2nnc(-c3cccc(C#N)n3)n2CCN1C(=O)c1ccc(-c2cccs2)cc1] | (R)-6-(8-methyl-7-(4-(thiophen-2-yl)benzoyl)-5,6,7,8-tetrahydro-[1,2,4]triazolo[4,3-a]pyrazin-3-yl)picolinonitrile | 426.49 |

In Table 1, the term "Cpd" means compound.

The compounds of Table 1 were named using ChemDraw® Ultra version 12.0 (CambridgeSoft, Cambridge, Mass., USA).

The compounds of Formula I can be prepared by different ways with reactions known to a person skilled in the art. Reaction schemes as described in the example section are illustrative only and should not be construed as limiting the invention in any way. According to one embodiment, compounds of Formula I can be prepared using the chiral synthesis of the invention detailed below.

The invention is further directed to the use of the compounds of the invention or pharmaceutically acceptable salts or solvates thereof as antagonists to the NK-3 receptor.

Accordingly, in a particularly preferred embodiment, the invention relates to the use of compounds of Formula I and subformulae in particular those of table 1 above, or pharmaceutically acceptable salts or solvates thereof, as NK-3 receptor antagonists.

Chiral Synthesis

As noted above, the invention relates to a novel process for the preparation of compounds of Formula II which comprises the above described steps a) to d).

In one embodiment, the process of the invention is directed to the preparation of 5,6,7,(8-substituted)-tetrahydro-[1,2,4]triazolo[4,3-a]pyrazine compounds of Formula II as defined above or salts or solvates thereof, wherein $R^{1'}$ and $Ar^{2'}$ are as defined above; and steps a) to d) are as follows:

a) reacting a compound of Formula A

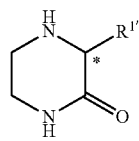

A wherein $R^{1'}$ is as defined above;
with a reagent resulting in an N-sp³ protective group on the amine nitrogen of compound of Formula A of Formula B1 or Formula B2

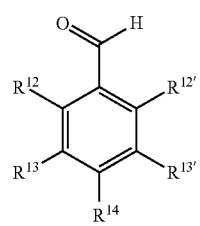

B-1

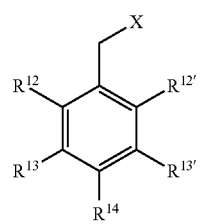

B-2 wherein,
$R^{12}$, $R^{12'}$, $R^{13}$, $R^{13'}$ and $R^{14}$ are H, or $R^{14}$ is methoxy and $R^{12}$, $R^{12'}$, $R^{13}$ and $R^{13'}$ are H, or $R^{12}$ and $R^{14}$ are methoxy and $R^{12'}$, $R^{13}$ and $R^{13'}$ are H, or $R^{12}$, $R^{12'}$ and $R^{14}$ are methoxy and $R^{13}$ and $R^{13'}$ are H, X is Cl, Br, I, OMs, OTs, OTf,
either through direct alkylation of the amine nitrogen when compound of Formula B2 is used, or in the presence of a reducing agent when a compound of Formula B1 is used to ultimately obtain a compound of Formula C-1

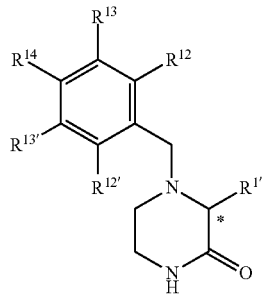

C-1 wherein $R^{1'}$, $R^{12}$, $R^{12'}$, $R^{13}$, $R^{13'}$ and $R^{14}$ are as defined above;

b) converting the compound of Formula C-1 with a tri(C1-C2 alkyl)oxonium salt (Meerwein-type reagents), or (C1-C2)alkylsulfate, or (C1-C2)chloroformate, or use of PCl₅/POCl₃/(C1-C2)hydroxyalkyl so as to obtain a compound of Formula D-1

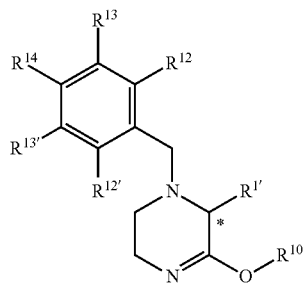

D-1 wherein $R^{1'}$, $R^{12}$, $R^{12'}$, $R^{13}$, $R^{13'}$ and $R^{14}$ are as defined above and $R^{10}$ is C1-C2 alkyl, in the presence of a base;

c) reacting the compound of Formula D-1 with a compound of Formula E

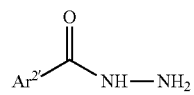

E or a salt or solvate thereof, wherein
$Ar^{2'}$ is defined as above with respect to Formula II;
so as to obtain a compound of Formula F-1.

49

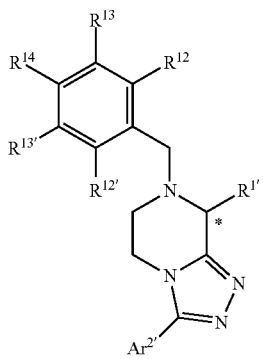

(F-1)

wherein R¹', R¹², R¹²', R¹³, R¹³', R¹⁴ and Ar²' are as defined above; and d) deprotecting the compound of Formula F-1 with a suitable deprotection reagent as defined herein to afford a compound of Formula II or an salt or solvate thereof.

Preferred compounds of Formula II and salts or solvates thereof are those wherein R¹' is linear or branched C1-C4 alkyl or C3-C4 cycloalkyl, each of said alkyl or cycloalkyl groups, groups being optionally substituted by one ester group; preferably R¹' is linear or branched C1-C4 alkyl or C3-C4 cycloalkyl; or R¹' is C1-C2 alkyl, optionally substituted by one ester group; preferably R¹' is methyl optionally substituted by one ester group, more preferably R¹' is methyl; and/or Ar²' is a 5- to 6-membered aryl or heteroaryl group, each of the aryl, or heteroaryl groups being optionally substituted by one or more group(s) selected from halo, alkyl, haloalkyl, cycloalkyl, aryl, heteroaryl, hydroxyl, alkoxy, alkylamino, carbamoyl, alkylcarbamoyl, carbamoylalkyl, carbamoylamino, alkylcarbamoylamino, or fused to the aryl or heteroaryl group may be one or more cycloalkyl, aryl, heterocyclyl or heteroaryl moiety, each of said substituents being optionally substituted by one or more further substituent(s) selected from halo, alkyl, haloalkyl, alkoxy, haloalkoxy; preferably Ar²' is a 5- to 6-membered aryl or heteroaryl group, each of the aryl, or heteroaryl groups being optionally substituted by one or more group(s) selected from halo, alkyl, haloalkyl, cycloalkyl, aryl, heteroaryl, hydroxyl, alkoxy, alkylamino, carbamoyl, alkylcarbamoyl, carbamoylalkyl, carbamoylamino, alkylcarbamoylamino, more preferably Ar²' is a 5- to 6-membered aryl or heteroaryl group, each of the aryl, or heteroaryl groups being optionally substituted by one or more group(s) selected from halo, alkyl, haloalkyl, cycloalkyl, aryl, heteroaryl, hydroxyl, alkylamino, still more preferably Ar²' is a 5- to 6-membered aryl or heteroaryl group, each of the aryl, or heteroaryl groups being optionally substituted by one or more group(s) selected from fluoro, branched or linear C1-C4 alkyl, C3-C4 cycloalkyl halo(C1)alkyl, cyclopropyl, aryl, hydroxyl, alkylamino; and most preferably Ar²' is a 5- to 6-membered heteroaryl group selected from the group consisting of rings (i), (ii) and (iii)

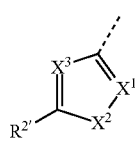

(i)

50

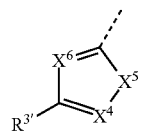

(ii)

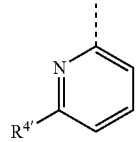

(iii)

wherein

X¹ is N or C—R⁶ wherein R⁶ is H, fluoro or methyl; preferably X¹ is C—R⁶ wherein R⁶ is H or methyl, more preferably X¹ is CH; and/or X² is O or S; preferably X² is S; and/or X³ is N, or X³ is CH under the condition that X¹ is N and X² is N—R⁷ wherein R⁷ is linear or branched C1-C3 alkyl or cyclopropyl; preferably X³ is N; and/or R²' is linear or branched C1-C4 alkyl, C1-C2 haloalkyl, linear or branched C2-C3 alkenyl, C3-C4 cycloalkyl, di(C1-C2 alkyl)amino, phenyl, 4-fluorophenyl, 2,4-difluorophenyl or N-morpholinyl; preferably R²' is methyl, ethyl, iso-propyl, C1 fluoroalkyl, cyclopropyl, dimethylamino, phenyl, 4-fluorophenyl, 2,4-difluorophenyl or or N-morpholinyl; more preferably R²' is methyl, ethyl, iso-propyl, trifluoromethyl or cyclopropyl, still more preferably R²' is methyl, ethyl or iso-propyl; most preferably R²' is methyl; and/or X⁴ is N or C—R⁸ wherein R⁸ is H or C1-C2 alkyl, X⁵ is O or S, X⁶ is N or X⁶ is CH under the condition that X⁴ is N and X⁵ is N—R⁹ wherein R⁹ is C1-C2 alkyl or C3 cycloalkyl, or X⁴ is N, X⁵ is N—R⁹ wherein R⁹ is methyl and X⁶ is CH; preferably X⁴ is N or C—R⁸ wherein R⁸ is H or methyl, X⁵ is O or S and X⁶ is N; more preferably X⁴ is N or C—R⁸ wherein R⁸ is H or methyl, X⁵ is S and X⁶ is N; and/or R³' is linear or branched C1-C4 alkyl, C1-C2 haloalkyl, linear or branched C2-C3 alkenyl, C3-C4 cycloalkyl, di(C1-C2 alkyl)amino, phenyl, 4-fluorophenyl, 2,4-difluorophenyl or N-morpholinyl; more preferably R³' is linear or branched C1-C4 alkyl or C3 cycloalkyl; even more preferably R³' is methyl or iso-propyl; and/or R⁴' is cyano, C1-C2 alkyl or hydroxyl, preferably R⁴' is cyano, methyl or hydroxyl, preferably R⁴' is methyl or hydroxyl, still more preferably R⁴' is methyl.

Particularly preferred compounds of Formula II are those listed in table 2 hereafter:

TABLE 2

| Cpd n° | Structure | Chemical name | MW |
|---|---|---|---|
| 1 | 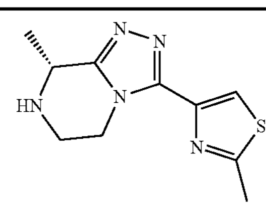 | (R)-2-methyl-4-(8-methyl-5,6,7,8-tetrahydro-[1,2,4]triazolo[4,3-a]pyrazin-3-yl)thiazole | 235.31 |

TABLE 2-continued

| Cpd n° | Structure | Chemical name | MW |
|---|---|---|---|
| 2 | 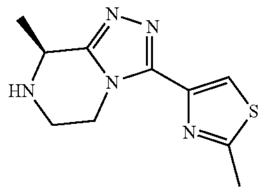 [SMILES: Cc1nc(-c2nnc3n2CCN[C@H]3C)cs1] | (S)-2-methyl-4-(8-methyl-5,6,7,8-tetrahydro-[1,2,4]triazolo[4,3-a]pyrazin-3-yl)thiazole | 235.31 |
| 3 | 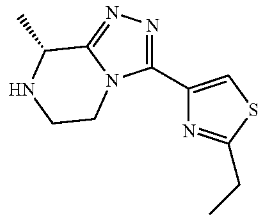 [SMILES: CCc1nc(-c2nnc3n2CCN[C@@H]3C)cs1] | (R)-2-ethyl-4-(8-methyl-5,6,7,8-tetrahydro-[1,2,4]triazolo[4,3-a]pyrazin-3-yl)thiazole | 249.34 |
| 4 | 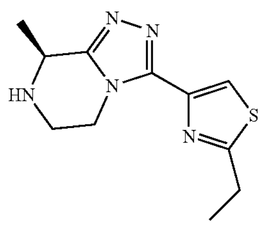 [SMILES: CCc1nc(-c2nnc3n2CCN[C@H]3C)cs1] | (S)-2-ethyl-4-(8-methyl-5,6,7,8-tetrahydro-[1,2,4]triazolo[4,3-a]pyrazin-3-yl)thiazole | 249.34 |
| 5 | 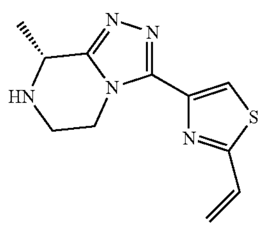 [SMILES: C=Cc1nc(-c2nnc3n2CCN[C@@H]3C)cs1] | (R)-4-(8-methyl-5,6,7,8-tetrahydro-[1,2,4]triazolo[4,3-a]pyrazin-3-yl)-2-vinylthiazole | 247.32 |
| 6 | 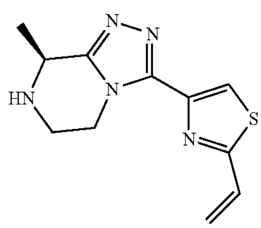 [SMILES: C=Cc1nc(-c2nnc3n2CCN[C@H]3C)cs1] | (S)-4-(8-methyl-5,6,7,8-tetrahydro-[1,2,4]triazolo[4,3-a]pyrazin-3-yl)-2-vinylthiazole | 247.32 |
| 7 | 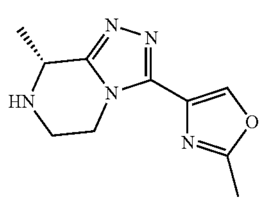 [SMILES: Cc1nc(-c2nnc3n2CCN[C@@H]3C)co1] | (R)-2-methyl-4-(8-methyl-5,6,7,8-tetrahydro-[1,2,4]triazolo[4,3-a]pyrazin-3-yl)oxazole | 219.24 |
| 8 | 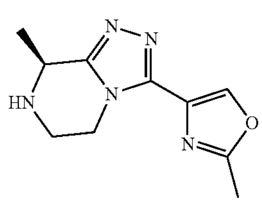 [SMILES: Cc1nc(-c2nnc3n2CCN[C@H]3C)co1] | (S)-2-methyl-4-(8-methyl-5,6,7,8-tetrahydro-[1,2,4]triazolo[4,3-a]pyrazin-3-yl)oxazole | 219.24 |
| 9 | | (R)-2-isopropyl-4-(8-methyl-5,6,7,8-tetrahydro-[1,2,4]triazolo[4,3-a]pyrazin-3-yl)oxazole | 247.30 |
| 10 | | (S)-2-isopropyl-4-(8-methyl-5,6,7,8-tetrahydro-[1,2,4]triazolo[4,3-a]pyrazin-3-yl)oxazole | 247.30 |
| 11 | | (R)-2-cyclopropyl-4-(8-methyl-5,6,7,8-tetrahydro-[1,2,4]triazolo[4,3-a]pyrazin-3-yl)oxazole | 245.28 |
| 12 | | (S)-2-cyclopropyl-4-(8-methyl-5,6,7,8-tetrahydro-[1,2,4]triazolo[4,3-a]pyrazin-3-yl)oxazole | 245.28 |
| 13 | | (R)-2,5-dimethyl-4-(8-methyl-5,6,7,8-tetrahydro-[1,2,4]triazolo[4,3-a]pyrazin-3-yl)thiazole | 249.34 |
| 14 | | (S)-2,5-dimethyl-4-(8-methyl-5,6,7,8-tetrahydro-[1,2,4]triazolo[4,3-a]pyrazin-3-yl)thiazole | 249.34 |

TABLE 2-continued

| Cpd n° | Structure | Chemical name | MW |
|---|---|---|---|
| 15 | 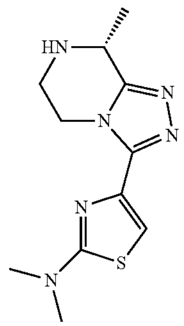 [SMILES: C[C@H]1NCCn2c(-c3csc(N(C)C)n3)nnc21] | (R)-N,N-dimethyl-4-(8-methyl-5,6,7,8-tetrahydro-[1,2,4]triazolo[4,3-a]pyrazin-3-yl)thiazol-2-amine | 264.35 |
| 16 | 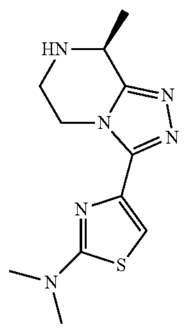 [SMILES: C[C@@H]1NCCn2c(-c3csc(N(C)C)n3)nnc21] | (S)-N,N-dimethyl-4-(8-methyl-5,6,7,8-tetrahydro-[1,2,4]triazolo[4,3-a]pyrazin-3-yl)thiazol-2-amine | 264.35 |
| 17 | 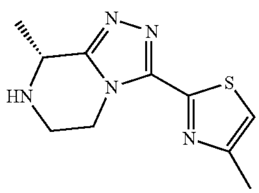 [SMILES: Cc1csc(-c2nnc3n2CCN[C@@H]3C)n1] | (R)-4-methyl-2-(8-methyl-5,6,7,8-tetrahydro-[1,2,4]triazolo[4,3-a]pyrazin-3-yl)thiazole | 235.31 |
| 18 | 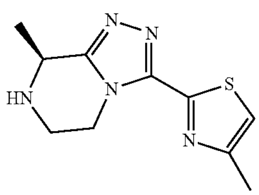 [SMILES: Cc1csc(-c2nnc3n2CCN[C@H]3C)n1] | (S)-4-methyl-2-(8-methyl-5,6,7,8-tetrahydro-[1,2,4]triazolo[4,3-a]pyrazin-3-yl)thiazole | 235.31 |
| 19 | 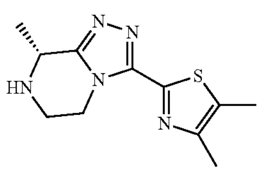 | (R)-4,5-dimethyl-2-(8-methyl-5,6,7,8-tetrahydro-[1,2,4]triazolo[4,3-a]pyrazin-3-yl)thiazole | 249.34 |
| 20 | 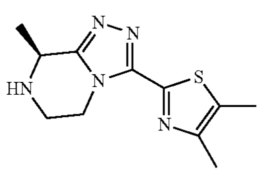 | (S)-4,5-dimethyl-2-(8-methyl-5,6,7,8-tetrahydro-[1,2,4]triazolo[4,3-a]pyrazin-3-yl)thiazole | 249.34 |
| 21 | 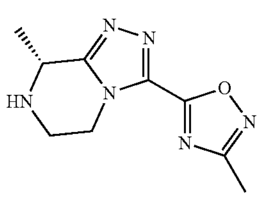 [SMILES: Cc1noc(-c2nnc3n2CCN[C@@H]3C)n1] | (R)-3-methyl-5-(8-methyl-5,6,7,8-tetrahydro-[1,2,4]triazolo[4,3-a]pyrazin-3-yl)-1,2,4-oxadiazole | 220.23 |
| 22 | 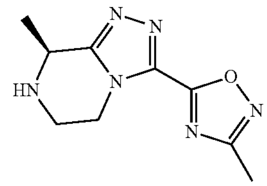 [SMILES: Cc1noc(-c2nnc3n2CCN[C@H]3C)n1] | (S)-3-methyl-5-(8-methyl-5,6,7,8-tetrahydro-[1,2,4]triazolo[4,3-a]pyrazin-3-yl)-1,2,4-oxadiazole | 220.23 |
| 23 | 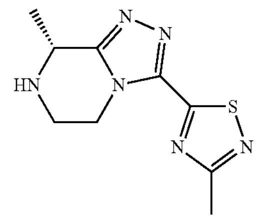 [SMILES: Cc1nsc(-c2nnc3n2CCN[C@@H]3C)n1] | (R)-3-methyl-5-(8-methyl-5,6,7,8-tetrahydro-[1,2,4]triazolo[4,3-a]pyrazin-3-yl)-1,2,4-thiadiazole | 236.30 |
| 24 | 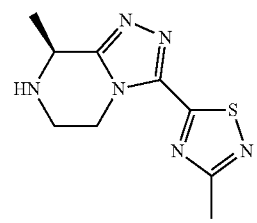 | (S)-3-methyl-5-(8-methyl-5,6,7,8-tetrahydro-[1,2,4]triazolo[4,3-a]pyrazin-3-yl)-1,2,4-thiadiazole | 236.30 |
| 25 | 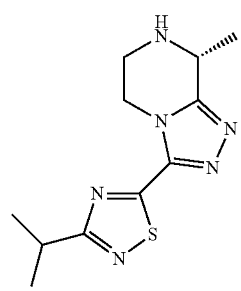 [SMILES: CC(C)c1nsc(-c2nnc3n2CCN[C@@H]3C)n1] | (R)-3-isopropyl-5-(8-methyl-5,6,7,8-tetrahydro-[1,2,4]triazolo[4,3-a]pyrazin-3-yl)-1,2,4-thiadiazole | 264.35 |
| 26 | 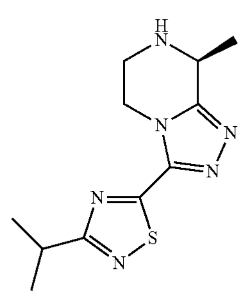 [SMILES: CC(C)c1nsc(-c2nnc3n2CCN[C@H]3C)n1] | (S)-3-isopropyl-5-(8-methyl-5,6,7,8-tetrahydro-[1,2,4]triazolo[4,3-a]pyrazin-3-yl)-1,2,4-thiadiazole | 264.35 |
| 27 | 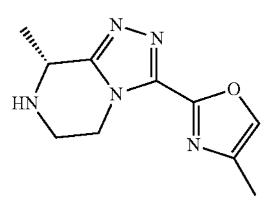 | (R)-4-methyl-2-(8-methyl-5,6,7,8-tetrahydro-[1,2,4]triazolo[4,3-a]pyrazin-3-yl)oxazole | 219.24 |
| 28 | 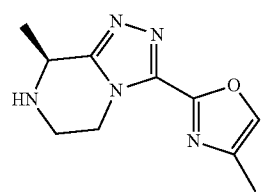 [SMILES: Cc1coc(-c2nnc3n2CCN[C@H]3C)n1] | (S)-4-methyl-2-(8-methyl-5,6,7,8-tetrahydro-[1,2,4]triazolo[4,3-a]pyrazin-3-yl)oxazole | 219.24 |

TABLE 2-continued

| Cpd n° | Structure | Chemical name | MW |
|---|---|---|---|
| 29 | 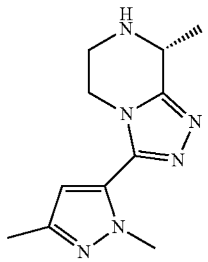 | (R)-3-(1,3-dimethyl-1H-pyrazol-5-yl)-8-methyl-5,6,7,8-tetrahydro-[1,2,4]triazolo[4,3-a]pyrazine | 232.29 |
| 30 | 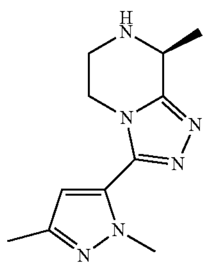 | (S)-3-(1,3-dimethyl-1H-pyrazol-5-yl)-8-methyl-5,6,7,8-tetrahydro-[1,2,4]triazolo[4,3-a]pyrazine | 232.29 |
| 31 | 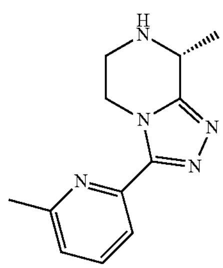 | (R)-8-methyl-3-(6-methylpyridin-2-yl)-5,6,7,8-tetrahydro-[1,2,4]triazolo[4,3-a]pyrazine | 229.28 |
| 32 | 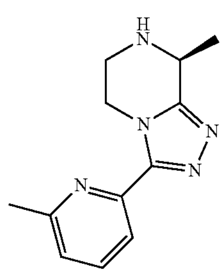 | (S)-8-methyl-3-(6-methylpyridin-2-yl)-5,6,7,8-tetrahydro-[1,2,4]triazolo[4,3-a]pyrazine | 229.28 |
| 33 | 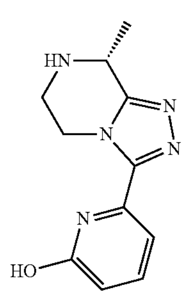 [SMILES: C[C@H]1NCCn2c(-c3cccc(O)n3)nnc21] | (R)-6-(8-methyl-5,6,7,8-tetrahydro-[1,2,4]triazolo[4,3-a]pyrazin-3-yl)pyridin-2-ol | 231.25 |
| 34 | 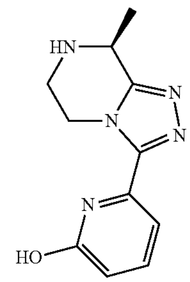 [SMILES: C[C@@H]1NCCn2c(-c3cccc(O)n3)nnc21] | (S)-6-(8-methyl-5,6,7,8-tetrahydro-[1,2,4]triazolo[4,3-a]pyrazin-3-yl)pyridin-2-ol | 231.25 |
| 35 | 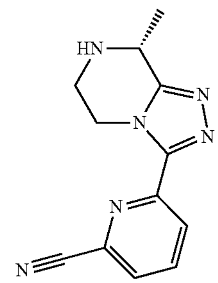 [SMILES: C[C@H]1NCCn2c(-c3cccc(C#N)n3)nnc21] | (R)-6-(8-methyl-5,6,7,8-tetrahydro-[1,2,4]triazolo[4,3-a]pyrazin-3-yl)picolinonitrile | 240.26 |
| 36 | 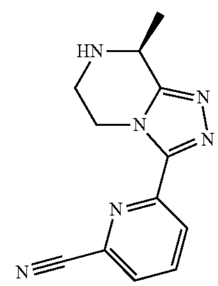 [SMILES: C[C@@H]1NCCn2c(-c3cccc(C#N)n3)nnc21] | (S)-6-(8-methyl-5,6,7,8-tetrahydro-[1,2,4]triazolo[4,3-a]pyrazin-3-yl)picolinonitrile | 240.26 |

The compounds of Table 2 were named using ChemDraw Ultra 12® purchased from CambridgeSoft (Cambridge, Mass., USA).

The below description of the process of the invention applies to the process of the invention as defined above, including all embodiments described.

Step a) of the process as defined above is the preparation of compounds of Formula C through reaction of the amine group of a compound of Formula A with a reagent resulting in a N-sp³ protective group, as defined herein, on the amine nitrogen of compound of Formula A using standard reductive amination conditions.

The compound of Formula A is advantageously selected from those wherein $R^{1'}$ is a C1-C4 alkyl, each of said alkyl groups being optionally substituted by one or more group(s) selected from halo or esters, preferably $R^{1'}$ is methyl.

This reaction results in the protection of the amine nitrogen of the piperazinone of Formula A with an above-defined N-sp³ protective group (compound of Formula C), in particular with a benzylic protective group when a compound of Formula B1 or B2 is used (compound of Formula C-1).

The reagent resulting in a N-sp³ protective group, as defined herein, on the amine nitrogen of compound of Formula A is advantageously a compound of Formula B1 or B2 as defined above. The compound of Formula B1 or B2 is advantageously selected from those wherein $R^{14}$ is methoxy and $R^{12}$, $R^{12'}$, $R^{13}$, and $R^{13'}$ are H, or $R^{12}$ and $R^{14}$ are methoxy and $R^{12'}$, $R^{13}$ and $R^{13'}$ are H, or $R^{12}$, $R^{12'}$ and $R^{14}$ are methoxy and $R^{13}$ and $R^{13'}$ are H, in particular the compound of Formula B is the one wherein $R^{12}$ and $R^{14}$ are methoxy and $R^{12'}$, $R^{13}$ and $R^{13'}$ are H; and/or The term "benzylic protective groups" according to the invention is defined as benzyl (Bn), 4-methoxybenzyl (PMB), 2,4-dimethoxybenzyl (DMB) and 2,4,6-trimethoxybenzyl (TMB), among which DMB and TMB, in particular DMB, are preferred.

These benzylic protective groups proved advantageous since their use resulted in significant reduction of racemization during the steps b), c) and d) as compared to when other protective groups such as Boc (tert-butyloxycarbonyl) and Cbz (carbobenzyloxy) were used to conduct steps b), c) and d).

Without being exclusively bound by any theory, Applicant considers two conjectures as potentially relevant to the significant improvements in the improved chiral synthesis procedure disclosed in this invention. Firstly, that N-sp$^3$ protective groups, as defined herein, e.g. Bn, PMB, DMB, TMB, in contrast to the "N-sp$^2$ protective groups", i.e. carbamates such as Boc, Cbz, Alloc (allyloxycarbonyl), may be considered less electron-withdrawing, thus rendering the hydrogen at the stereogenic carbon center less labile and, consequently, less prone to racemization. Secondly, the greater reaction efficiency in terms of reaction time and generally milder reaction conditions (e.g. obviating the need for large excess of Meerwein reagent) observed in both the imidate formation (step b) and cyclodehydration steps (step c) with N-sp$^3$ protective groups such as Bn, PMB, DMB likely contributes to retaining the chiral purity that originates from the starting material, e.g. a chiral form of 3-methyl-piperazin-2-one, and, consequently furnishing the intermediates thereof and the final products of this invention in high enantiomeric purity as defined herein.

As already set forth above, step a) is carried out in the presence of a reducing agent. The term "reducing agent" as used herein means all reagents that can reduce an imine to an amine, such as suitable hydrogenolytic conditions, including but not limited to using NaBH$_4$ and related derivatives, tri(C1-C2alkyl)silanes, boranes, and hydride-transfer reagents.

The reducing agent is advantageously an alkaline cation borohydride reagent, which is preferably selected from the group consisting of sodium borohydride, sodium cyanoborohydride, sodium triacetoxyborohydride, sodium triflurorace-toxyborohydride, more preferably the reducing agent is sodium triacetoxyborohydride.

Step a) is carried out according to standard procedures well known to those skilled in the art (See for example (a) Wuts, P. G. M.; Greene, T. W. In "Greene's Protective Groups in Organic Synthesis", Wiley-Interscience: New York, 4$^{th}$ Edition, Chap. 7, pp. 696-926, and (b) Kocieński, P. J. In "Protecting Groups", Georg Thieme Verlag: Stuttgart, New York; 3$^{rd}$ Edition, Chap. 8, pp. 487-643).

Intermediates of Formula A may be optionally purified by silica gel flash chromatography or silica gel chromatography, and/or precipitation, and/or trituration, and/or filtration, and/or recrystallization.

The second step of the process, step b), is the conversion of the ketopiperazine compounds of Formula C to iminoether compounds of Formula D, in particular of ketopiperazine compounds of Formula C-1 to iminoether compounds of Formula D-1.

Unlike the case with the N-sp$^2$ protective groups, such as Boc, with N-sp$^3$ protective groups, step b) proceeds without significant loss of chirality resulting in the corresponding products of good enantiomeric purity as defined herein.

The procedure involves a tri(C1-C2 alkyl)oxonium salt (Meerwein-type reagents), or (C1-C2)alkylsulfate, or (C1-C2)chloroformate, or use of PCl$_5$/POCl$_3$/(C1-C2)hydroxyalkyl, preferably tri(C1-C2 alkyl)oxonium salt (Meerwein-type reagents), or (C1-C2)alkylsulfate, more preferably tri (C1-C2 alkyl)oxonium salt, and even more preferably a tri(C2 alkyl)oxonium salt, such as Et$_3$OBF$_4$.

As set out above, step b) is carried out in the presence of a base.

Use of at least 2 equivalents of tri(C1-C2 alkyl)oxonium salt (1) with respect to the 3-substituted-piperazin-2-one was required to aid towards a complete conversion when step b) was carried out without a mild base additive, such as Na$_2$CO$_3$, as further discussed hereunder.

Without being bound by any theory, Applicant believes that formation of an acid such as HBF$_4$ that may be a side-product with the use of moisture-sensitive tri(C1-C2 alkyl)oxonium salt (Meerwein-type reagents) may additionally contribute to the variability in the product quality aforementioned. Interestingly, there exist two literature references (See (a) Sanchez, J. D. et al. *J. Org. Chem.* 2001, 66, 5731-5735; (b) Kende, A. S.; et al. *Org. Lett.* 2003, 5, 3205-3208) that cite the use of mild bases such as Na$_2$CO$_3$ in conjunction with the use of Meerwein reagent although without offering any explicit rationale or detailed experimental conditions. After extensive reaction optimization experiments, Applicant found that addition of a base, especially Na$_2$CO$_3$, with respect to the Meerwein reagent helped minimize racemization. Applicant further observed that use of a mild base additive, especially Na$_2$CO$_3$, appears to also help accelerate the reaction towards completion that in turn may contribute to minimizing racemization in such reactions.

The base is advantageously selected from the group consisting of sodium carbonate, sodium bicarbonate, potassium carbonate, cesium carbonate, preferably the base is sodium carbonate.

In a preferred embodiment, between 1 and 5, preferably about 1.8 mole equivalents with respect to tri(C1-C2 alkyl) oxonium salt of base are used.

The tri(C1-C2 alkyl)oxonium salt is advantageously selected from the group consisting of trimethyloxonium tetrafluoroborate, triethyloxonium tetrafluoroborate, preferably the tri(C1-C2 alkyl) oxonium salt is triethyloxonium tetrafluoroborate. In an advantageous embodiment, between 1 and 2, preferably about 1.4, mole equivalents of tri(C1-C2 alkyl)oxonium salt is used.

The iminoether synthesis step b) is advantageously carried out in an organic, preferably anhydrous, solvent, preferably dichloromethane.

The reaction is advantageously carried out at a temperature equal to or below the boiling point of the organic solvent; preferably the reaction is carried out at room temperature.

The term "room temperature" as used herein means a temperature comprised between 10° C. and 30° C., preferably about 20±5° C.

In one embodiment, especially in the case of the conversion of ketopiperazine compounds of Formula C-1 to iminoether compounds of Formula D-1, step b) is carried out in DCM, at room temperature with 1.8 equivalents with respect to tri(C1-C2 alkyl)oxonium salt of sodium carbonate.

Intermediates of Formula D may optionally be purified by flash or column chromatography on silica gel.

The third step of the process, step c), is the preparation of triazolopiperazine compounds of Formula F by condensation between an iminoether of Formula D and an acylhydrazide of Formula E or a salt or solvate thereof, especially the preparation of triazolopiperazine compounds of Formula F-1 by condensation between an iminoether of Formula D-1 and an acylhydrazide of Formula E or salt or solvate thereof.

Without being bound by any theory, Applicant believes that when using N-sp$^2$ protective groups, such as Boc, the inductive effect of the carbamate makes the proton at the C8 position more acidic, which could thus explain the observed racemization (deprotonation might occur in the presence of hydrazide).

Step c) is generally carried out at a temperature comprised between 50° C. and 135° C., preferably between 70° C. and 135° C.

In contrast, condensations with Boc-protected methylketopiperazine were typically conducted under very forcing conditions, such as 135° C., neat reaction medium, long reaction time (>24 h) or excessive application of microwave for several days. Such conditions were not readily amenable for scale-up, and in addition, non-reproducible chiral purity was also a problem with such harsh and protracted reaction conditions.

Intermediates of Formula F may optionally be purified by flash or column chromatography on silica gel.

The fourth step of the process, i.e. step d), entails deprotection of compounds of Formula F especially compounds of Formula F-1 with a suitable deprotection reagent.

The term "suitable deprotection reagent" according to the invention is defined as any reagent(s) allowing the removal of an N-sp$^3$ protective group as defined herein, in particular benzylic protective groups as defined herein. Examples of such reagents are reported in (a) Wuts, P. G. M.; Greene, T. W. In "Greene's Protective Groups in Organic Synthesis", Wiley-Interscience: New York, 4$^{th}$ Edition, Chap. 7, pp. 696-926, and (b) Kocieński, P. J. In "Protecting Groups", Georg Thieme Verlag: Stuttgart, New York; 3$^{rd}$ Edition, Chap. 8, pp. 487-643); suitable deprotection reagents include but are not limited to hydrogenolytic conditions (e.g. $H_2$, Pd/C) or acidolytic conditions (e.g. HCl, TFA).

Preferred deprotection reagents are selected from the group consisting of TFA, HCl, preferably HCl.

The more acid labile variants of the benzylic protective groups as defined herein, such as PMB, DMB and TMB, proved advantageous due to milder deprotection conditions required, thus consequently aiding in minimizing any racemization possible at this step.

Step d) is advantageously carried out in an organic solvent selected from 1,4-dioxane, dichloromethane, iso-propanol.

When using acidolytic deprotection conditions such as through the use of TFA or HCl, compounds of Formula II are thus obtained in their corresponding salt forms.

In one embodiment, step d) may be optionally followed by a conversion to the free base form.

In one embodiment, compounds of Formula II, either in salt or free base form, are converted using stereoisomeric salt-forming agents, such as chiral acids, to obtain stereoisomeric salts of Formula II in order to enhance the chemical purity and/or stereoisomeric purity of the final intermediate.

The aforesaid stereoisomeric salt-forming agents include but are not limited to mandelic acid, tartaric acid, dibenzoyl- and ditoluyl-tartaric acid, phenylpropionic acid, tartanilic acid derivatives in all relevant stereoisomeric forms, or more preferably mandelic acid, tartaric acid, dibenzoyl- and ditoluyl-tartaric acid, phenylpropionic acid in all relevant stereoisomeric forms.

In one embodiment, step d) is followed by an additional amide coupling step e) in which the compound of Formula II or salt or solvate thereof is reacted with a compound of Formula G

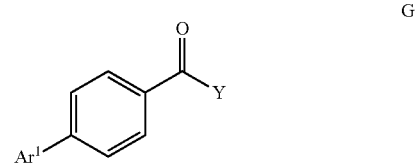

or a salt or solvate thereof, wherein
Ar$^1$ is phenyl, thiophen-2yl or 4-fluorophenyl, preferably phenyl or thiophen-2-yl;
Y is hydroxyl, halo, preferably F or Cl, more preferably hydroxyl and Cl, and even more preferably Cl;
to provide a compound of Formula H

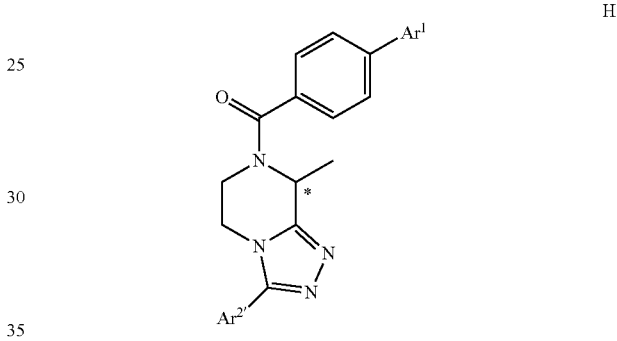

or a salt or solvate thereof wherein Ar$^2$' is as defined above with respect to Formula II and Ar$^1$ is as defined above with respect to Formula G.

Step e) is advantageously carried out in an organic, preferably anhydrous, solvent, selected from dichloromethane, acetonitrile, preferably in dichloromethane.

The reaction is advantageously carried out at a temperature equal to or below boiling point of the organic solvent, preferably at room temperature.

In the case of compounds of Formula G wherein Y is a halo, the reaction is carried out in the presence of a base selected from the group consisting of di-iso-propylethylamine, N-methylmorpholine, triethylamine, preferably N-methylmorpholine, and in the case of compounds of Formula G wherein Y is a hydroxyl, an activated anhydride, ester, acylurea derivative of the latter said compounds—formed through conventional amide bond forming reagent (s) involving the use of so-called activating groups, such as isobutylchloroformate, DIC, DCC, HOBt, HATU, HBTU, DEPBT under reaction conditions known to those skilled in the art, and more preferably with compounds of Formula G wherein Y is a halo, the reaction was carried out in the presence of a base selected from the group consisting of di-iso-propylethylamine, N-methylmorpholine, triethylamine, preferably N-methylmorpholine;

Enantiomeric excess values of compounds of Formula II or salt thereof were not determined since separation on chiral HPLC was difficult to achieve. However, chiral purity and enantiomeric excess of compounds of Formula G could be determined. Applicant has observed identical ee values for compounds of Formula D and amides of Formula H which confirmed both steps d) and e) proceed without any detectable racemisation (chiral LC).

In another aspect, the invention provides intermediates for the synthesis of compounds of Formula II, in particular according to the process of the invention. These intermediates are compounds of Formula D as defined above.

In one embodiment, compounds of Formula D are those of formula D-1

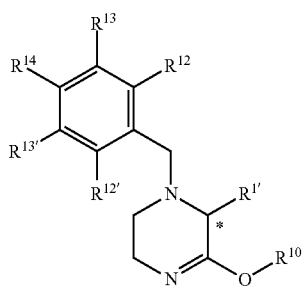

D-1 wherein $R^{1'}$ and $R^{10}$ are as defined with respect to Formula D; and $R^{12}$, $R^{12'}$, $R^{13}$, $R^{13'}$ and $R^{14}$ are H, or $R^{14}$ is methoxy and $R^{12}$, $R^{12'}$, $R^{13}$ and $R^{13'}$ are H, or $R^{12}$ and $R^{14}$ are methoxy and $R^{12'}$, $R^{13}$ and $R^{13'}$ are H, or $R^{12}$, $R^{12'}$ and $R^{14}$ are methoxy and $R^{13}$ and $R^{13'}$ are H.

Preferred compounds of Formula D-1 are those wherein: $R^{14}$ is methoxy and $R^{12}$, $R^{12'}$, $R^{13}$ and $R^{13'}$ are H, or $R^{12}$ and $R^{14}$ are methoxy and $R^{12'}$, $R^{13}$ and $R^{13'}$ are H, or $R^{12}$, $R^{12'}$ and $R^{14}$ are methoxy and $R^{13}$ and $R^{13'}$ are H, preferably $R^{12}$ and $R^{14}$ are methoxy and $R^{12'}$, $R^{13}$ and $R^{13'}$ are H, or $R^{12}$, $R^{12'}$ and $R^{14}$ are methoxy and $R^{13}$ and $R^{13'}$ are H, more preferably $R^{12}$ and $R^{14}$ are methoxy and $R^{12'}$, $R^{13}$ and $R^{13'}$ are H; and/or $R^{10}$ is ethyl.

A preferred compound of Formula D-1 is (R)-1-(2,4-dimethoxybenzyl)-5-ethoxy-6-methyl-1,2,3,6-tetrahydropyrazine.

As set forth above, the invention also provides compounds of Formula III as defined above. In one embodiment, compounds of Formula III or salts or solvates thereof are those wherein $R^{11}$ is H or

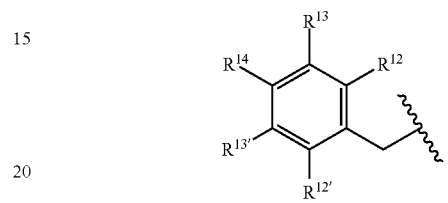

wherein $R^{12}$, $R^{12'}$, $R^{13}$, $R^{13'}$ and $R^{14}$ are H, or $R^{14}$ is methoxy and $R^{12}$, $R^{12'}$, $R^{13}$ and $R^{13'}$ are H, or $R^{12}$ and $R^{14}$ are methoxy and $R^{12'}$, $R^{13}$ and $R^{13'}$ are H, or $R^{12}$, $R^{12'}$ and $R^{14}$ are methoxy and $R^{13}$ and $R^{13'}$ are H; preferably $R^{14}$ is methoxy and $R^{12}$, $R^{12'}$, $R^{13}$ and $R^{13'}$ are H, or $R^{12}$ and $R^{14}$ are methoxy and $R^{12'}$, $R^{13}$ and $R^{13'}$ are H, or $R^{12}$, $R^{12'}$ and $R^{14}$ are methoxy and $R^{13}$ and $R^{13'}$ are H, preferably $R^{12}$ and $R^{14}$ are methoxy and $R^{12'}$, $R^{13}$ and $R^{13'}$ are H, or $R^{12}$, $R^{12'}$ and $R^{14}$ are methoxy and $R^{13}$ and $R^{13'}$ are H, more preferably $R^{12}$ and $R^{14}$ are methoxy and $R^{12'}$, $R^{13}$ and $R^{13'}$ are H; and $R^{1'}$ and $Ar^{2'}$ is as defined with respect to Formula II.

Particularly preferred compounds of Formula III are those listed in table 3 hereafter:

TABLE 3

| Cpd n° | Structure | Chemical name | MW |
|---|---|---|---|
| 1 | 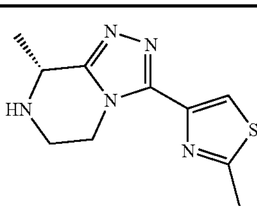 | (R)-2-methyl-4-(8-methyl-5,6,7,8-tetrahydro-[1,2,4]triazolo[4,3-a]pyrazin-3-yl)thiazole | 235.31 |
| 2 | 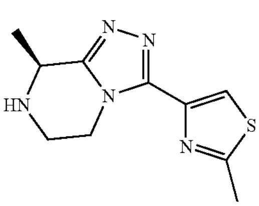 [SMILES: Cc1nc(-c2nnc3n2CCN[C@H]3C)cs1] | (S)-2-methyl-4-(8-methyl-5,6,7,8-tetrahydro-[1,2,4]triazolo[4,3-a]pyrazin-3-yl)thiazole | 235.31 |
| 3 | 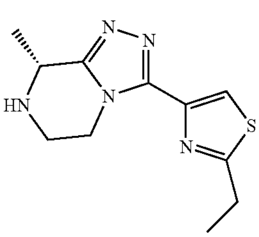 [SMILES: CCc1nc(-c2nnc3n2CCN[C@@H]3C)cs1] | (R)-2-ethyl-4-(8-methyl-5,6,7,8-tetrahydro-[1,2,4]triazolo[4,3-a]pyrazin-3-yl)thiazole | 249.34 |

TABLE 3-continued

| Cpd n° | Structure | Chemical name | MW |
|---|---|---|---|
| 4 | 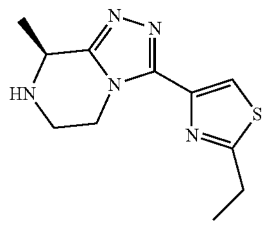 [SMILES: CCc1nc(-c2nnc3n2CCN[C@H]3C)cs1] | (S)-2-ethyl-4-(8-methyl-5,6,7,8-tetrahydro-[1,2,4]triazolo[4,3-a]pyrazin-3-yl)thiazole | 249.34 |
| 5 | 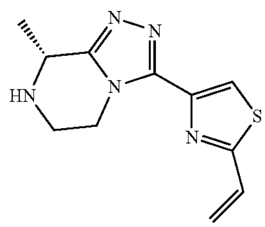 [SMILES: C=Cc1nc(-c2nnc3n2CCN[C@@H]3C)cs1] | (R)-4-(8-methyl-5,6,7,8-tetrahydro-[1,2,4]triazolo[4,3-a]pyrazin-3-yl)-2-vinylthiazole | 247.32 |
| 6 | 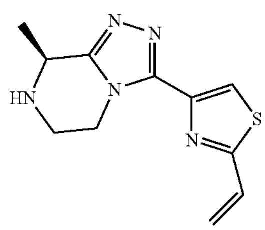 [SMILES: C=Cc1nc(-c2nnc3n2CCN[C@H]3C)cs1] | (S)-4-(8-methyl-5,6,7,8-tetrahydro-[1,2,4]triazolo[4,3-a]pyrazin-3-yl)-2-vinylthiazole | 247.32 |
| 7 | 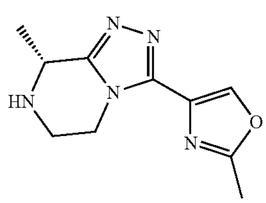 | (R)-2-methyl-4-(8-methyl-5,6,7,8-tetrahydro-[1,2,4]triazolo[4,3-a]pyrazin-3-yl)oxazole | 219.24 |
| 8 | 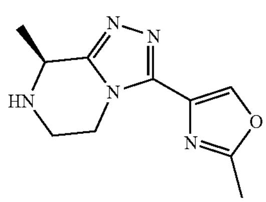 | (S)-2-methyl-4-(8-methyl-5,6,7,8-tetrahydro-[1,2,4]triazolo[4,3-a]pyrazin-3-yl)oxazole | 219.24 |
| 9 | 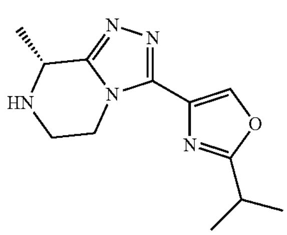 [SMILES: CC(C)c1nc(-c2nnc3n2CCN[C@@H]3C)co1] | (R)-2-isopropyl-4-(8-methyl-5,6,7,8-tetrahydro-[1,2,4]triazolo[4,3-a]pyrazin-3-yl)oxazole | 247.30 |
| 10 | 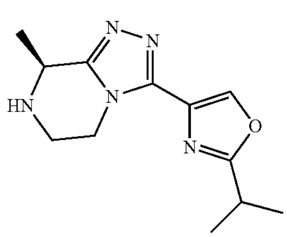 [SMILES: CC(C)c1nc(-c2nnc3n2CCN[C@H]3C)co1] | (S)-2-isopropyl-4-(8-methyl-5,6,7,8-tetrahydro-[1,2,4]triazolo[4,3-a]pyrazin-3-yl)oxazole | 247.30 |

TABLE 3-continued

| Cpd n° | Structure | Chemical name | MW |
|---|---|---|---|
| 11 | 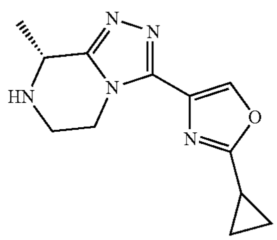 [SMILES: C[C@H]1NCCn2c(-c3coc(C4CC4)n3)nnc21] | (R)-2-cyclopropyl-4-(8-methyl-5,6,7,8-tetrahydro-[1,2,4]triazolo[4,3-a]pyrazin-3-yl)oxazole | 245.28 |
| 12 | 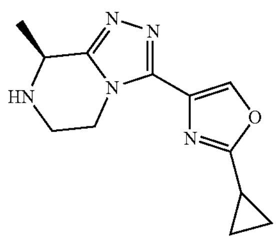 [SMILES: C[C@@H]1NCCn2c(-c3coc(C4CC4)n3)nnc21] | (S)-2-cyclopropyl-4-(8-methyl-5,6,7,8-tetrahydro-[1,2,4]triazolo[4,3-a]pyrazin-3-yl)oxazole | 245.28 |
| 13 | 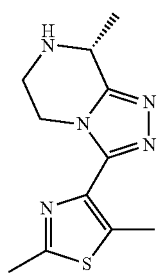 | (R)-2,5-dimethyl-4-(8-methyl-5,6,7,8-tetrahydro-[1,2,4]triazolo[4,3-a]pyrazin-3-yl)thiazole | 249.34 |
| 14 | 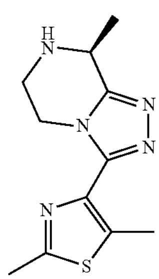 | (S)-2,5-dimethyl-4-(8-methyl-5,6,7,8-tetrahydro-[1,2,4]triazolo[4,3-a]pyrazin-3-yl)thiazole | 249.34 |
| 15 | 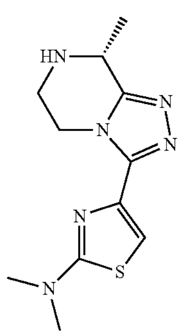 [SMILES: C[C@H]1NCCn2c(-c3csc(N(C)C)n3)nnc21] | (R)-N,N-dimethyl-4-(8-methyl-5,6,7,8-tetrahydro-[1,2,4]triazolo[4,3-a]pyrazin-3-yl)thiazol-2-amine | 264.35 |

TABLE 3-continued

| Cpd n° | Structure | Chemical name | MW |
|---|---|---|---|
| 16 | 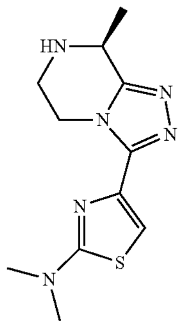 [SMILES: C[C@@H]1NCCn2c(-c3csc(N(C)C)n3)nnc21] | (S)-N,N-dimethyl-4-(8-methyl-5,6,7,8-tetrahydro-[1,2,4]triazolo[4,3-a]pyrazin-3-yl)thiazol-2-amine | 264.35 |
| 17 | 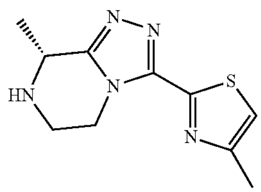 [SMILES: Cc1csc(-c2nnc3n2CCN[C@@H]3C)n1] | (R)-4-methyl-2-(8-methyl-5,6,7,8-tetrahydro-[1,2,4]triazolo[4,3-a]pyrazin-3-yl)thiazole | 235.31 |
| 18 | 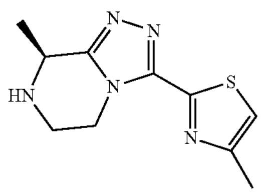 [SMILES: Cc1csc(-c2nnc3n2CCN[C@H]3C)n1] | (S)-4-methyl-2-(8-methyl-5,6,7,8-tetrahydro-[1,2,4]triazolo[4,3-a]pyrazin-3-yl)thiazole | 235.31 |
| 19 | 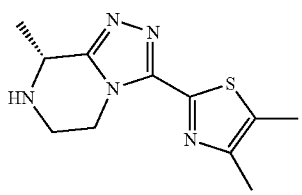 | (R)-4,5-dimethyl-2-(8-methyl-5,6,7,8-tetrahydro-[1,2,4]triazolo[4,3-a]pyrazin-3-yl)thiazole | 249.34 |
| 20 | 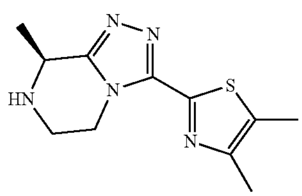 | (S)-4,5-dimethyl-2-(8-methyl-5,6,7,8-tetrahydro-[1,2,4]triazolo[4,3-a]pyrazin-3-yl)thiazole | 249.34 |
| 21 | 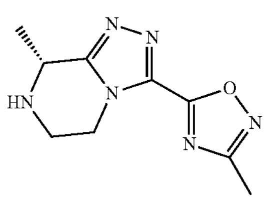 [SMILES: Cc1noc(-c2nnc3n2CCN[C@@H]3C)n1] | (R)-3-methyl-5-(8-methyl-5,6,7,8-tetrahydro-[1,2,4]triazolo[4,3-a]pyrazin-3-yl)-1,2,4-oxadiazole | 220.23 |
| 22 | 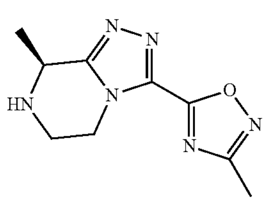 [SMILES: Cc1noc(-c2nnc3n2CCN[C@H]3C)n1] | (S)-3-methyl-5-(8-methyl-5,6,7,8-tetrahydro-[1,2,4]triazolo[4,3-a]pyrazin-3-yl)-1,2,4-oxadiazole | 220.23 |

TABLE 3-continued

| Cpd n° | Structure | Chemical name | MW |
|---|---|---|---|
| 23 | 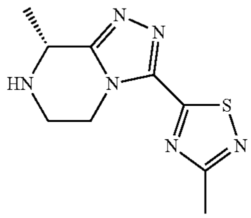 [SMILES: Cc1nsc(-c2nnc3n2CCN[C@@H]3C)n1] | (R)-3-methyl-5-(8-methyl-5,6,7,8-tetrahydro-[1,2,4]triazolo[4,3-a]pyrazin-3-yl)-1,2,4-thiadiazole | 236.30 |
| 24 | 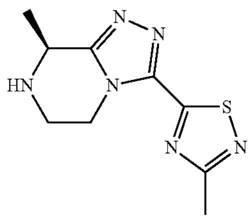 [SMILES: Cc1nsc(-c2nnc3n2CCN[C@H]3C)n1] | (S)-3-methyl-5-(8-methyl-5,6,7,8-tetrahydro-[1,2,4]triazolo[4,3-a]pyrazin-3-yl)-1,2,4-thiadiazole | 236.30 |
| 25 | 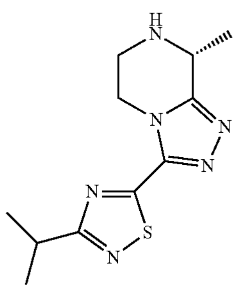 [SMILES: CC(C)c1nsc(-c2nnc3n2CCN[C@@H]3C)n1] | (R)-3-isopropyl-5-(8-methyl-5,6,7,8-tetrahydro-[1,2,4]triazolo[4,3-a]pyrazin-3-yl)-1,2,4-thiadiazole | 264.35 |
| 26 | 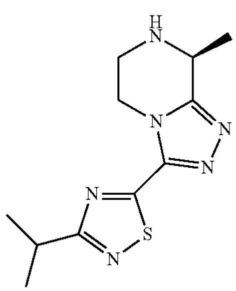 [SMILES: CC(C)c1nsc(-c2nnc3n2CCN[C@H]3C)n1] | (S)-3-isopropyl-5-(8-methyl-5,6,7,8-tetrahydro-[1,2,4]triazolo[4,3-a]pyrazin-3-yl)-1,2,4-thiadiazole | 264.35 |
| 27 | 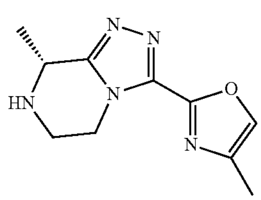 [SMILES: Cc1coc(-c2nnc3n2CCN[C@@H]3C)n1] | (R)-4-methyl-2-(8-methyl-5,6,7,8-tetrahydro-[1,2,4]triazolo[4,3-a]pyrazin-3-yl)oxazole | 219.24 |
| 28 | 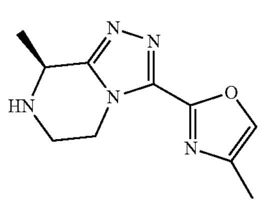 [SMILES: Cc1coc(-c2nnc3n2CCN[C@H]3C)n1] | (S)-4-methyl-2-(8-methyl-5,6,7,8-tetrahydro-[1,2,4]triazolo[4,3-a]pyrazin-3-yl)oxazole | 219.24 |

TABLE 3-continued

| Cpd n° | Structure | Chemical name | MW |
|---|---|---|---|
| 29 | 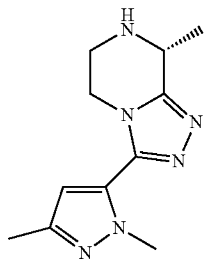 | (R)-3-(1,3-dimethyl-1H-pyrazol-5-yl)-8-methyl-5,6,7,8-tetrahydro-[1,2,4]triazolo[4,3-a]pyrazine | 232.29 |
| 30 | 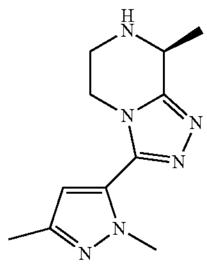 | (S)-3-(1,3-dimethyl-1H-pyrazol-5-yl)-8-methyl-5,6,7,8-tetrahydro-[1,2,4]triazolo[4,3-a]pyrazine | 232.29 |
| 31 | 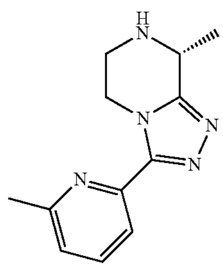 | (R)-8-methyl-3-(6-methylpyridin-2-yl)-5,6,7,8-tetrahydro-[1,2,4]triazolo[4,3-a]pyrazine | 229.28 |
| 32 | 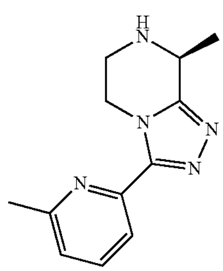 | (S)-8-methyl-3-(6-methylpyridin-2-yl)-5,6,7,8-tetrahydro-[1,2,4]triazolo[4,3-a]pyrazine | 229.28 |
| 33 | 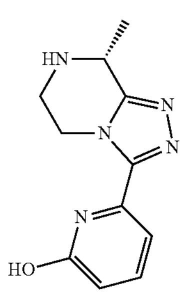 | (R)-6-(8-methyl-5,6,7,8-tetrahydro-[1,2,4]triazolo[4,3-a]pyrazin-3-yl)pyridin-2-ol | 231.25 |

TABLE 3-continued

| Cpd n° | Structure | Chemical name | MW |
|---|---|---|---|
| 34 | 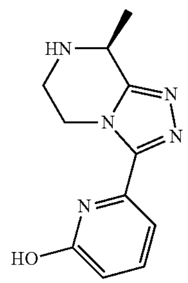 [SMILES: C[C@@H]1NCCn2c(-c3cccc(O)n3)nnc21] | (S)-6-(8-methyl-5,6,7,8-tetrahydro-[1,2,4]triazolo[4,3-a]pyrazin-3-yl)pyridin-2-ol | 231.25 |
| 35 | 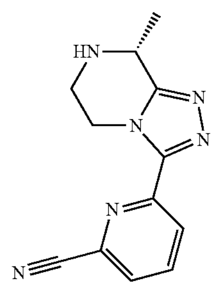 [SMILES: C[C@H]1NCCn2c(-c3cccc(C#N)n3)nnc21] | (R)-6-(8-methyl-5,6,7,8-tetrahydro-[1,2,4]triazolo[4,3-a]pyrazin-3-yl)picolinonitrile | 240.26 |
| 36 | 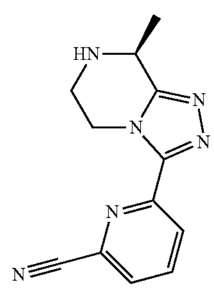 [SMILES: C[C@@H]1NCCn2c(-c3cccc(C#N)n3)nnc21] | (S)-6-(8-methyl-5,6,7,8-tetrahydro-[1,2,4]triazolo[4,3-a]pyrazin-3-yl)picolinonitrile | 240.26 |
| 37 | 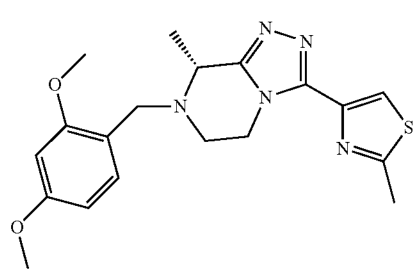 [SMILES: COc1ccc(CN2CCn3c(-c4csc(C)n4)nnc3[C@H]2C)c(OC)c1] | (R)-4-(7-(2,4-dimethoxybenzyl)-8-methyl-5,6,7,8-tetrahydro-[1,2,4]triazolo[4,3-a]pyrazin-3-yl)-2-methylthiazole | 385.48 |
| 38 | 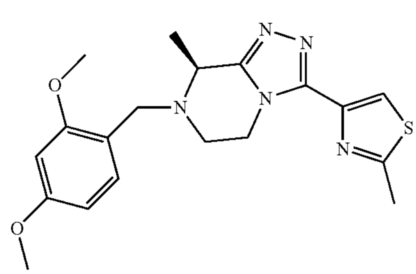 [SMILES: COc1ccc(CN2CCn3c(-c4csc(C)n4)nnc3[C@@H]2C)c(OC)c1] | (S)-4-(7-(2,4-dimethoxybenzyl)-8-methyl-5,6,7,8-tetrahydro-[1,2,4]triazolo[4,3-a]pyrazin-3-yl)-2-methylthiazole | 385.48 |

TABLE 3-continued

| Cpd nº | Structure | Chemical name | MW |
|---|---|---|---|
| 39 | 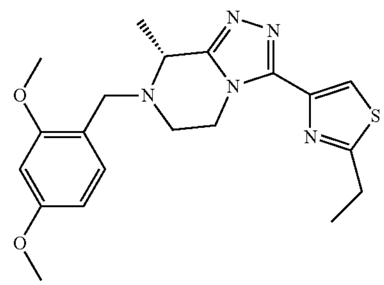 [SMILES: CCc1nc(-c2nnc3n2CCN(Cc2ccc(OC)cc2OC)[C@@H]3C)cs1] | (R)-4-(7-(2,4-dimethoxybenzyl)-8-methyl-5,6,7,8-tetrahydro-[1,2,4]triazolo[4,3-a]pyrazin-3-yl)-2-ethylthiazole | 399.51 |
| 40 | 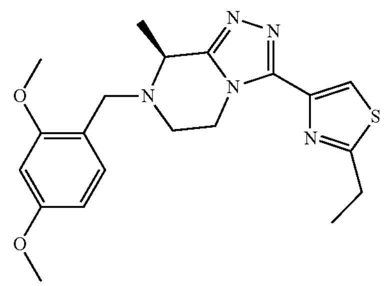 [SMILES: CCc1nc(-c2nnc3n2CCN(Cc2ccc(OC)cc2OC)[C@H]3C)cs1] | (S)-4-(7-(2,4-dimethoxybenzyl)-8-methyl-5,6,7,8-tetrahydro-[1,2,4]triazolo[4,3-a]pyrazin-3-yl)-2-ethylthiazole | 399.51 |
| 41 | 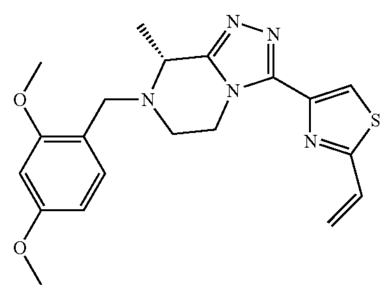 [SMILES: C=Cc1nc(-c2nnc3n2CCN(Cc2ccc(OC)cc2OC)[C@@H]3C)cs1] | (R)-4-(7-(2,4-dimethoxybenzyl)-8-methyl-5,6,7,8-tetrahydro-[1,2,4]triazolo[4,3-a]pyrazin-3-yl)-2-vinylthiazole | 397.49 |
| 42 | 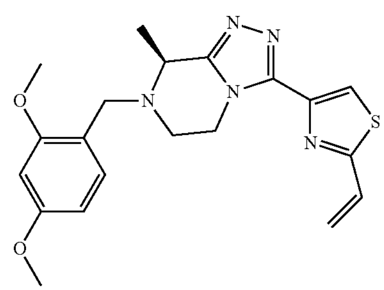 [SMILES: C=Cc1nc(-c2nnc3n2CCN(Cc2ccc(OC)cc2OC)[C@H]3C)cs1] | (S)-4-(7-(2,4-dimethoxybenzyl)-8-methyl-5,6,7,8-tetrahydro-[1,2,4]triazolo[4,3-a]pyrazin-3-yl)-2-vinylthiazole | 397.49 |
| 43 | 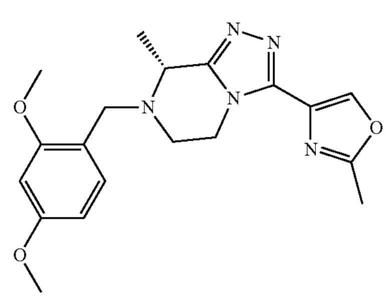 [SMILES: COc1ccc(CN2CCn3c(-c4coc(C)n4)nnc3[C@H]2C)c(OC)c1] | (R)-4-(7-(2,4-dimethoxybenzyl)-8-methyl-5,6,7,8-tetrahydro-[1,2,4]triazolo[4,3-a]pyrazin-3-yl)-2-methyloxazole | 369.42 |

TABLE 3-continued

| Cpd n° | Structure | Chemical name | MW |
|---|---|---|---|
| 44 | 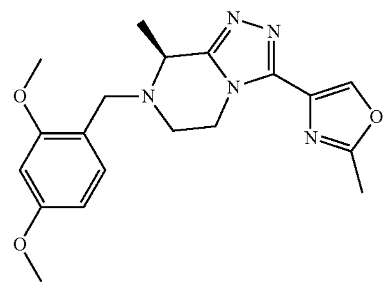 [SMILES: COc1ccc(CN2CCn3c(-c4coc(C)n4)nnc3[C@@H]2C)c(OC)c1] | (S)-4-(7-(2,4-dimethoxybenzyl)-8-methyl-5,6,7,8-tetrahydro-[1,2,4]triazolo[4,3-a]pyrazin-3-yl)-2-methyloxazole | 369.42 |
| 45 | 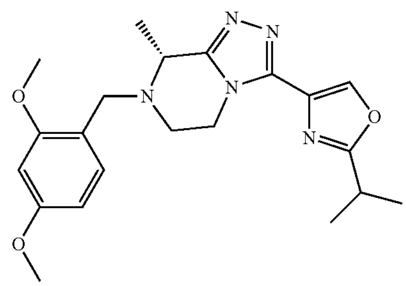 [SMILES: COc1ccc(CN2CCn3c(-c4coc(C(C)C)n4)nnc3[C@H]2C)c(OC)c1] | (R)-4-(7-(2,4-dimethoxybenzyl)-8-methyl-5,6,7,8-tetrahydro-[1,2,4]triazolo[4,3-a]pyrazin-3-yl)-2-isopropyloxazole | 397.47 |
| 46 | 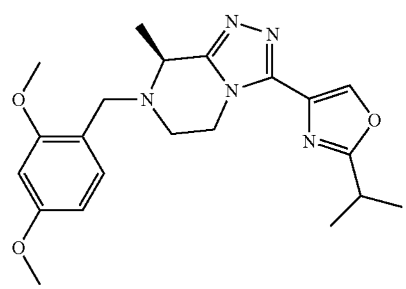 [SMILES: COc1ccc(CN2CCn3c(-c4coc(C(C)C)n4)nnc3[C@@H]2C)c(OC)c1] | (S)-4-(7-(2,4-dimethoxybenzyl)-8-methyl-5,6,7,8-tetrahydro-[1,2,4]triazolo[4,3-a]pyrazin-3-yl)-2-isopropyloxazole | 397.47 |
| 47 | 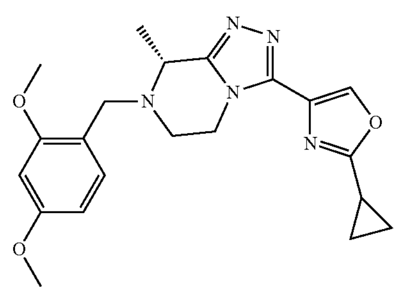 [SMILES: COc1ccc(CN2CCn3c(-c4coc(C5CC5)n4)nnc3[C@H]2C)c(OC)c1] | (R)-2-cyclopropyl-4-(7-(2,4-dimethoxybenzyl)-8-methyl-5,6,7,8-tetrahydro-[1,2,4]triazolo[4,3-a]pyrazin-3-yl)oxazole | 395.46 |
| 48 | 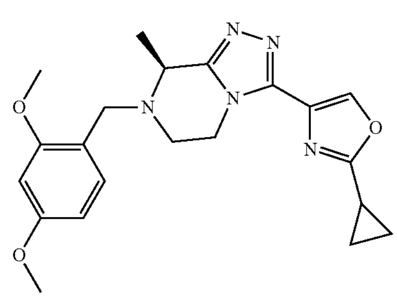 [SMILES: COc1ccc(CN2CCn3c(-c4coc(C5CC5)n4)nnc3[C@@H]2C)c(OC)c1] | (S)-2-cyclopropyl-4-(7-(2,4-dimethoxybenzyl)-8-methyl-5,6,7,8-tetrahydro-[1,2,4]triazolo[4,3-a]pyrazin-3-yl)oxazole | 395.46 |

TABLE 3-continued

| Cpd n° | Structure | Chemical name | MW |
|---|---|---|---|
| 49 | 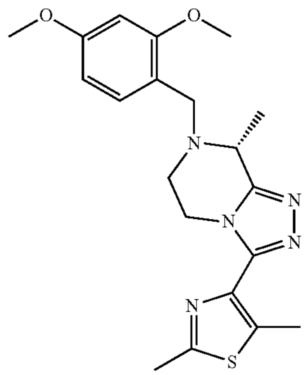 | (R)-4-(7-(2,4-dimethoxybenzyl)-8-methyl-5,6,7,8-tetrahydro-[1,2,4]triazolo[4,3-a]pyrazin-3-yl)-2,5-dimethylthiazole | 399.51 |
| 50 | 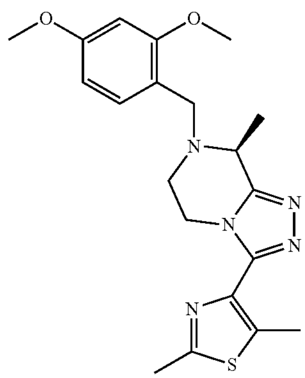 | (S)-4-(7-(2,4-dimethoxybenzyl)-8-methyl-5,6,7,8-tetrahydro-[1,2,4]triazolo[4,3-a]pyrazin-3-yl)-2,5-dimethylthiazole | 399.51 |
| 51 | 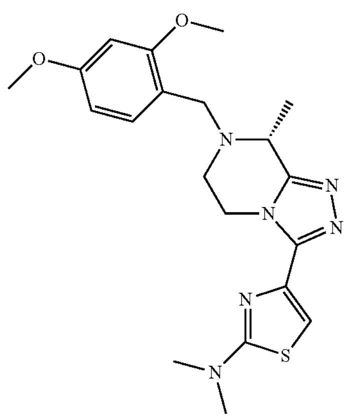 [SMILES: COc1ccc(CN2CCn3c(-c4csc(N(C)C)n4)nnc3[C@H]2C)c(OC)c1] | (R)-4-(7-(2,4-dimethoxybenzyl)-8-methyl-5,6,7,8-tetrahydro-[1,2,4]triazolo[4,3-a]pyrazin-3-yl)-N,N-dimethylthiazol-2-amine | 414.52 |
| 52 | 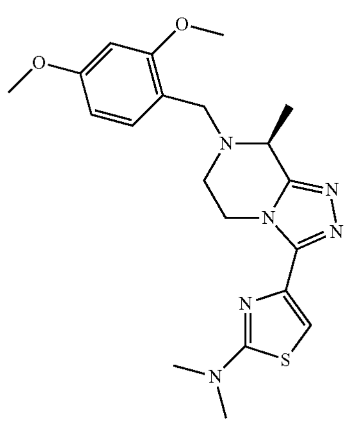 [SMILES: COc1ccc(CN2CCn3c(-c4csc(N(C)C)n4)nnc3[C@@H]2C)c(OC)c1] | (S)-4-(7-(2,4-dimethoxybenzyl)-8-methyl-5,6,7,8-tetrahydro-[1,2,4]triazolo[4,3-a]pyrazin-3-yl)-N,N-dimethylthiazol-2-amine | 414.52 |

TABLE 3-continued

| Cpd n° | Structure | Chemical name | MW |
|---|---|---|---|
| 53 | 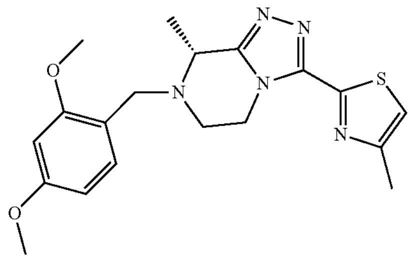 [SMILES: COc1ccc(CN2CCn3c(-c4nc(C)cs4)nnc3[C@H]2C)c(OC)c1] | (R)-2-(7-(2,4-dimethoxybenzyl)-8-methyl-5,6,7,8-tetrahydro-[1,2,4]triazolo[4,3-a]pyrazin-3-yl)-4-methylthiazole | 385.48 |
| 54 | 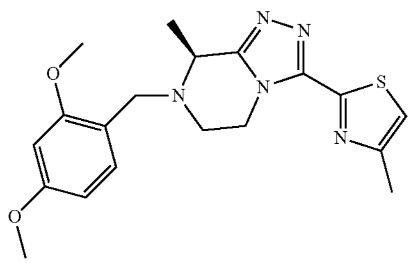 [SMILES: COc1ccc(CN2CCn3c(-c4nc(C)cs4)nnc3[C@@H]2C)c(OC)c1] | (S)-2-(7-(2,4-dimethoxybenzyl)-8-methyl-5,6,7,8-tetrahydro-[1,2,4]triazolo[4,3-a]pyrazin-3-yl)-4-methylthiazole | 385.48 |
| 55 | 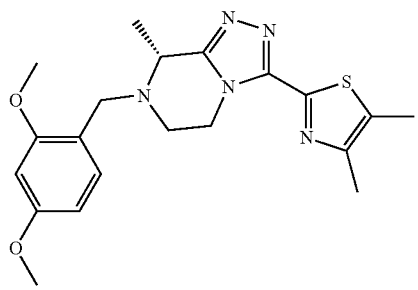 [SMILES: COc1ccc(CN2CCn3c(-c4nc(C)c(C)s4)nnc3[C@H]2C)c(OC)c1] | (R)-2-(7-(2,4-dimethoxybenzyl)-8-methyl-5,6,7,8-tetrahydro-[1,2,4]triazolo[4,3-a]pyrazin-3-yl)-4,5-dimethylthiazole | 399.51 |
| 56 | 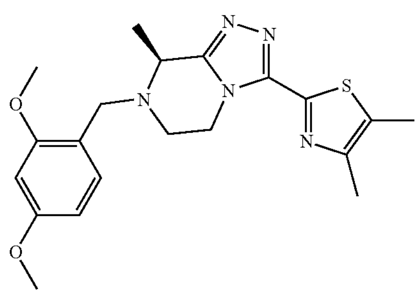 [SMILES: COc1ccc(CN2CCn3c(-c4nc(C)c(C)s4)nnc3[C@@H]2C)c(OC)c1] | (S)-2-(7-(2,4-dimethoxybenzyl)-8-methyl-5,6,7,8-tetrahydro-[1,2,4]triazolo[4,3-a]pyrazin-3-yl)-4,5-dimethylthiazole | 399.51 |
| 57 | 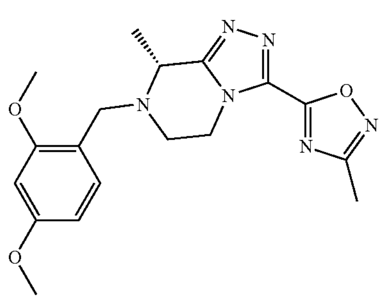 [SMILES: COc1ccc(CN2CCn3c(-c4nc(C)no4)nnc3[C@H]2C)c(OC)c1] | (R)-5-(7-(2,4-dimethoxybenzyl)-8-methyl-5,6,7,8-tetrahydro-[1,2,4]triazolo[4,3-a]pyrazin-3-yl)-3-methyl-1,2,4-oxadiazole | 370.41 |

TABLE 3-continued

| Cpd n° | Structure | Chemical name | MW |
|---|---|---|---|
| 58 | 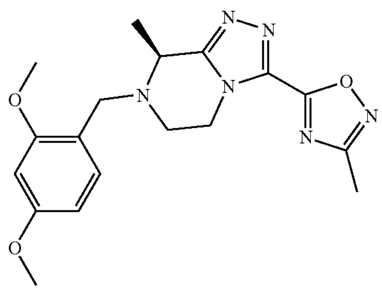 [SMILES: COc1ccc(CN2CCn3c(-c4nc(C)no4)nnc3[C@@H]2C)c(OC)c1] | (S)-5-(7-(2,4-dimethoxybenzyl)-8-methyl-5,6,7,8-tetrahydro-[1,2,4]triazolo[4,3-a]pyrazin-3-yl)-3-methyl-1,2,4-oxadiazole | 370.41 |
| 59 | 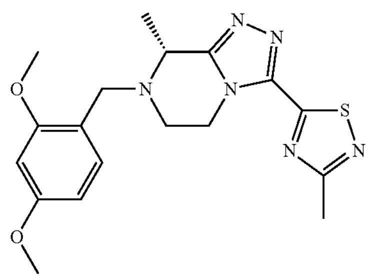 [SMILES: COc1ccc(CN2CCn3c(-c4nc(C)ns4)nnc3[C@H]2C)c(OC)c1] | (R)-5-(7-(2,4-dimethoxybenzyl)-8-methyl-5,6,7,8-tetrahydro-[1,2,4]triazolo[4,3-a]pyrazin-3-yl)-3-methyl-1,2,4-thiadiazole | 386.47 |
| 60 | 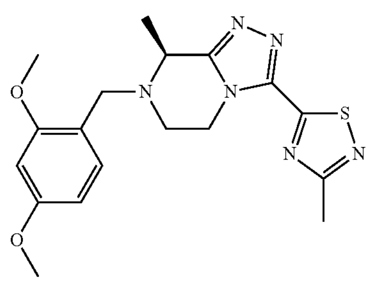 [SMILES: COc1ccc(CN2CCn3c(-c4nc(C)ns4)nnc3[C@@H]2C)c(OC)c1] | (S)-5-(7-(2,4-dimethoxybenzyl)-8-methyl-5,6,7,8-tetrahydro-[1,2,4]triazolo[4,3-a]pyrazin-3-yl)-3-methyl-1,2,4-thiadiazole | 386.47 |
| 61 | 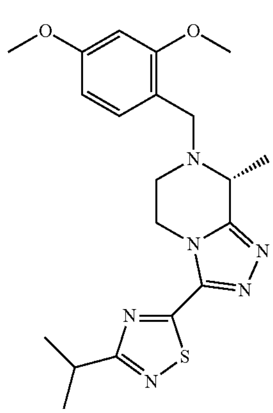 | (R)-5-(7-(2,4-dimethoxybenzyl)-8-methyl-5,6,7,8-tetrahydro-[1,2,4]triazolo[4,3-a]pyrazin-3-yl)-3-isopropyl-1,2,4-thiadiazole | 414.52 |

TABLE 3-continued

| Cpd n° | Structure | Chemical name | MW |
|---|---|---|---|
| 62 | 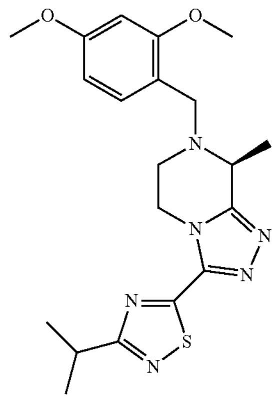 | (S)-5-(7-(2,4-dimethoxybenzyl)-8-methyl-5,6,7,8-tetrahydro-[1,2,4]triazolo[4,3-a]pyrazin-3-yl)-3-isopropyl-1,2,4-thiadiazole | 414.52 |
| 63 | 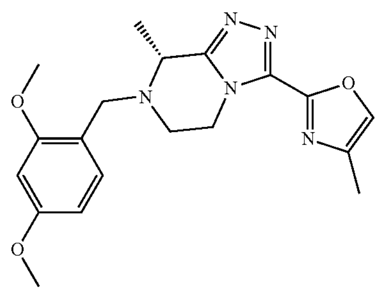 [SMILES: COc1ccc(CN2CCn3c(-c4nc(C)co4)nnc3[C@H]2C)c(OC)c1] | (R)-2-(7-(2,4-dimethoxybenzyl)-8-methyl-5,6,7,8-tetrahydro-[1,2,4]triazolo[4,3-a]pyrazin-3-yl)-4-methyloxazole | 369.42 |
| 64 | 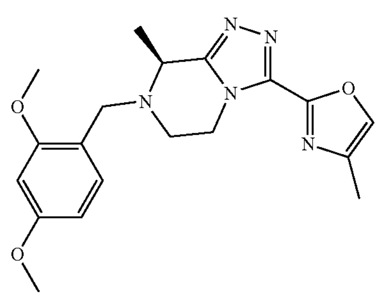 [SMILES: COc1ccc(CN2CCn3c(-c4nc(C)co4)nnc3[C@@H]2C)c(OC)c1] | (S)-2-(7-(2,4-dimethoxybenzyl)-8-methyl-5,6,7,8-tetrahydro-[1,2,4]triazolo[4,3-a]pyrazin-3-yl)-4-methyloxazole | 369.42 |
| 65 | 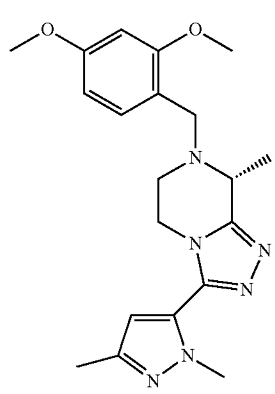 | (R)-7-(2,4-dimethoxybenzyl)-3-(1,3-dimethyl-1H-pyrazol-5-yl)-8-methyl-5,6,7,8-tetrahydro-[1,2,4]triazolo[4,3-a]pyrazine | 382.46 |

TABLE 3-continued

| Cpd n° | Structure | Chemical name | MW |
|---|---|---|---|
| 66 | 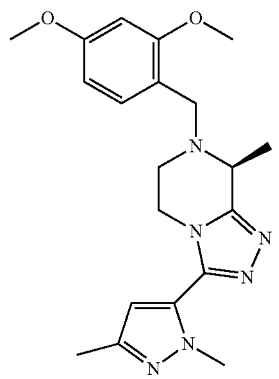 | (S)-7-(2,4-dimethoxybenzyl)-3-(1,3-dimethyl-1H-pyrazol-5-yl)-8-methyl-5,6,7,8-tetrahydro-[1,2,4]triazolo[4,3-a]pyrazine | 382.46 |
| 67 | 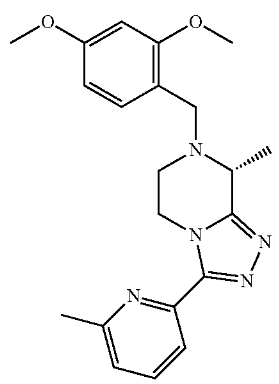 | (R)-7-(2,4-dimethoxybenzyl)-8-methyl-3-(6-methylpyridin-2-yl)-5,6,7,8-tetrahydro-[1,2,4]triazolo[4,3-a]pyrazine | 379.46 |
| 68 | 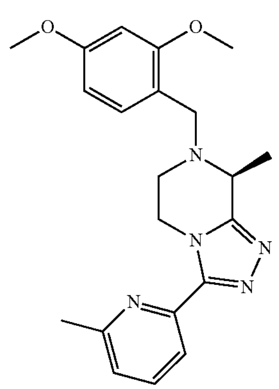 | (S)-7-(2,4-dimethoxybenzyl)-8-methyl-3-(6-methylpyridin-2-yl)-5,6,7,8-tetrahydro-[1,2,4]triazolo[4,3-a]pyrazine | 379.46 |
| 69 | 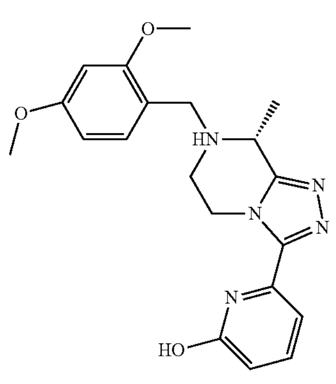 [SMILES: COc1ccc(CN2CCn3c(-c4cccc(O)n4)nnc3[C@H]2C)c(OC)c1] | (R)-6-(8-methyl-5,6,7,8-tetrahydro-[1,2,4]triazolo[4,3-a]pyrazin-3-yl)pyridin-2-ol compound with 1-ethyl-2,4-dimethoxybenzene (1:1) | 397.47 |

TABLE 3-continued

| Cpd n° | Structure | Chemical name | MW |
|---|---|---|---|
| 70 | 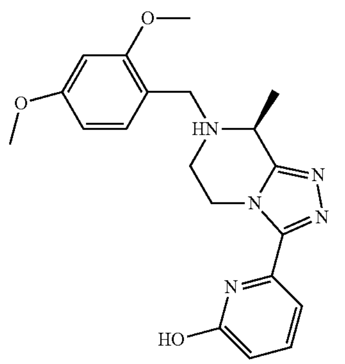 [SMILES: COc1ccc(CN2CCn3c(-c4cccc(O)n4)nnc3[C@@H]2C)c(OC)c1] | (S)-6-(8-methyl-5,6,7,8-tetrahydro-[1,2,4]triazolo[4,3-a]pyrazin-3-yl)pyridin-2-ol compound with 1-ethyl-2,4-dimethoxybenzene (1:1) | 397.47 |
| 71 | 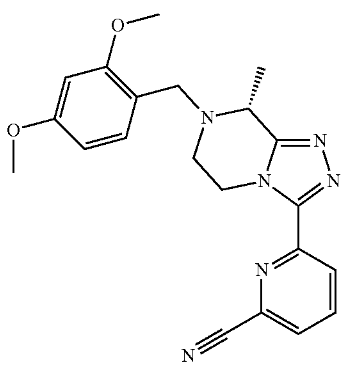 [SMILES: COc1ccc(CN2CCn3c(-c4cccc(C#N)n4)nnc3[C@H]2C)c(OC)c1] | (R)-6-(7-(2,4-dimethoxybenzyl)-8-methyl-5,6,7,8-tetrahydro-[1,2,4]triazolo[4,3-a]pyrazin-3-yl)picolinonitrile | 390.44 |
| 72 | 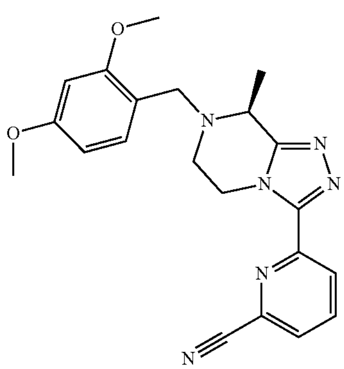 [SMILES: COc1ccc(CN2CCn3c(-c4cccc(C#N)n4)nnc3[C@@H]2C)c(OC)c1] | (S)-6-(7-(2,4-dimethoxybenzyl)-8-methyl-5,6,7,8-tetrahydro-[1,2,4]triazolo[4,3-a]pyrazin-3-yl)picolinonitrile | 390.44 |
| 73 | 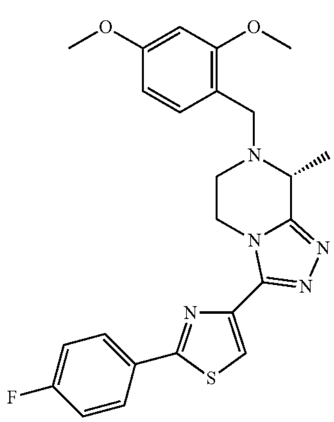 [SMILES: COc1ccc(CN2CCn3c(-c4csc(-c5ccc(F)cc5)n4)nnc3[C@H]2C)c(OC)c1] | (R)-4-(7-(2,4-dimethoxybenzyl)-8-methyl-5,6,7,8-tetrahydro-[1,2,4]triazolo[4,3-a]pyrazin-3-yl)-2-(4-fluorophenyl)thiazole | 465.54 |

TABLE 3-continued

| Cpd n° | Structure | Chemical name | MW |
|---|---|---|---|
| 74 | 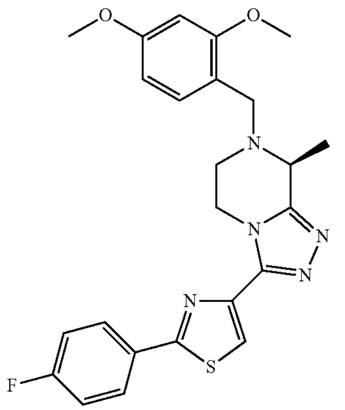 [SMILES: COc1ccc(CN2CCn3c(-c4csc(-c5ccc(F)cc5)n4)nnc3[C@@H]2C)c(OC)c1] | (S)-4-(7-(2,4-dimethoxybenzyl)-8-methyl-5,6,7,8-tetrahydro-[1,2,4]triazolo[4,3-a]pyrazin-3-yl)-2-(4-fluorophenyl)thiazole | 465.54 |

Compounds of Formula D, especially D-1, and Formula III, in particular (R)-1-(2,4-dimethoxybenzyl)-5-ethoxy-6-methyl-1,2,3,6-tetrahydropyrazine and those of table 3 above, or salts or solvates thereof are particularly interesting for the synthesis of chiral 5,6,7,(8-substituted)-tetrahydro-[1,2,4]triazolo[4,3-a]pyrazines, which are useful intermediates for the synthesis of pharmaceutical active ingredients, such as selective NK-3 receptor antagonists.

Accordingly, in another aspect, the invention relates to the use of these compounds or salts or solvates thereof for the synthesis of pharmaceutical active ingredients, such as selective NK-3 receptor antagonists.

APPLICATIONS

The compounds of the invention are therefore useful as medicaments, in particular in the prevention and/or treatment of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carninoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis.

The invention also provides for a method for delaying in patient the onset of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carninoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a pharmaceutically effective amount of a compound of Formula I or pharmaceutically acceptable salts or solvate thereof to a patient in need thereof.

Preferably, the patient is a warm-blooded animal, more preferably a human.

The compounds of the invention are also useful in the treatment of gynecological disorders and infertility. In particular, the invention provides methods to suppress the LH-surge in assisted conception.

The compounds of the invention are also useful to cause male castration and to inhibit the sex drive in men. This is of particular interest in the treatment of male sexual offenders.

The invention further provides the use of a compound of Formula I or a pharmaceutically acceptable salts or solvate thereof for the manufacture of a medicament for treating and/or preventing depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carninoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis in a patient.

Preferably, the patient is a warm-blooded animal, more preferably a human.

The invention further provides the use of a compound of Formula I or a pharmaceutically acceptable salts or solvate thereof for the manufacture of a medicament to suppress the LH-surge in assisted conception in a patient. Preferably the patient is a warm-blooded animal, more preferably a woman.

The invention further provides the use of a compound of Formula I or a pharmaceutically acceptable salts or solvate thereof for the manufacture of a medicament to cause male castration and to inhibit the sex drive in men. This is of particular interest in the treatment of male sexual offenders.

According to a further feature of the present invention there is provided a method for modulating NK-3 receptor activity, in a patient, preferably a warm blooded animal, and even more preferably a human, in need of such treatment, which comprises administering to said patient an effective amount of compound of the present invention, or a pharmaceutically acceptable salts or solvate thereof.

According to one embodiment, the compounds of the invention, their pharmaceutical acceptable salts or solvates may be administered as part of a combination therapy. Thus, are included within the scope of the present invention embodiments comprising coadministration of, and compositions and medicaments which contain, in addition to a compound of the present invention, a pharmaceutically acceptable salts or solvate thereof as active ingredient, additional therapeutic agents and/or active ingredients. Such multiple drug regimens, often referred to as "combination therapy", may be used in the treatment and/or prevention of any of the diseases or conditions mediated by or associated with NK-3 receptor modulation. The use of such combinations of therapeutic agents is especially pertinent with respect to the treatment of the above-mentioned disorders within a patient in need of treatment or one at risk of becoming such a patient.

In addition to the requirement of therapeutic efficacy, which may necessitate the use of active agents in addition to the NK-3 receptor modulator compounds of Formula I or pharmaceutical salts or acceptable solvates thereof, there may be additional rationales which compel or highly recommend the use of combinations of drugs involving active ingredients which represent adjunct therapy, i.e., which complement and supplement the function performed by the NK-3 receptor modulator compounds of the present invention. Suitable supplementary therapeutic agents used for the purpose of auxiliary treatment include drugs which, instead of directly treating or preventing a disease or condition mediated by or associated with NK-3 receptor modulation, treat diseases or conditions which directly result from or indirectly accompany the basic or underlying NK-3 receptor modulated disease or condition.

According to a further feature of the present invention, the compound of Formula I, a pharmaceutically acceptable salts or solvate thereof may be used in combination therapy with antipsychotic drugs (APD), to improve the efficacy and to minimize secondary effects associated to APD including but not limited to Dopamine 2/3 and 5-HT2 receptors antagonists. More particular the compound of Formula I, a pharmaceutically acceptable salts or solvate thereof may be used as an adjunct therapy in combination with an atypical antipsychotic drug, including but not limited to risperidone, clozapine, olanzapine, where the NK-3 receptor modulator may serve a role as dose-limiting for the atypical antipsychotic and therefore spare the patient from some of the side effect of those atypical antipsychotic drugs.

Thus, the methods of treatment and pharmaceutical compositions of the present invention may employ the compounds of Formula I or pharmaceutical acceptable solvates thereof in the form of monotherapy, but said methods and compositions may also be used in the form of multiple therapy in which one or more compounds of Formula I or their pharmaceutically acceptable salts or solvates are coadministered in combination with one or more other therapeutic agents.

In the above-described embodiment combinations of the present invention, the compound of Formula I, a pharmaceutically acceptable salts or solvate thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The invention also provides pharmaceutical compositions comprising a compound of Formula I or a pharmaceutically acceptable salts or solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salts or solvate thereof as active ingredient, additional therapeutic agents and/or active ingredients.

Another object of this invention is a medicament comprising at least one compound of the invention, or a pharmaceutically acceptable salts or solvate thereof, as active ingredient.

According to a further feature of the present invention there is provided the use of a compound of Formula I or a pharmaceutically acceptable salts or solvate thereof for the manufacture of a medicament for modulating NK-3 receptor activity in a patient, in need of such treatment, which comprises administering to said patient an effective amount of compound of the present invention, or a pharmaceutically acceptable salts or solvate thereof.

Preferably, the patient is a warm-blooded animal, more preferably a human.

As set forth above, the compounds of the invention, their pharmaceutically acceptable salts or solvates may be used in monotherapy or in combination therapy. Thus, according to one embodiment, the invention provides the use of a compound of the invention for the manufacture of a medicament for at least one of the purposes described above, wherein said medicament is administered to a patient in need thereof, preferably a warm-blooded animal, and even more preferably a human, in combination with at least one additional therapeutic agent and/or active ingredient. The benefits and advantages of such a multiple drug regimen, possible administration regimens as well as suitable additional therapeutic agents and/or active ingredients are those described above.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, of the at least one compound of the invention, e.g. about 10, 25, 50, 100, 200, 300 or 400 mg per unit dosage.

Usually, depending on the condition to be prevented or treated and the route of administration, the active compound of the invention will usually be administered between 0.01 to 100 mg per kilogram, more often between 0.1 and 50 mg, such as between 1 and 25 mg, for example about 0.5, 1, 5, 10, 15, 20 or 25 mg, per kilogram body weight of the patient per day, which may be administered as a single daily dose, divided over one or more daily doses, or essentially continuously, e.g. using a drip infusion.

DEFINITIONS

The definitions and explanations below are for the terms as used throughout the entire application, including both the specification and the claims.

When describing the compounds of the invention, the terms used are to be construed in accordance with the following definitions, unless indicated otherwise.

The term "halo" or "halogen" means fluoro, chloro, bromo, or iodo. Preferred halo groups are fluoro and chloro. The most preferred halo group is fluoro in the present invention unless otherwise indicated herein.

The term "alkyl" by itself or as part of another substituent refers to a hydrocarbyl radical of formula $C_nH_{2n+1}$ wherein n is a number greater than or equal to 1. Generally, alkyl groups of this invention comprise from 1 to 4 carbon atoms, preferably from 1 to 3 carbon atoms. Alkyl groups may be linear or branched.

Suitable alkyl groups include methyl, ethyl, n-propyl, i-propyl, n-butyl, i-butyl, s-butyl and t-butyl.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like. $C_{x-y}$-haloalkyl and Cx-Cy-alkyl refer to alkyl groups which comprise from x to y carbon atoms. Preferred haloalkyl groups are difluoromethyl, trifluoromethyl.

The term "alkenyl" as used herein refers to an unsaturated hydrocarbyl group, which may be linear or branched, comprising one or more carbon-carbon double bonds. Suitable alkenyl groups comprise between 2 and 3 carbon atoms. Examples of alkenyl groups are ethenyl (vinyl), 2-propenyl (allyl). The preferred alkenyl group herein is the vinyl group.

The term "thiophen-2-yl" as used herein means a group of formula

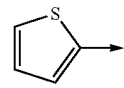

wherein the arrow defines the attachment point.

The term "cycloalkyl" as used herein is a cyclic alkyl group, that is to say, a monovalent, saturated, or unsaturated hydrocarbyl group having 1 or 2 cyclic structures. Cycloalkyl includes monocyclic hydrocarbyl groups only. Cycloalkyl groups may comprise 3 or more carbon atoms in the ring and generally, according to this invention comprise from 3 to 4, more preferably 3 carbon atoms. Examples of cycloalkyl groups include cyclopropyl and cyclobutyl, with cyclopropyl being particularly preferred.

The term "ester" or "esters" as used herein means a group selected the group consisting of unsubstituted C1-C4 alkyloxycarbonyl, unsubstituted phenyloxycarbonyl or unsubstituted phenyl(C1-C2 alkyl)oxycarbonyl.

Suitable ester groups include methyloxycarbonyl, ethyloxycarbonyl, n-propyloxycarbonyl, i-propyloxycarbonyl, n-butyloxycarbonyl, i-butyloxycarbonyl, s-butyloxycarbonyl, t-butyloxycarbonyl, phenyloxycarbonyl, benzyloxycarbonyl and phenethyloxycarbonyl, among which methyloxycarbonyl, ethyloxycarbonyl, propyloxycarbonyl, i-propyloxycarbonyl, phenyloxycarbonyl, and benzyloxycarbonyl are preferred.

The ring atoms of 5,6,7,(8-substituted)-[1,2,4]triazolo[4,3-a]pyrazines of the invention are numbered based on scheme below.

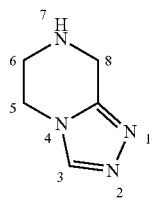

Bonds from an asymmetric carbon in compounds are generally depicted using a solid line (-), a zigzag line (⁓), a solid wedge (▬), or a dotted wedge (⋯). The use of either a solid or dotted wedge to depict bonds from an asymmetric carbon atom is meant to indicate that only the stereoisomer shown is meant to be included.

In the compounds of the invention, a dotted wedge (⋯). carrying a methyl at the C8 position is used to depict the (R)-enantiomer. A solid wedge (▬) would be used to depict the (S)-enantiomer.

The compounds of Formula II and subformulae thereof contain a stereogenic carbon center at position 8 and thus may exist as (R)- and (S)-enantiomers. The use of a solid line to depict the bond between position 8 of the ring and $R^{1'}$ with a star next to position 8 indicates that the individual enantiomers are meant, thus excluding racemic mixtures thereof.

A solid wedge (▬) for the bond between position 8 of the ring and $R^1$ is used to depict the (S)-enantiomer and a dotted wedge (⋯) for the bond between position 8 of the ring and $R^{1'}$ is used to depict the (R)-enantiomer.

For instance, (R)-8-methyl-3-(6-methylpyridin-2-yl)-5,6,7,8-tetrahydro-[1,2,4]triazolo[4,3-a]pyrazine is depicted as . . .

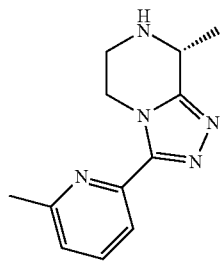

Prototropic tautomer equilibrium form may exist in certain compounds of Formula I'" thereby engendering either or both tautomers to exist; an example is illustrated below.

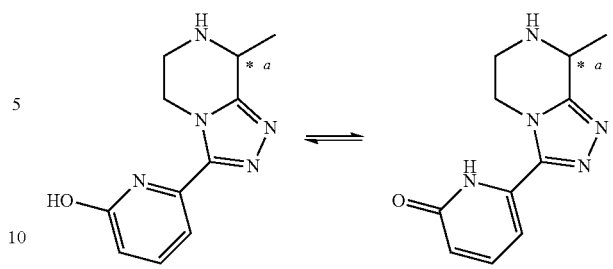

All tautomeric forms of compounds of the invention fall, wherever applicable, within the scope of the invention regardless of which specific tautomer is drawn or named.

The compounds of the invention may be in the form of pharmaceutically acceptable salts. Pharmaceutically acceptable salts of the compounds of Formulae I, II and III include the acid addition salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

The compounds of Formulae I, II or III of the invention may be prepared in salt form through the use of salt-formers. Suitable acids are preferably but not limited to those that are considered to form pharmaceutically acceptable salts (see for example: Wermuth, C. G.; Stahl, P. H. In "Handbook of Pharmaceutical Salts", Wiley-VCH: New York, 2002). Such salts may be formed to enhance chemical purity and/or enhance storage lifetime of the attendant salt intermediate. Examples of relevant salt-formers as aforementioned include in a non-limiting sense the following acids; through any and all stereoisomeric forms where applicable: HCl, sulfuric acid, phosphoric acid, acetic acid, ethanesulfonic acid, citric acid, lactic acid, maleic acid, mandelic acid, succinic acid, phenylpropionic acid, p-toluenesulfonic acid. Preferred salt-formers include HCl.

Pharmaceutically acceptable salts of compounds of Formulae I, II and III may be prepared by one or more of these methods:

(i) by reacting the compound of Formulae I, II or III with the desired acid;

(ii) by removing an acid-labile protecting group from a suitable precursor of the compound of Formulae I, II or III; or (iii) by converting one salt of the compound of Formulae I, II or III to another by reaction with an appropriate acid or by means of a suitable ion exchange column.

The term "solvate" is used herein to describe a compound in this invention that contains stoichiometric or sub-stoichiometric amounts of one or more pharmaceutically acceptable solvent molecule such as ethanol. The term "hydrate" refers to when the said solvent is water.

All references to compounds of Formulae I, II or III include references to salts, solvates, multi-component complexes and liquid crystals thereof.

The compounds of the invention include compounds of Formulae I, II or III as hereinbefore defined, including all polymorphs and crystal habits thereof, prodrugs, prodrugs and tautomers thereof and isotopically-labeled compounds of Formulae I, II or III.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formulae I, II or III above.

The invention also generally covers all pharmaceutically acceptable predrugs and prodrugs of the compounds of Formulae I, II or III.

The term "prodrug" as used herein means the pharmacologically acceptable derivatives of compounds of Formulae I, II or III, such as for example esters, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting the receipt of, or is receiving medical care or is/will be the object of a medical procedure.

The term "human" refers to a subject of both genders and at any stage of development (i.e. neonate, infant, juvenile, adolescent, adult).

The terms "treat", "treating" and "treatment, as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e.g. NK-3 antagonist) that is sufficient to achieve the desired therapeutic or prophylactic effect in the patient to which/whom it is administered.

The term "administration", or a variant thereof (e.g., "administering"), means providing the active agent or active ingredient (e. g. a NK-3 antagonist), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "antagonist" as used herein means a compound that competitively or non-competitively binds to a receptor at the same site as an agonist (for example, the endogenous ligand) and does not activate an intracellular response initiated by an active form of the receptor. An antagonist for a specific receptor, therefore, inhibits the intracellular response induced by an agonist to that specific receptor.

The term "sex hormone-dependent disease" as used herein means a disease which is exacerbated by, or caused by, excessive, inappropriate or unregulated sex hormone production. Examples of such diseases in men include but are not limited to benign prostatic hyperplasia (BPH), prostatic hyperplasia, metastatic prostatic carninoma, testicular cancer, androgen dependent acne, male pattern baldness and precocious puberty in boys. Examples of such diseases in women include but are not limited to endometriosis, abnormal puberty, uterine fibrosis, uterine fibroid tumor, hormone-dependent cancers (ovarian cancer, breast cancer), androgen-producing tumor (virilizing ovarian or adrenal tumor), hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), menorrhagia and adenomyosis (abnormal endometrial growth within the muscle of the uterus).

The term "Psychotic disorders" as used herein means a group of illnesses that affect the mind. These illnesses alter a patient's ability to think clearly, make good judgments, respond emotionally, communicate effectively, understand reality, and behave appropriately. When symptoms are severe, patient with psychotic disorders have difficulty staying in touch with reality and are often unable to meet the ordinary demands of daily life. Psychotic disorders include but are not limited to, schizophrenia, schizophreniform disorder, schizo-affective disorder, delusional disorder, brief psychotic disorder, shared psychotic disorder, psychotic disorder due to a general medical condition, substance-induced psychotic disorder or psychotic disorders not otherwise specified (Diagnostic and Statistical Manual of Mental Disorders, Ed. 4th, American Psychiatric Association, Washington, D.C. 1994).

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The expression "reagent resulting in a N-sp$^3$ protective group (PG) on the amine nitrogen of the compound of Formula A" means any such reagents that result in a cleavable protective group substitution(s) while retaining the protected nitrogen atom as a tertiary amine, i.e. in the N-sp$^3$ hybridized form. Specifically N-benzyl and in particular electron-rich substituted N-benzyl; especially N-benzyl substituted by one or more electron donating groups, such as for example alcohol groups, alkoxy groups (especially methoxy), amino groups, alkyl groups; are considered embodiments of the "N-sp$^3$ protective group" definition above. Examples of such reagents include, but are not limited to, benzaldehyde, 4-methoxybenzaldehyde, 2,4-dimethoxybenzaldehyde, and 2,4,6-trimethoxybenzaldehyde. Examples of N-benzyl or electron-rich substituted N-benzyl protective groups include, but are not limited to N-benzyl, N-4-methoxybenzyl, N-3,4-dimethoxybenzyl, N-3-methoxybenzyl, N-3,5-dimethoxybenzyl, N-2,4,6-trimethoxybenzyl. (See Wuts, P. G. M.; Greene, T. W. In "Greene's Protective Groups in Organic Synthesis", Wiley-Interscience: New York, 4$^{th}$ Edition, Chap. 7, pp. 696-926, and Kocieński, P. J. In "Protecting Groups", Georg Thieme Verlag: Stuttgart, New York; $3^{rd}$ Edition, Chap. 8, pp. 487-643).

The present invention will be better understood with reference to the following examples. These examples are intended to representative of specific embodiments of the invention, and are not intended as limiting the scope of the invention.

EXAMPLES

Chemistry Examples

Figure 1:
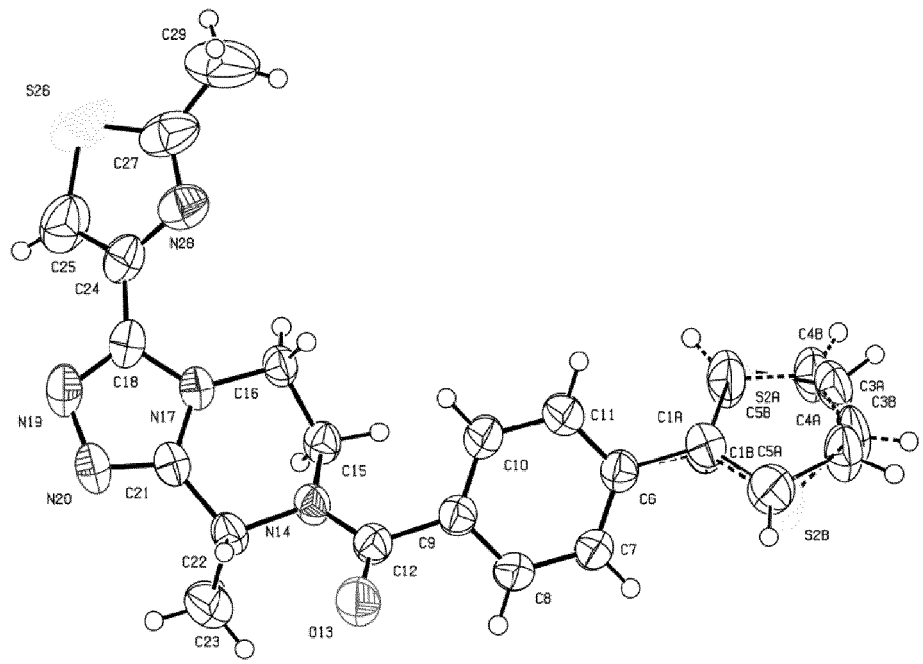
FIG. 1 shows X-ray crystal structure of compound no 1 (thermal displacement ellipsoids drawn at the 50% probability level).

All reported temperatures are expressed in degrees Celsius (° C.); all reactions were carried out at room temperature (RT) unless otherwise stated.

All reactions were followed by thin layer chromatography (TLC) analysis (TLC plates, silica gel 60 $F_{254}$, Merck) was used to monitor reactions, establish silica-gel flash chromatography conditions. All other TLC developing agents/visualization techniques, experimental set-up or purification procedures that were used in this invention, when not described in specific details, are assumed to be known to those conversant in the art and are described in such standard reference manuals as: i) Gordon, A. J.; Ford, R. A. "The Chemist's Companion—A Handbook of Practical Data, Techniques, and References", Wiley: New York, 1972; ii) Vogel's Textbook of Practical Organic Chemistry, Pearson Prentice Hall: London, 1989.

HPLC-MS spectra were typically obtained on an Agilent LCMS using electrospray ionization (ESI). The Agilent instrument includes an autosampler 1200, a binary pump 1100, an ultraviolet multi-wavelength detector 1100 and a 6100 single-quad mass-spectrometer. The chromatography column used was Sunfire 3.5 μm, C18, 3.0×50 mm in dimensions.

Eluent typically used was a mixture of solution A (0.1% TFA in $H_2O$) and solution B (0.1% TFA in MeCN).

Gradient was applied at a flow rate of 1.3 mL per minute as follows: gradient A: held the initial conditions of 5% solution B for 0.2 min, increased linearly to 95% solution B in 6 min, held at 95% during 1.75 min, returned to initial conditions in 0.25 min and maintained for 2.0 min; gradient B: held the initial conditions of 5% solution B for 0.2 min, increased linearly to 95% in 2.0 min, held at 95% during 1.75 min, returned to initial conditions in 0.25 min and maintained for 2 min.

Determination of chiral purity was made using chiral HPLC that was performed on an Agilent 1100 (binary pump and a ultraviolet multi wavelength detector) with manual or automatic (Autosampler 1100) injection capabilities. Columns used were CHIRALPAK IA 5 μm, 4.6×250 mm or CHIRALPAK IB 5 μm, 4.6×250 mm in isocratic mode. Choice of eluent was predicated on the specifics of each separation. Further details concerning the chiral HPLC methods used are provided below.

Method A: column CHIRALPAK IA 5 μm, 4.6×250 mm, eluent: EtOAc plus 0.1% of DEA, flow rate: 1.0 mL per minute; UV detection at 254 nm; column at RT, eluent was used as sample solvent.

Method A': column CHIRALPAK IA 5 μm, 4.6×250 mm, eluent: EtOAc plus 0.1% of DEA, flow rate: 1.5 mL per minute; UV detection at 254 nm; column at RT, eluent was used as sample solvent.

Method B: column CHIRALPAK IA 5 μm 4.6×250 mm, eluent: hexane/isopropanol/dichlormethane (3:1:1 v/v) plus 0.1% of DEA, flow rate: 1.0 mL per minute; UV detection at 254 nm, column at RT, eluent was used as sample solvent.

Method B': column CHIRALPAK IA 5 μm 4.6×250 mm, eluent: hexane/isopropanol/dichlormethane (3:1:1 v/v) plus 0.1% of DEA, flow rate: 1.5 mL per minute; UV detection at 254 nm, column at RT, eluent was used as sample solvent.

Method C: column CHIRALPAK IB 5 μm 4.6×250 mm, eluent: hexane/ethanol (7:3 v/v) plus 0.1% of DEA, flow rate: 1.0 mL $min^{-1}$, mL per minute; UV detection at 254 nm, column at RT, eluent was used as sample solvent.

Method C': column CHIRALPAK IA 5 μm 4.6×250 mm, eluent: hexane/ethanol (1:1 v/v) plus 0.1% of DEA, flow rate: 1.0 mL per minute; UV detection at 254 nm, column at RT, eluent was used as sample solvent.

Preparative HPLC purifications were typically carried out on a Waters FractionLynx instrument. This instrument consists of a fraction collector, a 2767 sample manager, a pump control a module II, a 515 HPLC pump, a 2525 binary gradient module, a switching valve, a 2996 photodiode array detector and a Micromass ZQ mass spectrometer. The chromatography column used was Waters Sunfire 5 μm, C18, 19×100 mm, or XBridge 5 μm, C18, 19×100 mm depending on the type of eluent system employed, i.e. low pH or high pH conditions.

For high-pH HPLC purifications, eluent typically consisted of a mixture of solution A (0.04 M ammonium bicarbonate in $H_2O$ plus 0.1% of conc. $NH_4OH$) and solution B was MeCN. The gradient was adapted depending on the impurity profile in each sample purified, thereby allowing sufficient separation between the impurities and the desired compound.

Chiral preparative HPLC purifications were performed on an Agilent 1200 instrument (preparative pump 1200 and ultraviolet multi wavelength detector 1200) with manual injection. The chiral columns used are as follows: CHIRALPAK IA 5 μm, 20×250 mm, CHIRALPAK IA 5 μm, 10×250 mm or a CHIRALPAK IB 5 μm, 10×250 mm. All chiral HPLC methods were employed in an isocratic mode. The eluent mixture was selected based on the analytical chiral HPLC experiment (see above) that provided the best chiral separation.

$^1$H (300 MHz) and $^{13}$C NMR (75 MHz) spectra were recorded on a Bruker Avance DRX 300 instrument. Chemical shifts are expressed in parts per million, (ppm, δ units). Coupling constants are expressed in Hertz (Hz). Abbreviations for multiplicities observed in NMR spectra are as follows: s (singlet), d (doublet), t (triplet), q (quadruplet), m (multiplet), br (broad).

Solvents, reagents and starting materials were purchased and used as received from commercial vendors unless otherwise specified.

The following abbreviations are used:
Boc: tert-butoxycarbonyl,
Cpd: compound,
DCM: Dichloromethane,
DEA: diethylamine,
DMA: N,N-dimethylacetamide,
DMB: 2,4-dimethoxybenzyl,
DMB-CHO: 2,4-dimethoxybenzaldehyde,
DMF: N,N-dimethylformamide,
ee: Enantiomeric excess,
eq: Equivalent(s),
Et: Ethyl,
EtOAc: Ethyl acetate,
EtOH: Ethanol,
g: Gram(s),
h: Hour(s),
IPA: isopropanol,
L: Liter(s),
MeOH: Methanol,
μL: Microliter(s),
mg: Milligram(s),
mL: Milliliter(s),
mmol: Millimole(s),
min: Minute(s),
NMM: N-methylmorpholine
P: UV purity at 254 nm or 215 nm determined by HPLC-MS,
PMB: 4-methoxybenzyl,
PMB-CHO: 4-methoxybenzaldehyde,
RT: Room temperature,
tBu: tert-Butyl,
TFA: trifluoroacetic acid,
THF: Tetrahydrofuran,
TLC: Thin layer chromatography,
TMS: trimethylsylil,
Y: Yield.

The intermediates and compounds described below were named using ChemDraw® Ultra version 12.0 (Cambridge-Soft, Cambridge, Mass., USA).

I. Racemic Synthesis

I.1. General Synthetic Scheme for Racemic Synthesis

Most compounds of the invention were synthesized using the methodology described in Scheme 1, which represents the racemic product synthesis. The racemic products were subjected to chiral HPLC for chiral separation.

Scheme 1: General racemic synthetic scheme for the preparation of the compounds of the invention.

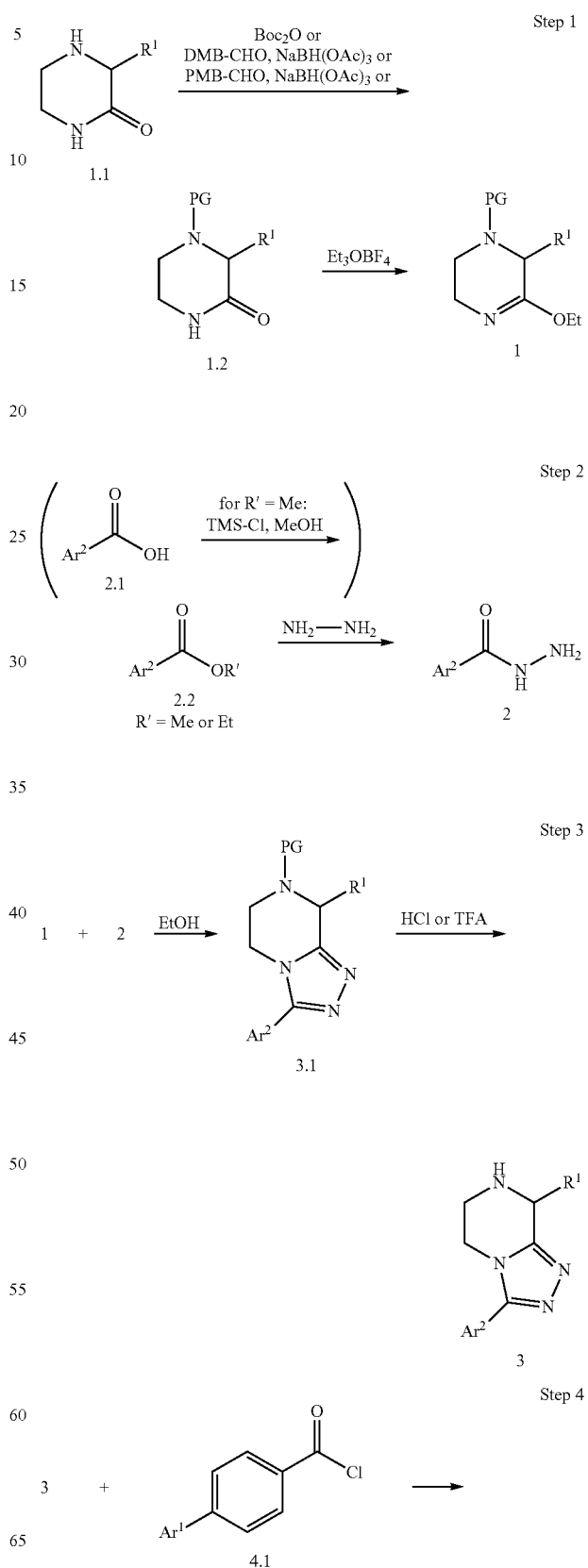

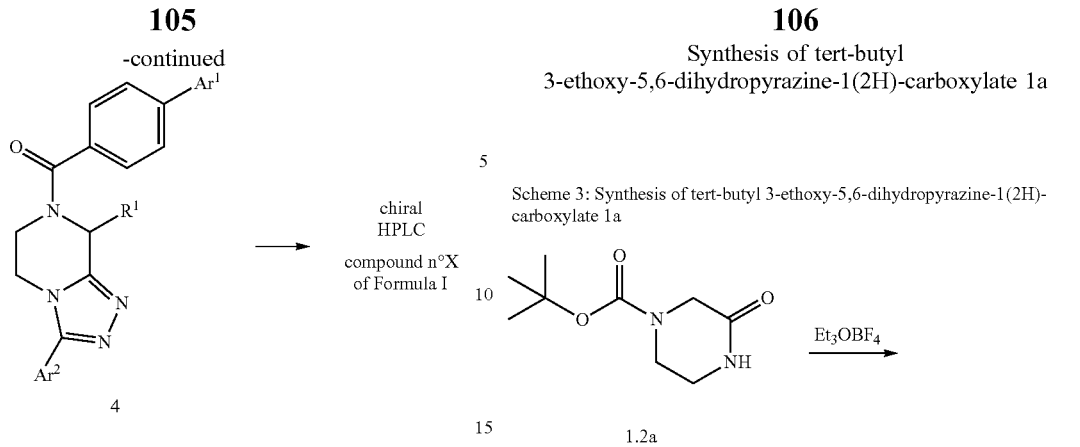

The general synthetic scheme comprises the following steps:

Step 1: Ketopiperazine 1.1 was protected and converted to iminoether 1 by using the Meerwein reagent (Et$_3$OBF$_4$).

Step 2: Ester 2.2 was subsequently converted to acyl hydrazide 2. Ester 2.2 may be obtained be esterification of acid 2.1.

Step 3: Cyclodehydration between the acyl hydrazide 2 and the iminoether 1 furnished the protected triazolopiperazine 3.1. Thereafter, 3.1 was subjected to acidolytic deprotection to obtain 3.

Step 4: The thus obtained triazolopiperazine intermediate 3 was acylated through reaction with the appropriate acid chloride 4.1 to obtain the racemic final target structure represented by the general Formula 4. The chiral final compounds were subsequently obtained by purification using preparative chiral HPLC.

I.2. Step 1: Protection and Conversion to Iminoether 1

Method A: Boc Protection and Conversion to Iminoether 1

Method A is the procedure used for the synthesis of the iminoether intermediates 1 with a Boc protection and is detailed below:

Scheme 2: Protection with Boc group and conversion to iminoether 1

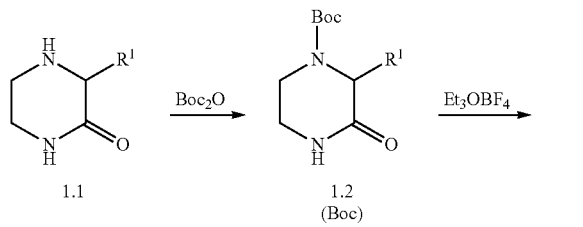

Method A is illustrated by the synthesis of intermediates 1a and 1b wherein R1 is H and Me respectively.

Synthesis of tert-butyl 3-ethoxy-5,6-dihydropyrazine-1(2H)-carboxylate 1a

Scheme 3: Synthesis of tert-butyl 3-ethoxy-5,6-dihydropyrazine-1(2H)-carboxylate 1a

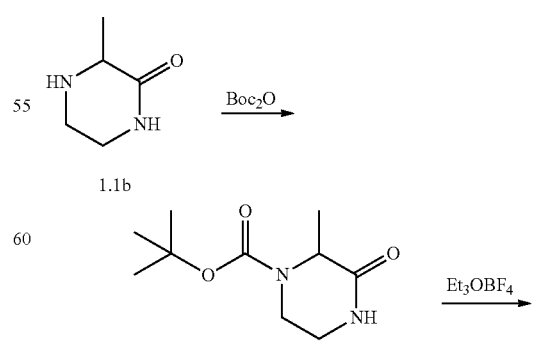

To a pre-made solution of triethyloxonium tetrafluoroborate (2.3 g, 0.012 mol) in anhydrous DCM (20 mL) was added 1.2a (2 g, 0.01 mol) at 0° C. After the addition was completed, the ice-bath was removed, and the reaction mixture was allowed to warm to RT and stirred for an additional hour (reaction progress monitored by LCMS). Upon completion of the reaction, a saturated solution of NaHCO$_3$ (500 mL) was slowly added to the reaction mixture and it was stirred for 5 min. The organic layer was separated and the aqueous layer was further extracted with DCM (200 mL). The combined organic layers were subsequently washed with brine, dried over MgSO$_4$, filtered and further dried in vacuo to obtain the title intermediate 1a as viscous yellow oil. Yield: 2.03 g (88%). $^1$H NMR (CDCl$_3$): δ: 4.1 (q, J=7.1, 2H), 3.85 (s, 2H), 3.5 (m, 1H), 3.35 (t, J=5.1, 2H), 1.45 (s, 9H), 1.3 (t, J=7.1, 3H).

Synthesis of tert-butyl 3-ethoxy-2-methyl-5,6-dihydropyrazine-1(2H)-carboxylate 1b Scheme 4: Synthesis of tert-butyl 3-ethoxy-2-methyl-5,6-dihydropyrazine-1(2H)-carboxylate 1b

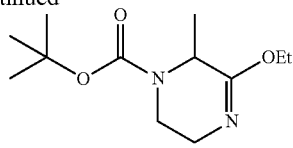

1b

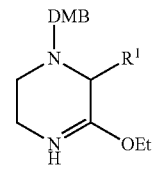

1 (DMB)

Step 1: Synthesis of tert-butyl 2-methyl-3-oxopiperazine-1-carboxylate 1.2b

NEt$_3$ (20 mL, 145 mmol) was added to a solution of 3-methylpiperazin-2-one 1.1b (15 g, 131 mmol) in anhydrous DCM (200 mL) under N$_2$ at RT. After 10 min stirring, the reaction mixture was cooled to 0° C. and Boc$_2$O (33 g, 151 mmol). The reaction mixture was stirred at RT for 1 h and thereupon washed with 0.5M HCl (150 mL), brine (150 mL), dried over MgSO$_4$, filtered and concentrated to constant weight furnishing 2.2 as yellow oil (20.2 g, 72%). LCMS: P=100%, retention time=2.0 min, (M+H-tBu)$^+$: 159

Step 2: Synthesis of tert-butyl 3-ethoxy-2-methyl-5,6-dihydropyrazine-1(2H)-carboxylate 1b To a solution of 1.2b (24 g, 87 mol) in anhydrous DCM (250 mL) at 0° C. under N$_2$ atmosphere was added a pre-made solution of triethyloxonium tetrafluoroborate (19.92 g, 105 mmol) in anhydrous DCM (50 mL). The reaction mixture was allowed to warm to RT and stirred for 30 min whereupon saturated solution of NaHCO$_3$ (400 mL) was added. The extracted aqueous layer was then washed with DCM (200 ml) and the combined organic extracts were subsequently washed with brine (300 mL), dried over MgSO$_4$, filtered and further dried in vacuo to obtain the title intermediate 1b as colorless oil. (20.7 g, 98%). LCMS: P=98%, retention time=1.8 min, (M+H+H$_2$O)$^+$: 261; $^1$H-NMR (CDCl$_3$): δ 4.30 (br, 1H), 4.11-4.01 (m, 2H), 3.84 (br, 1H), 3.48-3.40 (m, 2H), 2.90 (br, 1H), 1.32 (d, J=6.9, 3H), 1.26 (t, J=7.1, 3H).

Method B: Protection Using Benzyl Derivative Protecting Groups Such as DMB and Conversion to Iminoether 1

Method B is the procedure used for the synthesis of the iminoether intermediates 1 with a benzyl derivative protecting group such as DMB and is detailed below:

Scheme 5: Protection with DMB group and conversion to iminoether 1

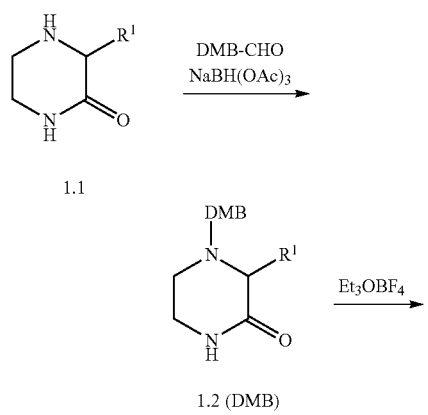

Method B is illustrated by the synthesis of intermediates 1c and 1d wherein R1 is Me and the protecting group is DMB and PMB respectively.

Synthesis of 1-(2,4-dimethoxybenzyl)-5-ethoxy-6-methyl-1,2,3,6-tetrahydropyrazine 1c Scheme 6: Synthesis of 1-(2,4-dimethoxybenzyl)-5-ethoxy-6-methyl-1,2,3,6-tetrahydropyrazine 1c

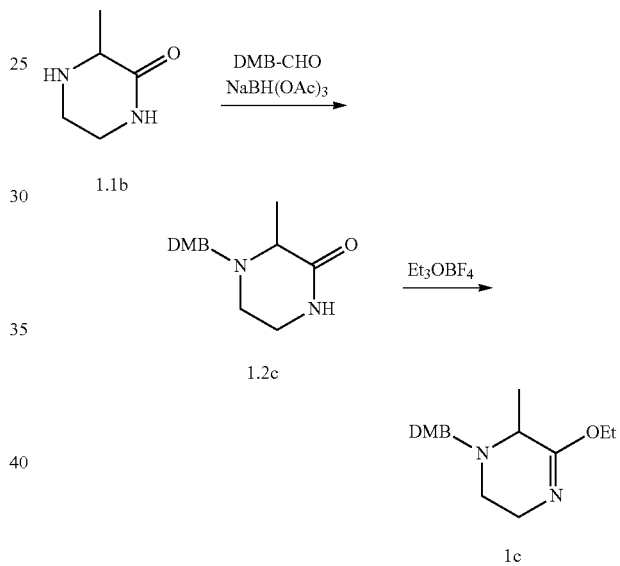

Step 1: Synthesis 4-(2,4-dimethoxybenzyl)-3-methylpiperazin-2-one 1.2c

In a round-bottom flask, were sequentially introduced 3-methylpiperazin-2-one (10 g, 88 mmol), 2,4-dimethoxybenzaldehyde (16 g, 96 mmol), acetic acid (6.5 ml, 114 mmol) and sodium triacetoxyborohydride (22.3 g, 105 mmol) in commercial anhydrous acetonitrile (750 mL), at RT, under N$_2$ atmosphere. The reaction was stirred at RT overnight. The reaction mixture was quenched carefully at 0° C. with saturated NaHCO$_3$ solution (100 mL) until no more bubbling was observed. Aqueous and organic layers were separated. The aqueous layer was extracted with EtOAc (3×300 mL) and the combined organic layers were washed with brine, dried over MgSO$_4$, filtered, and concentrated under reduced pressure to afford the title compound as yellow oil. The crude compound was then purified on silica gel (DCM/MeOH: 98/2 to 95/5) to afford the desired product 1.2c as a pale yellow oil (20.6 g, 78 mmol, 89%). LCMS: P=97%, retention time=1.6 min, (M+H)$^+$: 265.

In the case of PMB and TMB protection, 4-methoxybenzaldehyde or 2,4,6-trimethoxybenzaldehyde was used instead of 2,4-dimethoxybenzaldehyde to furnish 4-(4-methoxybenzyl)-3-methylpiperazin-2-one or 4-(2,4,6-trimethoxy benzyl)-3-methylpiperazin-2-one.

Step 2: 1-(2,4-dimethoxybenzyl)-5-ethoxy-6-methyl-1,2,3,6-tetrahydropyrazine 1c Oven-dried (115° C.) sodium carbonate (18.6 g, 98 mmol, 2.25 eq.) was placed in a 500 mL round-bottom flask. The round-bottom flask was backfilled with Ar and then capped with a rubber septum. A solution of 4-(2,4-dimethoxybenzyl)-3-methylpiperazin-2-one 1.2c (20.6 g, 78 mmol, 1 eq.) in anhydrous DCM (250 mL) was added, followed by triethyloxonium tetrafluoroborate (18.6 g, 98 mmol, 1.25 eq.) in one portion. Thereafter, the reaction mixture was stirred further at RT for 1 h whereupon the reaction mixture was diluted with water (250 mL). The aqueous layer was extracted with DCM (3×150 mL). The organic layers were combined, dried over MgSO$_4$, filtered and concentrated under reduced pressure. The crude compound was then purified on silica gel (EtOAc) to afford the desired product 1c as orange oil. Yield: 13.2 g, 58%. LCMS: P=93%, retention time=1.8 min, (M+H+H$_2$O)$^+$: 311; $^1$H-NMR (CDCl$_3$): δ 7.23 (d, J=8.8 Hz, 1H), 6.48 (d, J=8.8 Hz, 1H), 6.44 (s, 1H), 4.02 (m, 2H), 3.92 (s, 3H), 3.91 (s, 3H), 3.86 (d, J$_{AB}$=14.0 Hz, 1H), 3.46 (d, J$_{AB}$=14.0 Hz, 1H), 3.44 (m, 2H), 3.10 (m, 1H), 2.79 (m, 1H), 2.32 (m, 1H), 1.35 (d, J=6.8 Hz, 3H), 1.24 (t, J=6.0 Hz, 3H).

Starting step 2 from 4-(4-methoxybenzyl)-3-methylpiperazin-2-one allowed to isolate 1-(4-methoxybenzyl)-5-ethoxy-6-methyl-1,2,3,6-tetrahydropyrazine 1d. LCMS: P=95%, retention time=1.8 min, (M+H+H$_2$O)$^+$: 281.

I.3. Step 2: Formation of Acyl Hydrazide 2

Method C: Acyl Hydrazide 2

Method C is the procedure used for the synthesis of the acyl hydrazides 2 and is detailed below:

Scheme 7: Formation of acylhydrazide 2

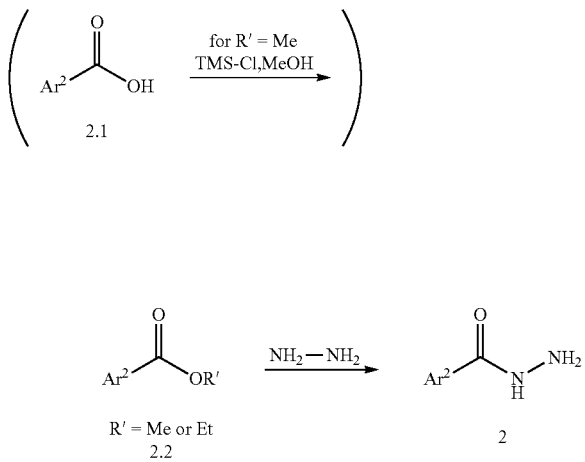

Method C is illustrated by the synthesis of intermediate 2a, 2k and 2r.

Synthesis of 2-methylthiazole-4-carbohydrazide 2a

Scheme 8: Synthesis of 2-methylthiazole-4-carbohydrazide 2a

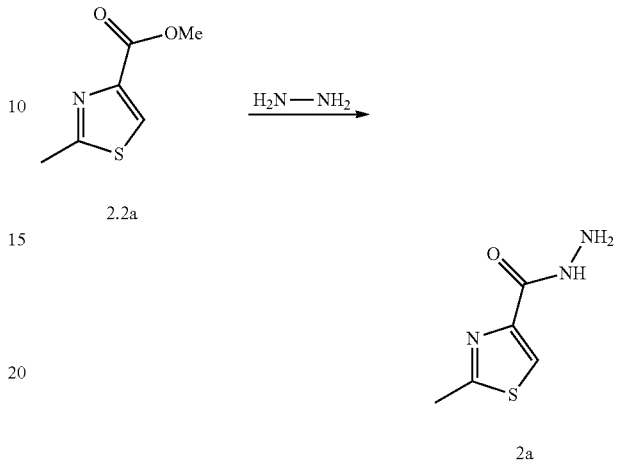

In a 100 mL round-bottom flask equipped with a condenser, ethyl 2-methylthiazole-4-carboxylate 2.2a (10 g, 58.4 mmol, 1 eq.) was dissolved in anhydrous EtOH (25 mL) and treated at RT with hydrazine monohydrate (17.0 mL, 354.4 mmol, 6 eq.). The resulting yellow solution was heated at reflux temperature for 14 h. After allowing the reaction mixture to come to RT, the solution was concentrated under reduced pressure to afford 13.4 g of a brown oil. Co-evaporations using 3×200 mL of a mixture of commercial anhydrous DCM:MeOH (1:1) were performed to remove residual water. The residue was then recrystallized from hot EtOH (60 mL). The obtained crystals were filtered and washed with cooled (0° C.) EtOH (2×30 mL). The orange solid was dried under vacuum for 1 h to afford 2a. Yield: 5.85 g, 64%. LCMS: P=100%, retention time=0.5 min, (M+H)$^+$: 158; $^1$H-NMR (CDCl$_3$): δ 8.32 (br, 1H), 7.96 (s, 1H), 4.07 (br, 2H), 2.70 (s, 3H).

In one embodiment 1.2 to 20 equivalents of hydrazine hydrate was used to carry out this reaction using a temperature range from RT to reflux.

In one embodiment, hydrazide 2 was recrystallized and/or precipitated.

The following intermediates were also prepared from the ad hoc carboxylic acids, methyl or ethyl esters using General Method C:

intermediate 2b: 2-trifluoromethylthiazole-4-carbohydrazide, methyl ester precursor was previously synthesized using conventional esterification method (such as TMS-Cl in methanol) from commercially available acid;

intermediate 2c: 2-ethylthiazole-4-carbohydrazide;

intermediate 2d: 2-vinylthiazole-4-carbohydrazide, tert-butyl 2-(4-(hydrazinecarbonyl)thiazol-2-yl)ethylcarbamate was used as precursor of the vinyl moiety, commercially available ethyl 2-(2-aminoethyl)thiazole-4-carboxylate dihydrochloride was previously Boc-protected and then esterified using conventional methods;

intermediate 2e: 2-methyloxazole-4-carbohydrazide;

intermediate 2f: 2-isopropyloxazole-4-carbohydrazide, ethyl ester precursor was previously synthesized from condensation of isobutyramide and ethyl 3-bromo-2-oxopropanoate according to WO2009/70485 A1;

intermediate 2g: 2-cyclopropyloxazole-4-carbohydrazide, ethyl ester was made as described above;
intermediate 2h: 2,5-dimethylthiazole-4-carbohydrazide, methyl ester precursor was previously synthesized using conventional esterification method (such as TMS-Cl in methanol) from commercially available acid;
intermediate 2i: tert-butyl (4-(hydrazinecarbonyl)thiazol-2-yl)carbamate, ethyl 2-((tert-butoxycarbonyl)amino)thiazole-4-carboxylate precursor was previously Boc-protected using conventional method.
intermediate 2j: 2-isopropylthiazole-4-carbohydrazide.

Synthesis of 4-methylthiazole-2-carbohydrazide 2k

Scheme 9: Synthesis of 4-methylthiazole-2-carbohydrazide 2k

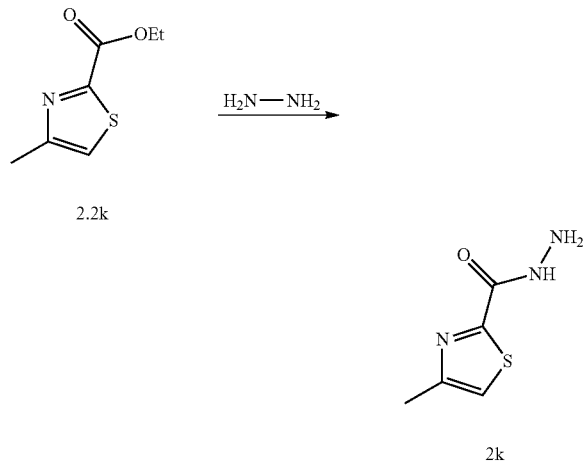

In a 100 mL round-bottom flask equipped with a condenser, 4-methylthiazole-2-carboxylate 2.2k (500 mg, 2.92 mmol, 1 eq.) was dissolved in anhydrous EtOH (5 mL) and treated at RT with hydrazine monohydrate (216 μL, 4.46 mmol, 1.5 eq.). The resulting solution was heated at reflux temperature for 18 hours. After allowing the reaction mixture to come to RT, the solution was concentrated under reduced pressure and the obtained crude was purified on a pad of silica (eluent: DCM/MeOH: 100/0 to 97/3) to afford 266 mg of 2k as a white solid (266 mg, 1.69 mmol, 57%). LCMS: P=90%, retention time=0.7 min, (M+H)$^+$: 158.

The following intermediates were also prepared from the ad hoc carboxylic acids methyl or ethyl esters using General Method C:
Intermediate 2l: 4,5-dimethylthiazole-2-carbohydrazide, prepared from ester 5.3. This latter was prepared in two steps from commercial thiazole 5.1 (procedure adapted from Castells, J. et al., *Tetrahedron Lett.*, 1985, 26, 5457-5458).

Scheme 10: Synthesis of methyl 4,5-dimethylthiazole-2-carboxylate 2.2l

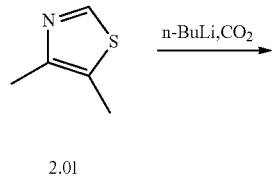

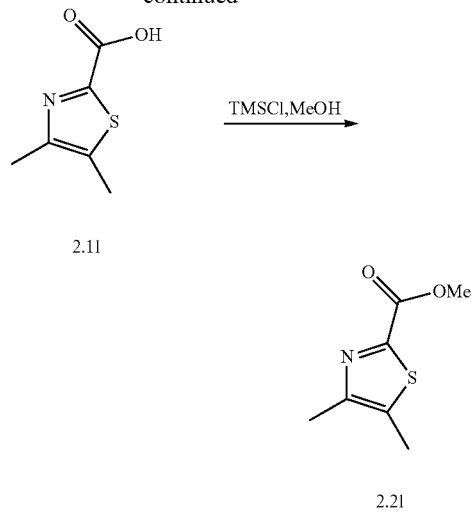

Step 1: Synthesis of 4,5-dimethylthiazole-2-carboxylic acid 2.1l

A solution of 2.0l (3.0 g, 25.7 mmol, 1 eq.) in dry THF (50 mL) was degassed using vacuum pump and backfilled with $N_2$ (repeated three times). The solution was then cooled to −78° C. and n-butyllithium (2.5M in hexanes, 11.3 mL, 28.3 mmol, 1.1 eq.) was added. The solution was stirred for 30 min at −78° C. and then the solution was placed under $CO_2$ atmosphere (bubbling directly into the solution). After 1 hour of stirring at −78° C., the solution was allowed to warm to room temperature. HCl 1N (25 mL) and EtOAc (200 mL) were added. After separation of both phases, the aqueous phase was extracted with DCM (2×100 mL). The organic phases were combined, washed with water, dried over $MgSO_4$, filtered and concentrated under reduced pressure to afford acid 2.1l (3.0 g, 6.30 mmol) which was used in the next step without further purification.

Step 2: Synthesis of methyl 4,5-dimethylthiazole-2-carboxylate 2.2l

To a solution of acid 2.1l (3.0 g, 6.30 mmol, 1 eq.) in commercial dry MeOH (12 mL) was added at RT chlorotrimethylsilane (4.0 mL, 31.5 mmol, 5 eq.) dropwise. The resulting solution was stirred at 60° C. for 14 hours. The reaction mixture was cooled down to RT, diluted with DCM (100 mL) and quenched with a saturated solution of $NaHCO_3$ (50 mL). The aqueous phase was extracted with DCM (2×50 mL). The organic phases were combined, washed with brine (100 mL), dried over $MgSO_4$, filtered and concentrated under reduced pressure. The crude was purified by flash chromatography on silica gel (eluent Pet. Ether/EtOAc: 100/0 to 80/20) to afford 2.2l (1.32 g, 7.7 mmol, 55%). LCMS: P=33%, retention time=2.1 min, (M+H)$^+$: 172.

Intermediate 2m: 3-methyl-1,2,4-oxadiazole-5-carbohydrazide, prepared from ester 2.2m using General Method C. This latter was prepared in one step from acetimidamide 2.0m (adapted from Street Leslie J. et al, *J. Med. Chem.*, 2004, 47(14), 3642-3657).

Scheme 11: Synthesis of ethyl 3-methyl-1,2,4-oxadiazole-5-carboxylate 2.2m

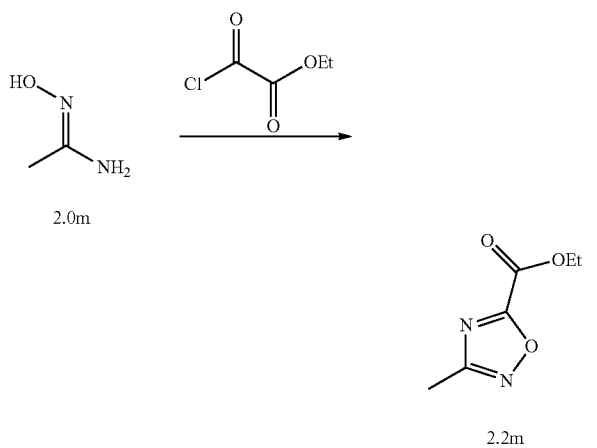

To a solution of (E)-N'-hydroxyacetimidamide 2.0m (1.0 g, 13.50 mmol, 1 eq.) and pyridine (4.35 mL, 54.0 mmol, 4 eq.) in dry DCM (40 mL) was added at RT ethyloxalyl chloride (2.4 g, 18.0 mmol, 1.3 eq.). The solution was stirred at reflux for 14 hours. The reaction mixture was cooled down to RT and quenched with NH₄Cl sat. (30 mL). The aqueous phase was extracted with DCM (2×50 mL). The organic phases were combined, washed with NaHCO₃ sat. (50 mL), dried over MgSO₄, filtered and concentrated under reduced pressure to give 2.2m as yellow oil (1.32 g, 8.45 mmol, 63%) which was used in the next step without further purification. LCMS: P=92%, retention time=2.0 min, (M+H)⁺: 157.

Intermediate 2n: 3-methyl-1,2,4-thiadiazole-5-carbohydrazide, prepared from ester 2.2m using General Method C. This latter was prepared in one step from acetamide 2.0n, reagents 2.0n' and 2.0n'' (adapted from U.S. Pat. No. 5,583,092A1).

Scheme 12: Synthesis of methyl 3-methyl-1,2,4-thiadiazole-5-carboxylate 2.2n

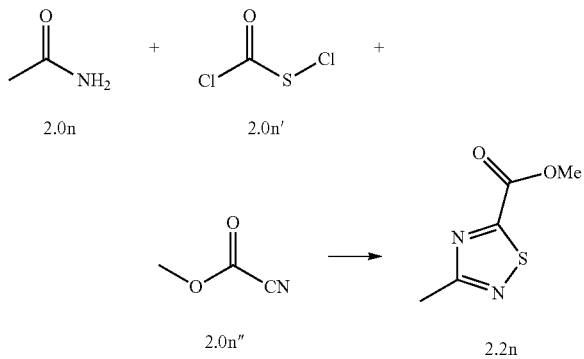

A solution of 2.0n (500 mg, 8.46 mmol, 1 eq.), and 2.0n' (820 µL, 9.31 mmol, 1.2 eq.) in dry toluene (23 mL) was stirred at reflux for 2 hours. The solvent was then evaporated under reduced pressure and the residue was dissolved again in toluene (11.3 mL). 2.0n'' (2.0 mL, 25.4 mmol, 3 eq.) was added to the solution and the resulting mixture was stirred at reflux for 4 hours. The solvent was evaporated and the obtained crude was purified by flash chromatography on silica gel (eluent: DCM 100%) to obtain the desired ester 2.2n (150 mg, 0.95 mmol, 11%) as a brown oil. LCMS: P=97%, retention time=1.8 min, (M+H)⁺: 159.

Intermediate 2o: 4-methyloxazole-2-carbohydrazide. Prepared from ester 2.2o using General Method C. This latter was prepared in one step from 4-methyloxazole 2.0o.

Scheme 13: Synthesis of methyl 4-methyloxazole-2-carboxylate 2.2o

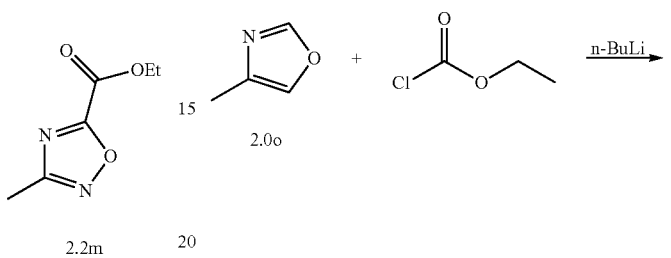

To a solution of 2.0o (1.0 g, 12.0 mmol, 1 eq.) in commercially dry THF (50 mL) was added at −78° C. under Ar atmosphere n-BuLi (2.5M in hexanes, 5.30 mL, 13.24 mmol, 1.1 eq.). After 30 minutes of stirring at −78° C., ethylchloroformate (1.16 mL, 12.13 mmol, 1.0 eq.) was added dropwise. After 30 minutes of stirring, the dry ice bath was removed and the resulting solution was allowed to warm to RT and stirred for 14 hours. HCl 1N (15 mL) and EtOAc (30 mL) were added. After separation of both phases, the aqueous phase was extracted with DCM (2×10 mL). The organic phases were combined, washed with brine (20 mL), dried over MgsO₄, filtered and concentrated under reduced pressure. The obtained crude was purified by flash chromatography on silica gel (eluent: DCM/MeOH: 100/0 to 99.5/0.5) to afford ester 2.2o (240 mg, 1.55 mmol, 13%) as a colorless oil. LCMS: P=96%, retention time=2.0 min, (M+H)⁺: 156.

Intermediate 2p: 3-isopropyl-1,2,4-thiadiazole-5-carbohydrazide, prepared from ester 2.2p using General Method C. This latter was prepared in one step from isobutyramide 2.0p, reagents 2.0p' and 2.0p'' as depicted below.

Scheme 14: Synthesis of methyl 3-isopropyl-1,2,4-thiadiazole-5-cardoxylate 2.2p

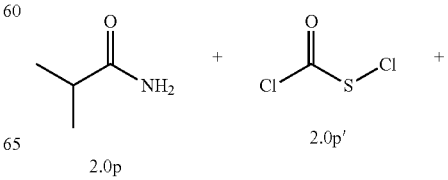

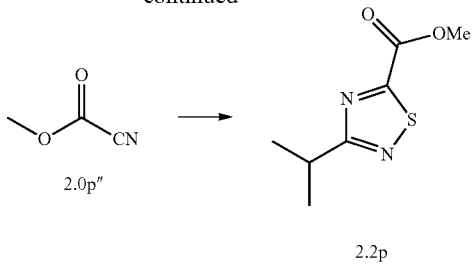

A solution of 2.0p (500 mg, 5.74 mmol, 1 eq.), and 2.0p' (555 μL, 6.31 mmol, 1.2 eq.) in dry toluene (15 mL) was stirred at reflux for 2 hours. The solvent was then evaporated under reduced pressure and the residue was dissolved again in toluene (7.6 mL). 2.0p" (900 μL, 11.34 mmol, 2 eq.) was added to the solution and the resulting mixture was stirred at reflux for 4 hours. The solvent was evaporated and the obtained crude 2.2p (587 mg, 3.15 mmol, 55%) was used in the next step without further purification. LCMS: P=45%, retention time=2.3 min, (M+H)$^+$: 187.

Intermediate 2q: 1,3-dimethyl-1H-pyrazole-5-carbohydrazide was prepared from commercial ethyl ester using General Method C.

Synthesis of 6-methylpicolinohydrazide 2r

Scheme 15: Synthesis of 6-methylpicolinohydrazide 2r.

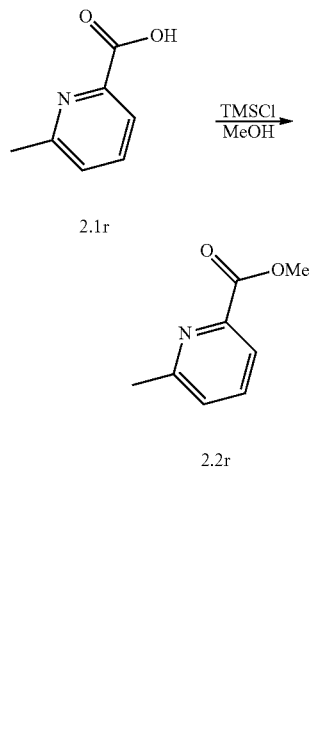

Step 1: Synthesis of methyl 6-methylpicolinate 2.2r

To a solution of 6-methylpicolinic acid 2.1r (3 g, 21.88 mmol) in anhydrous MeOH (70 mL) at RT under N$_2$ atmosphere was added TMS-Cl (13.88 mL, 109 mmol). The reaction mixture was left stirring at 60° C. overnight whereupon the mixture was concentrated under reduced pressure to afford 5.51 g of yellow oil used without further purification in next step. LCMS: P=95%, retention time=1.02 min, (M+H)$^+$: 152.

Step 2: Synthesis of 6-methylpicolinohydrazide 2r

To a solution of crude methyl 6-methylpicolinate 2.2r (5.51 g, 21.88 mmol) in EtOH (22 mL) at RT was added hydrazine monohydrate (10.61 mL, 219 mmol). The reaction mixture was heated to reflux for 90 min. After allowing the reaction mixture to reach RT, the solution was concentrated under reduced pressure and purified by silica gel chromatography (eluent: DCM/MeOH: 100/0 to 96/4) to afford the desired product 2r as white solid (2.34 g, 15.48 mmol, 71%). LCMS: P=100%, retention time=0.54 min, (M+H)$^+$: 152.

In one embodiment 2.5 to 20 equivalents of hydrazine hydrate was used to carry out this reaction using a temperature range from RT to reflux.

In one embodiment, hydrazide 2 was recrystallized and/or precipitated. The following intermediates were also prepared from the ad hoc carboxylic acids or carboxylic acid ethyl ester using General Method C:

intermediate 2s: 6-hydroxypicolinohydrazide, intermediate 2t: 6-bromopicolinohydrazide.

I.4. Step 3: Cyclodehydration Leading to Triazolopiperazine 3

Method D: Cyclodehydration and Acydolysis-Boc Protection

Method D is the procedure used for the synthesis of the triazolopiperazine 3 and is detailed below:

Scheme 16: Cyclodehydration leading to triazolopiperazine

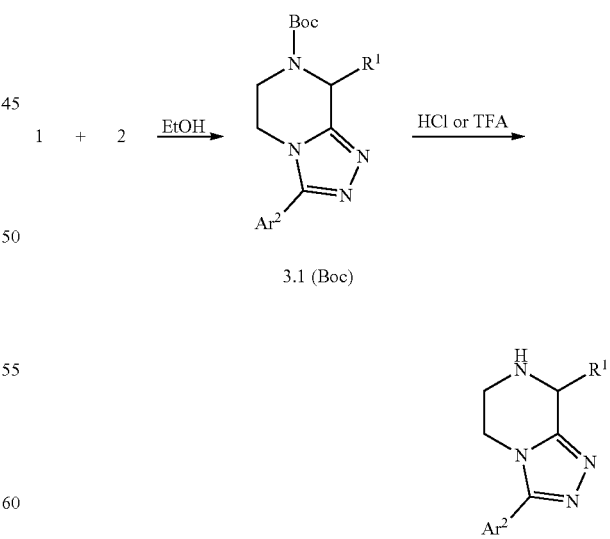

Method D is illustrated by the synthesis of intermediates 3a, 3f and 3g wherein the protecting group is Boc.

Synthesis of 2-methyl-4-(5,6,7,8-tetrahydro-[1,2,4]triazolo[4,3-a]pyrazin-3-yl)thiazole hydrochloride 3a Scheme 17: Synthesis of 2-methyl-4-(5,6,7,8-tetrahydro-[1,2,4]triazolo[4,3-a]pyrazin-3-yl)thiazole hydrochloride 3a

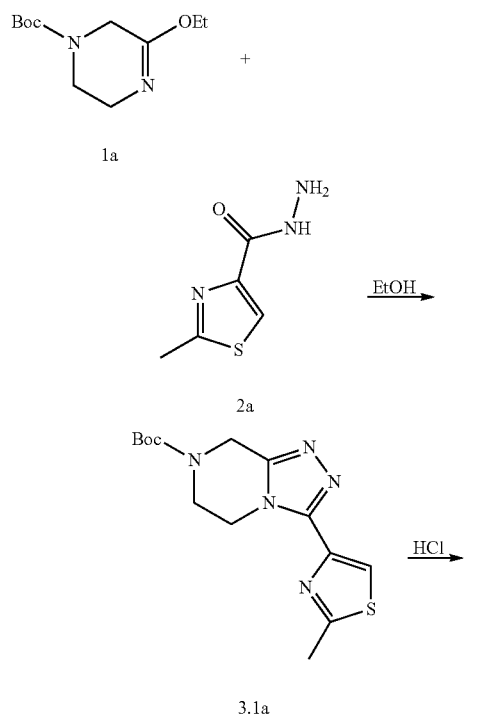

Step 1: Synthesis of tert-butyl 8-methyl-3-(2-methylthiazol-4-yl)-5,6-dihydro-[1,2,4]triazolo[4,3-a]pyrazine-7(8H)-carboxylate 3.1a In a 100 mL round-bottom flask equipped with a condenser, imino-ether 1b (1.089 g, 4.77 mmol, 1 eq.) was dissolved in commercial anhydrous EtOH (20 mL), to which was added 2-methylthiazole-4-carbohydrazide 2a (750 mg, 4.77 mmol, 1 eq.) in one portion. The resulting solution was stirred under reflux overnight. The reaction mixture was cooled down to RT and the solvent was removed under reduced pressure. The crude compound was then purified on silica gel (DCM/MeOH: 99/1 to 98/2) to afford the desired product 3.1a as white solid (1.07 g, 3.33 mmol, 70%). LCMS: P=100%, retention time=2.1 min, (M+H)$^+$: 321.

Step 2 Synthesis of 2-methyl-4-(8-methyl-5,6,7,8-tetrahydro-[1,2,4]triazolo[4,3-a]pyrazin-3-yl)thiazolehydrochloride 3a HCl 4M solution in 1,4-dioxane (8.32 mL, 33.3 mmol) was added in one portion to a solution of 3.1a (1.07 g, 3.33 mmol) in commercial iso-propanol (20 mL). The reaction mixture was stirred at 60° C. After 1.5 h (complete conversion by LC-MS), the reaction mixture was allowed to cool to room temperature and then further cooled to 0° C. with an ice bath. Thereupon, 10 mL of Et$_2$O was added. After 15 min stirring, the precipitate was filtered and dried in vacuo to afford 3a as white solid. Yield: 736 mg (86%). LCMS: P=97%, retention time=0.5 min, (M+H)$^+$: 222.

The following intermediates were also prepared from the ad hoc reagents and intermediates using General Method D:

intermediate 3b: 4-(5,6,7,8-tetrahydro-[1,2,4]triazolo[4,3-a]pyrazin-3-yl)-2-(trifluoromethyl)thiazole hydrochloride, from intermediates 1a and 2b;

intermediate 3c: 4-(5,6,7,8-tetrahydro-[1,2,4]triazolo[4,3-a]pyrazin-3-yl)-2-vinylthiazole, from intermediates 1a and 2d then the Boc aminoethyl derivative obtained 3.1c was deprotected in acidic conditions (as step 2 above using only 2 eq of HCl in dioxane) followed by dimethylamine elimination (using 10 eq of NaH and MeI at RT), then vinyl derivative 3.1.c obtained was subjected to step 2 above to afford 3c;

intermediate 3d: 4-(5,6,7,8-tetrahydro-[1,2,4]triazolo[4,3-a]pyrazin-3-yl)-2-isopropyloxazole hydrochloride, from intermediates 1a and 2f;

intermediate 3e: 2-isopropyl-4-(5,6,7,8-tetrahydro-[1,2,4]triazolo[4,3-a]pyrazin-3-yl)thiazole hydrochloride, from intermediates 1a and 2j.

Synthesis of 4-methyl-2-(5,6,7,8-tetrahydro-[1,2,4]triazolo[4,3-a]pyrazin-3-yl)thiazole 3f Scheme 18: Synthesis of 4-methyl-2-(5,6,7,8-tetrahydro-[1,2,4]triazolo[4,3-a]pyrazin-3-yl)thiazole 3f

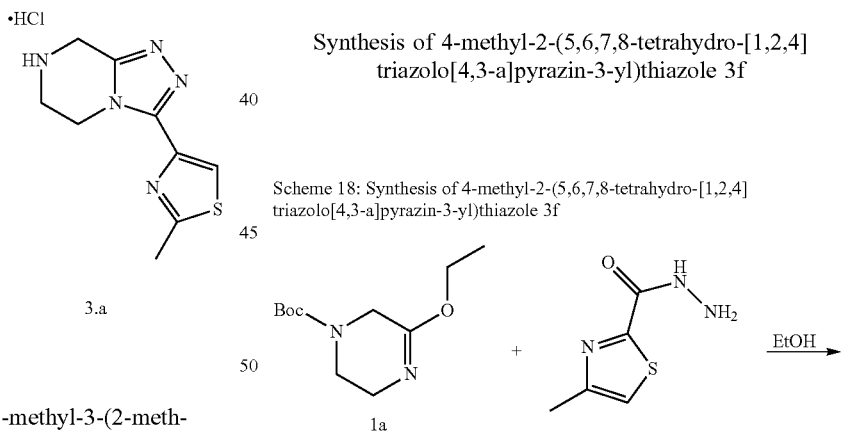

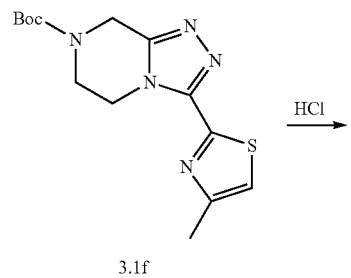

-continued

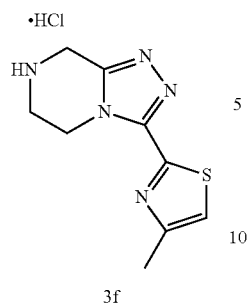

3f

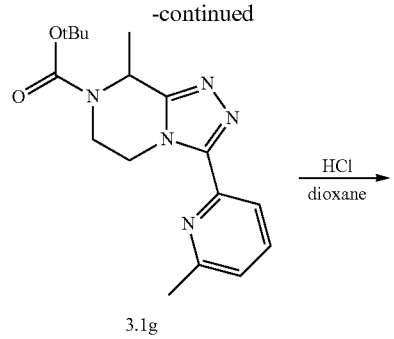

3.1g

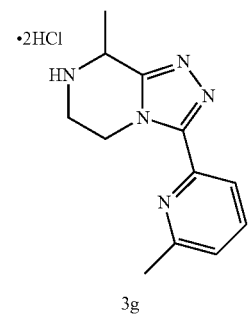

3g

Step 1: Synthesis of tert-butyl 3-(4-methylthiazol-2-yl)-5,6-dihydro-[1,2,4]triazolo[4,3-a]pyrazine-7(8H)-carboxylate 3.1f Imino-ether 1a (148 mg, 0.649 mmol, 1 eq.) was dissolved in anhydrous EtOH (3 mL) at RT, to which was added 2-methylthiazole-4-carbohydrazide 2k (102 mg, 0.649 mmol, 1 eq.). The resulting solution was stirred under reflux overnight. The reaction mixture was cooled to RT and the solvent was removed under reduced pressure. The crude compound was then purified on silica gel (DCM/MeOH: 99/1 to 98/2) to afford the desired product 3.1f as yellow solid (174 mg, 83%). LCMS: P=93%, retention time=2.2 min, (M+H)$^+$: 322.

Step 2 Synthesis of 2-methyl-4-(8-methyl-5,6,7,8-tetrahydro-[1,2,4]triazolo[4,3-a]pyrazin-3-yl)thiazolehydrochloride 3f 4M HCl in dioxane (2.71 mL, 10.83 mmol) was added to a solution of Boc-triazolopiperazine 3.1f (1.07 g, 3.33 mmol) in iso-propanol (3 mL) at RT. The reaction mixture was stirred at 60° C. After 1.5 h (complete conversion by LC-MS), the reaction mixture was allowed to cool to room temperature and then further cooled to 0° C. with an ice bath. Thereupon, 5 mL of Et$_2$O was added. After 30 min stirring, the precipitate was filtered off and dried in vacuo to afford 3f as a white solid (132 mg, 95%). LCMS: P=97%, retention time=0.9 min, (M+H)$^+$: 222.

Synthesis of 8-methyl-3-(6-methylpyridin-2-yl)-5,6,7,8-tetrahydro-[1,2,4]triazolo[4,3-n]pyrazine 3g Scheme 19: Synthesis of 8-methyl-3-(6-methylpyridin-2-yl)-5,6,7,8-tetrahydro-[1,2,4]triazolo [4,3-a]pyrazine 3g

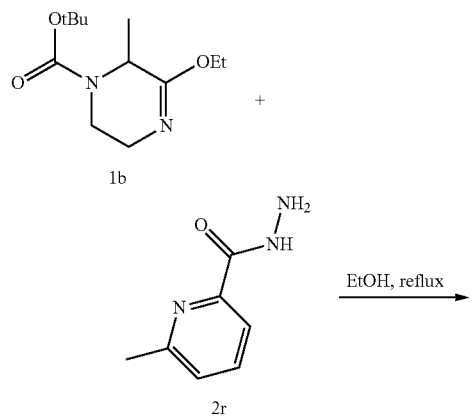

Step 1: Synthesis of tert-butyl 8-methyl-3-(6-methylpyridin-2-yl)-5,6-dihydro-[1,2,4]triazolo[4,3-a]pyrazine-7(8H)-carboxylate 3.1g Iminoether 1b (468 mg, 1.93 mmol, 1 eq.) was dissolved in anhydrous EtOH (2 mL), to which was added carbohydrazide 2r (270 mg, 1.79 mmol, 1 eq.). The resulting mixture was stirred at 135° C. in oil bath for 63 h. The reaction mixture was allowed to reach RT whereupon volatiles were removed under reduced pressure. The crude compound was then purified using silica gel chromatography (DCM/MeOH: 99/1 to 98/2) to afford the desired product 3.1g as yellow oil (380 mg, 1.15 mmol, 65%). LCMS: P=95%, retention time=2.2 min, (M+H)$^+$: 330.

Step 2: Synthesis of 8-methyl-3-(6-methylpyridin-2-yl)-5,6,7,8-tetrahydro-[1,2,4]triazolo[4,3-a]pyrazine 3g dihydrochloride salt 4M HCl in dioxane (5.77 mL, 23.07 mmol) was added to a solution of 3.1g (380 mg, 1.15 mmol) in iso-propanol (10 mL). The reaction mixture was stirred at 60° C. for 1 h. The reaction mixture was allowed reach RT and then further cooled to 0° C. The precipitate eventually obtained was filtered and dried in vacuo to afford 3g as yellow solid. (367 mg, quant.). LCMS: P=92%, retention time=0.2 min, (M+H)$^+$: 230.

The following intermediates were also prepared from the ad hoc reagents and intermediates using General Method D:
intermediate 3h: 6-(8-methyl-5,6,7,8-tetrahydro-[1,2,4]triazolo[4,3-a]pyrazin-3-yl)pyridin-2-ol hydrochloride salt, from intermediates 1c and 2s;
intermediate 3i: 3-(6-bromopyridin-2-yl)-8-methyl-5,6,7,8-tetrahydro-[1,2,4]triazolo[4,3-a]pyrazine dihydrochloride salt, from intermediates 1b and 2t.
Method E: Cyclodehydration and Acydolysis—DMB Protection
Method E is the procedure used for the synthesis of the triazolopiperazine 3 and is detailed below:

Scheme 20: Cyclodeshydratation leading to triazolopiperazine 3

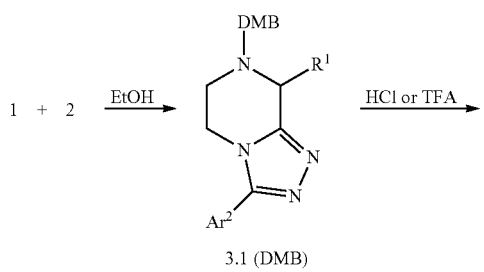

3.1 (DMB)

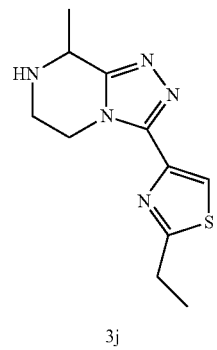

3j

Step 1: Synthesis of 4-(7-(2,4-dimethoxybenzyl)-8-methyl-5,6,7,8-tetrahydro-[1,2,4]triazolo[4,3-a]pyrazin-3-yl)-2-ethylthiazole 3.1j In a 10 mL round-bottom flask equipped with a condenser, imino-ether 1c (790 mg, 2.70 mmol, 1 eq.) was dissolved in anhydrous EtOH (2.5 mL), to which was added 2-methyl-thiazole-4-carbohydrazide 2c (462 mg, 2.70 mmol, 1 eq.) in one portion. The resulting solution was stirred at 135° C. overnight. Thereafter, the reaction mixture was brought to RT and the volatiles removed under reduced pressure. The crude compound was then purified using silica gel chromatography (DCM/MeOH: 99/1 to 98/2) to afford the desired product 3.1j as yellow solid (837 mg, 2.10 mmol, 78%). LCMS: P=97%, retention time=1.9 min, (M+H)$^+$: 400.

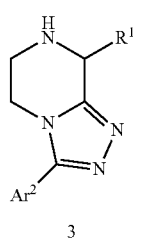

3

Method E is illustrated by the synthesis of intermediates 3j and 3q wherein the protecting group is DMB.

Synthesis of 2-ethyl-4-(8-methyl-5,6,7,8-tetrahydro-[1,2,4]triazolo[4,3-c a]pyrazin-3-yl)thiazole 3j Step 2 Synthesis of 2-ethyl-4-(8-methyl-5,6,7,8-tetrahydro-[1,2,4]triazolo[4,3-a]pyrazin-3-yl)thiazole 3j In a round-bottom flask containing 10 ml DCM was added 4-(7-(2,4-dimethoxybenzyl)-8-methyl-5,6,7,8-tetrahydro-[1,2,4]triazolo[4,3-a]pyrazin-3-yl)-2-ethylthiazole 3.1j (0.837 g, 2.10 mmol). Then, TFA (10.48 mL, 141 mmol), was added to the reaction mixture at RT. After 30 min stirring, the mixture was concentrated. Then ca 25 mL DCM was added to the residue thus obtained, and washed with saturated NaHCO$_3$ (15 mL). The aqueous layer was extracted twice with 25 mL of DCM, the organic layers were washed with 25 mL of brine, dried over MgSO$_4$, filtered and concentrated under reduced pressure to obtain crude 3e as a pink oil (500 mg, 96%). The crude 3j was directly used in the next step without further purification.

In one embodiment, alternative work-up equally used involved treatment of the dried residue obtained above with 4 M HCl/dioxane (20 eq.) at RT under stirring. After 5 min, Et$_2$O was added to help precipitation. This precipitate was filtered off under vacuum, washed with Et$_2$O and dried under high vacuum to furnish 3j.

The following intermediates were also prepared from the ad hoc reagents and intermediates using General Method E: intermediate 3k: 4-(8-methyl-5,6,7,8-tetrahydro-[1,2,4]triazolo[4,3-a]pyrazin-3-yl)-2-vinylthiazole from intermediates 1c and 2d; the Boc aminoethyl derivative 3.1k isolated after condensation was first Boc-deprotected (8 eq of HCl/dioxane). Following dimethylamine elimination (using 10 eq of NaH and MeI at RT), the vinyl moiety obtained was then DMB-deprotected as in step 2 above to furnish 3k; intermediate 3l: 2-methyl-4-(8-methyl-5,6,7,8-tetrahydro-[1,2,4]triazolo[4,3-a]pyrazin-3-yl)oxazole, from intermediates 1c and 2e;

Scheme 21: Synthesis of 2-ethyl-4-(8-methyl-5,6,7,8-tetrahydro-[1,2,4]triazolo[4,3-a]pyrazin-3-yl)thiazole 3j

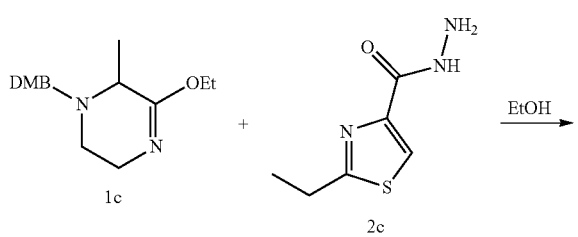

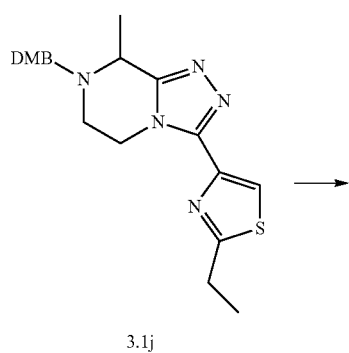

3.1j intermediate 3m 2-isopropyl-4-(8-methyl-5,6,7,8-tetrahydro-[1,2,4]triazolo[4,3-a]pyrazin-3-yl)oxazole, from intermediates 1c and 2f;

intermediate 3n: 2-cyclopropyl-4-(8-methyl-5,6,7,8-tetrahydro-[1,2,4]triazolo[4,3-a]pyrazin-3-yl)oxazole, from intermediates 1c and 2g;

intermediate 3o: 2,5-dimethyl-4-(8-methyl-5,6,7,8-tetrahydro-[1,2,4]triazolo[4,3-a]pyrazin-3-yl)thiazole, from intermediates 1c and 2h;

intermediate 3p: 4-(8-methyl-5,6,7,8-tetrahydro-[1,2,4]triazolo[4,3-a]pyrazin-3-yl)thiazol-2-amine, from intermediates 1c and 2g.

Synthesis of 4,5-dimethyl-2-(8-methyl-5,6,7,8-tetrahydro-[1,2,4]triazolo[4,3-a]pyrazin-3-yl)thiazole hydrochloride 3q Scheme 22: Synthesis of 4,5-dimethyl-2-(8-methyl-5,6,7,8-tetrahydro-[1,2,4]triazolo[4,3-a]pyrazin-3-yl)thiazole hydrochloride 3q

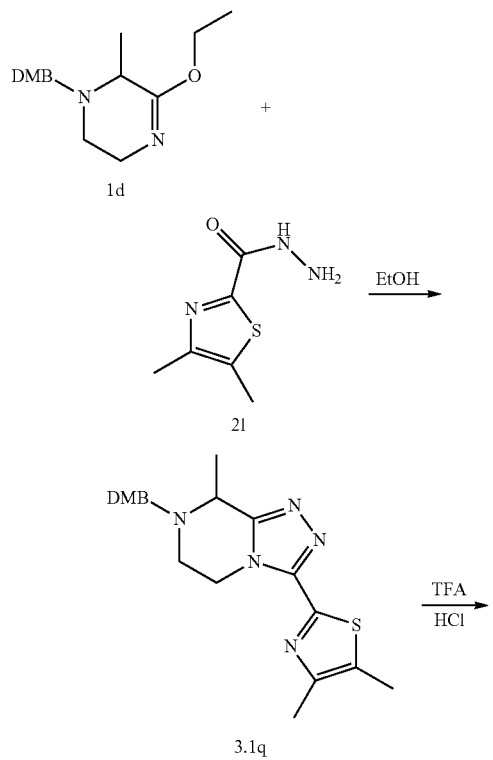

Step 1: Synthesis of 2-(7-(2,4-dimethoxybenzyl)-8-methyl-5,6,7,8-tetrahydro-[1,2,4]triazolo[4,3-a]pyrazin-3-yl)-4,5-dimethylthiazole 3.1q Iminoether 1d (768 mg, 2.63 mmol, 1 eq.) was dissolved in anhydrous EtOH (5 mL), to which was added 4,5-dimethylthiazole-2-carbohydrazide 2l (450 mg, 2.63 mmol, 1 eq.) and the resultant reaction mixture was refluxed for 48 hours. The reaction mixture was then brought to RT and the volatiles was removed under reduced pressure, whereupon the isolated crude was purified using silica gel chromatography (DCM/MeOH: 100/0 to 98/2) to afford the desired product 3.1q (786 mg, 1.93 mmol, 74%). LCMS: P=65%, retention time=1.9 min, (M+H)$^+$: 400.

Step 2: Synthesis of 4,5-dimethyl-2-(8-methyl-5,6,7,8-tetrahydro-[1,2,4]triazolo[4,3-a]pyrazin-3-yl)thiazole 3c To 3.1q (0.786 g, 1.97 mmol) in anhydrous DCM (6.6 mL) at RT was added TFA (9.1 mL, 148 mmol) and the mixture refluxed for 30 min whereupon the volatiles were removed under vacuum. 4M HCl in dioxane (5 mL, 20 mmol) was added dropwise at RT with stirring. After 5 min, Et$_2$O was added to help precipitation of the product, whereupon it was filtered, washed with Et$_2$O and dried under vacuum to afford 3q (729 mg, 100%). LCMS: P=100%, retention time=1.6 min, (M+H)$^+$: 250.

In one embodiment 20 eq. of TFA at RT in DCM (1:1 mixture DCM/TFA v/v) was used to carry out this reaction.

The following intermediates were also prepared from the ad hoc reagents and intermediates using General Method E:

intermediate 3r: 3-methyl-5-(8-methyl-5,6,7,8-tetrahydro-[1,2,4]triazolo[4,3-a]pyrazin-3-yl)-1,2,4-oxadiazole hydrochloride, from intermediates 1c and 2m;

intermediate 3s: 3-methyl-5-(8-methyl-5,6,7,8-tetrahydro-[1,2,4]triazolo[4,3-a]pyrazin-3-yl)-1,2,4-thiadiazole hydrochloride, from intermediates 1c and 2n;

intermediate 3t: 4-methyl-2-(8-methyl-5,6,7,8-tetrahydro-[1,2,4]triazolo[4,3-a]pyrazin-3-yl)oxazole hydrochloride, from intermediates 1c and 2o;

intermediate 3u: 3-isopropyl-5-(8-methyl-5,6,7,8-tetrahydro-[1,2,4]triazolo[4,3-a]pyrazin-3-yl)-1,2,4-thiadiazole hydrochloride, from intermediates 1c and 2p.

Method F: Cyclodehydration and Acydolysis—PMB Protection

Method F is the procedure used for the synthesis of the triazolopiperazine 3 and is detailed below:

Scheme 23: Cyclodeshydratation leading to triazolopiperazine 3

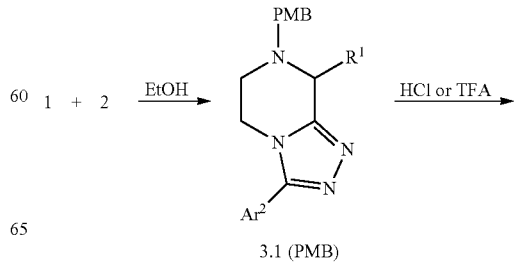

3.1 (PMB)

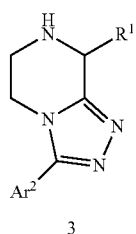

Method F is illustrated by the synthesis of intermediate 3v wherein the protecting group is PMB.

Synthesis of 4-methyl-2-(8-methyl-5,6,7,8-tetrahydro-[1,2,4]triazolo[4,3-a]pyrazin-3-yl)thiazole 3v Scheme 24: Synthesis of 4-methyl-2-(8-methyl-5,6,7,8-tetrahydro-[1,2,4]triazolo[4,3-a]pyrazin-3-yl)thiazole 3v

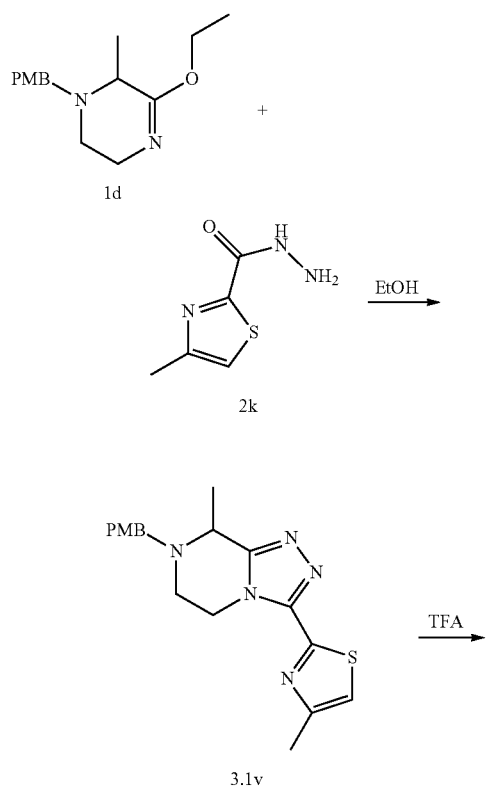

Step 1: Synthesis of 2-(7-(4-methoxybenzyl)-8-methyl-5,6,7,8-tetrahydro-[1,2,4]triazolo[4,3-a]pyrazin-3-yl)-4-methylthiazole 3.1v Imino-ether 1d (444 mg, 1.69 mmol, 1 eq.) was dissolved in anhydrous EtOH (5 mL), to which was added 2-methyl-thiazole-4-carbohydrazide 2k (266 mg, 1.69 mmol, 1 eq.) and the resultant solution was refluxed for 24 h. The reaction mixture was cooled to RT and the solvent was removed under reduced pressure. The crude compound was then purified on silica gel (DCM/MeOH: 99/1 to 98/2) to afford the desired product 3.1v as a pale yellow solid (383 mg, 1.07 mmol, 64%). LCMS: P=75%, retention time=1.9 min, (M+H)$^+$: 356.

Step 2: Synthesis of 4-methyl-2-(8-methyl-5,6,7,8-tetrahydro-[1,2,4]triazolo[4,3-a]pyrazin-3-yl)thiazole 3v Anhydrous DCM (2.5 mL) was added at RT to 2-(7-(4-methoxybenzyl)-8-methyl-5,6,7,8-tetrahydro-[1,2,4]triazolo[4,3-a]pyrazin-3-yl)-4-methylthiazole 3.1v (443 mg, 1.246 mmol, 1 eq.). TFA (2.5 mL, 33.5 mmol, 27 eq.) was then added and the reaction mixture refluxed for 15 h. The reaction was quenched by addition of NaHCO$_3$ sat. solution. The layers were separated and the aqueous layer was basified to pH ~14 with NaOH 1M solution and was extracted with DCM (3×70 mL). Combined organic layers were washed with brine (~70 mL), dried over MgSO4, filtered and concentrated under reduced pressure to afford 3v after vacuum during for 3 h without mass variation. (342 mg, 100%). LCMS: P=100%, retention time=1.2 min, (M+H)$^+$: 236.

The following intermediate was also prepared from the ad hoc reagents and intermediates using General Method F:

Intermediate 3w: 3-(1,3-dimethyl-1H-pyrazol-5-yl)-8-methyl-5,6,7,8-tetrahydro-[1,2,4]triazolo[4,3-a]pyrazine, from intermediates 1d and 2q.

I.5. Step 4: Acylation Leading to Final Products

Method G: Acylation and Chiral HPLC Purification

Method G is the procedure used for the synthesis of the racemic product 4 and its purification to obtain final compounds no X of general Formula I. Method G is detailed below:

Scheme 25: Acylation and chiral HPLC purification

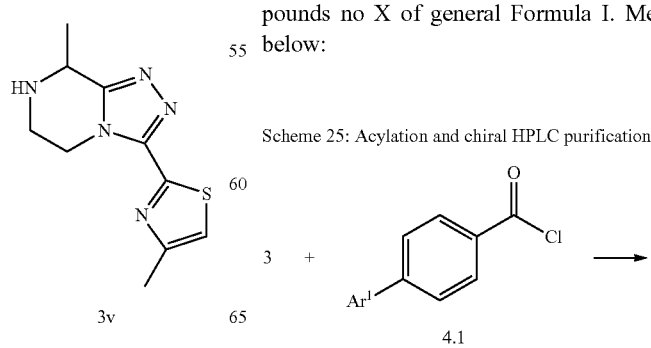

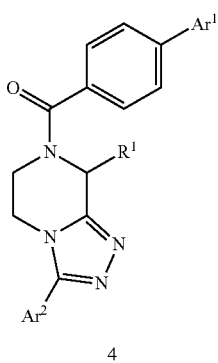

Method G is illustrated by the synthesis of compounds no 5, 19, 29 and 33 of general Formula I.

Synthesis of (3-(2-ethylthiazol-4-yl)-8-methyl-5,6-dihydro-[1,2,4]triazolo[4,3-a]pyrazin-7(8H)-yl)(4-(thiophen-2-yl)phenyl)methanone 4a and (R)-(3-(2-ethylthiazol-4-yl)-8-methyl-5,6-dihydro-[1,2,4]triazolo[4,3-a]pyrazin-7(8H)-yl)(4-(thiophen-2-yl)phenyl)methanone compound no 5

Scheme 26: Synthesis of compounds 4a and n°5

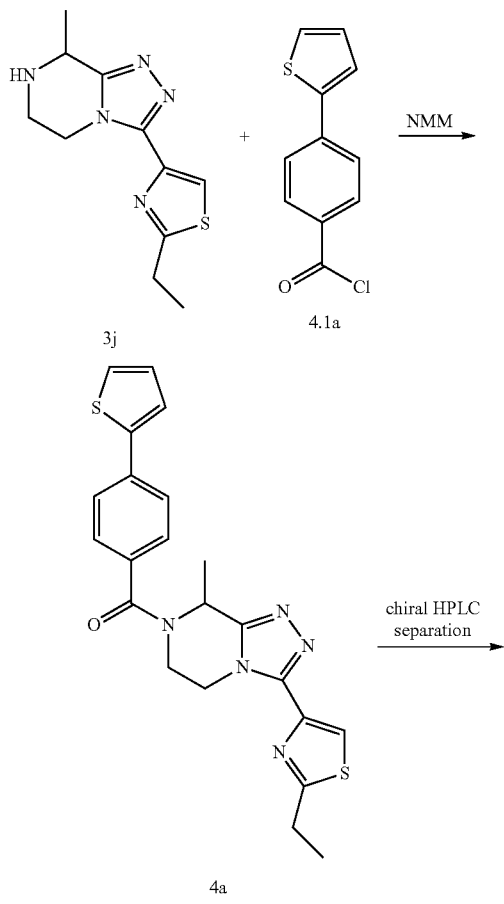

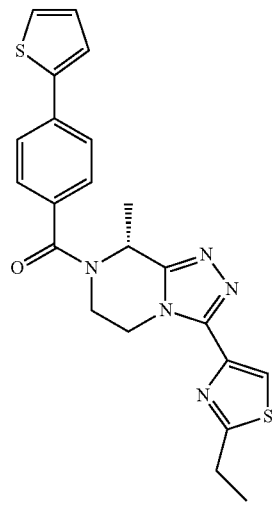

compound n° 5

To a solution of crude 3j (250 mg, 1.003 mmol, 1 eq.) in anhydrous DCM (10 mL) were added, at RT, 4-(thiophen-2-yl)benzoyl chloride 4.1a (290 mg, 1.303 mmol, 1.3 eq.), followed by N-methylmorpholine (0.359 mL, 3.51 mmol, 3.5 eq.) dropwise over 15 sec. The reaction mixture was stirred at RT for 10 minutes and the milky suspension was poured into 10 mL of 1 M HCl solution. The aqueous phase was extracted with DCM (3×10 mL). The organic phases were combined, washed with 1 M NaOH (20 mL), brine (20 mL), dried over $MgSO_4$ and evaporated to dryness. The residue was solubilized in DCM (4 mL) and $Et_2O$ was slowly added (5 mL) to induce precipitation. The solid was filtered off, washed with 2 mL of $Et_2O$ and dried under vacuum to afford 4a as yellow powder (234 mg, 0.537 mmol, 54%). LCMS: P=97%, retention time=2.4 min, $(M+H)^+$: 436.

4a was purified by chiral preparative HPLC according to the abovementioned method to yield title compound no 5 as a white powder. LCMS: P=100%, retention time=4.3 min, $(M+H)^+$: 436; Chiral HPLC retention time: 14.0 min; ee>99%; $^1$H-NMR (CDCl$_3$): δ 8.02 (s, 1H), 7.70 (d, J=8.2, 2H), 7.47 (d, J=8.2, 2H), 7.31 (m, 2H), 7.12 (m, 1H), 5.77 (br, 1H), 4.83 (m, 1H), 4.63 (br, 1H), 4.26 (m, 1H), 3.53 (m, 1H), 3.07 (d, J=7.5, 2H), 1.74 (d, J=6.9, 3H), 1.43 (t, J=7.5, 3H).

Synthesis of (8-methyl-3-(4-methylthiazol-2-yl)-5,6-dihydro-[1,2,4]triazolo[4,3-a]pyrazin-7(8H)-yl)(4-(thiophen-2-yl)phenyl)methanone 4b and (R)-(8-methyl-3-(4-methylthiazol-2-yl)-5,6-dihydro-[1,2,4]triazolo[4,3-a]pyrazin-7(8H)-yl)(4-(thiophen-2-yl)phenyl)methanone compound no 19

Scheme 27: Synthesis of compounds 4b and n°19

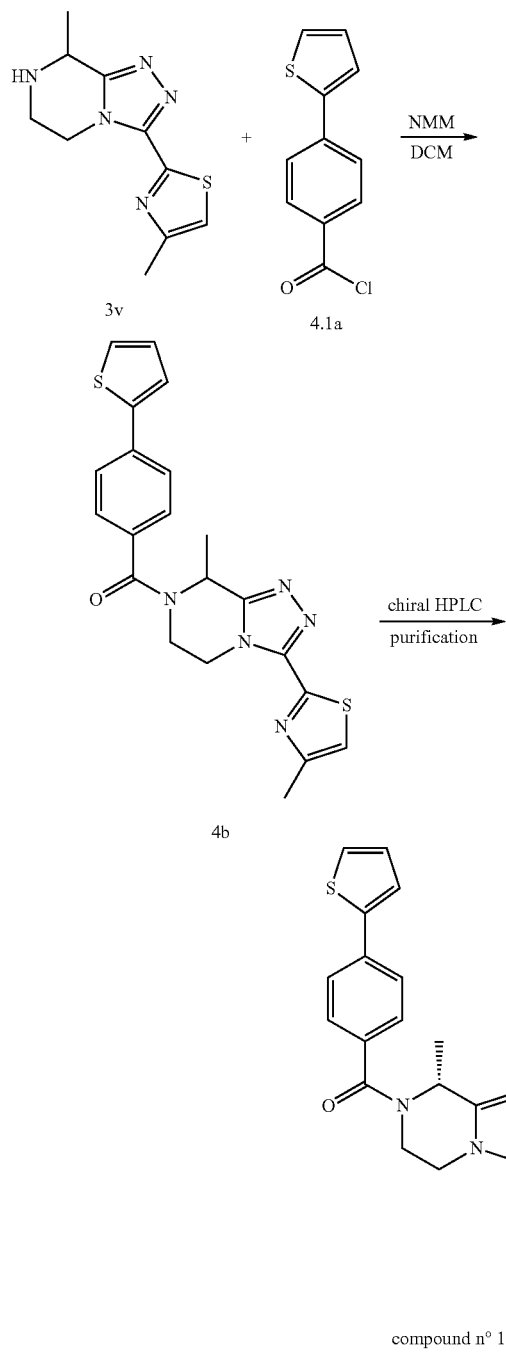

4b compound n° 19

To a solution of 3v (342 mg, 1.25 mmol, 1 eq.) in commercial anhydrous DCM (12 mL) at RT were added 4-(thiophen-2-yl)benzoyl chloride 4.1a (326 mg, 1.464 mmol, 1.17 eq.), followed by N-methylmorpholine (0.128 mL, 1.25 mmol, 1.0 eq.) dropwise over 15 sec. The reaction mixture was stirred at RT for 15 minutes and then diluted with DCM (60 mL). The organic layer was washed with water (40 mL), brine (50 mL), dried over MgSO₄, filtered and evaporated under reduced pressure. The residue was purified on silica gel (DCM/MeOH: 98/2) to afford 4b as yellow oil with 88% purity by LCMS. Diethylether (10 mL) was added on obtained oil and mixture was sonicated. A white solid precipitated and was filtered. The filtrate was concentrated under reduced pressure and diethylether (5 mL) was added on the residue. After sonication, a second white precipitate was filtered. Both precipitates were merged to afford 4b as white solid (189 mg, 36%). LCMS: P=99%, retention time=4.4 min, (M+H)$^+$: 422.

4b was purified by chiral preparative HPLC according to the abovementioned method to yield title compound no 19 as white powder. LCMS: P=100%, retention time=4.3 min, (M+H)$^+$: 422; Chiral HPLC retention time: 6.6 min, ee=94%; $^1$H-NMR (CDCl$_3$): δ 7.70 (d, J=8.2, 2H), 7.48 (d, J=8.2, 2H), 7.40-7.35 (m, 2H), 7.13-7.11 (m, 1H), 7.00 (m, 1H), 5.81 (br, 1H), 4.95 (dd, J$_1$=3.3, J$_2$=14.0, 1H), 4.60 (br, 1H), 4.27 (td, J$_1$=3.9, J$_2$=12.7, 1H), 3.51 (m, 1H), 2.50 (s, 3H), 1.75 (d, J=6.9, 3H).

When hydrochloride salt of 3 was used, 2.2 eq. of N-methylmorpholine were added.

Synthesis of compound no 29: (R)-[1,1'-biphenyl]-4-yl(8-methyl-3-(6-methylpyridin-2-yl)-5,6-dihydro-[1,2,4]triazolo[4,3-a]pyrazin-7(8H)-yl)methanone Scheme 28: Synthesis of compounds 4c and n°29

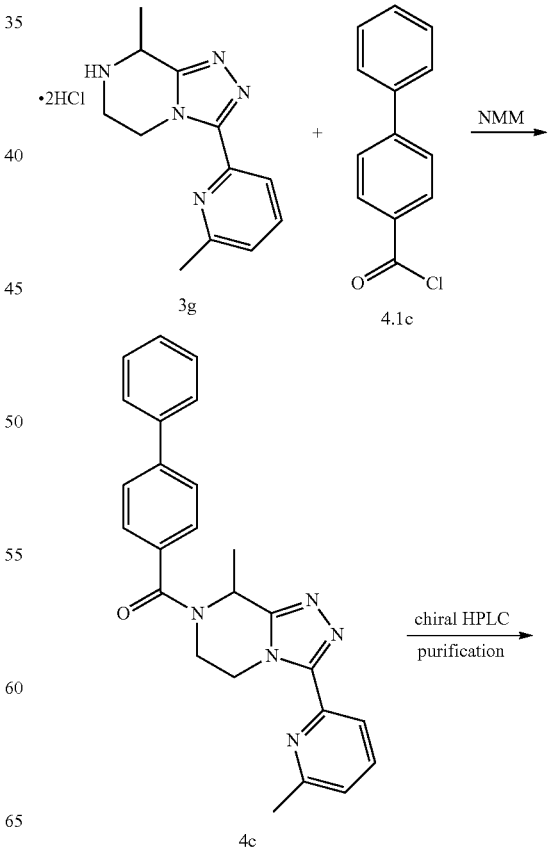

4c

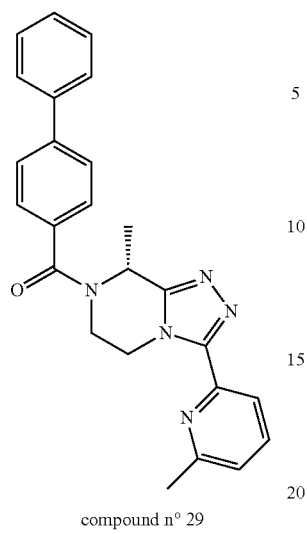

compound n° 29

To a solution of 3g (500 mg, 1.65 mmol, 1 eq.) in anhydrous DCM (10 mL) were added at RT [1,1'-biphenyl]-4-carbonyl chloride 4.1c (430 mg, 1.98 mmol, 1.2 eq.), followed by N-methylmorpholine (507 µL, 4.96 mmol, 3.00 eq.). The reaction mixture was stirred at RT for 30 min. whereupon saturated NaHCO$_3$ solution (10 mL) and DCM (5 mL) were added to the reaction mixture. The organic phase was extracted, dried over MgSO$_4$, filtered and concentrated under reduced pressure. The crude product was purified using silica gel chromatography (eluent: DCM/MeOH: 98:2) to afford 268 mg of 4c. LCMS: P=98%, retention time=4.2 min, (M+H)$^+$: 410.

4c was purified by chiral preparative HPLC according to the abovementioned method to yield title compound no 29 as a white powder. LCMS: P=100%, retention time=4.2 min, (M+H)$^+$: 410; Chiral HPLC retention time: 4.7 min; ee>99%. $^1$H-NMR (CDCl$_3$): δ 8.11 (d, J=7.7, 1H), 7.67-7.40 (m, 10H), 7.20 (d, J=6.7, 1H), 5.78 (bs, 1H), 5.00 (dd, J$_1$=3.3, J$_2$=14.0, 1H), 4.67 (br, 1H), 4.37 (m, 1H), 3.51 (m, 1H), 2.58 (s, 3H), 1.76 (d, J=6.9, 3H).

The procedure used for the synthesis of compound no 33 is the following:

Scheme 29: Synthesis of compound n°33.

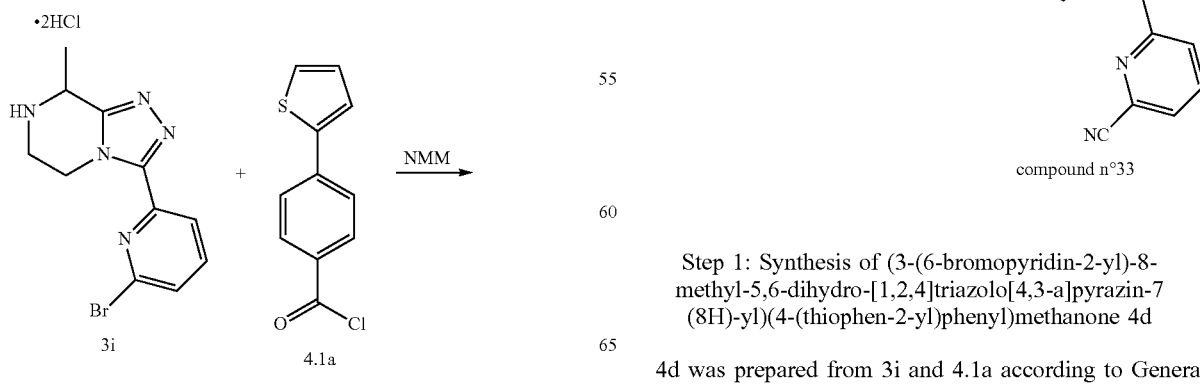

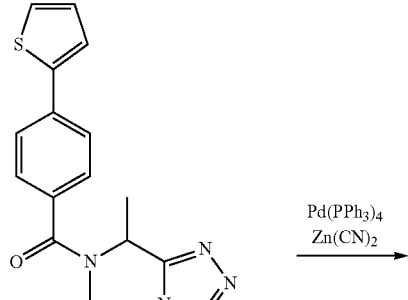

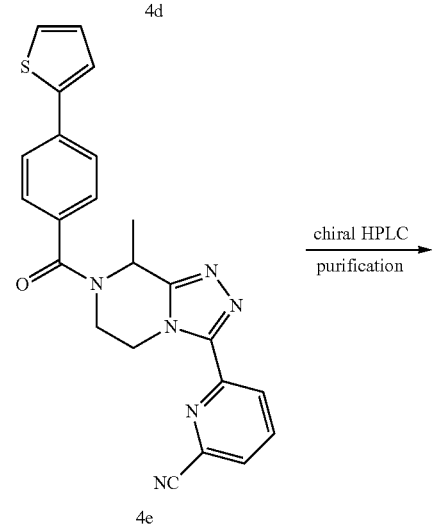

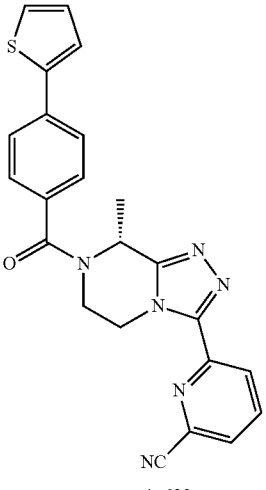

compound n°33

Step 1: Synthesis of (3-(6-bromopyridin-2-yl)-8-methyl-5,6-dihydro-[1,2,4]triazolo[4,3-a]pyrazin-7(8H)-yl)(4-(thiophen-2-yl)phenyl)methanone 4d 4d was prepared from 3i and 4.1a according to General Method G.

Step 2: Synthesis of 6-(8-methyl-7-(4-(thiophen-2-yl)benzoyl)-5,6,7,8-tetrahydro-[1,2,4]triazolo[4,3-a]pyrazin-3-yl)picolinonitrile 4e A mixture of 4d (140 mg, 0.291 mmol) and zinc cyanide (137 mg, 1.166 mmol) in DMA (2 mL) at RT was degassed. Then Pd(PPh$_3$)$_4$ (67.4 mg, 0.058 mmol) was added (67.4 mg, 0.058 mmol). The reaction mixture was stirred at 115° C. for 30 min. whereupon DCM (30 mL) was added and the organic layer extract was washed with water (2×30 mL), dried over MgSO$_4$, filtered and concentrated under reduced pressure. The residue was purified using silica gel chromatography (DCM/MeOH: 100/0 to 98/2) to afford 4d as white solid (8 mg, 6%). LCMS: P=90%, rt=4.2 min, (M+H)$^+$: 427.

4d was purified by chiral preparative HPLC according to the abovementioned method to yield title compound no 33 as white powder. LCMS: P=100%, retention time=4.2 min, (M+H)$^+$: 427; Chiral HPLC retention time: 18.8 min; ee=98%.

II. Chiral Synthesis

II.1. General Synthetic Scheme for Chiral Synthesis

Compounds of the invention were synthesized using the chiral process of the invention described in Scheme 30.

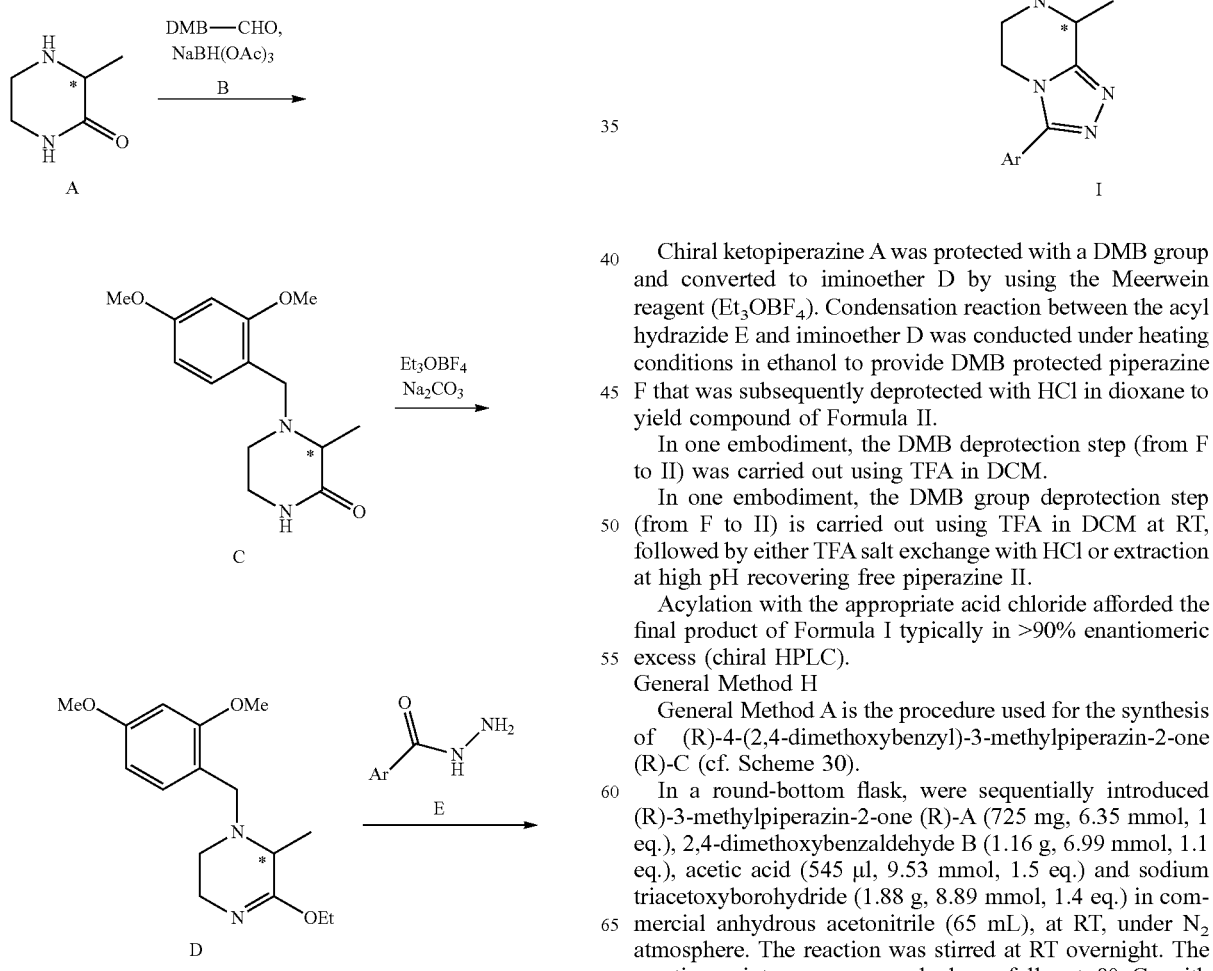

Chiral ketopiperazine A was protected with a DMB group and converted to iminoether D by using the Meerwein reagent (Et$_3$OBF$_4$). Condensation reaction between the acyl hydrazide E and iminoether D was conducted under heating conditions in ethanol to provide DMB protected piperazine F that was subsequently deprotected with HCl in dioxane to yield compound of Formula II.

In one embodiment, the DMB deprotection step (from F to II) was carried out using TFA in DCM.

In one embodiment, the DMB group deprotection step (from F to II) is carried out using TFA in DCM at RT, followed by either TFA salt exchange with HCl or extraction at high pH recovering free piperazine II.

Acylation with the appropriate acid chloride afforded the final product of Formula I typically in >90% enantiomeric excess (chiral HPLC).

General Method H

General Method A is the procedure used for the synthesis of (R)-4-(2,4-dimethoxybenzyl)-3-methylpiperazin-2-one (R)-C (cf. Scheme 30).

In a round-bottom flask, were sequentially introduced (R)-3-methylpiperazin-2-one (R)-A (725 mg, 6.35 mmol, 1 eq.), 2,4-dimethoxybenzaldehyde B (1.16 g, 6.99 mmol, 1.1 eq.), acetic acid (545 µl, 9.53 mmol, 1.5 eq.) and sodium triacetoxyborohydride (1.88 g, 8.89 mmol, 1.4 eq.) in commercial anhydrous acetonitrile (65 mL), at RT, under N$_2$ atmosphere. The reaction was stirred at RT overnight. The reaction mixture was quenched carefully at 0° C. with saturated NaHCO₃ solution (100 mL) until no more bubbling was observed. Aqueous and organic layers were separated. The aqueous layer was extracted with EtOAc (3×100 mL) and the combined organic layers were washed with brine, dried over MgSO₄, filtered, and concentrated under reduced pressure to afford the title compound as yellow oil. The crude compound was then purified on silica gel (DCM/MeOH: 98/2 to 95/5) to afford the desired product (R)-C as a viscous pale yellow oil. Yield: 1.65 g, 98%. LCMS: P=100%, retention time=1.6 min, (M+H)⁺: 265; chiral HPLC retention time=41.5 min, ee>99%; ¹H-NMR (CDCl₃): δ 7.23 (d, J=8.9, 1H), 6.49 (d, J=8.9, 1H), 6.46 (s, 1H), 6.29 (br, 1H), 3.81 (s, 3H), 3.80 (s, 3H), 3.78 (d, $J_{AB}$=15.0, 1H), 3.49 (d, $J_{AB}$=15.0, 1H), 3.27 (m, 2H), 3.19 (m, 1H), 2.95 (m, 1H), 2.48 (m, 1H), 1.48 (d, J=6.8, 3H).

The (S)-4-(2,4-dimethoxybenzyl)-3-methylpiperazin-2-one (S)-C was also prepared using General Method H starting from (S)-3-methylpiperazin-2-one (S)-A. Yield: 300 mg, 99%. LCMS: P=100%, retention time=1.6 min, (M+H)⁺: 265; chiral HPLC retention time=26.6 min, ee>99%.

General Method I:

General Method I is the procedure used for the synthesis of (R)-1-(2,4-dimethoxybenzyl)-5-ethoxy-6-methyl-1,2,3,6-tetrahydropyrazine (R)-D (cf. Scheme 30) as detailed below.

Oven dried (115° C.) sodium carbonate (2.48 g, 23.40 mmol, 2.25 eq.) was placed in a round-bottom flask. The round-bottom flask was backfilled with Ar and then capped with a rubber septum. A solution of (R)-4-(2,4-dimethoxybenzyl)-3-methylpiperazin-2-one (R)-C (2.75 g, 10.40 mmol, 1 eq.) in anhydrous DCM (35 mL) was added, followed by freshly prepared triethyloxonium tetrafluoroborate (2.48 g, 13.05 mmol, 1.25 eq.) in one portion. Thereafter the reaction mixture was stirred further at RT for 1 hour, whereupon the reaction mixture was diluted with saturated aqueous NaHCO₃ (100 mL). The aqueous layer was extracted with DCM (3×200 mL). The organic layers were combined, dried over MgSO₄, filtered and concentrated under reduced pressure to afford 3.1 g of yellow oil. The crude compound was then purified on silica gel (EtOAc/MeOH: 99/1) to afford the desired product (R)-D as a pale yellow oil. Yield: 1.44 g, 48%. LCMS: P=95%, retention time=1.8 min, (M+H2O+H)⁺: 311; chiral HPLC retention time=12.3 min, ee>97%. ¹H-NMR (CDCl₃): δ 7.23 (d, J=8.8, 1H), 6.48 (d, J=8.8, 1H), 6.44 (s, 1H), 4.02 (m, 2H), 3.92 (s, 6H), 3.86 (d, $J_{AB}$=14.0, 1H), 3.46 (d, $J_{AB}$=14.0, 1H), 3.44 (m, 2H), 3.10 (m, 1H), 2.79 (m, 1H), 2.32 (m, 1H), 1.35 (d, J=6.8, 3H), 1.24 (t, J=6.0, 3H).

The (S)-1-(2,4-dimethoxybenzyl)-5-ethoxy-6-methyl-1,2,3,6-tetrahydropyrazine(S)-D was also prepared using General Method I starting from (S)-C (46 mg, 0.16 mmol, 59%). LCMS: P=100%, retention time=1.8 min, (M+H2O+H)⁺: 311; chiral HPLC retention time=11.3 min, ee=96%.

General Method J:

General Method J is the procedure used for the synthesis of hydrazide E.a (cf scheme 31) as detailed below.

Scheme 31: Synthesis of 2-methylthiazole-4-carbohydrazide E.a

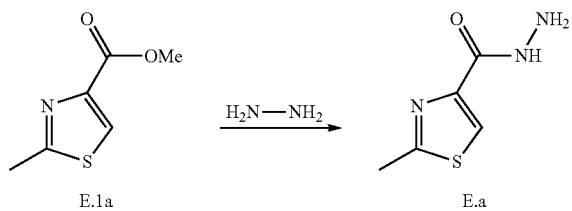

Synthesis of 2-methylthiazole-4-carbohydrazide E.a

In a 100 mL round-bottom flask equipped with a condenser, ethyl 2-methylthiazole-4-carboxylate E.1a (10 g, 58.4 mmol, 1 eq.) was dissolved in anhydrous EtOH (25 mL) and treated at RT with hydrazine monohydrate (17.0 mL, 354.4 mmol, 6 eq.). The resulting yellow solution was heated at reflux temperature for 14 h. After allowing the reaction mixture to come to RT, the solution was concentrated under reduced pressure to afford 13.4 g of a brown oil. Co-evaporations using 3×200 mL of a mixture of commercial anhydrous DCM:MeOH (1:1) were performed to remove residual water. The residue was then recrystallized from hot EtOH (60 mL): after total dissolution, the mixture was then allowed to cool down to RT and then put at 0° C. (with an ice bath) for 40 min. The obtained crystals were filtered and washed with cooled (0° C.) EtOH (2×30 mL). The orange solid was dried under vacuum for 1 h to afford E.a (5.85 g, 37.2 mmol, 64%). LCMS: P=100%, retention time=0.5 min, (M+H)⁺: 158; ¹H-NMR (CDCl₃): δ 8.32 (br, 1H), 7.96 (s, 1H), 4.07 (br, 2H), 2.70 (s, 3H).

General Method K:

General Method K is the general procedure used for the synthesis of chiral triazolopiperazine intermediates F (cf. scheme 30) and is detailed below in scheme 32 with the synthesis of (R)-4-(7-(2,4-dimethoxybenzyl)-8-methyl-5,6,7,8-tetrahydro-[1,2,4]triazolo[4,3-a]pyrazin-3-yl)-2-methylthiazole(R)-F.a.

Scheme 32: Synthesis of (R)-4-(7-(2,4-dimethoxybenzyl)-8-methyl-5,6,7,8-tetrahydro-[1,2,4]triazolo[4,3-a]pyrazin-3-yl)-2-methylthiazole(R)-F.a

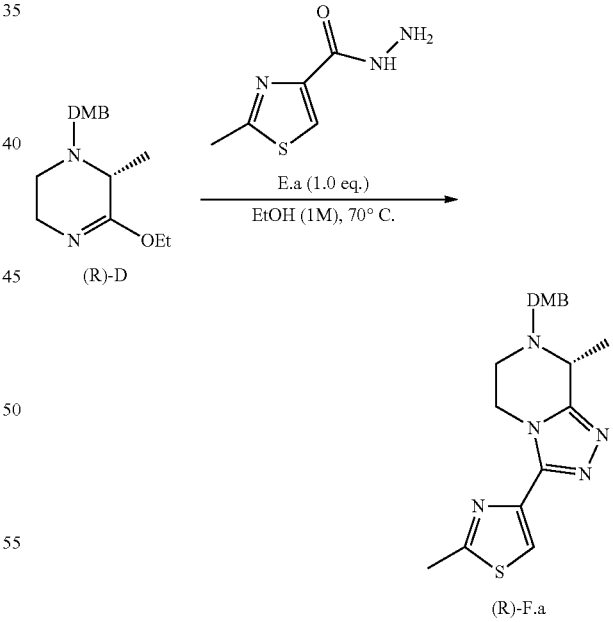

In a 50 mL round-bottom flask equipped with a condenser, imino-ether (R)-D (4.51 g, 14.96 mmol, 1 eq.) was dissolved in anhydrous EtOH (15 mL), to which was added 2-methylthiazole-4-carbohydrazide E.a (2.35 g, 14.96 mmol, 1 eq.) in one portion. The resulting solution was stirred at 70° C. for 6 hours. The reaction mixture was cooled down to RT and the solvent was removed under reduced pressure. The crude compound was then purified by silica gel chromatography (DCM/MeOH: 99/1 to 95/5) to afford the desired product (R)-F.a as pale yellow foamy solid. Yield: 3.78 g, 65%. LCMS: P=96%, retention time=1.8 min, (M+H)$^+$: 386; chiral HPLC retention time=13.9 min, ee=95%; $^1$H-NMR (CDCl$_3$): δ 7.85 (s, 1H), 7.19 (s, 1H), 6.41 (m, 2H), 4.38 (m, 1H), 4.16 (m, 1H), 3.96 (m, 1H), 3.86 (d, J$_{AB}$=15.0, 1H), 3.74 (s, 3H), 3.73 (s, 3H), 3.56 (d, J$_{AB}$=15.0, 1 H), 3.11 (m, 1H), 2.66 (s, 3H), 2.62 (m, 1H), 1.64 (d, J=6.6, 3H); $^{13}$C-NMR (CDCl$_3$): δ 166.2, 160.2, 158.8, 154.6, 148.1, 143.1, 130.9, 118.8, 118.2, 104.2, 98.5, 77.6, 77.2, 76.8, 70.4, 70.2, 55.4, 55.4, 55.8, 50.2, 45.8, 44.2, 19.2, 17.7, 15.7.

In a round-bottom flask equipped with a condenser, imino-ether (R)-D (890 mg, 3.04 mmol, 1 eq.) was dissolved in anhydrous EtOH (3 mL), to which was added 2-methyl-thiazole-4-carbohydrazide E.a (479 mg, 3.04 mmol, 1 eq.). The resulting solution was stirred at 70° C. for 7 hours, then brought to RT and the volatiles removed under reduced pressure. The crude compound was then purified by silica gel chromatography (DCM/MeOH: 99/1 to 95/5) to afford the desired product F.a as pale yellow oil. Yield: 685 mg, 58%. LCMS: P=96%, retention time=1.8 min, (M+H)$^+$: 386; chiral HPLC retention time: 14.3 min, ee=95%; $^1$H-NMR (CDCl$_3$): δ 7.85 (s, 1H), 7.19 (s, 1H), 6.41 (m, 2H), 4.38 (m, 1H), 4.16 (m, 1H), 3.96 (m, 1H), 3.86 (d, J$_{AB}$=15.0, 1H), 3.74 (s, 3H), 3.73 (s, 3H), 3.56 (d, J$_{AB}$=15.0, 1H), 3.11 (m, 1H), 2.66 (s, 3H), 2.62 (m, 1H), 1.64 (d, J=6.6, 3H).

The (S)-4-(7-(2,4-dimethoxybenzyl)-8-methyl-5,6,7,8-tetrahydro-[1,2,4]triazolo[4,3-a]pyrazin-3-yl)-2-methylthiazole(S)-F.a was also prepared using General Method K starting from (S)-D (36 mg, 0.09 mmol, 54%). LCMS: P=90%, retention time=1.8 min, (M+H)$^+$: 386; chiral HPLC retention time=21.0 min, ee=94.0%.

General Method L:

General Method E is the general procedure used for the synthesis of compounds of Formula II salts (cf. compounds II in scheme 30) and is detailed below in scheme 33 with the synthesis of compound no 11-1: (R)-8-methyl-3-(2-methylthiazol-4-yl)-5,6,7,8-tetrahydro-[1,2,4]triazolo[4,3-a]pyrazin-7-ium chloride(R)-II-1.

In a 50 mL round-bottom flask equipped with a condenser, were introduced (R)-F.a (262 mg, 0.68 mmol, 1 eq.) followed by a solution of HCl 4 M in dioxane (3.4 mL, 13.60 mmol, 20 eq.) in one portion. The resulting yellow solution was stirred at 100° C. After 6 hours, i-PrOH (6 mL) was added to the hot reaction mixture. The solution was then allowed to reach RT by removing the oil bath. Et$_2$O (15 mL) was then added and the obtained precipitate was filtered off, washed with Et$_2$O (3 mL) and air-dried overnight to afford (R)-II-1 (235 mg, 0.86 mmol, 100%) as a pink solid which was used in the next step without further purification.

The (S)-2-methyl-4-(8-methyl-5,6,7,8-tetrahydro-[1,2,4]triazolo[4,3-a]pyrazin-3-yl)thiazole(S)-II-1 was prepared using TFA procedure, starting from (S)-F.a as followed:

(S)-F.a (36 mg, 0.09 mmol, 1 eq.) was dissolved in dry DCM (500 μL). TFA (467 μL, 6.0 mmol, 65 eq.) was added dropwise at RT. After 30 minutes, the dark pink reaction mixture was quenched carefully with a saturated solution of NaHCO$_3$ (10 mL). The aqueous phase was extracted with DCM (3×10 mL). Organic phases were combined, washed with brine (10 mL), dried over MgSO4, filtered and concentrated under reduced pressure to afford the free amine (S)-II-1 as white solid (43 mg, 0.183 mmol, 100%) which was used in the next step without further purification.

Determination of Enantiomeric Excess:

As aforementioned, given that chiral LC determination of % ee proved difficult for compounds of Formula II, specifically due to technical chiral LC issues in dealing with such amines, the % ee was determined through the product formed at the subsequent step wherein the amine was acylated to furnish the final products exemplified through but not limited to compound no 1 of Formula I.

General Method M:

General Method M is the general procedure used for the synthesis of chiral triazolopiperazine compounds of the invention and is detailed below with the synthesis of (R)-(8-methyl-3-(2-methylthiazol-4-yl)-5,6-dihydro-[1,2,4]triazolo[4,3-a]pyrazin-7(8H)-yl) (4-(thiophen-2-yl)phenyl)methanone (R)-compound no 1 of Formula I (hereunder noted I-1).

Scheme 33: Synthesis of compound n°1 hydrochloride: (R)-8-methyl-3-(2-methylthiazol-4-yl)-5,6,7,8-tetrahydro-[1,2,4]triazolo[4,3-a]pyrazin-7-ium chloride(R)-II-1

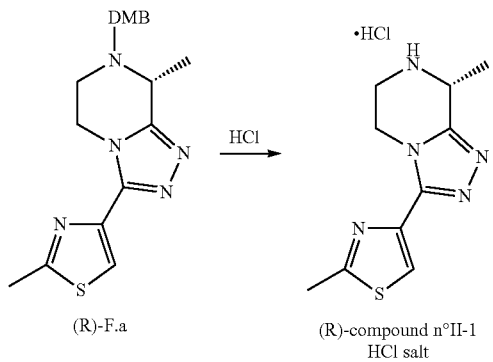

Scheme 34: Synthesis of (R)-I-1

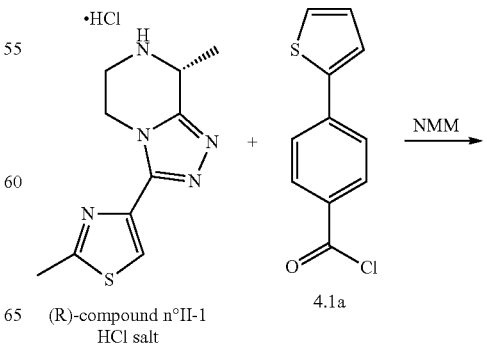

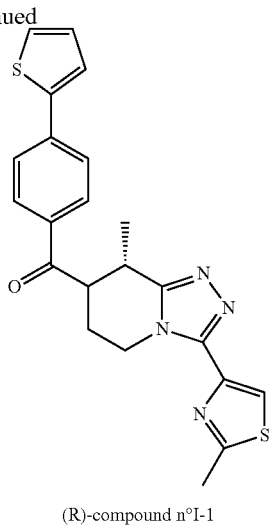

(R)-compound n°I-1

To a solution of crude (R)-II-1 (235 mg, 0.67 mmol, 1 eq.) in anhydrous DCM (10 mL) were added at 0° C. 4-(thiophen-2-yl)benzoyl chloride 4.1a (165 mg, 0.742 mmol, 1.3 eq.), followed by N-methylmorpholine (163 µL, 1.48 mmol, 2.2 eq.) dropwise over 15 sec. The reaction mixture was stirred at RT for 10 minutes and, the milky suspension was poured into 10 mL of 1 M HCl. The aqueous phase was extracted with DCM (3×10 mL). The organic phases were combined, washed with 1 M NaOH (20 mL), brine (20 mL), dried over MgSO$_4$ and evaporated to dryness. The crude compound was purified by silica gel chromatography (eluent: EtOAc/MeOH: 98/2) to afford the desired product (R)-I-1 as a white foam. Yield: 158 mg, 55%. LCMS: P=97%, retention time=4.0 min, (M+H)$^+$: 422; Chiral HPLC retention time=15.4 min, ee=95%; $^1$H-NMR (CDCl$_3$): δ 7.93 (s, 1H), 7.61 (d, J=7.9, 2H), 7.40 (d, J=7.9, 2H), 7.31 (m, 2H), 7.04 (m, 1H), 5.73 (m, 1H), 4.78 (m, 1H), 4.46 (m, 1H), 4.14 (m, 1H), 3.47 (m, 1H), 2.70 (s, 3H), 1.68 (d, J=6.7, 3H). $^{13}$C-NMR (CDCl3): δ 170.3, 166.5, 151.9, 148.0, 142.4, 136.4, 128.1, 125.8, 124.0, 119.3, 77.4, 77.0, 76.6, 44.8, 30.7, 19.6, 19.1.

Identical % ee was obtained for compounds (R)-I-1 and (R)-F.a thus confirming that no detectable racemization occurs during the acidolytic deprotection and N-acylation steps.

Compound (S)-(8-methyl-3-(2-methylthiazol-4-yl)-5,6-dihydro-[1,2,4]triazolo[4,3-a]pyrazin-7(8H)-yl)(4-(thiophen-2-yl)phenyl)methanone (S)-I-1 was also prepared using General Method F starting from (S)-II-1(16 mg, 38.0 µmol, 40%). LCMS: P=90%, retention time=4.0 min, (M+H)$^+$: 386.1; chiral HPLC retention time=11.0 min, ee=92%.

X-Ray Crystallographic Characterization of Compound (R)-I-1.

Compound(R)-I-1 was characterized by single crystal X-ray spectroscopy thus establishing the configuration of the more active enantiomer as being the (R)-configuration (see FIG. 1).

Method.

All data were recorded on a MAR345 image plate (MAR-RESEARCH) using MoKα radiation (λ=0.71073). X-rays were generated on a RIGAKU rotating anode generator with power settings of 50 KV and 70 mA. A Zr filter is used to eliminate the MoKα radiation. A suitable crystal was chosen under a microscope, mounted in a nylon loop and aligned on the goniometer prior to the x-ray experiment. A total of 174 images corresponding to a 2.0° phi rotation were collected at room temperature. The reflections on the diffraction images were indexed and integrated using the Automar data processing suite (MARRESEARCH). During the integration the friedel pairs were kept unmerged in order to preserve the anomalous signal needed for absolute structure determination. Xprep (Bruker) was used to determine the spacegroup and to generate the reflection and instruction files for structure determination and subsequent refinement. Structure solution was performed by SHELXS and the refinement was done by SHELXL ("A short history of SHELX". Sheldrick, G. M. (2008). Acta Cryst. A64, 112-122). The free rotation around the C6-C1 (C1A or C1B) results in rotational isomerism in a 58/42% ratio as seen in FIG. 1 below. As depicted in the X-ray Figure below the chirality of C22 carbon atom is established as R. (H. D. Flack (1983). "On Enantiomorph-Polarity Estimation". Acta Cryst A39: 876-881; J. Appl. Cryst. (2008), 41, 96-103.)

X-Ray Crystallographic Characterization of Compound (S)-I-1.

Figure 2:
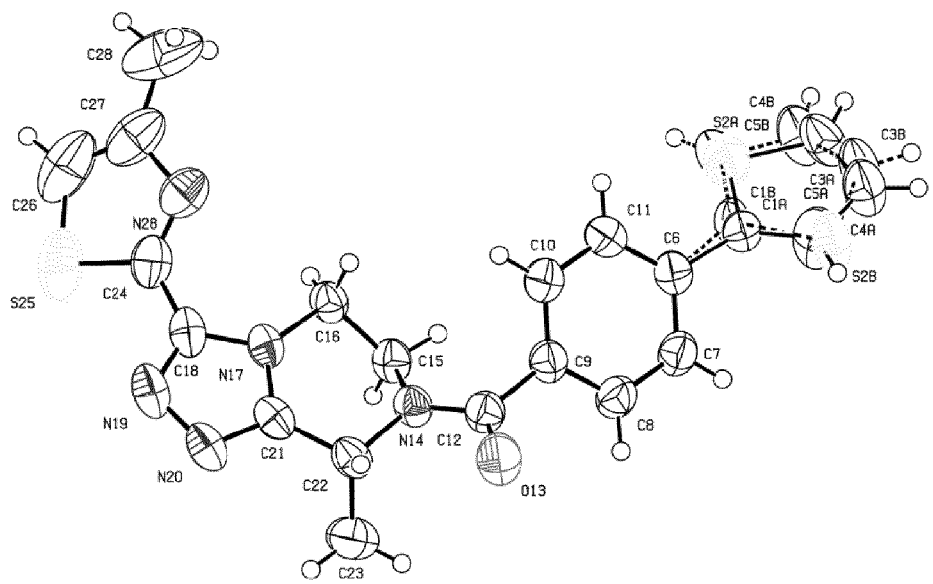
FIG. 2 shows X-ray crystal structure of compound no 19 (thermal displacement ellipsoids drawn at the 50% probability level).

Compound(S)-I-1 was characterized by single crystal X-ray spectroscopy thus establishing the configuration of the more active enantiomer as being the (R)-configuration (see FIG. 2).

Method.

All data were recorded on a MAR345 image plate (MAR-RESEARCH) using MoKα radiation (λ=0.71073). X-rays were generated on a RIGAKU rotating anode generator with power settings of 50 KV and 70 mA. A Zr filter is used to eliminate the MoKα radiation. A suitable crystal was chosen under a microscope, mounted in a nylon loop and aligned on the goniometer prior to the x-ray experiment. A total of 174 images corresponding to a 2.5° phi rotation were collected at room temperature. The reflections on the diffraction images were indexed and integrated using the Automar data processing suite (MARRESEARCH). During the integration the friedel pairs were kept unmerged in order to preserve the anomalous signal needed for absolute structure determination. Xprep (Bruker) was used to determine the spacegroup and to generate the reflection and instruction files for structure determination and subsequent refinement. Structure solution was performed by SHELXS and the refinement was done by SHELXL ("A short history of SHELX". Sheldrick, G. M. (2008). Acta Cryst. A64, 112-122). The free rotation around the C6-C1 (C1A or C1B) results in rotational isomerism in a 58/42% ratio as seen in FIG. 1 below. As depicted in the X-ray Figure below the chirality of C22 carbon atom is established as R. (H. D. Flack (1983). "On Enantiomorph-Polarity Estimation". Acta Cryst A39: 876-881; J. Appl. Cryst. (2008), 41, 96-103.)

It can be readily appreciated that related compounds of the invention may be synthesized from the ad hoc reagents using the general methods and procedures described herein.

III. X-Ray Crystallographic Characterization

III.1. Compound No 1

Compound no 1 was characterized by single crystal X-ray spectroscopy thus establishing the configuration of the more active enantiomer as the (R)-configuration (see FIG. 1).

Methods.

All data were recorded on a MAR345 image plate (MAR-RESEARCH) using MoKα radiation (λ=0.71073). X-rays were generated on a RIGAKU rotating anode generator with power settings of 50 KV and 70 mA. A Zr filter is used to eliminate the MoKα radiation. A suitable crystal was chosen under a microscope, mounted in a nylon loop and aligned on the goniometer prior to the x-ray experiment. A total of 174 images corresponding to a 2.0° phi rotation were collected at room temperature. The reflections on the diffraction images were indexed and integrated using the Automar data processing suite (MARRESEARCH). During the integration the friedel pairs were kept unmerged in order to preserve the anomalous signal needed for absolute structure determination. Xprep (Bruker) was used to determine the spacegroup and to generate the reflection and instruction files for structure determination and subsequent refinement. Structure solution was performed by SHELXS and the refinement was done by SHELXL ("A short history of SHELX". Sheldrick, G. M. (2008). Acta Cryst. A64, 112-122). The free rotation around the C6-C1 (C1A or C1B) results in rotational isomerism in a 58/42% ratio as seen in FIG. 1 below. As depicted in the X-ray FIG. 1 the chirality of C22 carbon atom is established as R. (H. D. Flack (1983). "On Enantiomorph-Polarity Estimation". Acta Cryst A39: 876-881; J. Appl. Cryst. (2008), 41, 96-103.)

III.2. Compound No 19

Compound no 19 in the present invention was characterized by single crystal X-ray spectroscopy that established the configuration of the more active enantiomer as (R) (see FIG. 2).

Methods.

All data were recorded on a MAR345 image plate (MAR-RESEARCH) using MoKα radiation ($\lambda$=0.71073). X-rays were generated on a RIGAKU rotating anode generator with power settings of 50 KV and 70 mA. A Zr filter is used to eliminate the MoKα radiation. A suitable crystal was chosen under a microscope, mounted in a nylon loop and aligned on the goniometer prior to the x-ray experiment. A total of 103 images corresponding to a 1.5° phi rotation were collected at room temperature. The reflections on the diffraction images were indexed and integrated using the Automar data processing suite (MARRESEARCH). During the integration the friedel pairs were kept unmerged in order to preserve the anomalous signal needed for absolute structure determination. Xprep (Bruker) was used to determine the spacegroup and to generate the reflection and instruction files for structure determination and subsequent refinement. Structure solution was performed by SHELXS and the refinement was done by SHELXL ("A short history of SHELX". Sheldrick, G. M. (2008). Acta Cryst. A64, 112-122). The free rotation around the C6-C1 (C1A or C1B) results in rotational isomerism in a 56/44% ratio as seen in FIG. 2 below. As depicted in the X-ray FIG. 2 the chirality of C22 carbon atom is established as R. (H. D. Flack (1983). "On Enantiomorph-Polarity Estimation". Acta Cryst A39: 876-881; J. Appl. Cryst. (2008), 41, 96-103.)

IV. Summary of Methods and Reagents Used for the Synthesis of the Compounds of the Invention Compounds of the invention of general Formula I were synthesized from the ad hoc reagents and intermediates using the general methods and procedures described above. Table 4 hereunder recapitulates the intermediates and general methods used for each compound as well as LCMS analytical data.

TABLE 4

| Cpd n° | Triazolo piperazine intermediate | Acyl chloride intermediate | General method | LCMS Purity (%) | LCMS Retention time (min) | LCMS [M + H]+ | Chiral HPLC Retention time (S-enantiomer) (min) | Chiral HPLC Retention time (R-enantiomer) (min) | Chiral HPLC Method name | ee (R) (%) |
|---|---|---|---|---|---|---|---|---|---|---|
| 1 | II-1 | 4-(thiophen-2-yl)benzoyl chloride | General Method M | 97 | 3.97 | 422 | 11.1 | 15.3 | A | 95.3 |
| 2 | II-1 | [1,1'-biphenyl]-4-carbonyl chloride | General Method M | 97 | 4.07 | 416 | 10.9 | 14.1 | A | 93.0 |
| 3 | 3a | 4-(thiophen-2-yl)benzoyl chloride | General Method G | 95 | 3.97 | 408 | — | — | — | — |
| 4 | 3b | 4-(thiophen-2-yl)benzoyl chloride | General Method G | 97 | 4.44 | 462 | — | — | — | — |
| 5 | 3j | 4-(thiophen-2-yl)benzoyl chloride | General Method G | 100 | 4.31 | 436 | 10.0 | 14.0 | A | 99.5 |
| 6 | 3j | [1,1'-biphenyl]-4-carbonyl chloride | General Method G | 99 | 4.34 | 430 | 6.5 | 10.4 | B | 99.5 |
| 7 | 3k | 4-(thiophen-2-yl)benzoyl chloride | General Method G | 100 | 4.28 | 434 | 10.0 | 15.0 | A | 99.6 |
| 8 | 3k | [1,1'-biphenyl]-4-carbonyl chloride | General Method G | 100 | 4.36 | 428 | 9.9 | 14.3 | A | 99.0 |
| 9 | 3c | 4-(thiophen-2-yl)benzoyl chloride | General Method G | 95 | 4.13 | 420 | — | — | — | — |
| 10 | 3c | [1,1'-biphenyl]-4-carbonyl chloride | General Method G | 95 | 4.22 | 414 | — | — | — | — |
| 11 | 3l | 4-(thiophen-2-yl)benzoyl chloride | General Method G | 100 | 3.74 | 406 | 10.6 | 15.2 | A | 96.0 |
| 12 | 3l | [1,1'-biphenyl]-4-carbonyl chloride | General Method G | 99 | 3.87 | 400 | 10.1 | 13.6 | A | 99.4 |
| 13 | 3m | 4-(thiophen-2-yl)benzoyl chloride | General Method G | 98 | 4.32 | 434 | 9.2 | 13.5 | A | 99.9 |

TABLE 4-continued

| Cpd n° | Triazolo piperazine intermediate | Acyl chloride intermediate | General method | LCMS Purity (%) | LCMS Retention time (min) | LCMS [M + H]+ | Chiral HPLC Retention time (S-enantiomer) (min) | Chiral HPLC Retention time (R-enantiomer) (min) | Chiral HPLC Method name | ee (R) (%) |
|---|---|---|---|---|---|---|---|---|---|---|
| 14 | 3d | 4-(thiophen-2-yl)benzoyl chloride | General Method G | 94 | 4.17 | 420 | — | — | — | — |
| 15 | 3n | 4-(thiophen-2-yl)benzoyl chloride | General Method G | 96 | 4.14 | 432 | 7.0 | 9.7 | B | 99.9 |
| 16 | 3o | 4-(thiophen-2-yl)benzoyl chloride | General Method G | 100 | 4.13 | 436 | 8.2 | 10.9 | A | 64 |
| 17 | 3p | 4-(thiophen-2-yl)benzoyl chloride | General Method G furnished aminothiazole 4that was then dimethylated using conventional method | 98 | 4.03 | 451 | 18.1 | 14.2 | C | 96.0 |
| 18 | 3e | 4-(thiophen-2-yl)benzoyl chloride | General Method G | 92 | 4.36 | 436 | — | — | — | — |
| 19 | 3v | 4-(thiophen-2-yl)benzoyl chloride | General Method G | 100 | 4.30 | 422 | 5.9 | 6.6 | A | 94.0 |
| 20 | 3v | [1,1'-biphenyl]-4-carbonyl chloride | General Method G | 99 | 4.41 | 416 | 6.3 | 8.7 | B | 99.5 |
| 21 | 3f | [1,1'-biphenyl]-4-carbonyl22chloride | General Method G | 98 | 4.52 | 402 | — | — | — | — |
| 22 | 3q | 4-(thiophen-2-yl)benzoyl chloride | General Method G | 99 | 4.52 | 436 | 6.6 | 8.5 | B | 99.0 |
| 23 | 3r | 4-(thiophen-2-yl)benzoyl chloride | General Method G | 100 | 4.01 | 407 | 6.5 | 8.7 | B (3/2/0.5 ratio used) | 99.8 |
| 24 | 3s | 4-(thiophen-2-yl)benzoyl chloride | General Method G | 100 | 4.24 | 423 | 6.34 | 7.73 | B- | 99.0 |
| 25 | 3u | 4-(thiophen-2-yl)benzoyl chloride | General Method G | 97 | 4.84 | 451 | 5.3 | 7.7 | B- | 93.0 |
| 26 | 3t | 4-(thiophen-2-yl)benzoyl chloride | General Method G | 100 | 4.02 | 406 | 7.3 | 10.1 | B- | 99.6 |
| 27 | 3t | [1,1'-biphenyl]-4-carbonyl chloride | General Method G | 100 | 4.09 | 400 | 6.5 | 8.5 | B | 99.9 |
| 28 | 3w | 4-(thiophen-2-yl)benzoyl chloride | General Method G | 100 | 3.85 | 419 | 7.3 | 9.2 | B | 96.0 |
| 29 | 3g | [1,1'-biphenyl]-4-carbonyl chloride | General Method G | 100 | 4.21 | 410 | 3.5 | 4.7 | B' | 99.9 |
| 30 | 3g | 4-(thiophen-2-yl)benzoyl chloride | General Method G | 100 | 4.11 | 416 | 4.6 | 5.4 | A' | 99.0 |
| 31 | 3h | 4-(thiophen-2-yl)benzoyl chloride | General Method G | 100 | 4.48 | 418 | 8.0 | 13.4 | C' | 98.0 |
| 32 | 3h | [1,1'-biphenyl]-4-carbonyl chloride | General Method G | 100 | 3.57 | 412 | 7.3 | 9.0 | C' | 97.0 |
| 33 | 3i | 4-(thiophen-2-yl)benzoyl chloride | Method G | 99 | 4.19 | 427 | 16.2 | 17.3 | C' | 98.5 |

In Table 4, the term "Cpd" means compound.

In Table 4 the configuration of each peak separated by chiral LC was established with compound no 1, compound no 19 directly, and applied to the other cases by analogy. The indirect configurational assignment aforesaid was always confirmed through biological activity determination that was conclusive given the acute stereochemical SAR.

BIOLOGY EXAMPLES

Functional Assay

Aequorin Assay with Human NK-3 Receptor

Changes in intracellular calcium levels are a recognized indicator of G protein-coupled receptor activity. The efficacy of compounds of the invention to inhibit NKA-mediated NK-3 receptor activation was assessed by an in vitro Aequorin functional assay. Chinese Hamster Ovary recombinant cells expressing the human NK3 receptor and a construct that encodes the photoprotein apoaequorin were used for this assay. In the presence of the cofactor coelenterazine, apoaequorin emits a measurable luminescence that is proportional to the amount of intracellular (cytoplasmic) free calcium.

Antagonist Testing

The antagonist activity of compounds of the invention is measured following pre-incubation (3 minutes) of the compound with the cells, followed by addition of the reference agonist (NKA) at a final concentration equivalent to the $EC_{80}$ (3 nM) and recording of emitted light (FDSS 6000 Hamamatsu) over the subsequent 90-second period. The intensity of the emitted light is integrated using the reader software. Compound antagonist activity is measured based on the inhibition of the luminescence response to the addition of Neurokinin A.

Inhibition curves are obtained for compounds of the invention and the concentrations of compounds which inhibit 50% of reference agonist response ($IC_{50}$) were determined (see results in table 5 below). The $IC_{50}$ values shown in table 5 indicate that compounds of the invention are potent NK-3 antagonist compounds.

TABLE 5

| Compound n° | $IC_{50}$ (nM) |
|---|---|
| 1 | 16 |
| 2 | 28 |
| 3 | 83 |
| 4 | 50 |
| 5 | 3 |
| 6 | 10 |
| 7 | 3 |
| 8 | 7 |
| 9 | 18 |
| 10 | 20 |
| 11 | 34 |
| 12 | 58 |
| 13 | 2 |
| 14 | 47 |
| 15 | 9 |
| 16 | 30 |
| 17 | 7 |
| 18 | 10 |
| 19 | 8 |
| 20 | 11 |
| 21 | 33 |
| 22 | 21 |
| 23 | 33 |
| 24 | 2 |
| 25 | 3 |
| 26 | 12 |
| 27 | 51 |
| 28 | 37 |
| 29 | 18 |
| 30 | 11 |
| 31 | 18 |

Competitive Binding Assays

The affinity of compounds of the invention for the human NK-3 receptor was determined by measuring the ability of compounds of the invention to competitively and reversibly displace a well-characterized NK3 radioligand.

$^3$H-SB222200 Binding Competition Assay with Human NK-3 Receptor

The ability of compounds of the invention to inhibit the binding of the NK-3 receptor selective antagonist $^3$H-SB222200 was assessed by an in vitro radioligand binding assay. Membranes were prepared from Chinese hamster ovary recombinant cells stably expressing the human NK3 receptor. The membranes were incubated with 5 nM $^3$H-SB222200(ARC) in a HEPES 25 mM/NaCl 0.1M/$CaCl_2$ 1 mM/$MgCl_2$ 5 Mm/BSA 0.5%/Saponin 10 µg/ml buffer at pH 7.4 and various concentrations of compounds of the invention. The amount of $^3$H-SB222200 bound to the receptor was determined after filtration by the quantification of membrane associated radioactivity using the TopCount-NXT reader (Packard). Competition curves were obtained for compounds of the invention and the concentration that displaced 50% of bound radioligand ($IC_{50}$) were determined by linear regression analysis and then the apparent inhibition constant ($K_i$) values were calculated by the following equation: $K_i=IC_{50}/(1+[L]/K_d)$ where [L] is the concentration of free radioligand and $K_d$ is its dissociation constant at the receptor, derived from saturation binding experiments (Cheng and Prusoff, 1973) (see results in table 6 below).

Table 6 shows biological results obtained using the $^3$H-SB222200 binding competition assay with compounds of the invention. These results indicate that compounds of the invention display potent affinity for the human NK-3 receptor.

TABLE 6

| Compound n° | $K_i$ (nM) |
|---|---|
| 1 | 16 |
| 2 | 26 |
| 3 | 83 |
| 4 | 56 |
| 5 | 5 |
| 6 | 11 |
| 7 | 4 |
| 8 | 7 |
| 9 | 19 |
| 10 | 36 |
| 11 | 44 |
| 12 | 70 |
| 13 | 3 |
| 14 | 42 |
| 15 | 11 |
| 16 | 32 |
| 17 | 7 |
| 18 | 20 |
| 19 | 6 |
| 20 | 12 |
| 21 | 38 |
| 22 | 21 |
| 23 | 29 |
| 25 | 3 |
| 27 | 51 |
| 28 | 68 |
| 29 | 23 |
| 30 | 10 |
| 31 | 22 |

Selectivity Assay

Selectivity of the compounds of the invention was determined over the other human NK receptors, namely NK-1 and NK2 receptors.

Human NK1

The affinity of compounds of the invention for the NK1 receptor was evaluated in CHO recombinant cells which express the human NK1 receptor. Membrane suspensions were prepared from these cells. The following radioligand: [$^3$H] substance P (PerkinElmer Cat#NET111520) was used in this assay. Binding assays were performed in a 50 mM Tris/5 mM $MnCl_2$/150 mM NaCl/0.1% BSA at pH 7.4. Binding assays consisted of 25 µl of membrane suspension (approximately 5 µg of protein/well in a 96 well plate), 50 µl of compound or reference ligand (Substance P) at increasing concentrations (diluted in assay buffer) and 2 nM [$^3$H] substance P. The plate was incubated 60 min at 25° C. in a water bath and then filtered over GF/C filters (Perkin Elmer, 6005174, presoaked in 0.5% PEI for 2 h at room temperature) with a Filtration unit (Perkin Elmer). The radioactivity retained on the filters was measured by using the TopCount-NXT reader (Packard). Competition curves were obtained for compounds of the invention and the concentrations of compounds which displaced 50% of bound radioligand (IC$_{50}$) were determined and then apparent inhibition constant Ki values were calculated by the following equation: Ki=IC$_{50}$/(1+[L]/K$_D$) where [L] is the concentration of free radioligand and K$_D$ is its dissociation constant at the receptor, derived from saturation binding experiments (Cheng and Prusoff, 1973).

Human NK2

The affinity of compounds of the invention for the NK2 receptor was evaluated in CHO recombinant cells which express the human NK2 receptor. Membrane suspensions were prepared from these cells. The following radioligand [$^{125}$I]-Neurokinin A (PerkinElmer Cat#NEX252) was used in this assay. Binding assays were performed in a 25 mM HEPES/1 mM CaCl2/5 mM MgCl2/0.5% BSA/10 µg/ml saponin, at pH 7.4. Binding assays consisted of 25 µl of membrane suspension (approximately 3.75 µg of protein/well in a 96 well plate), 50 µl of compound or reference ligand (Neurokinin A) at increasing concentrations (diluted in assay buffer) and 0.1 nM [$^{125}$I]-Neurokinin A. The plate was incubated 60 min at 25° C. in a water bath and then filtered over GF/C filters (Perkin Elmer, 6005174, presoaked in assay buffer without saponine for 2 h at room temperature) with a Filtration unit (Perkin Elmer). The radioactivity retained on the filters was measured by using the TopCount-NXT reader (Packard). Competition curves were obtained for compounds of the invention and the concentrations of compounds which displaced 50% of bound radioligand (IC$_{50}$) were determined and then apparent inhibition constant Ki values were calculated by the following equation: Ki=IC$_{50}$/(1+[L]/K$_D$) where [L] is the concentration of free radioligand and K$_D$ is its dissociation constant at the receptor, derived from saturation binding experiments (Cheng and Prusoff, 1973).

The compounds of the invention, which were tested in the above NK-1 and NK-2 described assays, demonstrated a low affinity at the human NK-1 and human NK-2 receptors: more than 200 fold shift of the Ki compared to the human NK-3 receptor (table 7). Thus, compounds according to the invention have been shown to be selective over NK1 and NK2 receptors.

TABLE 7

| Compound n° | NK1 Ki (µM) | NK2 Ki (µM) | NK3 Ki (nM) |
| --- | --- | --- | --- |
| 1 | 12.7 | 14.0 | 16 |
| 3 | >>10 (<10% inhibition at 10 µM) | >>10 (<10% inhibition at 10 µM) | 83 |
| 11 | >>10 (<10% inhibition at 10 µM) | >>10 (<25% inhibition at 10 µM) | 44 |
| 17 | for the racemate: 6.06 | for the racemate: 9.95 | 7 |
| 23 | for the racemate: >>10 (<10% inhibition at 10 µM) | for the racemate: >>10 (<25% inhibition at 10 µM) | 29 |

TABLE 7-continued

| Compound n° | NK1 Ki (µM) | NK2 Ki (µM) | NK3 Ki (nM) |
| --- | --- | --- | --- |
| 30 | 17.2 | 5.93 | 10 |
| 31 | >>10 (<10% inhibition at 10 µM) | >>10 (<10% inhibition at 10 µM) | 22 | hERG Inhibition Assay

The human Ether-a-go-go Related Gene (hERG) encodes the inward rectifying voltage gated potassium channel in the heart (I$_{Kr}$) which is involved in cardiac repolarisation. I$_{Kr}$ current inhibition has been shown to elongate the cardiac action potential, a phenomenon associated with increased risk of arrhythmia. I$_{Kr}$ current inhibition accounts for the vast majority of known cases of drug-induced QT-prolongation. A number of drugs have been withdrawn from late stage clinical trials due to these cardiotoxic effects, therefore it is important to identify inhibitors early in drug discovery.

The hERG inhibition study aims at quantifying the in vitro effects of compounds of the invention on the potassium-selective IK$_f$ current generated in normoxic conditions in stably transfected HEK 293 cells with the human ether-a-go-go-related gene (hERG).

Whole-cell currents (acquisition by manual patch-clamp) elicited during a voltage pulse were recorded in baseline conditions and following application of tested compounds (5 minutes of exposure). The concentrations of tested compounds (0.3 µM; 3 µM; 10 µM; 30 µM) reflect a range believed to exceed the concentrations at expected efficacy doses in preclinical models.

The pulses protocol applied is described as follow: the holding potential (every 3 seconds) was stepped from −80 mV to a maximum value of +40 mV, starting with −40 mV, in eight increments of +10 mV, for a period of 1 second. The membrane potential was then returned to −55 mV, after each of these incremented steps, for 1 second and finally repolarized to −80 mV for 1 second.

The current density recorded were normalized against the baseline conditions and corrected for solvent effect and time-dependent current run-down using experimental design in test compound free conditions.

Inhibition curves were obtained for compounds and the concentrations which decreased 50% of the current density determined in the baseline conditions (IC$_{50}$) were determined. All compounds for which the IC$_{50}$ value is above 10 µM are not considered to be potent inhibitors of the hERG channel whereas compounds with IC$_{50}$ values below 1 µM are considered potent hERG channel inhibitors.

When tested in the hERG inhibition assay, compounds of the invention were determined to have IC$_{50}$ values as shown in Table 8.

TABLE 8

| Compound n° | IC$_{50}$ (µM) |
| --- | --- |
| 1 | >30 |
| 2 | >30 |
| 3 | 26 |
| 4 | >30 |
| 11 | >30 |
| 19 | 17 |
| 22 | 12 |
| 29 | 25 |
| 31 | 20 |

In Vivo Assay to Assess Compound Activity in Rat

The effect of compounds of the invention to inhibit luteinizing hormone (LH) secretion and decrease circulating androgen levels are determined by the following biological studies.

Castrated Male Rat Model to Assess the Effect of Compound of Invention on Circulating Levels of Luteinizing Hormone (LH).

In humans and rodents, castration is well-precedented to permit heightened, persistent GnRH signaling and consequent elevation of circulating LH. Thus, a castrated rat model is used to provide a broad index for measurement of LH inhibition as a marker of test compound inhibition of the GnRH signaling pathway.

Castrated adult male Sprague-Dawley (SD) rats (150-175 g) were purchased from Janvier (St Berthevin, France). All animals were housed 3 per cage in a temperature-controlled room (22±2° C.) and 50±5% relative humidity with a 12 hour light/12 hour dark photoperiod (lights off at 6 h00 pm). The animals were allowed 2 weeks of postoperative recovery prior to study. Animals were handled on a daily basis. Standard diet and tap water were provided ad libitum. Animal cage litters were changed once a week. On the study day, animals were acclimated to the procedure room for a period of one hour prior to the initiation of the experiment.

Compounds of the invention were formulated as apyrogen water with 90 g/L (2-Hydroxypropyl)-β-CycloDextrin.

After basal sampling (T0) a single dose of compounds of the invention or vehicle was administrated intravenously to rats. Blood was then collected at 60 min post dosing. Blood samples were obtained via tail vein bleed, drawn into EDTA-containing tubes and centrifuged immediately. Plasma samples were collected and stored in a −80° C. freezer until assayed. Serum LH levels were determined using radioimmunoassay kit from RIAZEN—Rat LH, Zentech (Liège, Belgium). Baseline was defined as the initial basal blood sample.

Figure 3:
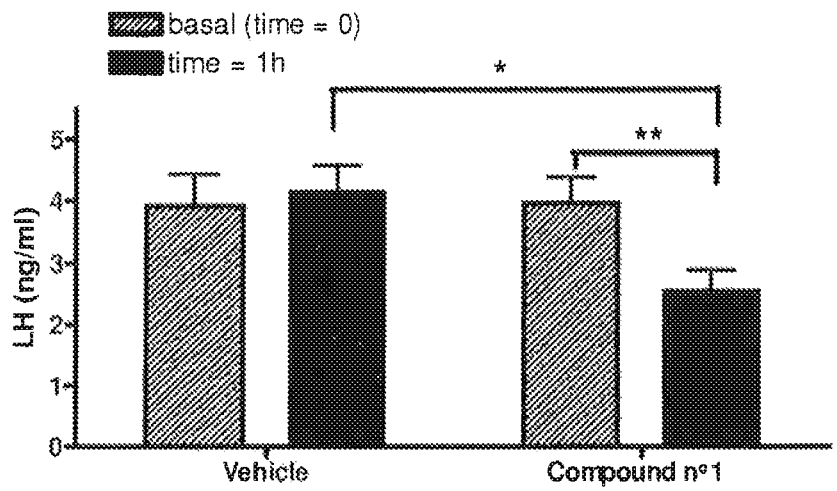
FIG. 3 shows the effects of a single intravenous 10 mg/kg dose of compound no 1 on lutenizing hormone ('LH') plasma levels in castrated male, Sprague-Dawley rats measured 1 hour after dosing. LH levels are expressed as means±S.E.M. The vehicle is 9% 2-hydroxypropyl-β-cyclodextrin/$H_2O$ (w/w). Vehicle, N=10 rats; Compound no 1, N=9 rats.

When tested in the castrated male rat model described above, the compound no 1 significantly suppressed circulating LH levels (FIG. 3).

Figure 4:
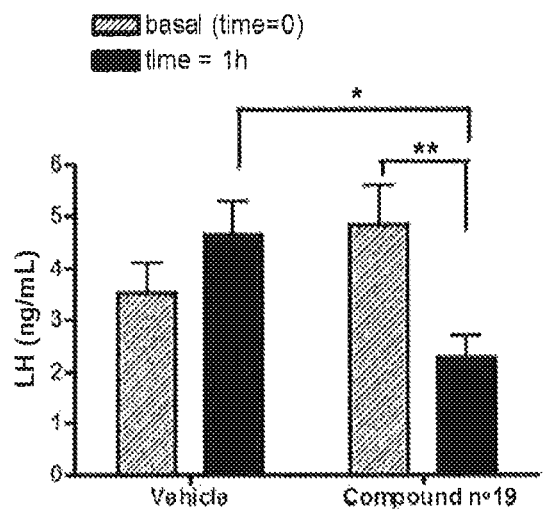
FIG. 4 shows the effects of a single intravenous 10 mg/kg dose of compound no 19 on lutenizing hormone ('LH') plasma levels in castrated male, Sprague-Dawley rats measured 1 hour after dosing. LH levels are expressed as means±S.E.M. The vehicle is 9% 2-hydroxypropyl-β-cyclodextrin/H2O (w/w). Vehicle, n=5 rats; Compound no 19, n=5 rats.

When tested in the castrated male rat model described above, the compound no 19 significantly suppressed circulating LH levels (FIG. 4).

Gonad-Intact Adult Male to Assess the Effect of Compounds of the Invention on Circulating Levels of Testosterone.

Gonad-intact adult male Sprague-Dawley (SD) rats (225-385 g N=3/group were housed in a temperature-controlled room (22±2° C.) and 50±5% relative humidity with a 12 hour light/12 hour dark photoperiod (lights off at 6 h00 pm). Rat chow and tap water were made available to rats, ad libitum. After basal blood sampling, free-moving rats were intravenously injected at time=0 min with either a single dose of compound or vehicle. Blood was then collected at times 1, 5, 15, 90, 150, 210 min into tubes containing EDTA as anticoagulant and centrifuged immediately. Plasma samples were collected and stored in a −80° C. freezer until assayed. Plasma testosterone levels were determined using a radioimmunoassay kit (Immunotech).

Compound no 1 was formulated in 9% 2-hydroxypropyl-β-cyclodextrin/H2O (w/w). A single dose of 50 mg/kg of compound no 1 was intravenously injected.

Figure 5:
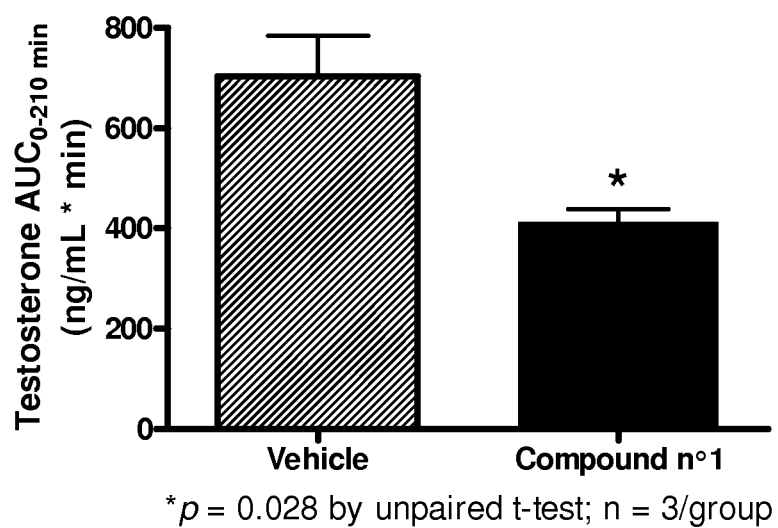
FIG. 5 shows the effects of a single intravenous 50 mg/kg dose of compound no 1 on testosterone plasma levels in male, Sprague-Dawley rats. N=3 rats per treatment group. Testosterone levels were measured just prior to dosing and at times 1, 5, 15, 90, 150, 210 min after dosing to derive a time-response curve. Data are expressed as the testosterone area under the curve ('AUC')±S.E.M. The vehicle is 9% 2-hydroxypropyl-β-cyclodextrin/$H_2O$ (w/w).

When tested in gonad-intact male rats, compound no 1 significantly suppressed plasma testosterone levels over the 210 minute test period (FIG. 5).

The invention claimed is:

1. A compound of Formula I:

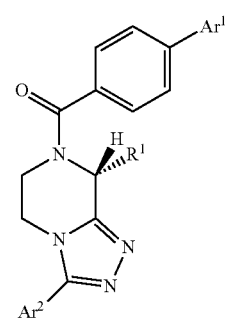

and pharmaceutically acceptable solvates thereof, wherein $Ar^1$ is unsubstituted thiophen-2-yl, unsubstituted phenyl, or 4-fluorophenyl;

$R^1$ is H or methyl;

$Ar^2$ is of general Formula (i), (ii) or (iii):

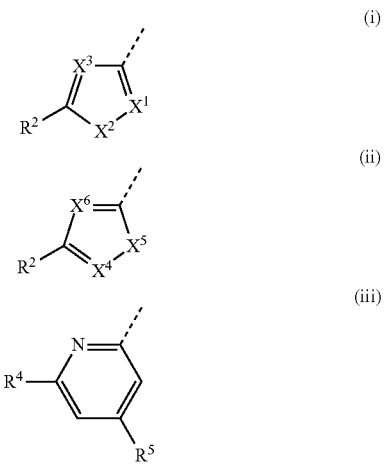

wherein $R^2$ is linear or branched C1-C4 alkyl, C1-C2 haloalkyl, linear or branched C2-C3 alkenyl, C3-C4 cycloalkyl or di(C1-C2 alkyl)amino;

$X^1$ is N or C—$R^6$ wherein $R^6$ is H, fluoro or C1-C2 alkyl;

$X^2$ is O or S;

$X^3$ is N, or $X^3$ is CH under the condition that $X^1$ is N and $X^2$ is N—$R^7$ wherein $R^7$ is linear or branched C1-C3 alkyl or cyclopropyl;

$R^3$ is linear or branched C1-C4 alkyl or C3-C4 cycloalkyl;

$X^4$ is N or C—$R^8$ wherein $R^8$ is H or C1-C2 alkyl;

$X^5$ is O or S;

$X^6$ is N, or $X^6$ is CH under the condition that $X^4$ is N and $X^5$ is N—$R^9$ wherein $R^9$ is linear or branched C1-C3 alkyl or cyclopropyl;

$R^4$ is halo, cyano, methyl, or hydroxyl;

$R^5$ is H or halo;

with the condition that when $Ar^2$ is of Formula (iii), then $R^1$ is methyl; and the compound of Formula I is not (3-(2-isobutylthiazol-4-yl)-5,6-dihydro-[1,2,4]triazolo[4,3-a]pyrazin-7(8H)-yl)(4-(thiophen-2-yl)phenyl)methanone;

[1,1'-biphenyl]-4-yl(8-methyl-3-(6-methylpyridin-2-yl)-5,6-dihydro-[1,2,4]triazolo[4,3-a]pyrazin-7(8H)-yl)methanone;

(8-methyl-3-(6-methylpyridin-2-yl)-5,6-dihydro-[1,2,4]triazolo[4,3-a]pyrazin-7(8H)-yl)(4-(thiophen-2-yl)phenyl)methanone.

2. The compound of claim 1 having Formula I':

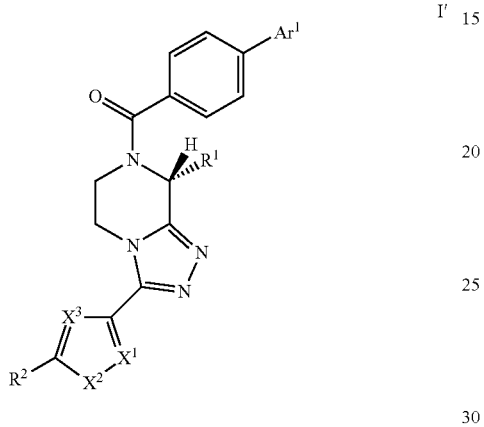

and pharmaceutically acceptable solvates thereof, wherein $Ar^1$ is unsubstituted thiophen-2-yl, unsubstituted phenyl, or 4-fluorophenyl;

$R^1$ is H or methyl;

$R^2$ is linear or branched C1-C4 alkyl, C1-C2 haloalkyl, linear or branched C2-C3 alkenyl, C3-C4 cycloalkyl or di(C1-C2 alkyl)amino;

$X^1$ is N or C—$R^6$ wherein $R^6$ is H, fluoro or C1-C2 alkyl;

$X^2$ is O or S;

$X^3$ is N, or $X^3$ is CH under the condition that $X^1$ is N and $X^2$ is N—$R^7$ wherein $R^7$ is linear or branched C1-C3 alkyl or cyclopropyl.

3. The compound of claim 1 having Formula I'1

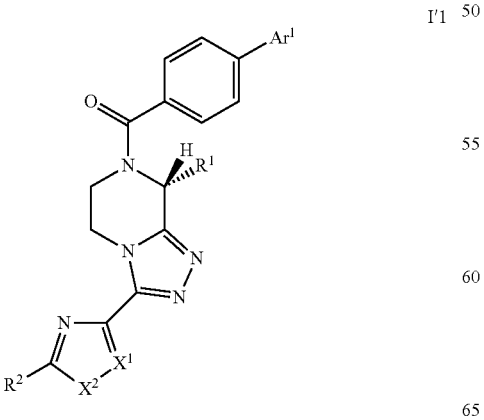

and pharmaceutically acceptable solvates thereof.

4. The compound of claim 1 selected from Formulae I'a and I'b

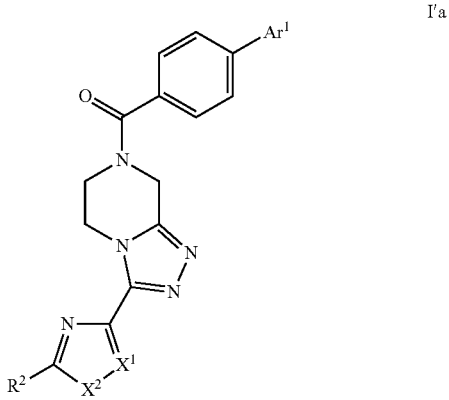

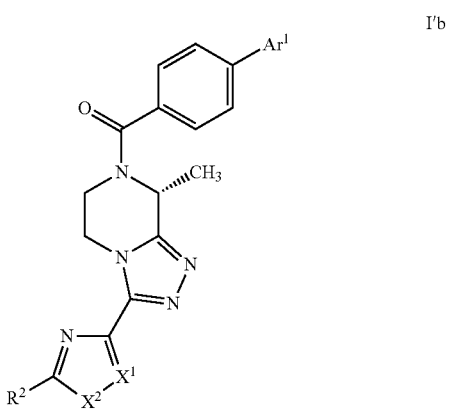

and pharmaceutically acceptable solvates thereof.

5. The compound of claim 1 selected from Formulae I'c, I'd

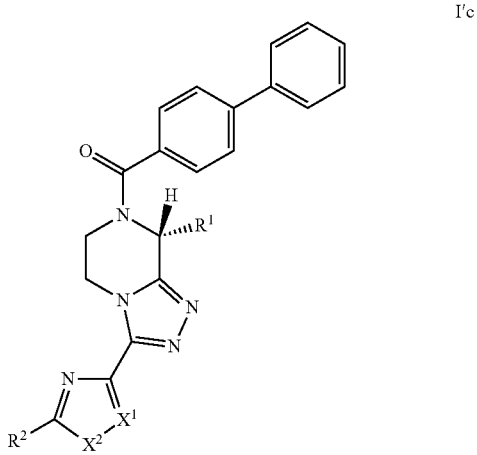

-continued
I'd
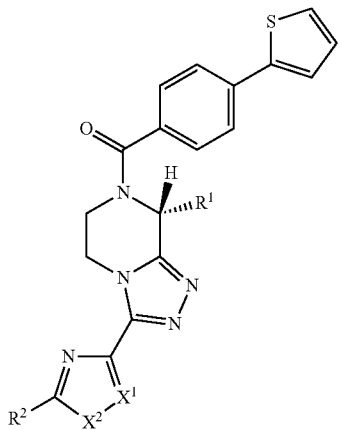
and pharmaceutically acceptable solvates thereof.
6. The compound of claim 1 selected from Formulae I'e, I'f
I'e
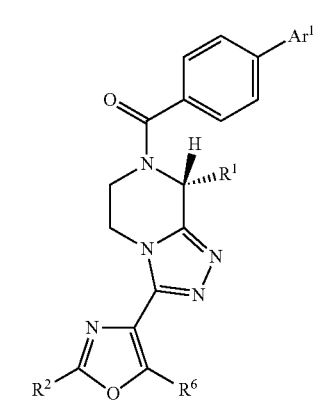
I'f
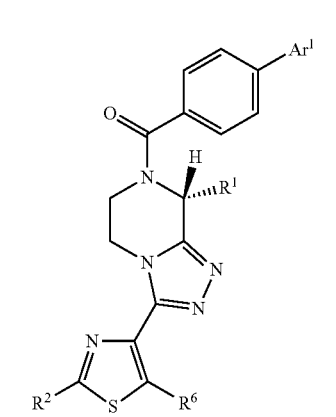
and pharmaceutically acceptable solvates thereof.
7. The compound of claim 1 selected from Formulae I'e-1, I'e-2, I'f-1, I'f-2
I'e-1
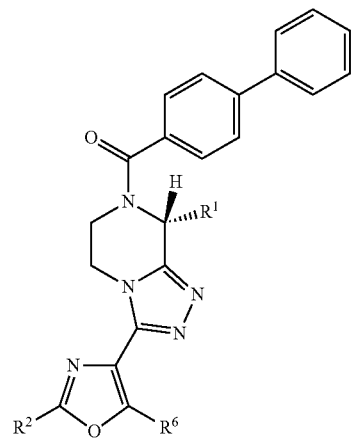
I'f-1
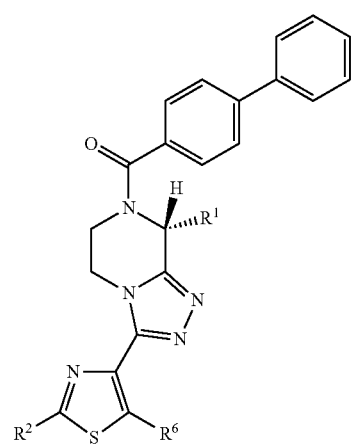
I'e-2
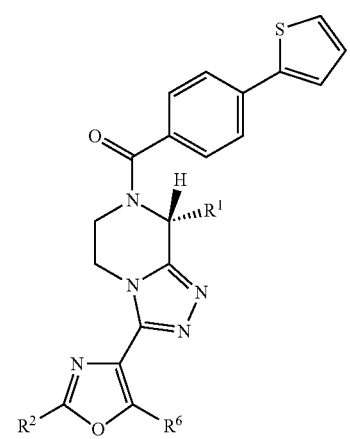

-continued

I'-f-2

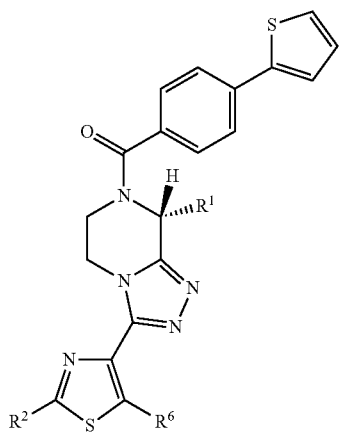

and pharmaceutically acceptable solvates thereof.

8. The compound of claim 1 having Formula I'e-3

I'e-3

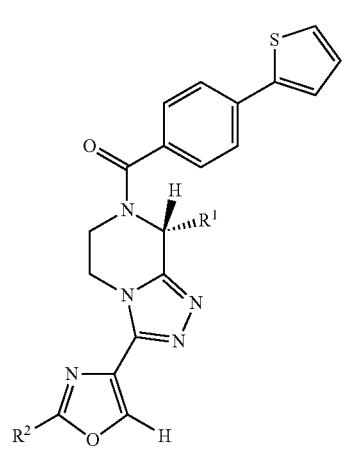

and pharmaceutically acceptable solvates thereof.

9. The compound of claim 1 having Formula I'f-3

I'f-3

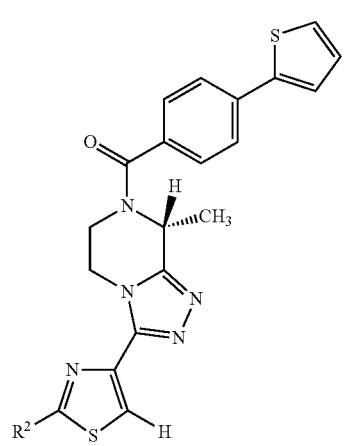

and pharmaceutically acceptable solvates thereof.

10. The compound of claim 1 having Formulae I'g, I'h and I'i

I'g

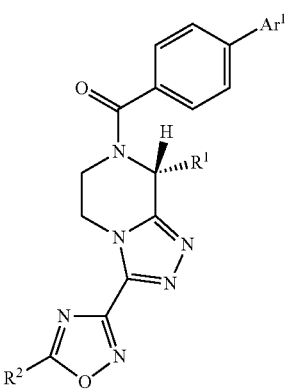

I'h

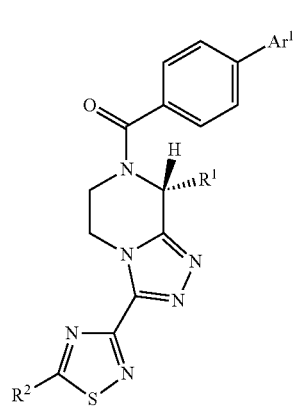

I'i

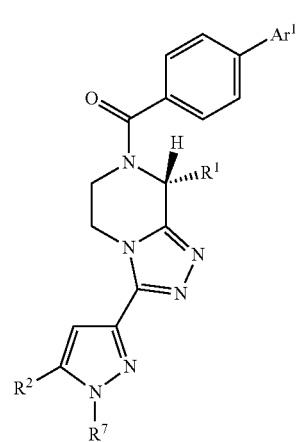

and pharmaceutically acceptable solvates thereof.

11. The compound of claim 1 having Formula I″:

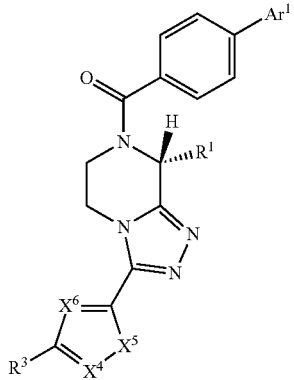

I″ and pharmaceutically acceptable solvates thereof, wherein
Ar¹ is unsubstituted thiophen-2-yl, unsubstituted phenyl, or 4-fluorophenyl;
$R^1$ is H or methyl;
$R^3$ is linear or branched C1-C4 alkyl or C3-C4 cycloalkyl;
$X^4$ is N or C—$R^8$ wherein $R^8$ is H or C1-C2 alkyl;
$X^5$ is O or S;
$X^6$ is N, or $X^6$ is CH under the condition that $X^4$ is N and $X^5$ is N—$R^9$ wherein $R^9$ is linear or branched C1-C3 alkyl or cyclopropyl.

12. The compound of claim 1 selected from Formulae I″a, I″b

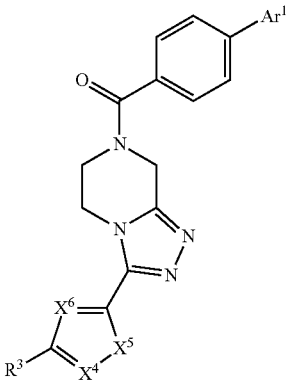

I″a

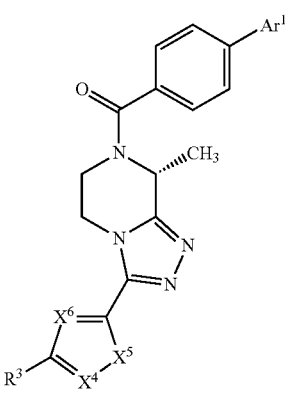

I″b and pharmaceutically acceptable solvates thereof.

13. The compound of claim 1 selected from Formulae II″c, I″d

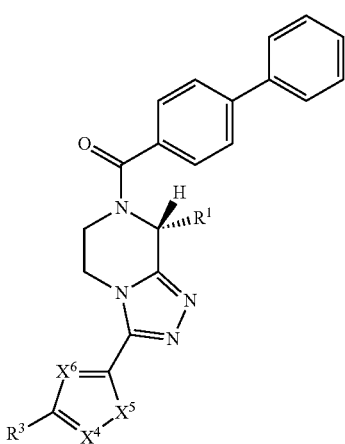

I″c

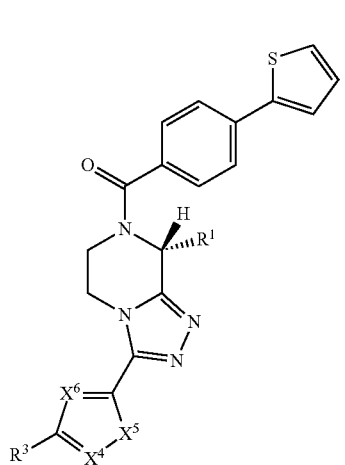

I″d and pharmaceutically acceptable solvates thereof.

14. The compound of claim 1 selected from Formulae II″e, I″f, I″g, I″h and I″i

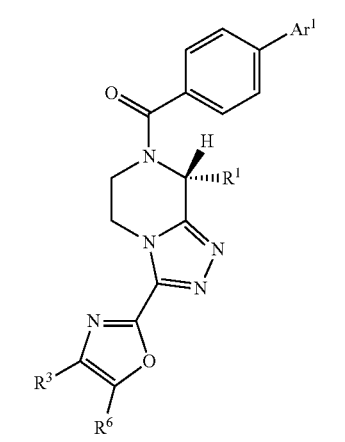

I″e

-continued
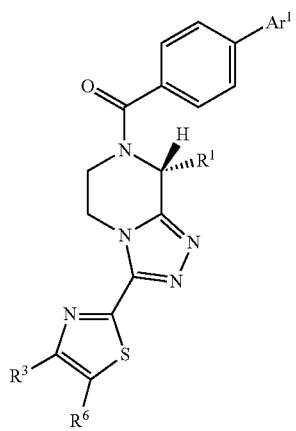
I″f
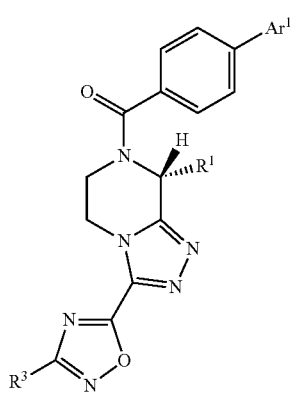
I″g
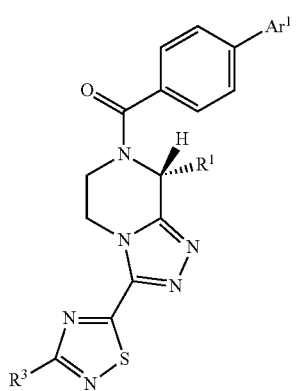
I″h
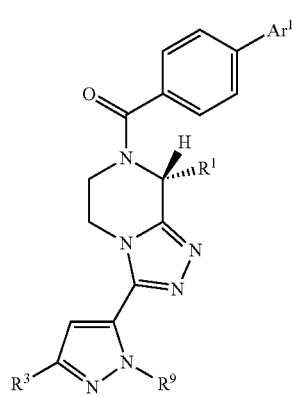
I″i
and pharmaceutically acceptable solvates thereof.
15. The compound of claim 14 selected from Formulae I″e-1, I″f-1, I″g-1, I″h-1, I″i-1, I″e-2, I″f-2, I″g-2, I″h-2 and I″i-2
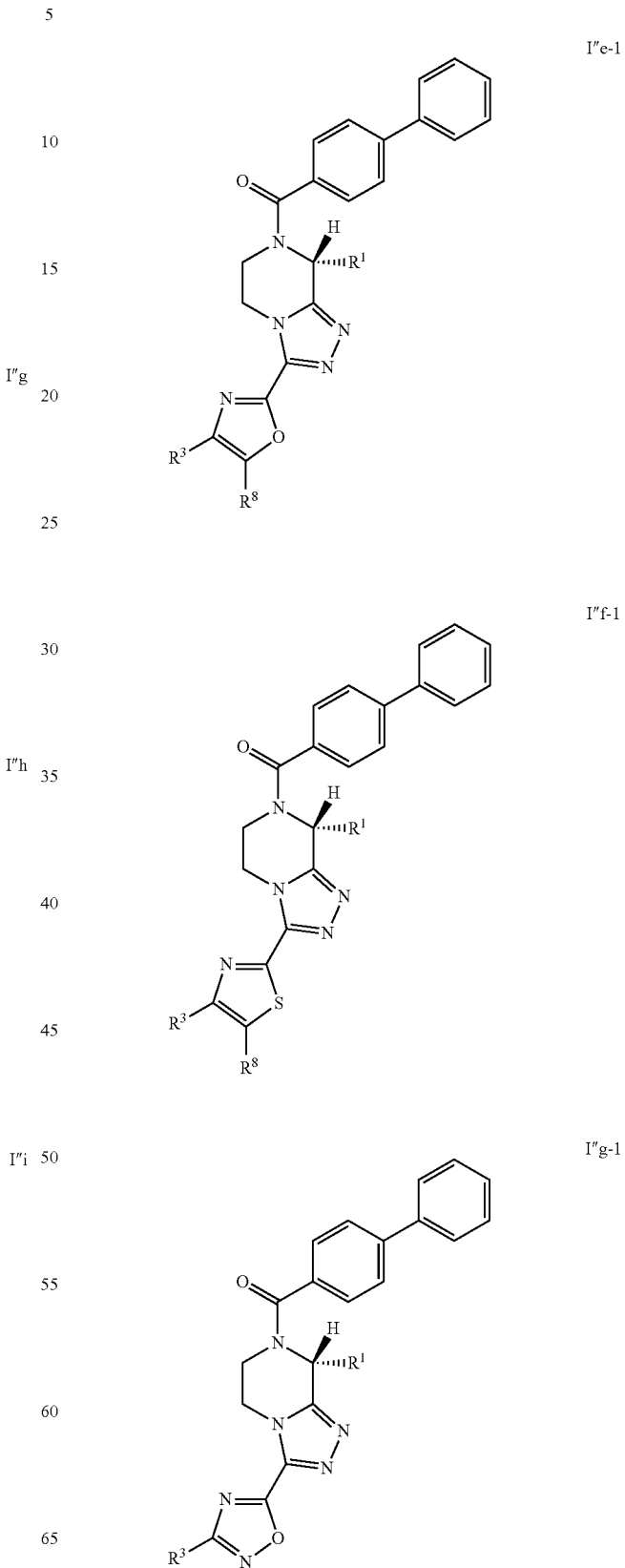

I″h-1
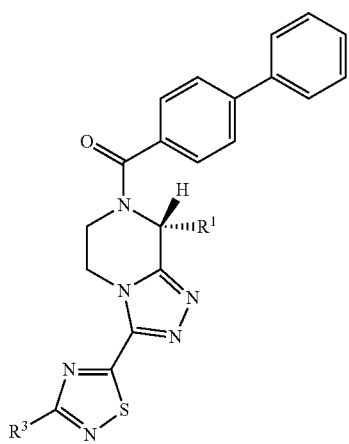
I″i-1
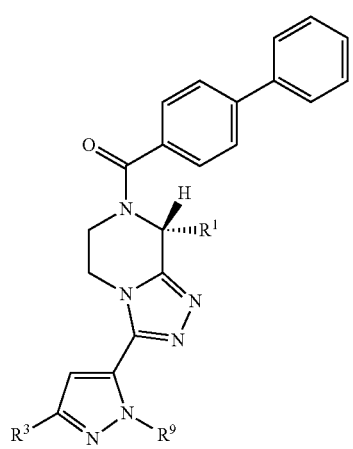
I″e-2
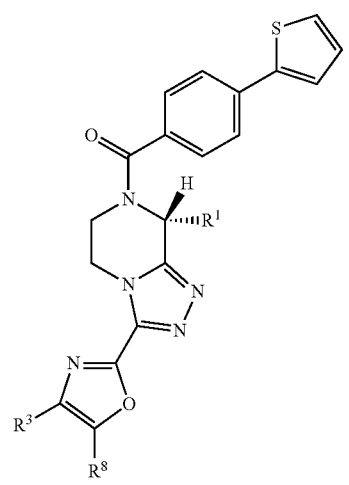
I″f-2
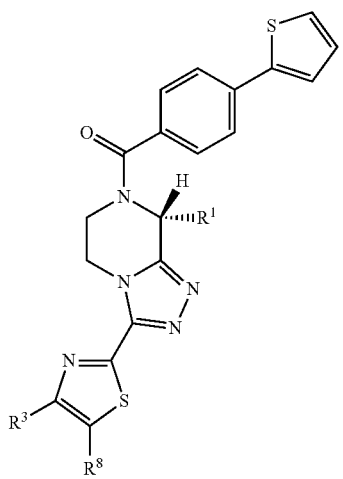
I″g-2
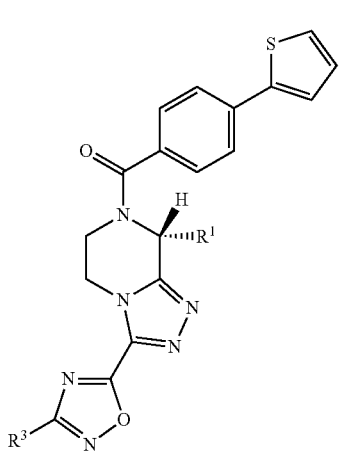
I″h-2
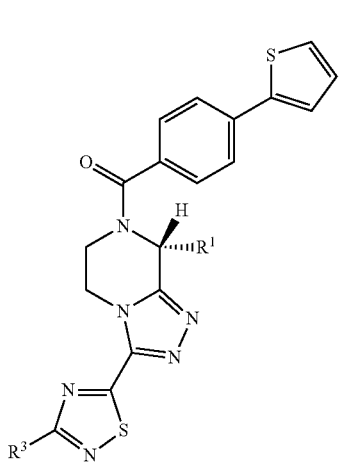

-continued

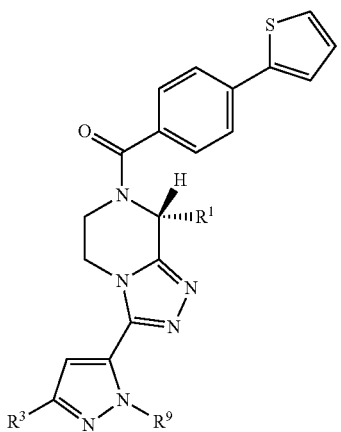

I″i-2 and pharmaceutically acceptable solvates thereof.

16. The compound of claim 1 having Formula I'":

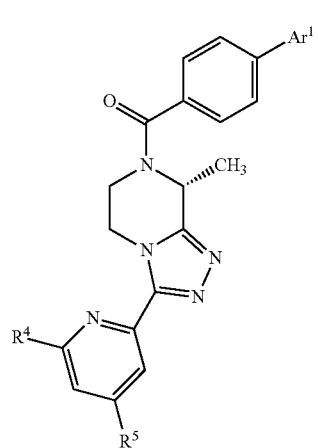

I'"

and pharmaceutically acceptable solvates thereof, wherein

Ar$^1$ is unsubstituted phenyl, unsubstituted thiophen-2-yl or 4-fluorophenyl;

R$^4$ is halo, cyano, methyl, or hydroxyl;

R$^5$ is H or halo.

17. The compound of claim 1 selected from Formulae I'"a and I'"b

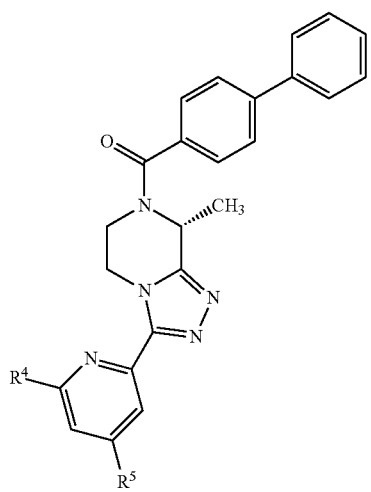

I'"a

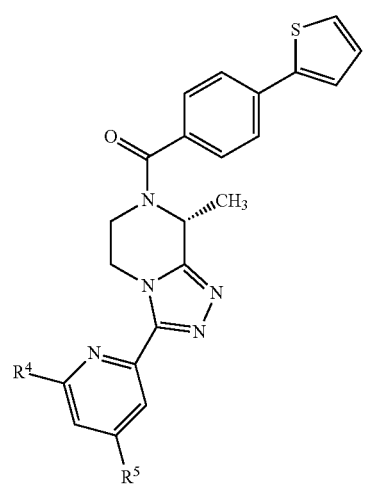

I'"b and pharmaceutically acceptable solvates thereof.

18. The compound of claim 1 selected from the group consisting of:

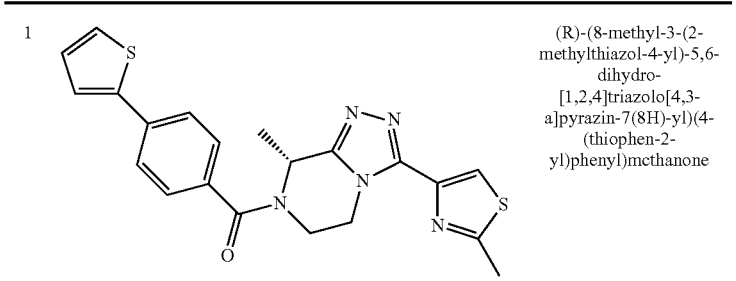

(R)-(8-methyl-3-(2-methylthiazol-4-yl)-5,6-dihydro-[1,2,4]triazolo[4,3-a]pyrazin-7(8H)-yl)(4-(thiophen-2-yl)phenyl)methanone -continued

| | | |
|---|---|---|
| 2 | | (R)-[1,1'-biphenyl]-4-yl(8-methyl-3-(2-methylthiazol-4-yl)-5,6-dihydro-[1,2,4]triazolo[4,3-a]pyrazin-7(8H)-yl)methanone |
| 3 | | (3-(2-methylthiazol-4-yl)-5,6-dihydro-[1,2,4]triazolo[4,3-a]pyrazin-7(8H)-yl)(4-(thiophen-2-yl)phenyl)methanone |
| 4 | | (4-(thiophen-2-yl)phenyl)(3-(2-(trifluoromethyl)thiazol-4-yl)-5,6-dihydro-[1,2,4]triazolo[4,3-a]pyrazin-7(8H)-yl)methanone |
| 5 | | (R)-(3-(2-ethylthiazol-4-yl)-8-methyl-5,6-dihydro-[1,2,4]triazolo[4,3-a]pyrazin-7(8H)-yl)(4-(thiophen-2-yl)phenyl)methanone |
| 6 | | (R)-[1,1'-biphenyl]-4-yl(3-(2-ethylthiazol-4-yl)-8-methyl-5,6-dihydro-[1,2,4]triazolo[4,3-a]pyrazin-7(8H)-yl)methanone |

| | | |
|---|---|---|
| 7 | 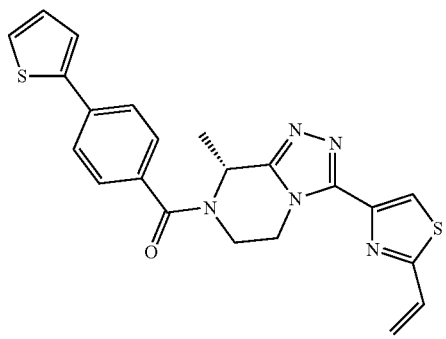 [SMILES: C=Cc1nc(-c2nnc3n2CCN(C(=O)c2ccc(-c4cccs4)cc2)[C@@H]3C)cs1] | (R)-(8-methyl-3-2-vinylthiazol-4-yl)-5,6-dihydro-[1,2,4]triazolo[4,3-a]pyrazin-7(8H)-yl)(4-(thiophen-2-yl)phenyl)methanone |
| 8 | 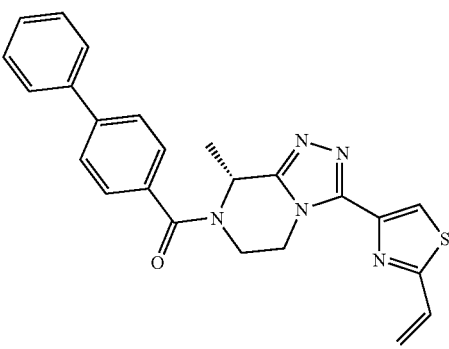 [SMILES: C=Cc1nc(-c2nnc3n2CCN(C(=O)c2ccc(-c4ccccc4)cc2)[C@@H]3C)cs1] | (R)-[1,1'-biphenyl]-4-yl(8-methyl-3-(2-vinylthiazol-4-yl)-5,6-dihydro-[1,2,4]triazolo[4,3-a]pyrazin-7(8H)-yl)methanone |
| 9 | 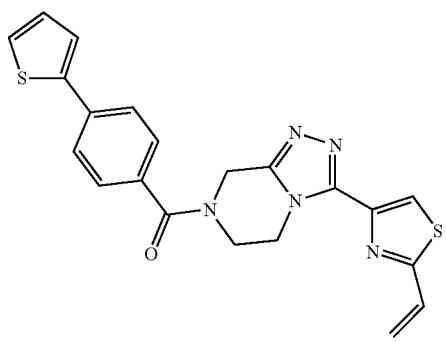 [SMILES: C=Cc1nc(-c2nnc3n2CCN(C(=O)c2ccc(-c4cccs4)cc2)C3)cs1] | (4-(thiophen-2-yl)phenyl)(3-(2-vinylthiazol-4-yl)-5,6-dihydro-[1,2,4]triazolo[4,3-a]pyrazin-7(8H)-yl)methanone |
| 10 | 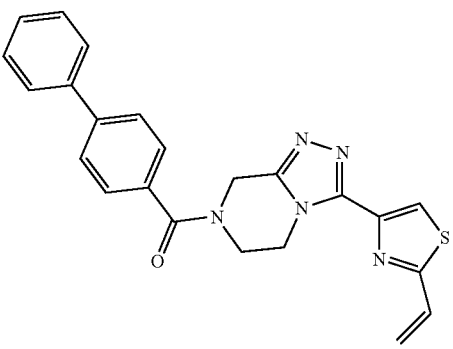 [SMILES: C=Cc1nc(-c2nnc3n2CCN(C(=O)c2ccc(-c4ccccc4)cc2)C3)cs1] | [1,1'-biphenyl]-4-yl(3-(2-vinylthiazol-4-yl)-5,6-dihydro-[1,2,4]triazolo[4,3-a]pyrazin-7(8H)-yl)methanone |

| | | |
|---|---|---|
| 11 | 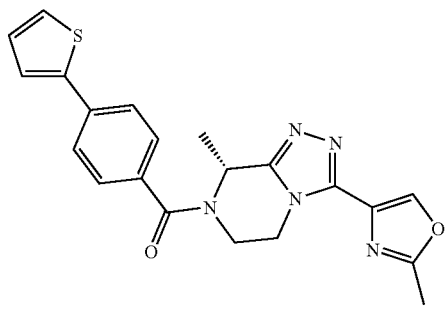 [SMILES: Cc1nc(-c2nnc3n2CCN(C(=O)c2ccc(-c4cccs4)cc2)[C@@H]3C)co1] | (R)-(8-methyl-3-(2-methyloxazol-4-yl)-5,6-dihydro-[1,2,4]triazolo[4,3-a]pyrazin-7(8H)-yl)(4-(thiophen-2-yl)phenyl)methanone |
| 12 | 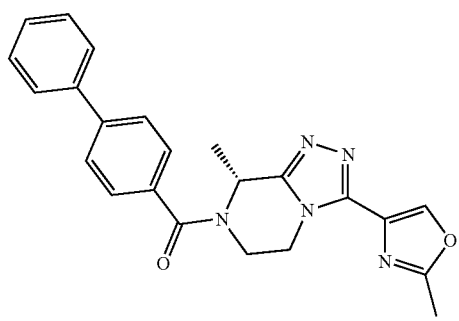 [SMILES: Cc1nc(-c2nnc3n2CCN(C(=O)c2ccc(-c4ccccc4)cc2)[C@@H]3C)co1] | (R)-[1,1'-biphenyl]-4-yl(8-methyl-3-(2-methyloxazol-4-yl)-5,6-dihydro-[1,2,4]triazolo[4,3-a]pyrazin-7(8H)-yl)methanone |
| 13 | 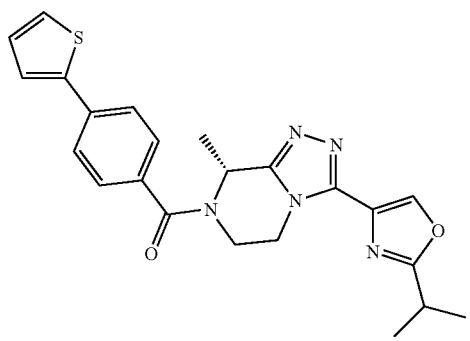 [SMILES: CC(C)c1nc(-c2nnc3n2CCN(C(=O)c2ccc(-c4cccs4)cc2)[C@@H]3C)co1] | (R)-(3-(2-isopropyloxazol-4-yl)-8-methyl-5,6-dihydro-[1,2,4]triazolo[4,3-a]pyrazin-7(8H)-yl)(4-(thiophen-2-yl)phenyl)methanone |
| 14 | 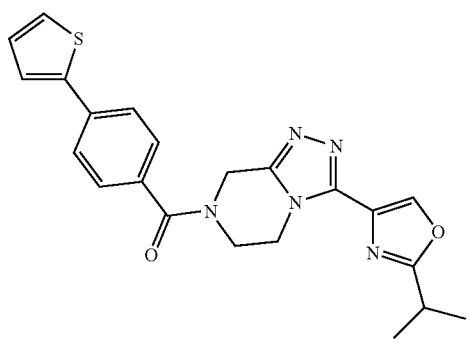 [SMILES: CC(C)c1nc(-c2nnc3n2CCN(C(=O)c2ccc(-c4cccs4)cc2)C3)co1] | (3-(2-isopropyloxazol-4-yl)-5,6-dihydro-[1,2,4]triazolo[4,3-a]pyrazin-7(8H)-yl)(4-(thiophen-2-yl)phenyl)methanone |

| | | |
|---|---|---|
| 15 | 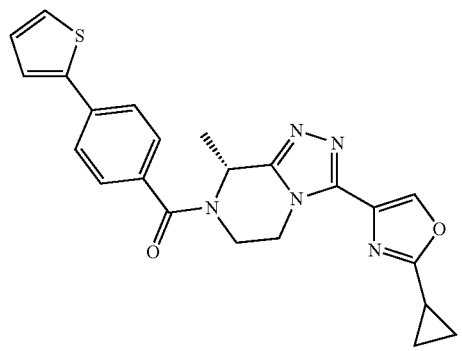 [SMILES: C[C@@H]1c2nnc(-c3coc(C4CC4)n3)n2CCN1C(=O)c1ccc(-c2cccs2)cc1] | (R)-(3-(2-cyclopropyloxazol-4-yl)-8-methyl-5,6-dihydro-[1,2,4]triazolo[4,3-a]pyrazin-7(8H)-yl)(4-(thiophen-2-yl)phenyl)methanone |
| 16 | 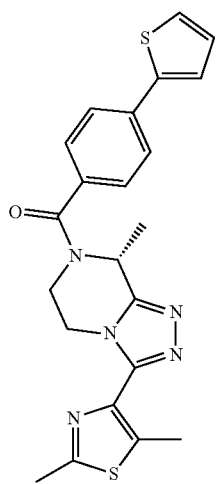 [SMILES: Cc1nc(-c2nnc3n2CCN(C(=O)c2ccc(-c4cccs4)cc2)[C@@H]3C)c(C)s1] | (R)-(3-(2,5-dimethylthiazol-4-yl)-8-methyl-5,6-dihydro-[1,2,4]triazolo[4,3-a]pyrazin-7(8H)-yl)(4-(thiophen-2-yl)phenyl)methanone |
| 17 | 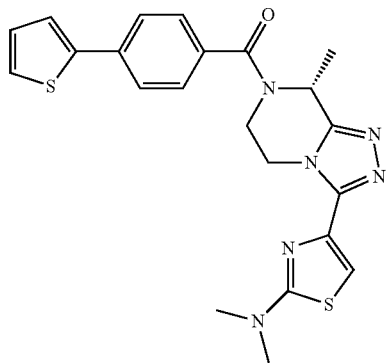 [SMILES: C[C@@H]1c2nnc(-c3csc(N(C)C)n3)n2CCN1C(=O)c1ccc(-c2cccs2)cc1] | (R)-(3-(2-(dimethylamino)thiazol-4-yl)-8-methyl-5,6-dihydro-[1,2,4]triazolo[4,3-a]pyrazin-7(8H)-yl)(4-(thiophen-2-yl)phenyl)methanone |
| 18 | 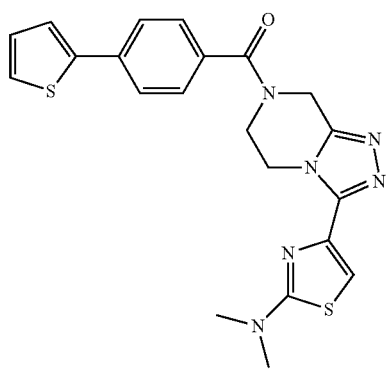 [SMILES: CN(C)c1nc(-c2nnc3n2CCN(C(=O)c2ccc(-c4cccs4)cc2)C3)cs1] | (3-(2-isopropylthiazol-4-yl)-5,6-dihydro-[1,2,4]triazolo[4,3-a]pyrazin-7(8H)-yl)(4-(thiophen-2-yl)phenyl)methanone |

-continued

| | | |
|---|---|---|
| 19 | 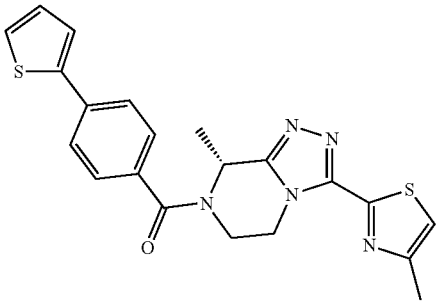 [SMILES: Cc1csc(-c2nnc3n2CCN(C(=O)c2ccc(-c4cccs4)cc2)[C@@H]3C)n1] | (R)-(8-nnethyl-3-(4-methylthiazol-2-yl)-5,6-dihydro-[1,2,4]triazolo[4,3-a]pyrazin-7(8H)-yl)(4-(thiophen-2-yl)phenyl)methanone |
| 20 | 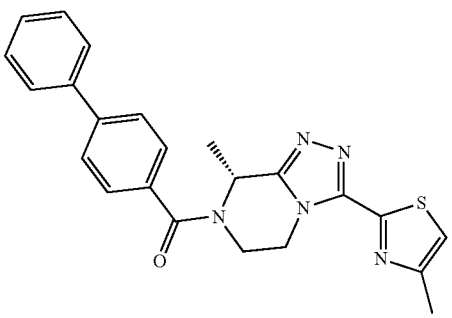 | (R)-[1,1'-biphenyl]-4-yl(8-methyl-3-(4-methylthiazol-2-yl)-5,6-dihydro-[1,2,4]triazolo[4,3-a]pyrazin-7(8H)-yl)methanone |
| 21 | 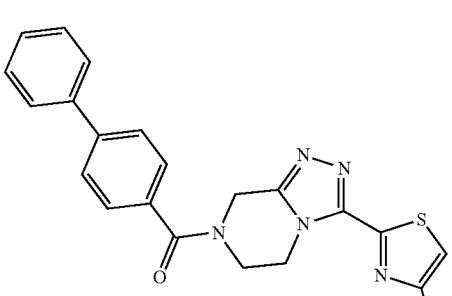 | [1,1'-biphenyl]-4-yl(3-(4-methylthiazol-2-yl)-5,6-dihydro-[1,2,4]triazolo[4,3-a]pyrazin-7(8H)-yl)methanone |
| 22 | 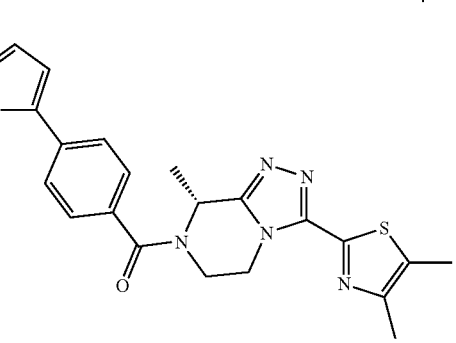 | (R)-(3-(4,5-dimethylthiazol-2-yl)-8-methyl-5,6-dihydro-[1,2,4]triazolo[4,3-a]pyrazin-7(8H)-yl)(4-(thiophen-2-yl)phenyl)methanone |
| 23 | 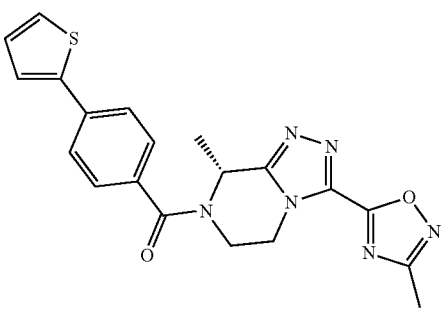 [SMILES: Cc1noc(-c2nnc3n2CCN(C(=O)c2ccc(-c4cccs4)cc2)[C@@H]3C)n1] | (R)-(8-nnethyl-3-methyl-1,2,4-(oxadiazol-5-yl)-5,6-dihydro-[1,2,4]triazolo[4,3-a]pyrazin-7(8H)-yl)(4-(thiophen-2-yl)phenyl)methanone |

| | | |
|---|---|---|
| 24 | 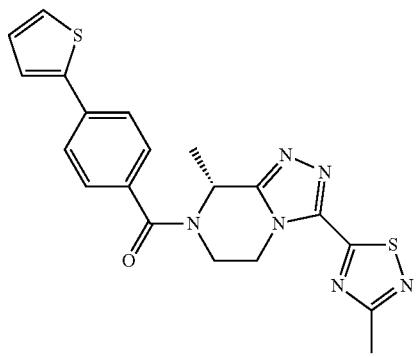 [SMILES: Cc1nsc(-c2nnc3n2CCN(C(=O)c2ccc(-c4cccs4)cc2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(4-(thiophen-2-yl)phenyl)methanone |
| 25 | 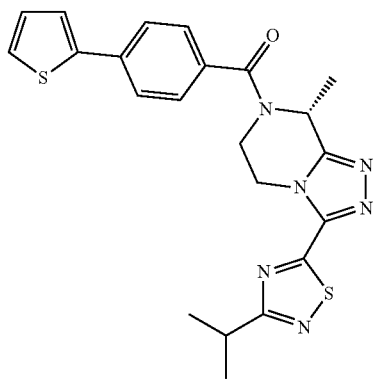 [SMILES: CC(C)c1nsc(-c2nnc3n2CCN(C(=O)c2ccc(-c4cccs4)cc2)[C@@H]3C)n1] | (R)-(3-(3-isopropyl-1,2,4-thiadiazol-5-yl)-8-methyl-5,6-dihydro-[1,2,4]triazolo[4,3-a]pyrazin-7(8H)-yl)(4-(thiophen-2-yl)phenyl)methanone |
| 26 | 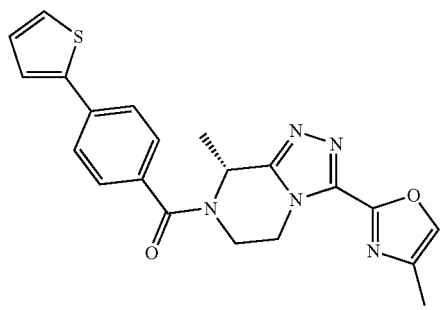 [SMILES: Cc1coc(-c2nnc3n2CCN(C(=O)c2ccc(-c4cccs4)cc2)[C@@H]3C)n1] | (R)-(8-methyl-3-(4-methyloxazol-2-yl)-5,6-dihydro-[1,2,4]triazolo[4,3-a]pyrazin-7(8H)-yl)(4-(thiophen-2-yl)phenyl)methanone |
| 27 | 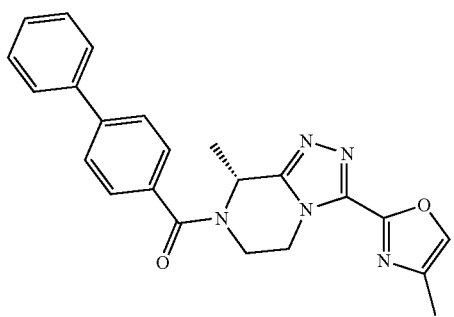 [SMILES: Cc1coc(-c2nnc3n2CCN(C(=O)c2ccc(-c4ccccc4)cc2)[C@@H]3C)n1] | (R)-[1,1'-biphenyl]-4-yl(8-methyl-3-(4-methyloxazol-2-yl)-5,6-dihydro-[1,2,4]triazolo[4,3-a]pyrazin-7(8H)-yl)methanone |

| | | |
|---|---|---|
| 28 | 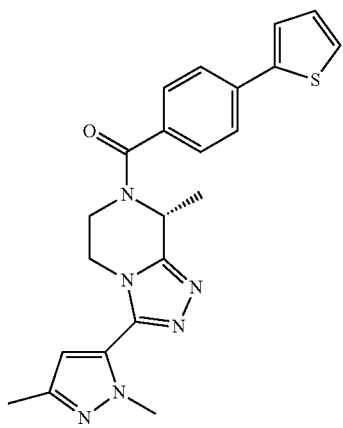 [SMILES: Cc1cc(-c2nnc3n2CCN(C(=O)c2ccc(-c4cccs4)cc2)[C@@H]3C)n(C)n1] | (R)-(3-(1,3-dimethyl-1H-pyrazol-5-yl)-8-methyl-5,6-dihydro-[1,2,4]triazolo[4,3-a]pyrazin-7(8H)-yl)(4-(thiophen-2-yl)phenyl)methanone |
| 29 | 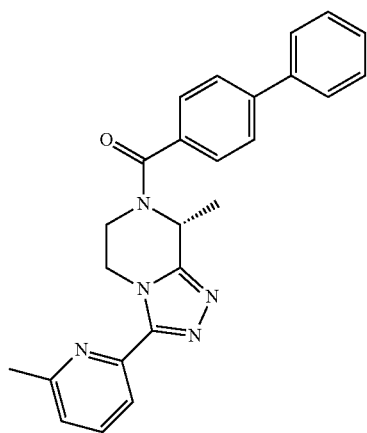 [SMILES: Cc1cccc(-c2nnc3n2CCN(C(=O)c2ccc(-c4ccccc4)cc2)[C@@H]3C)n1] | (R)-[1,1'-biphenyl]-4-yl(8-methyl-3-(6-methylpyridin-2-yl)-5,6-dihydro-[1,2,4]triazolo[4,3-a]pyrazin-7(8H)-yl)methanone |
| 30 | 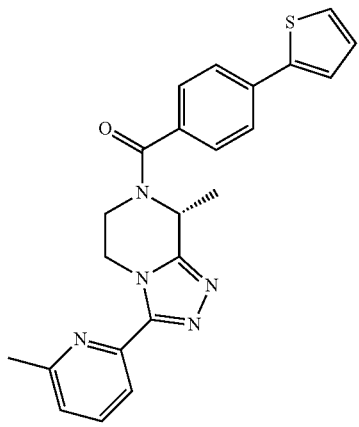 [SMILES: Cc1cccc(-c2nnc3n2CCN(C(=O)c2ccc(-c4cccs4)cc2)[C@@H]3C)n1] | (R)-(8-methyl-3-(6-methylpyridin-2-yl)-5,6-dihydro-[1,2,4]triazolo[4,3-a]pyrazin-7(8H)-yl)(4-(thiophen-2-yl)phenyl)methanone |

| | | |
|---|---|---|
| 31 | 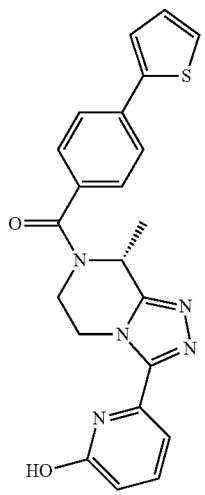 [SMILES: C[C@@H]1c2nnc(-c3cccc(O)n3)n2CCN1C(=O)c1ccc(-c2cccs2)cc1] | (R)-(3-(6-hydroxypyridin-2-yl)-8-methyl-5,6-dihydro-[1,2,4]triazolo[4,3-a]pyrazin-7(8H)-yl)(4-(thiophen-2-yl)phenyl)methanone |
| 32 | 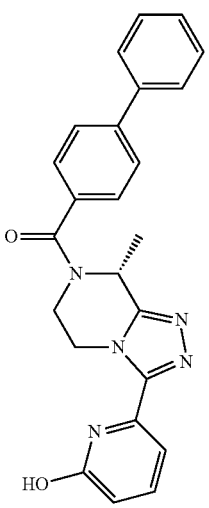 [SMILES: C[C@@H]1c2nnc(-c3cccc(O)n3)n2CCN1C(=O)c1ccc(-c2ccccc2)cc1] | (R)-[1,1'-biphenyl]-4-yl(3-(6-hydroxypyridin-2-yl)-8-methyl-5,6-dihydro-[1,2,4]triazolo[4,3-a]pyrazin-7(8H)-yl)methanone |
| 33 | 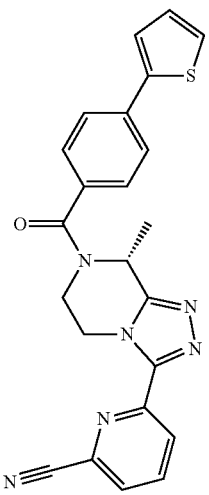 [SMILES: C[C@@H]1c2nnc(-c3cccc(C#N)n3)n2CCN1C(=O)c1ccc(-c2cccs2)cc1] | (R)-6-(8-methyl-7-(4-(thiophen-2-yl)benzoyl)-5,6,7,8-tetrahydro-[1,2,4]triazolo[4,3-a]pyrazin-3-yl)picolinonitrile | and pharmaceutically acceptable solvates thereof.

19. A pharmaceutical composition comprising a compound according to claim 1 or a pharmaceutically acceptable solvate thereof and at least one pharmaceutically acceptable carrier, diluent, excipient and/or adjuvant.

20. Medicament comprising a compound according to claim 1 or a pharmaceutically acceptable solvate thereof.

* * * * *

UNITED STATES PATENT AND TRADEMARK OFFICE
CERTIFICATE OF CORRECTION

| | | |
|---|---|---|
| PATENT NO. | : 9,475,814 B2 | |
| APPLICATION NO. | : 14/349595 | |
| DATED | : October 25, 2016 | |
| INVENTOR(S) | : Hamid R. Hoveyda et al. | |

It is certified that error appears in the above-identified patent and that said Letters Patent is hereby corrected as shown below:

In the Claims

Column 158, Line 45, in the preamble of Claim 14, formula number "II"e" should read -- I"e --;

Column 158, Line 50, Claim 14, formulae I"e, that portion of the formula reading "$R^6$" should read -- $R^8$ --; and Column 159, Line 1, Claim 14, formulae I"f, that portion of the formula reading "$R^6$" should read -- $R^8$ --.

Signed and Sealed this
Thirtieth Day of May, 2017

Michelle K. Lee
*Director of the United States Patent and Trademark Office*